(12) United States Patent
Reimer et al.

(10) Patent No.: US 12,076,234 B2
(45) Date of Patent: Sep. 3, 2024

(54) STABILIZED FABRIC MATERIAL FOR MEDICAL DEVICES

(71) Applicant: Abbott Laboratories, Abbott Park, IL (US)

(72) Inventors: Jay Reimer, Shoreview, MN (US); Paul E. Ashworth, Danbury, WI (US)

(73) Assignee: Abbott Laboratories, Abbott Park, IL (US)

( * ) Notice: Subject to any disclaimer, the term of this patent is extended or adjusted under 35 U.S.C. 154(b) by 49 days.

(21) Appl. No.: 17/937,723

(22) Filed: Oct. 3, 2022

(65) Prior Publication Data
US 2023/0089253 A1 Mar. 23, 2023

Related U.S. Application Data

(60) Division of application No. 17/038,832, filed on Sep. 30, 2020, which is a continuation-in-part of
(Continued)

(51) Int. Cl.
*A61F 2/24* (2006.01)
*D03D 1/00* (2006.01)
(Continued)

(52) U.S. Cl.
CPC .......... *A61F 2/2415* (2013.01); *A61F 2/2418* (2013.01); *D03D 1/00* (2013.01);
(Continued)

(58) Field of Classification Search
CPC ............ A61F 2/2418; A61F 2002/0068; A61F 2230/0069; D10B 2509/06
See application file for complete search history.

(56) References Cited

U.S. PATENT DOCUMENTS

| 2,852,811 A | 9/1958 | Petriello |
| 3,657,744 A | 4/1972 | Ersek |

(Continued)

FOREIGN PATENT DOCUMENTS

| EP | 1318775 B1 | 11/2006 |
| EP | 2435250 A1 | 4/2012 |

(Continued)

OTHER PUBLICATIONS

<https://www.thefreedictionary.com/single-knit>; accessed Jul. 24, 2020.

(Continued)

*Primary Examiner* — Paul B Prebilic
(74) *Attorney, Agent, or Firm* — SLEMAN & LUND LLP

(57) ABSTRACT

A stabilized fabric composed of a mesh or a woven fabric is disclosed as are methods of their manufacture, the manufacture of medical devices made using a stabilized fibers and stabilized medical devices are all disclosed. Fabrics can be stabilized by several techniques including: using mechanical, chemical and/or energetic fasteners at warp and weft intersections in the weave; by using various weaving techniques and fibers. Meshes can be stabilized when properly dimensioned and arranged junctions and struts of the necessary properties are used. All of these stabilized fabrics can be made of synthetic polymer materials such as ultrahigh molecular weight PE or PP and expanded PTFE.

16 Claims, 77 Drawing Sheets

Related U.S. Application Data application No. 16/899,205, filed on Jun. 11, 2020, which is a continuation-in-part of application No. 16/713,356, filed on Dec. 13, 2019, said application No. 17/038,832 is a continuation-in-part of application No. 16/899,084, filed on Jun. 11, 2020.

(60) Provisional application No. 62/925,402, filed on Oct. 24, 2019, provisional application No. 62/925,379, filed on Oct. 24, 2019, provisional application No. 62/925,391, filed on Oct. 24, 2019, provisional application No. 62/925,412, filed on Oct. 24, 2019, provisional application No. 62/779,176, filed on Dec. 13, 2018, provisional application No. 62/925,418, filed on Oct. 24, 2019, provisional application No. 62/925,410, filed on Oct. 24, 2019.

(51) Int. Cl.
  *D03D 9/00* (2006.01)
  *A61F 2/00* (2006.01)

(52) U.S. Cl.
  CPC ........ *D03D 9/00* (2013.01); *A61F 2002/0068* (2013.01); *A61F 2220/0058* (2013.01); *A61F 2230/0069* (2013.01); *A61F 2240/001* (2013.01); *D10B 2321/021* (2013.01); *D10B 2321/022* (2013.01); *D10B 2321/042* (2013.01); *D10B 2509/06* (2013.01)

(56) References Cited

U.S. PATENT DOCUMENTS

| | | |
|---|---|---|
| 4,056,854 A | 11/1977 | Boretos |
| 4,222,126 A | 9/1980 | Boretos |
| 4,610,688 A | 9/1986 | Silvestrini |
| 4,610,918 A | 9/1986 | Effenberger |
| 4,876,049 A | 10/1989 | Aoyama |
| 5,411,552 A | 5/1995 | Andersen |
| 5,545,214 A | 8/1996 | Stevens |
| 5,562,729 A | 10/1996 | Purdy |
| 5,855,601 A | 1/1999 | Bessler |
| 5,957,948 A | 9/1999 | Mariant |
| 5,957,949 A | 9/1999 | Leonhardt |
| 6,458,153 B1 | 10/2002 | Bailey |
| 6,540,782 B1 | 4/2003 | Snyders |
| 6,821,297 B2 | 11/2004 | Snyders |
| 7,109,135 B2 | 9/2006 | Taghavi |
| 7,393,360 B2 | 7/2008 | Spenser |
| 7,510,575 B2 | 3/2009 | Spenser |
| 7,530,253 B2 | 5/2009 | Spenser |
| 7,585,321 B2 | 9/2009 | Cribier |
| 7,682,390 B2 | 3/2010 | Seguin |
| 7,923,094 B1 | 4/2011 | Harding |
| 8,758,389 B2 | 6/2014 | Glimsdale |
| 8,992,608 B2 | 3/2015 | Haug |
| 9,056,006 B2 | 6/2015 | Edelman |
| 9,241,794 B2 | 1/2016 | Braido |
| 9,289,296 B2 | 3/2016 | Braido |
| 9,326,856 B2 | 5/2016 | Schraut |
| 9,629,714 B2 | 4/2017 | Letac |
| 10,022,211 B2 | 7/2018 | Braido |
| 10,039,640 B2 | 8/2018 | Grundeman |
| 10,052,204 B2 | 8/2018 | McLean |
| 10,299,915 B2 | 5/2019 | Edelman |
| 2001/0021872 A1 | 9/2001 | Bailey |
| 2003/0078652 A1 | 4/2003 | Sutherland |
| 2003/0209835 A1 | 11/2003 | Chun |
| 2004/0088046 A1 | 5/2004 | Speziali |
| 2005/0137682 A1 | 6/2005 | Justino |
| 2006/0190074 A1 | 8/2006 | Hill |
| 2006/0235511 A1 | 10/2006 | Osborne |
| 2008/0020182 A1 | 1/2008 | Gregg |
| 2009/0105813 A1 | 4/2009 | Chambers |
| 2009/0117334 A1 | 5/2009 | Sogard |
| 2010/0094392 A1 | 4/2010 | Nguyen |
| 2012/0078352 A1 | 3/2012 | Wang |
| 2012/0171917 A1 | 7/2012 | Rasmussen |
| 2013/0150956 A1 | 6/2013 | Yohanan |
| 2013/0197631 A1 | 8/2013 | Bruchman |
| 2014/0005771 A1 | 1/2014 | Braido |
| 2014/0005772 A1 | 1/2014 | Edelman |
| 2014/0107772 A1 | 4/2014 | Li |
| 2014/0249567 A1 | 9/2014 | Adams |
| 2014/0277417 A1 | 9/2014 | Schraut |
| 2015/0091219 A1 | 4/2015 | Munnelly |
| 2015/0127100 A1 | 5/2015 | Braido |
| 2015/0157455 A1 | 6/2015 | Hoang |
| 2015/0157456 A1 | 6/2015 | Armstrong |
| 2015/0182332 A1 | 7/2015 | Edelman |
| 2015/0223932 A1 | 8/2015 | Dixon |
| 2015/0320556 A1 | 11/2015 | Levi |
| 2016/0100939 A1 | 4/2016 | Armstrong |
| 2016/0158012 A1 | 6/2016 | Anderl |
| 2016/0220359 A1 | 8/2016 | Backus |
| 2016/0220360 A1 | 8/2016 | Lin |
| 2016/0317305 A1 | 11/2016 | Pelled |
| 2017/0014227 A1 | 1/2017 | Boden |
| 2017/0065408 A1 | 3/2017 | Grundeman |
| 2017/0071729 A1 | 3/2017 | Wrobel |
| 2017/0086971 A1 | 3/2017 | Braido |
| 2017/0189172 A1 | 7/2017 | Grundeman |
| 2017/0189175 A1 | 7/2017 | Justino |
| 2017/0196688 A1 | 7/2017 | Christianson |
| 2017/0258585 A1 | 9/2017 | Marquez |
| 2017/0296332 A1 | 10/2017 | Harder |
| 2017/0325944 A1 | 11/2017 | Erzberger |
| 2018/0055631 A1 | 3/2018 | Morin |
| 2018/0055632 A1 | 3/2018 | Hill |
| 2018/0078368 A1 | 3/2018 | Vidlund |
| 2018/0116780 A1 | 5/2018 | Laine |
| 2018/0133003 A1 | 5/2018 | Levi |
| 2018/0296341 A1 | 10/2018 | Noe |
| 2019/0015192 A1 | 1/2019 | Nakazawa |
| 2019/0117387 A1 | 4/2019 | Li |
| 2019/0117390 A1 | 4/2019 | Neethling |
| 2019/0201190 A1 | 7/2019 | Dakin |
| 2019/0328525 A1 | 10/2019 | Noe |
| 2019/0351099 A1 | 11/2019 | McCarthy |
| 2020/0022807 A1 | 1/2020 | Karciauskas |
| 2020/0093590 A1 | 3/2020 | Reimer |
| 2020/0188095 A1 | 6/2020 | Liu |
| 2021/0045868 A1 | 2/2021 | Reimer |
| 2021/0121290 A1 | 4/2021 | Alkhatib |
| 2021/0315690 A1 | 10/2021 | Morin |
| 2021/0393400 A1 | 12/2021 | Alkhatib |

FOREIGN PATENT DOCUMENTS

| | | |
|---|---|---|
| EP | 2926766 A1 | 10/2015 |
| EP | 2949292 A1 | 12/2015 |
| EP | 2926766 B1 | 2/2016 |
| WO | 0224119 A1 | 3/2002 |
| WO | 2007013999 A2 | 2/2007 |
| WO | 2010138143 A1 | 12/2010 |
| WO | 2014008207 A1 | 1/2014 |
| WO | 2015169870 | 11/2015 |
| WO | 2016164197 A1 | 10/2016 |
| WO | 2018121341 A1 | 7/2018 |
| WO | 2018149587 A1 | 8/2018 |
| WO | 2020123945 | 6/2020 |

OTHER PUBLICATIONS

Adam Augustyn, Weaving, 2008, https://www.britannica.com/technology/weaving#ref290551, accessed on Oct. 11, 2019.

Basic Weaves, Cotton Incorporated, 2019, <https://www.cottonworks.com/topics/sourcing-manufacturing/weaving/the-art-of-weaving-basic-weaves/>, accessed on Oct. 11, 2019.

Basir et al., "Flexible mechanoprosthesis made from woven ultra-high-molecular-weight polyethylene fibers: proof of concept in a

(56) References Cited

OTHER PUBLICATIONS chronic sheep model"; Interactive Cardiovascular and Thoracic Surgery, Dec. 1, 2017, pp. 942-949, vol. 25, No. 6.
Bedford Cords, TextileSchool4U.Blogspot.com, 2013, http://textileschool4u.blogspot.com/2013/12/bedford-cords.html, accessed on Oct. 11, 2019.
Difference between Warp Rib Weave and Weft Rib Weave, Define Textile, 2019, <http://www.definetextile.com/2013/05/difference-between-warp-rib-weave-and.html>, accessed on Oct. 23, 2019.
Double Cloth, Mar. 20, 2019, https://en.wikipedia.Org/wiki/Double_cloth#cite_ref-text_2-0 https://en.wikipedia.org/wiki/Double_cloth, accessed on Oct. 11, 2019.
Honeycomb, The Free Dictionary, https://www.thefreedictionary.com/waffle+weave, accessed on Oct. 11, 2019.
International Search Report including the Written Opinion from Application No. PCT/US2019/066237 mailed Mar. 3, 2020, 13 pages.
International Search Report including the Written Opinion from Application No. PCT/US2020/037239 mailed Mar. 11, 2020, 16 pages.
Leno Weaves, Serial 512. Ed. 1., International Textbook Co., <https://www2.cs.arizona.edu/patterns/weaving/monographs/ics512.pdf>, accessed on Oct. 11, 2019.
Plain weave, Encyclopaedia Brittanica, Dec. 17, 2010, <https://www.britannica.com/technology/plain-weave> accessed on Oct. 11, 2019.
Rib-Knit, Merriam-Webster, 2019, <https://www.merriam-webster.com> /dictionary/rib-knit, accessed on Oct. 11, 2019.
Tapestry Weaving Basics, 2019, <https://www.mirrixlooms.com/pages/> tapestryweaving-basics, accessed on Oct. 11, 2019.
Twill weave, 2019, <https://www.dictionary.com/browse/twill-weave>, accessed on Oct. 11, 2019.
Warp knitting, Sep. 15, 2019, <https://en.wikipedia.org/wiki/> Warp_knitting, accessed on Oct. 11, 2019.
Watson, Kate Heintz et al., Textiles and Clothing, 1907, Home Economics Association, pp. 77.
What is a Herringbone Weave?, Shirts of Holland B.V., 2019, <https://sleeve7.com/blog/what-is-a-herringbone-weave/ >, accessed on Oct. 11, 2019.
Yamagishi M, Kurosawa H., "Outflow Reconstruction of Tetralogy of Fallot Using a Gore-Tex Valve," The Annals of Thoracic Surgery, Dec. 1, 1993, pp. 1411-1416, vol. 56, No. 6.

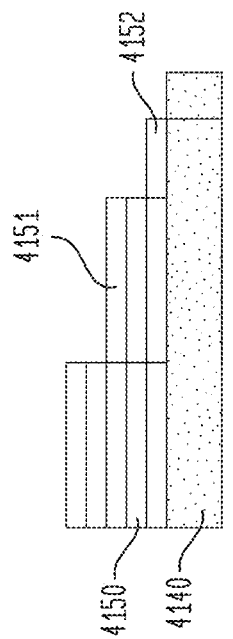
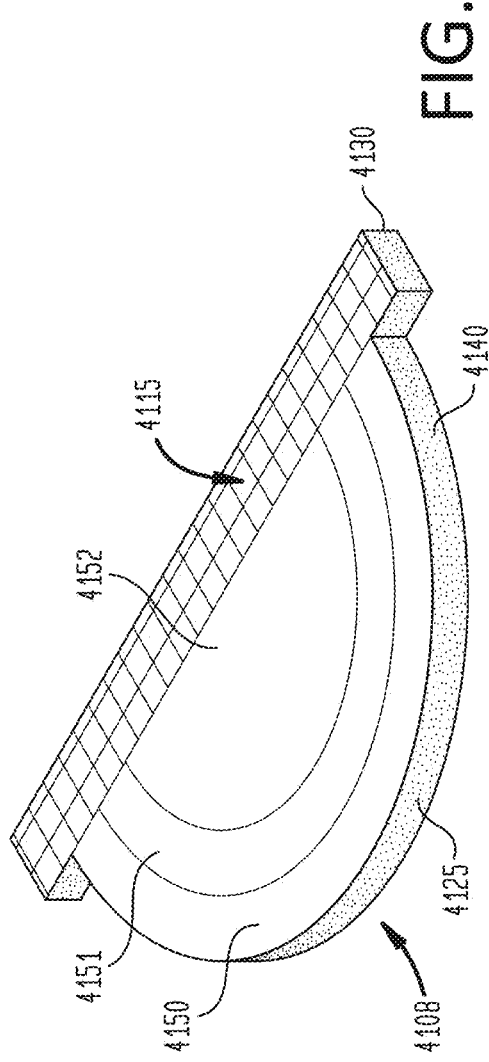
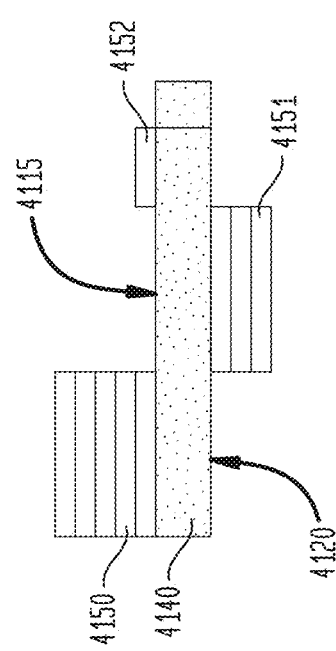
FIG. 41
FIG. 41B
FIG. 41A

STABILIZED FABRIC MATERIAL FOR MEDICAL DEVICES

CROSS-REFERENCE TO RELATED APPLICATIONS

The present application is a divisional application of U.S. application Ser. No. 17/038,832, filed Sep. 30, 2020, now U.S. Pat. No. 11,547,557, which is a continuation-in-part of U.S. patent application Ser. No. 16/899,205, filed Jun. 11, 2020, which is continuation-in-part of U.S. patent application Ser. No. 16/713,356, filed Dec. 13, 2019, which claims the benefit of the filing dates of United States Provisional Patent Application Nos. 62/779,176, filed Dec. 13, 2018; 62/925,379, filed Oct. 24, 2019; 62/925,391, filed Oct. 24, 2019; 62/925,402, filed Oct. 24, 2019; and 62/925,412, filed Oct. 24, 2019, the disclosures of all of which are hereby incorporated by reference herein.

U.S. application Ser. No. 17/038,832 is also a continuation-in-part of U.S. patent application Ser. No. 16/899,084, filed Jun. 11, 2020, which claims the benefit of the filing dates of U.S. Provisional Patent Application Nos. 62/925,410, filed Oct. 24, 2019; and 62/925,418, filed Oct. 24, 2019, the disclosures of all of which are hereby incorporated by reference herein.

BACKGROUND OF THE DISCLOSURE

The present disclosure relates to synthetic fabric materials that can be used in various medical devices and the medical devices including the synthetic fabric materials. For purposes of discussing the state of the art, however, prosthetic heart valves, and particularly collapsible/expandable prosthetic heart valves useful for delivery through a catheter or trocar, will be exemplified.

Prosthetic heart valves, including surgical heart valves and collapsible/expandable heart valves intended for transcatheter aortic valve replacement ("TAVR") or transcatheter mitral valve replacement ("TMVR"), are well known in the patent literature. (See U.S. Pat. Nos. 3,657,744; 4,056,854; 5,411,552; 5,545,214; 5,855,601; 5,957,948; 6,458,153; 6,540,782; 7,510,575; 7,585,321; 7,682,390; and 9,326,856; and U.S. Pub. No. 2015/0320556.) Surgical or mechanical heart valves may be sutured into a native annulus of a patient during an open-heart surgical procedure, for example. Collapsible/expandable heart valves may be delivered into a patient via a tube-like delivery apparatus such as a catheter, a trocar, a laparoscopic instrument, or the like to avoid a more invasive procedure such as full open-chest, open-heart surgery. As used herein, reference to a "collapsible/expandable" heart valve includes heart valves that are formed with a small cross-section that enables them to be delivered into a patient through a tube-like delivery apparatus in a minimally invasive procedure, and then expanded to an operable once in place, as well as heart valves that, after construction, are first collapsed to a small cross-section for delivery into a patient and then expanded to an operable size once in place.

Collapsible/expandable prosthetic heart valves typically take the form of a one-way valve structure (often referred to herein as a valve assembly) mounted to/within an expandable stent. In general, these collapsible/expandable heart valves include a self-expanding or balloon-expandable stent, often made of nitinol or steel. The one-way valve assembly mounted to/within the stent includes one or more leaflets, and may also include a cuff or skirt. The cuff may be disposed on the stent's interior or luminal surface, its exterior or abluminal surface, and/or on both surfaces. (See U.S. Pat. Nos. 6,458,153; 7,585,321; 8,992,608; 9,241,794; and 9,289,296; and U.S. Pub. No. 2015/0320556.) A cuff ensures that blood does not just flow around the valve leaflets if the valve or valve assembly are not optimally seated in a valve annulus. A cuff, or a portion of a cuff disposed on the exterior of the stent, can help retard leakage around the outside of the valve (the latter known as paravalvular leakage or "PV" leakage).

Leaflets, cuffs and valve assemblies for prosthetic heart valves may be derived from various natural tissues or synthetic materials. Commercial natural tissues that have been chemically treated or "fixed" are often used. For example, leaflets could be made of bovine pericardium and cuffs could be made of porcine pericardium. (See, e.g., U.S. Pat. No. 5,957,949 at 6:23-33; U.S. Pat. No. 6,458,153 at 8:28-40; U.S. Pat. No. 5,855,601 at 6:21-30; and U.S. Pat. No. 7,585,321 at 13:5-36.) Other materials that may be used include various synthetic polymers including, without limitation, polytetrafluoroethylene (PTFE) or polyester (see U.S. Pat. No. 5,855,601 at 6:29-31; U.S. Pat. Nos. 10,039,640; 10,022,211; 9,056,006; and 10,299,915; and U.S. Pub. Nos. 2018/0055632; 2017/0258585; 2018/0078368; 2019/0201190; Basir et al., "Flexible mechanoprosthesis made from woven ultra-high-molecular-weight polyethylene fibers: proof of concept in a chronic sheep model"; Interactive CardioVascular and Thoracic Surgery, 25(2017) 942-949; Yamagishi and Kurosawa, "Outflow Reconstruction of Tetralogy of Fallot Using a Gore-Tex Valve;" Ann. Thorac Surg. 1993; 56:1414-17), and elastic materials including silicone rubber and polyurethanes. (See U.S. Pat. No. 6,540,782 at 6:2-5.) These materials have been used in the form of continuous sheets, porous felts (U.S. Pat. No. 6,540,782 at 6:17-23) or woven fabrics. (See also U.S. Pat. Nos. 10,039,640; 10,299,915; 10,022,211; and 4,610,688; and U.S. Pub. Nos. 2018/0055632; 2017/0258585; and 2018/0078368.) Valve components and valve assemblies may be attached to a collapsible/expandable stent or frame by sutures or may be molded, glued, or soldered to the stent. (See U.S. Pat. No. 7,585,321 at 13:30-31.)

Mesh has been used in various surgical applications and in intravascular procedures as well. U.S. Pat. Nos. 6,974,586 and 6,375,670 describe the use of a mesh made from, inter alia, woven or interlaced wires, fibers or filaments.

Despite the disclosure of various natural tissues and synthetic materials for possible uses in various medical devices, little is often disclosed about the specifics of the structure and compositions of such elements beyond illustrations of their general structure and a generic identification of polymers that can be used. Those generalized disclosures show that, while the concept of polymer-based implantable medical devices, and in particular valves, is known, actually successfully taking the broad concept to working solutions is far more challenging. Therefore, there exists a need for further improvements in the materials for these devices and the devices made therefrom.

Another problem that may be encountered with medical devices formed from synthetic materials is a change in the properties, structure and/or performance of those materials after implantation. Using an expandable heart valve as an example, the free edge of one or more leaflets may retract or curl after implantation which can impact the completeness of coaptation of the leaflets and thereby result in leakage or regurgitation. Leaflet retraction has been observed before. See, Amir Basir, et al., noted above. This can cause a reduction in the rejection fraction of oxygenated blood pumped out of the heart and into the balance of the circulatory system and thus a reduction in pumping efficiency. This means that the heart must work harder to supply sufficient oxygen to the tissues and organs of the body.

BRIEF SUMMARY OF THE DISCLOSURE

The present invention is a stabilized fabric which comprises a stabilized woven fabric (a term which includes knitted fabrics) or a mesh, methods of stabilizing a woven fabric or a mesh, and stabilized medical devices made from a stabilized fabric as described herein. The present invention also comprises stabilized fabrics and stabilized medical devices comprising at least one component that is produced from a stabilized fabric that is resistant to conformation changes caused by tissue growth.

The disclosure describes stabilized polymer fabric materials (also referred to herein as "stabilized fabric(s)"). Stabilized fabrics include not only a stabilized woven fabric but also a mesh, unless the context suggests otherwise (such as when discussing a weaving technique or the relationship of warp and weft fibers). Stabilized fabric materials in accordance with the invention may be used for construction of, and as components of, stabilized medical devices including, without limitation: venous valves, occluders, prosthetic vascular conduits, grafts, and embolic protection devices, fabrics for treating hernias, skin patches, vaginal patches, cardiac patches, adhesion barriers, surgical heart valves (those requiring open chest surgery to implant) and collapsible/expandable prosthetic heart valves which can be implanted using a catheter such as trans-femorally, trans-apically, and trans-septally. These include expandable aortic valves, expandable mitral valves, expandable tricuspid valves and expandable pulmonary valves.

When the stabilized fabric used in stabilized medical device is a woven fabric, it comprises a woven polymer fabric having warp and weft fibers that meet at a plurality of intersections. In one embodiment, at least one of this plurality of intersections is stabilized by being mechanically fastened, chemically fastened or energetically fastened or is stabilized by weaving. "Fastened" and "fastening" in the context of a stabilized fabric of this invention means that one or more of the intersections is acted upon for reasons other than attaching the fabric to another piece of fabric, a stent, or some other structure of the medical device. Moreover, the intersections in question which result in a stabilized fabric are generally located in a portion of the fabric that is subject to movement in operation, and generally not located in a portion of the fabric that are attached to another structure or to itself (such as a portion of the fabric that is folded over and retained by being sutured).

Mechanically fastened means using a mechanical device such as, without limitation, a suture or a staple to bind one or more fiber intersections. Chemically fastening means something, such as, without limitation, using a glue or adhesive to bind one or more of the fiber intersections. Energetically fastening means using one or more types of energy to weld and therefore bind one or more fiber intersections. Stabilized by weaving means altering the nature of the weave and or the nature of the fibers to create additional friction and to restrict relative motion of the fibers at or adjacent one or more of the fiber intersections. This can be done by a number of techniques, such as, without limitation, by increasing the weave density of a localized area of the fabric, using fibers of variable thickness, using fibers of greater than usual thickness, using a denser weave or by controlling the weave pattern.

When the stabilized fabric used in a stabilized medical device is a mesh, it will be appreciated that a mesh is not woven and does not have intersections formed of fibers crossing one another. It is a continuous web or matrix of struts and junctions and, assuming the right materials and physical properties are employed, is intrinsically more stable than an un-stabilized fabric of similar material and physical dimensions. Thus, in the context of a stabilized fabric which is a mesh or a stabilized medical device made using a mesh, the mesh need not include further mechanical, chemical, energetic fastening or stabilizing by weaving. So long as the mesh is produced of the correct materials having the correct physical properties, it will be stabilized. That said, additional stability might be obtained by employing some of these same techniques and are therefore contemplated in addition.

In one particular embodiment, there is provided a balloon expandable or self-expandable prosthetic heart valve which can be implanted using a catheter trans-femorally, trans-apically, or trans-septally for replacement of a native aortic valve, mitral valve, tricuspid valve or pulmonary valve. The valve comprises at least one leaflet produced from a stabilized fabric (stabilized woven fabric or mesh) as just described. When the leaflet is composed of a stabilized woven fabric, the woven fabric has warp and weft fibers that meet at a plurality of intersections at least one of which is stabilized by being mechanically fastened, chemically fastened or energetically fastened or is stabilized by weaving. In some embodiments, the stabilized intersections are at least located in portions of the leaflet that are subject to movement during operation, and often not portions attached to another structure or to itself (such as a portion of the fabric that is folded over and retained by being sutured). When the leaflet is composed of a mesh, the entire leaflet may be composed of that mesh or mesh may be only disposed in that portion of the leaflet that is not attached to another structure or to itself (such as a portion of the fabric that is folded over and retained by being sutured) and thereby restricted in movement.

In another embodiment, the stabilized medical devices and/or fabrics of the invention are resistant to changes in conformation caused by tissue growth. That is to say that the stabilized fabrics or stabilized medical devices made therefrom provide a conformation that, following implantation, is closer to the original conformation of that fabric than would result from implanting an otherwise identical fabric or device that has not been stabilized as described. When the stabilized fabric or stabilized medical device resistant to changes in conformation caused by tissue growth is composed of a stabilized woven fabric, the woven fabric has warp and weft fibers that meet at a plurality of intersections, a sufficient number of relevant intersections are stabilized by being mechanically fastened, chemically fastened or energetically fastened or is stabilized by weaving so as to resist changes in conformation caused by tissue growth. Preferably, the stabilized intersections are located in a portion of the device where the fabric is subject to movement during operation and often not to portions that are not attached to another structure or to itself (such as a portion of the fabric that is folded over and retained by being sutured). When the stabilized fabric or stabilized medical device is composed of a mesh, the mesh is composed of a polymer, and has a structure, thickness, pore/dimple density, etc., that would resist changes in conformation caused by tissue growth.

In one particular embodiment, there is provided a balloon expandable or self-expandable prosthetic heart valves which can be implanted using a catheter such as trans-femorally, trans-apically, or trans-septally for replacement of a native aortic valve, mitral valve, tricuspid valve or pulmonary valve. The valve comprises at least one leaflet produced with a stabilized fabric (stabilized woven fabric or mesh) that would resist changes in conformation caused by tissue growth. When the leaflet is composed of a stabilized woven fabric, the woven fabric has warp and weft fibers that meet at a plurality of intersections. A sufficient number of these intersections have been stabilized by being mechanically fastened, chemically fastened or energetically fastened or is stabilized by weaving so as to provide a leaflet that is resistant to changes in conformation caused by tissue growth. In particular, intersections are fastened in a portion of the leaflet subject to movement in operation. In some embodiments, these stabilized intersections are not located in a portion of the leaflet that is attached to another structure or to itself (such as a portion of the fabric that is folded over and retained by being sutured). When the stabilized valve comprises, a leaflet composed of a mesh, the mesh is composed of materials and has physical properties rendering it resistant to changes in conformation caused by tissue growth. The entire leaflet may be composed of that mesh or mesh may be only disposed in that portion of the leaflet that is not attached to another structure or to itself (such as a portion of the fabric that is folded over and retained by being sutured).

The stabilized fabrics of the disclosure include uncoated woven fabrics, uncoated meshes, partially coated woven fabrics, partially coated/meshes, coated woven fabrics, and coated meshes. When the stabilized fabric is a woven fabric, it is made from interlaced fibers and includes, inter alia, woven fabrics, knitted fabrics, and the like. The woven fabric materials described herein include at least some synthetic fibers, such as, for example, fibers made from polyolefins such as polytetrafluoroethylene (PTFE) (which includes expanded and stretched PTFE and PTFE of any molecular weight) (also known as Teflon®), polyethylenes including those of any molecular weight (e.g., ultra-high molecular weight polyethylene (UHMWPE)), and polypropylenes including those of any molecular weight (e.g., ultra-high molecular weight polypropylene (UHMWPP), as well as polyurethanes, PEEK, polyvinyl alcohols, silicones, rayons, polyesters, aramids, spandex, or combinations, blends and copolymers thereof. These same polymer materials may also be used to produce a stabilized fabric mesh of the present invention. Meshes are not constructed from interlaced fibers but instead from a continuous web of these same polymers.

The uncoated woven fabrics used to produce the stabilized fabrics of the invention may have at least one of the following properties: a thread count of at least about 150 fibers per square inch, and the thread count need not be symmetrical; a high density weave of generally at least 300 fibers or more per square inch; a tensile strength of at least 50N and in some embodiments, 100 N or more; and/or an areal density of between 0.5 and 1.3 ounces/yard$^2$ (the areal density being the mass of the fabric per square yard). The uncoated fabric may have a thickness of between about 10 μm and about 200 μm. For these properties specifically, and physical properties of woven fabrics discussed herein in general, they refer to properties of the woven fabric before any coating or stabilization. Just as an example, mechanical fasteners could increase the thickness in a localized area. Tensile strength could increase and deflection or bending stiffness could increase. Therefore, unless the context suggests otherwise, references to the properties of a woven fabric means before stabilization.

These same thicknesses are applicable to layers made of a mesh instead of or in addition to a woven polymer fabric layer. The mesh generally contains pores and/or divots which are analogous to the gaps between fibers in a woven fabric. Pores traverse the entire thickness of the mesh having two openings, one on each major surface. Divots have only on opening. Pores and divots therefore have at least one opening and in each case, the size of the opening can vary widely from a micron$^2$ to much larger. In general, the openings have an average area which could range from about 100 microns$^2$ to about 5,000 microns$^2$. That is to say that each pore or divot has at least one opening and each such opening has an area. The average area of the openings of these pores/divots in this embodiment runs from about 100 microns$^2$ to about 5,000 microns$^2$. In another embodiment, these openings have an average area that ranges from between about range from about 1,000 to about 3,000 microns$^2$. In one embodiment, the mesh has a pore density (a term which is used to cover the density of pores and/or divots) of about 1 to about 25% of the total area and in still another embodiment, the pore density is about 5 to about 15%.

In some embodiments the woven polymeric fabric or polymer mesh, may be coated with at least one polymer layer to form a coated fabric. "Coated" as used herein means that the stabilized fabric has a polymer layer or coating applied to at least a portion of it after the woven fabric or mesh has otherwise been formed. And coatings, unless specified otherwise are applied to a woven fabric that has been stabilized or to a mesh. Although the order is not important. It will be appreciated that a mesh is generally stable because it is not made of fibers that can move relative to each other—it is a fixed web. Nonetheless it can be further stabilized by adding a coating. But coatings may be added for reasons other than stabilization and the use of a coated, partially coated, or uncoated mesh, coated for additional stabilization or to alter or improve its properties are both contemplated. A woven fabric on the other hand, has fibers that can move and may not be as intrinsically stable as a mesh of similar dimensions, physical properties and materials. A coating could be used to alter or improve properties of a woven fabric other than providing stability. Indeed, a coating could be applied to a fabric before or after, for example, a laser is used to "spot weld" a plurality of fiber intersections—a step which is primarily intended to enhance stability. Unless a coating is described as being used as a means to impart stabilization herein, it is contemplated that its use is to alter or improve some other property of the woven fabric. And when a coated or partially coated stabilized woven fabric is described, that will generally mean a fabric that is stabilized by a technique or device other than that coating. Also, coatings for stabilization might be applied using different materials, in a different way to a different area of the fabric. Coatings may be formed of a single polymer layer, multiple polymer layers, and/or patterns of discrete polymer layers on one or more surfaces of the stabilized fabric. Where multiple polymer coatings are used, they may be the same or different in terms of thickness, composition, number of layers and/or location. In some embodiments, the polymer coating may provide improved or altered properties to the fabric relative to the uncoated fabric. These altered properties may include, without limitation, one or more of: (1) adjusting the porosity of the fabric, (2) adjusting surface roughness, (3) altering strength, abrasion resistance, and/or flexibility, (4) altering lubricity, (5) providing weight or rigidity to portions of the fabric, (6) promoting folding in specific regions, (7) altering cell adhesion to the fabric, and (8) retention or release of a therapeutic agent.

The polymers which may be used for the coatings include all of those previously identified for use for the fabric. In addition, in some embodiments, the polymer coating can be bioabsorbable, biodegradable, and/or bio-erodible. Exemplary bioabsorbable, biodegradable, and/or bio-erodible polymers may include poly-glycolic acid, poly-L-lactic acid, copolymers of poly-glycolic acid, poly-L-lactic acid, polycaprolactone, poly-DL lactic acid, polytrimethylene carbonate, polydioxanone, poliglecaprone and polyglactin. Such bioabsorbable, biodegradable, and/or bio-erodible polymers may be provided as a coating on a surface in a thickness sufficient to delay tissue growth on the coated surface.

A single polymer coating layer may be used on one major surface of a fabric layer or multiple layers of the same or different polymer materials may be used on both major surfaces. Indeed, up to about 20 layers may be used on any surface or edge of the fabric. The total thickness of all such coatings can range from a minimum of about 0.50 μm to a maximum of about 100 μm per side of the fabric.

The coating may also be a partial coating and/or a contoured coating. Partially coated means that some portion of a major surface or edge is uncoated while other portions are coated. Contoured surfaces may be coated completely, but to different thicknesses or degrees. Either or both may be used to provide specific structural features to a side or edge of a coated fabric, to provide different patterns, and the like. Partial coatings may alter flexibility, provide extra resistance against wear from contact, can add weight, can help maintain a desired shape, can help prevent fraying or unravelling of the fabric, facilitate attachment, add strength, etc., to a localized area of the fabric and any structure made from that fabric. Coated (including partially coated) and uncoated fabrics may be provided with grommets to facilitate attachment while reducing damage that can come from the use of, for example, sutures. Coated and uncoated fabrics may also be constructed with indicia to assist in placement or confirming operability during surgery. Structures made from uncoated fabrics, coated fabrics, and partially coated fabrics include, without limitation: the elements of a valve assembly used in a collapsible/expandable heart valve such as interior cuffs, exterior cuffs, and leaflets. In some embodiments, one or more coatings or partial coatings are applied to a stabilized fabric. In other embodiments, one or more partial coatings may be applied to stabilize the woven fabric or mesh buy being placed in specific areas in need of stabilization—such as the free edge of a leaflet.

In another embodiment, leaflets, cuffs or other structures may be reinforced, weighted, or have their flexibilities altered by the addition of other features, with or without coatings. For example, a row of sutures could be added, of varying number of stiches, in a line or other desired shape, across the full length of the structure or any portion thereof. The properties can be altered based on the number and density of stiches, the number of sutures applied and the pattern in which they are applied. For example, by using one or more sutures extending from an attachment edge to a free edge of a leaflet, alternating stiffening and more flexible zones or "hinges" can be created. A suture could also be stitched to at least a portion of the attachment edge and/or the free edge of a leaflet to provide reinforcement and/or weight and/or to introduce or preserve a shape. In an alternate aspect of this embodiment, instead of or in addition to a coating and/or a suture, localized portions of denser weaves can be used for the same purposes—at the attachment edge, the free edge, and/or across at least a portion of a major surface of the leaflet. And in still another aspect of this embodiment, wires, such as a steel or nitinol wire could be used and inserted into the weave along the attachment edge, the free edge or across a major surface of a leaflet, for example. Wires or sutures or other structures could also be applied by gluing, laminating, etc. to a coated or uncoated fabric of the invention. For example, a wire could be disposed between a fabric material and a coating or layer laminated thereto at the free edge of a leaflet. The wire or other reinforcement may extend across the entire edge, just a portion of it, and may be continuous or discontinuous.

And while sutures, partial coatings and increased localized weave density can provide weight and reinforcement as just discussed, it has been found that these techniques, and other techniques discussed herein, can be useful in forming a stabilized fabric. Medical devices produced using synthetic materials could exhibit changes in shape, size, flexibility or other properties during use (collectively referred to herein as a change in "conformation.") which could interfere with important functions of the device. Changes in conformation could result from one, or a combination of factors. A woven fabric material could exhibit changes in the regularity of the woven pattern over time—fibers moving relative to each other or changing the size and shape of gaps between them or the nature and orientation of the intersections of warp and weft fibers. As discussed in more detail, it is believed that these changes in conformation can come from inter alia the growth of tissue onto and/or into the fabric (or a mesh). Moreover, woven fabrics might stretch over time. Flexibility could be altered. Or the shape/orientation of the woven fabric could change—effectively shrinking, curling, retracting and the like. This too could happen to a mesh. As will be readily appreciated, the causes of this change in conformation are complex and not completely understood. It may be rooted in the types of cells that attach to portions of the woven fabric and how they attach thereto exerting their influence to tighten or misshape localized structures. Or it could be simple mechanical stretching with repeated use, exposure to body temperatures, the friction from motion or blood moving past it, etc. Using an expandable prosthetic heart valve as an example, the free edge of one or more prosthetic leaflets may retract or curl after implantation which can impact the completeness of coaptation of the leaflets and thereby result in leakage or regurgitation. This conformation change in the leaflet material can ultimately cause a reduction in the rejection fraction of oxygenated blood pumped out of the heart and into the balance of the circulatory system and thus a reduction in pumping efficiency. This means that the heart must work harder to supply sufficient oxygen to the tissues and organs of the body.

However, it has now been discovered that controlling and retarding changing conformation and other similar phenomena can be achieved by stabilizing the weave of the fabric to maintain the relative spacing of its fibers and their geometry relative to each other. This can also be accomplished by using a mesh. Whether caused by cell attachment or some other biological or physiological cause, by movement while in use, material stretching or shrinking, exposure to body temperatures, tissues, fluids, or otherwise, the individual fibers of a weave can moved over time relative to other fibers of the weave. Just for example, instead of woven fibers being perpendicular and crossing each other to form roughly right angles, they can become moved forming more acute and obtuse angles. Instead of defining a regular pattern or roughly square openings between the fibers, the openings can become distorted into irregular polygons such as, without limitation, parallelograms, rhombus, trapezium and isosceles trapezium, kites or other irregular quadrilaterals. The size of these openings can vary along with the relative spacing of the adjacent fibers. And the fiber contour can become more extreme as they protrude further in one or more directions. A change in conformation has been found to occur in fabrics that have been implanted into test animals once they are harvested and analyzed. Irrespective of the cause, it has now been found that controlling the structure of the fabric to prevent changes in its original structure reduce or retard changes in a woven fabric's conformation.

Any way to accomplish this stabilization and control of the original woven fabric structure and inhibit conformation changes is contemplated. As noted earlier, sutures and suture lines can serve to add weight and localized rigidity or reinforcement to a woven fabric. And, of course, sutures can be used to secure the leaflet, cuff, or other structure to a superstructure such as a stent. But sutures have not been used in the past to stabilize a woven fabric, particularly by using it in an area of the fabric which is not secured to another structure. Sutures, or other fasteners such as staples, could be used for stabilizing the structure of the weave and in particular, in the case of an expandable valve, proximate to the free end or other area of a leaflet or cuff wherein the suture does not affix the leaflet to another structure. On a micro level, individual intersections of fibers (e.g. where warp and weft fibers cross over or under each other), where they cross at, for example, right angles (90 degrees), could be sutured together, fastened, or otherwise tied off to make their relative movement more difficult. The fastener applies pressure and friction to prevent movement of the individual fibers at the intersection. Not every intersection of a fabric need be sutured or otherwise fastened in this way to form a stabilized fabric. Selected intersections in the region of interest could be fastened while others are not. It is also possible to suture or fasten a small region to form a localized "groups" or "gather" of intersections and the action of gathering them can help lock in the conformation of the remaining portion of the weave in that area. Fasteners could be staggered or placed in a specific pattern.

Instead of, and/or in addition to a mechanical fastener, a chemical fastener, such as an adhesive, could be used to help maintain the intended weave conformation. Where fibers cross, adhesive(s) could be used to lock the fibers in place. This could again be done by applying an adhesive to the fibers at individual intersections and allowing the adhesive to set or cure. Alternatively, the adhesive could be applied to groups or gathers of the fibers and fiber intersections. Adhesives could be applied at where the fibers are in intimate contact or the intersection could be coated with an adhesive. And the adhesives could be applied in staggered spots or groups or in some other pattern. The adhesive could be self-curing and or could be activated with heat, light, activators such that where fibers cross, adhesion occurs. Adhesive could be applied to individual intersections or groups of intersections in a pattern including a staggered pattern. And still another alternative is to use a partial coating, on one or both sides of the fabric to lock the fibers into their intended positions and orientations. The adhesive could be applied to the fiber before the manufacturing process (e.g. weaving) or to the bulk fabric.

Energy in the form of heat, pressure, laser, high intensity light, ultrasonics, vibration, gases, radiofrequency, friction, spin welding, electrical current and the like could be used, alone or with mechanical and/or adhesive fasteners, to melt or otherwise "weld" fibers together at their intersections to form a stabilized fabric. Again, this can be done at individual intersections. As an alternative, a larger "spot" can be treated with heat, pressure, or one of the other sources of energy mentioned so that all of the intersections in that spot are welded together while the surrounding intersections are untouched. Energy could be applied in this way to an entire area such that the weave of the fabric in that area is impacted but other portions of the fabric are not. As an example, heat could be applied along the entire free edge of a prosthetic heart valve leaflet and for a few millimeters inward from the edge. This would weld substantially all of the fiber intersections proximate that edge and immobilize the weave fibers at and near that edge. The rest of the structure of the prosthetic leaflet would be relatively unaffected—however, the fused strip at the free edge could influence the shape, flexibility, and other properties of the overall prosthetic leaflet.

In an alternative, the intersections of warp and weft fibers could remain relatively unaltered (not mechanically fastened, not glued together, not welded) when compared to the fibers of the weave extending between the intersections. These fibers could be altered to preserve the original conformation (shape, orientation and relative positions of the individual fibers) and thereby produce a fabric that is resistant to a change in conformation such as by tissue growth during operation. And in another alternative, the fabric could be woven from fibers of undulating or variable thickness. Those undulations when woven into the fabric, increase the friction between fibers and can allow them to "nest" at various intersections making their relative movement more difficult. In another possibility, the fibers could be woven from relatively thicker and or wider fibers. A mixed weave is also possible. Relatively thicker and/or wider fibers could also have an undulating or variable thickness or could be woven with same—all the warp fibers having a relatively uniform thickness and widths and every other weft fiber having an undulating surface.

Another approach which can be used, alone or in combination with any or all of those just described, is the use of a localized increase in weave density. Relative to the rest of the woven fabric, a higher weave density has more intersections and its fibers are closer together. Proximity, lack of freedom of movement, and the increased collective friction at the increased number of intersections make it relatively more difficult to distort the fibers of the fabric in this region. "Localized" in this context means that something less than about 50% of the area of a side of the woven fabric includes a higher weave density than the remainder of the fabric used in that element or medical device—prior to its use. A localized increase in weave density can be accomplished as part of the initial weaving process or additional fibers could be woven into a specific area of a pre-woven fabric. The fibers used to increase the weave density in a localized area need not be the same as those used to produce the woven fabric overall. Relative to the weave density of the remainder of the fabric, this localized weave density increase could be by as much as 50%. In some embodiments, however, the increase is between about 20% to about 40% of the weave density of the rest of the fabric.

Instead of through localized weave density changes, this resistance to a change in conformation might also be accomplished by using a fabric having an overall denser weave to create the leaflet (or other medical device) than would otherwise have been used. For example, U.S. patent application Ser. No. 16/899,205, filed Jun. 11, 2020 discloses using a fabric with an areal density of at least $0.65\pm0.1$ ounces/yard$^2$ and an areal density of about at most about $1.3\pm0.1$ ounces/yard$^2$. Using a material of even denser weave, not just in a localized, area might provide the same overall benefit in terms of preserving the original conformation of the woven fabric.

Another aspect of a weave can impact stability as well, namely the type of weave. Certain weaves may intrinsically reduce the freedom of movement of individual fibers or pack them in closer. Any such weave may be used and these can include, without limitation, a Plain weave, Rib weave, Basket weave, Twill Weave, Herringbone weave, Satin weave, Sateen weave, Leno weave, Oxford Weave, Bedford cord weave, Waffle weave, Pile weave, Jacquard weave, Dobby weave, Crepe weave, Lappet weave, Tapestry Weave, Striped weave, Checquered weave, or Double cloth weave. Weaves can include any number of warp and weft fibers such as, for twills as an example, a 2/1 twill, a 3/1 twill, a 2/1 twill, a 2/2 twill, a 3/2 twill, a 4/2 twill, a 3/3 twill, a 6/2 twill, and for satin weaves a 4 harness satin weave, 5 harness satin weave, Finally, in place of a stabilized woven polymer fabric as described herein, a mesh can be used to provide the same or similar stability and allow a material to resist changes in conformation when implanted due to, for example, tissue growth. For example, a collapsible and/or expandable heart valve, or surgical valve could be constructed using a coated or uncoated mesh for its leaflets, its cuff, and/or its sewing ring with the resulting valve being resistant to leaflet retraction or other change in conformation. Indeed, an uncoated, partially coated, or fully coated polymer mesh can be used with, or as a substitute for any of the woven polymer fabrics described herein and used to produce any of the medical devices described herein. To produce a medical device with a stabilized mesh, and indeed one resistant to changes in conformation due to tissue growth, it is important that the polymer used, the physical dimensions of the mesh—size of the struts and their length, number and size of the junctions, size of the openings and the density of pores or divots, and the like, and the resulting physical properties, must be sufficient to reduce the impact of tissue growth on the original structure of the mesh after implantation.

In still a further embodiment, the medical device or an element thereof, such as a leaflet and/or cuff, could be constructed or attached so as to form a pleat or fold across a major surface thereof.

Another embodiment of the disclosure provides a method of manufacturing a collapsible/expandable valve prosthesis that includes providing an uncoated stabilized polymeric fabric or mesh as just discussed having a top surface and a bottom surface (first and second major surfaces); providing a polymer such as, without limitation, an ultra-high molecular weight polyolefin; and applying the polymer to the top surface and/or the bottom surface of the stabilized fabric (including a mesh) to form a coated stabilized woven fabric or coated mesh. One or more polymer films may be laminated to one or more surfaces of a woven fabric or mesh by gluing or the application of energy as noted earlier. A polymer coating layer may also be formed on the stabilized fabric by applying a liquid polymer material to a surface of the woven fabric or mesh and allowing it to solidify, cross-link, or otherwise become an adhered layer. This may be done by, for example, spray coating a polymer on one or more sides of the stabilized fabric, dip coating, and the like. Other techniques for applying the polymer coating include, for example, 3D printing. Partial coatings may be applied to a limited portion of the stabilized fabric or mesh as just discussed or may be formed by applying a complete coating to the fabric or mesh and removing portions by, for example, ablation.

The stabilized fabric or mesh, as well as any medical device made using that stabilized fabric or mesh, may undergo sterilization. This may be done with a variety of sterilization modalities, for example, with ethylene oxide, peracetic acid, nitrogen oxide, e-beam, steam, gamma radiation, carbon dioxide and chemical liquid sterilant.

Various methods of forming the components of medical devices, including valve components and valve assemblies, may be used. These include mechanical methods, for example cutting with scissors or a blade. Other techniques include, for example, cautery; stamping; chemical, laser, ultrasonic, or water jet cutting, bio-glue, folding or lamination.

One embodiment of a useful coated, partially coated or uncoated stabilized fabric is a high density woven fabric of a polyethylene, a polypropylene or a PTFE, or blends or copolymers thereof, the woven fabric having a thread count of 300-500×100-300 fibers per square inch, a tensile strength of at least 65N, an areal density of at least 0.65±0.1 ounces/yard$^2$, and a thickness of approximately 50-100 μm or the stabilized fabric comprises a mesh of the invention made from this same material and thickness and containing pores and/or divots having at least one opening having an average area which could range from about 100 microns$^2$ to about 5,000 microns$^2$ and/or a pore density or divot density of about 1 to about 25 In the case of the stabilized woven fabric, stabilization is achieved by mechanically fastening individual intersections without fastening that portion of the fabric to another structure, mechanically fastening bundles of intersections without fastening that portion of the fabric to another structure, chemically adhering individual intersections, chemically adhering bundles of intersections, welding individual intersections by the application of energy, welding bundles of intersections by the application of energy, increasing the weave density of a localized area of the fabric, using fibers of variable thickness, and/or coating a localized area of the fabric.

In another embodiment, a useful coated, partially coated or uncoated stabilized fabric which is composed of a woven fabric of a polyethylene (such as UHMWPE), a polypropylene (such as UHMWPP), or a halogenated polymer (such as UHMWPTFE or expanded or e-PTFE), or blends or copolymers thereof, before being stabilized the woven fabric has a thread count of 300-500×100-300 fibers per square inch, a tensile strength of at least 65N, an areal density of at least 0.5±0.1 ounces/yard$^2$, and a thickness of approximately 20-200 μm. Stabilization of these woven fabrics may be achieved: mechanically such as by mechanically fastening individual intersections without fastening that portion of the fabric to another structure, mechanically fastening bundles of intersections without fastening that portion of the fabric to another structure (collectively "mechanically"); chemically such as by chemically adhering individual intersections, chemically adhering bundles of intersections (collectively "chemically"); energetically such as by welding individual intersections by the application of energy, welding bundles of intersections by the application of energy (collectively "energetically"); through the weave by increasing the weave density of a localized area of the fabric, using fibers of variable thickness, using fibers of different thickness, using a denser weave or by controlling the weave pattern (collectively "weaving") and/or using a coating such as by coating a localized area of the fabric.

In one embodiment the woven fabric is stabilized by weaving, mechanically, chemically or energetically. In another embodiment the woven fabric is stabilized by weaving, mechanically, or energetically. Alternatively, the stabilized fabric comprises a mesh of the invention made from these same materials and thickness and containing pores or divots each having openings having an average area that ranges from between about range from about 1,000 to about 3,000 microns2 and/or a pore density or divot density from about 5 to about 15%.

In another embodiment, a useful coated, partially or uncoated stabilized fabric is a woven fabric of ultra-high molecular weight polyethylene or e-PTFE having a thread count of 440×220 fibers per square inch. In a particular embodiment, the uncoated fabric has a tensile strength of at least about 75N, an areal density of at least 0.65±0.1 ounces/yard$^2$, and a maximum thickness of approximately 50-100 μm stabilized by weaving, mechanically, chemically or energetically and in still another embodiment the woven fabric is stabilized by weaving, mechanically, or energetically. In an alternative for this embodiment, the stabilized fabric comprises a mesh of the invention made from these same materials and thickness and containing pores or divots each with at least one opening having an average area that ranges from between about range from about 1,000 to about 3,000 microns$^2$ and/or a pore density or divot density is about 5 to about 15%.

In another embodiment, a useful coated, partially coated or uncoated stabilized fabric is a woven fabric of ultra-high molecular weight polyethylene or e-PTFE having a thread count of 440×220 fibers per square inch. In a particular embodiment, the uncoated fabric has a tensile strength of at least about 75N, an areal density of at least 0.5±0.05 ounces/yard$^2$, and a thickness of approximately 50-100 μm stabilized by weaving, mechanically, chemically or energetically and in still another embodiment the woven fabric is stabilized by weaving, mechanically, or energetically. In an alternative for this embodiment, the stabilized fabric comprises a mesh of the invention made from this same material and the same thickness and containing pores and/or divots having at least one opening having an average area which could range from about 100 microns$^2$ to about 5,000 microns$^2$ and/or a pore density or divot density of about 1 to about 25%.

In another embodiment, a useful coated, partially coated or uncoated stabilized fabric is a woven fabric of ultra-high molecular weight polyethylene or e-PTFE having a thread count of 300-500×100-300 fibers per square inch. In a particular embodiment, the uncoated fabric has a tensile strength of at least 75N, an areal density of about 0.8±0.05 ounces/yard$^2$, and a thickness of approximately 76 μm stabilized by weaving, mechanically, chemically or energetically and in still another embodiment the woven fabric is stabilized by weaving, mechanically, or energetically. In an alternative for this embodiment the stabilized fabric comprises a mesh of the invention made from these same materials and thickness and having pores or divots with openings having an average area that ranges from between about range from about 1,000 to about 3,000 microns$^2$ and/or a pore density or divot density is about 5 to about 15%.

In another embodiment, a useful coated, partially coated or uncoated stabilized fabric is a woven fabric of ultra-high molecular weight polyethylene or e-PTFE having a thread count of 440×220 fibers per square inch. In a particular embodiment, the uncoated fabric has a tensile strength of at least about 75N, an areal density of at least 0.65±0.05 ounces/yard$^2$, and a thickness of approximately 50 μm stabilized by weaving, mechanically, chemically or energetically and in still another embodiment the woven fabric is stabilized by weaving, mechanically, or energetically. In an alternative for this embodiment the stabilized fabric comprises a mesh of the invention made from this same material and thickness and containing pores and/or divots having at least one opening having an average area which could range from about 100 microns$^2$ to about 5,000 microns$^2$ and/or a pore density or divot density of about 1 to about 25%.

In another embodiment, the invention is a useful uncoated, coated or partially coated stabilized fabric that is a high-density woven fabric of PE or PTFE having a thread count of 300-500×100-300 fibers per square inch. In a particular embodiment, the uncoated fabric has a tensile strength of at least about 75N, an areal density of at least 0.65±0.05 ounces/yard$^2$, and a thickness of approximately 250 μm or less stabilized by weaving, mechanically, chemically or energetically and in still another embodiment the woven fabric is stabilized by weaving, mechanically, or energetically. In an alternative for this embodiment the stabilized fabric comprises a mesh of the invention made from this same material and thickness containing pores and/or divots having at least one opening having an average area which could range from about 100 microns$^2$ to about 5,000 microns$^2$ and/or a pore density or divot density of about 1 to about 25%.

In some embodiments, the stabilized fabric material used in a medical device as described herein, is produced from a woven fabric or mesh that, before being stabilized, has a thickness of between about 1 μm and about 1,000 μm and in some embodiments, between about 1 μm and about 500 μm and in still others, between about 5 μm and about 300 μm. It also may have a tensile strength of at least about 35 N and in some embodiments at least about 50 N. In still other embodiments, the fabric material will have a tensile strength of at least about 70 N.

In particular for the valve components of expandable or surgical valves, including leaflets and cuffs, the stabilized fabric materials (woven fabric or mesh) used may exhibit one or more of the properties described in Table 1 below before being stabilized. It should be understood that, although Table 1 lists various characteristics with values grouped in a "broader range" and a "narrower range," the fabric material may include any combination of characteristics from the "broader range" and the "narrower range," and further, the fabric material may include in some instances characteristics that are outside the "broader range" and the "narrower range."

TABLE 1

| Test Type/Characteristic | Test Method | Broader Range | Narrower Range |
|---|---|---|---|
| Thickness (Leaflets) | ASTM D1777-96 | 5 μm-500 μm | 50 μm-350 μm |
| Thickness (Cuffs) | ASTM D1777-96 | 1 μm-300 μm | 5 μm-200 μm |
| Thickness (Occluder) | ASTM D1777-96 | 1 μm-1,000 μm | 1 μm-350 μm |
| Ultimate tensile strength | ASTM D5035-11 ASTM D882-12 | 1-500 MPa | 25-250 MPa |
| Tear strength | ASTM D2261-13 | 5-100 lbF | 10-40 lbF |

TABLE 1-continued

| Test Type/Characteristic | Test Method | Broader Range | Narrower Range |
|---|---|---|---|
| Permeability | ISO7198 | 1-2,000 mL/cm²/min | 10-1,200 |
| Suture Retention (where leaflet or cuff are attached via sutures | ISO7198 | 10-100N | 30-70N |
| Stiffness/Flexural Rigidity | ASTM D1388-14 | .001-8 cm | .001-4 cm |
| Stretch | ASTM D6614-07 | 1-400% | 3-50% |

In some embodiments, leaflets and/or cuffs formed of a stabilized UHMWPE fabric or mesh that, prior to stabilization and/or coating, may have one or more of: a thickness of about 250 μm or less, a tensile strength of at least about 75N and preferably at least about 90N; a stiffness/flexural rigidity of about 3.0+/−1.75 cm; a permeability of about 850-950 mL/cm2/min; a suture retention meeting ISO7198; a stretch/strain of about 20-25%; and a tear strength meeting or exceeding ASTM D2261-13. For a leaflet or cuff formed of an expanded or stretched PTFE, the overall properties can be similar. Where made of a woven fabric, the stabilized fabric is stabilized by weaving, mechanically, chemically or energetically and in still another embodiment the woven fabric is stabilized by weaving, mechanically, or energetically. In an alternative for this embodiment the stabilized fabric comprises a mesh of the invention made from this same material and thickness containing pores and/or divots having at least one opening having an average area which could range from about 100 microns² to about 5,000 microns² and/or a pore density or divot density of about 1 to about 25%. It should be noted that the "permeability" characteristic described above may apply particularly to fabrics/meshes that are coated with another material, or uncoated fabrics/meshes that have been exposure to blood for a time where the interaction of the blood with the fabric reduces the permeability of the uncoated fabric over time.

An embodiment of the invention is therefore a stabilized replacement heart valve comprising: a self-expandable or balloon-expandable stent; and a valve assembly sutured to the stent, the valve assembly comprising a cuff and a prosthetic leaflet at least one of which is composed of a coated or uncoated stabilized woven polymer fabric having warp and weft fibers that meet at a plurality of intersections, or a mesh, having at least one of: (i) an ultimate tensile strength between 25 MPa and 250 MPa; (ii) a tear strength of between 10 lbF and 40 lbF; (iii) a permeability of between 10 mL/cm²/min- and 1,200 mL/cm²/min; (iv) a suture retention of between 30 N and 70 N; (v) a stiffness/flexural rigidity of between 0.001 cm and 4 cm; and (vi) a stretch of between 3% and 50%; wherein the prosthetic leaflet has a thickness of between about 5 μm and about 500 μm and the cuff has a thickness of between about 1 μm and about 300 μm stabilized by weaving, mechanically, chemically or energetically and in still another embodiment the woven fabric is stabilized by weaving, mechanically, or energetically.

That stabilized replacement heart valve could also comprise: a self-expandable or balloon-expandable stent; and a valve assembly sutured to the stent, the valve assembly comprising a cuff and a prosthetic leaflet at least one of which is composed of a coated, partially coated, or uncoated polymer mesh The mesh has pores or divots each having at least one openings and wherein the average area of their which could range from about 100 microns² to about 5,000 microns². In another embodiment, the average area ranges from between about 1,000 to about 3,000 microns². In one embodiment, the mesh has a pore density (and/or divot density as noted earlier) of about 1 to about 25% and in still another embodiment, the pore density is about 5 to about 15%. The materials used to produce this mesh, the number of layers used, the number and types of coating, etc., their properties, and their thickness are the same as previously described for the woven fabrics described herein. In a particular embodiment, when used in prosthetic leaflets the mesh material has a thickness of between about 5 μm and about 500 μm and when used in a cuff the mesh material has a thickness of between about 1 μm and about 300 μm.

Thus in one embodiment of the disclosure, there is provided a replacement heart valve which is specifically designed to replace or repair a native aortic, native pulmonary, native tricuspid, or native mitral valve, the replacement heart valve being made using a stabilized fabric. The stabilized fabric comprises either a mesh or a stabilized woven fabric.

If a mesh, the stabilized fabric is composed an uncoated mesh, a partially coated mesh or a coated mesh composed of one or more polymer materials which may be polyolefins such as polytetrafluoroethylene (PTFE) (including expanded (e-PTFE), stretched, low molecular weight, medium molecular weight, high molecular weight and ultra-high molecular weight (UHMW)), polyethylenes (PE) (including low, medium, high and ultra-high molecular weight polyethylene (UHMWPE—e.g., having an average molecular weight of between about 2 and about 7.5 million atomic mass units)), and polypropylene (PP) (including low, medium, high and ultra-high molecular weight polypropylene (UHMWPP)), as well as polyurethane, PEEK, polyvinyl alcohol, silicone, rayon, polyesters, aramid, and spandex. The uncoated mesh has a thickness of between about 1 μm and about 500 μm. And the mesh has pores and/or divots having at least which have openings having an average area ranging from about 100 microns² to about 5,000 microns², a pore density (divot density) of about 1 to about 25%, or both. In another embodiment, the mesh is composed an uncoated mesh or a partially coated mesh composed of one or more polymer materials which may be a PTFE, a PE, or a PP and either pores and/or divots having openings having an average area ranging from about 1,000 to about 3,000 microns² or a pore density (divot density) of about 5 to about 15%, or both.

Methods of making medical devices such as heart valves as described herein include: forming one of the described stabilized fabrics into a component of a medical device, such as at least one leaflet or a cuff, and attaching it to other parts of the medical device or forming it into a medical device—such as by creating a valve assembly from the leaflet or cuff produced from the stabilized fabric and attaching it to a support or stent.

BRIEF DESCRIPTION OF THE DRAWINGS

This disclosure may be best understood by reference to the following description taken in conjunction with the accompanying drawing figures in which:

FIG. 41 is a schematic perspective view of a leaflet formed from another coated stabilized or non-stabilized woven fabric according to the present disclosure;

FIG. 41A is a cross-sectional view of a variant of the leaflet of FIG. 41;

FIG. 41B is a cross-sectional view of a further variant of the leaflet of FIG. 41;

DETAILED DESCRIPTION

Figure 1A:
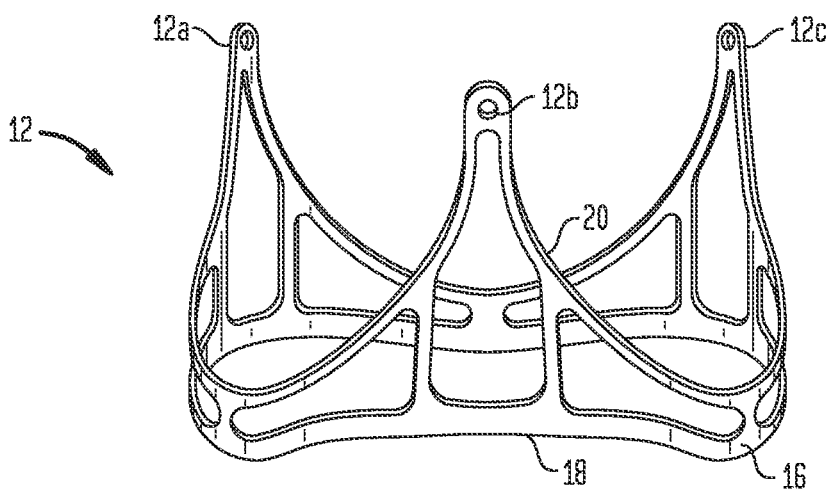
FIG. 1A is a perspective view of a frame of a surgical prosthetic heart valve according to the prior art.

"Stabilized" in the context of a stabilized medical device or stabilized fabric in accordance with the invention means a suitable mesh or a woven or knitted fabric having warp and weft fibers that meet at a plurality of intersections. At least one, and in general, a plurality of these intersections is stabilized by being mechanically fastened, chemically fastened or energetically fastened or is stabilized by weaving. "Fastened" and "fastening" in the context of a stabilized fabric of this invention means that one or more of the intersections is acted upon so as to increase the localized friction between crisscrossing fibers or locking them in place. Alternatively, stabilized in connection with weaving means altering the nature of the weave and/or the nature of the fibers to create additional friction and to restrict relative motion of the fibers at or adjacent fiber intersections. This can be done by a number of techniques, such as, without limitation, by increasing the weave density of a localized area of the fabric, using fibers of variable thickness, using fibers of greater than usual thickness, using a denser weave or by controlling the weave pattern. In one embodiment, stabilized woven fabrics include sufficient fastened intersection, located an appropriate, so as to render it resistant to changes in conformation.

"Conformation" in accordance with the present invention means the original relative position of the fibers, intersections, and gaps of a woven fabric and the original relative position of the struts, junctions and pores/divots of a mesh. Medical devices produced using synthetic materials could exhibit changes in shape, size, flexibility or other properties during use which could interfere with important functions of the device. As noted earlier, changes in conformation could result from one, or a combination of factors. A woven fabric material could exhibit changes in the regularity of the woven pattern over time—fibers moving relative to each other or changing the size and shape of gaps between them. Woven fabrics might stretch over time. Flexibility could be altered. Or it could be simple mechanical stretching with repeated use, exposure to body temperatures, the friction from motion or blood moving past it, etc. In some embodiments, stabilized medical devices made from stabilized fabrics will be resistant to changes in conformation by virtue of being stabilized.

Fabrics and medical devices made therefrom may in some other embodiments be stabilized such that they are resistant to changes in conformation caused by tissue growth. The term "tissue growth" as used herein is meant to encompass cells and tissues that may attach and/or grow onto and into the medical device and the materials it is made from. But it embraces more than that—indeed it is used herein to encompass the attachment, growth and/or accumulation of any biological or physiological materials and molecules within the body including, without limitation, cells, tissues, proteins, collagen, calcium, proteases, growth factors and the like. It has been found that these biological and physiological processes can cause a change in conformation of the fabric and any device made from it which could alter its ability to function as intended. This may be rooted in the types of cells that attach to portions of the fabric and how they attach thereto exerting their influence to tighten or misshape localized structures. But that process, and the materials that cause these issues are not completely understood. However, fabrics, meshes and medical devices made therefrom can be designed which are resistant to changes in conformation caused by these processes, again, herein, collectively referred to as "tissue growth." When implanted into a patient, the stabilized fabrics and/or devices of the invention retain relatively more of their original conformation than would result from implanting an otherwise identical fabric or device that has not been stabilized.

When one wants to evaluate a fabric or device produced from it to determine the extent of conformation change, or resistance to conformation changes caused by tissue growth during implantation in a patient, one can perform a visual inspection and a trained observer will be able to assess the results. But other more objective measures are also available. Speaking of a woven fabric, one can compare the distance between roughly parallel warp and weft fibers or intersections before and after implantation. For example, first and second weft fibers are selected which are spaced apart from each other by an initial distance. A first weft fiber could be chosen and a second weft fiber that is ten fibers away from the first fiber can be chosen and the distance between them measured. The distance between these two first and second weft fibers can be measured again after the valve is recovered from a patient or animal model following implantation for several weeks or longer. Those distances can be compared. In the alternative, the distance between a first and a second intersection spaced apart from each other, for example 10 intersections spaced apart in the warp or weft direction can be measured before implantation and after implantation in a model. Note that when reference is made to a "model" and more specifically a "sheep model" herein, it means a sheep is preferred unless, for size or other reasons known in the art, a sheep is not an appropriate model. In that case a pig is used.

Figure 86:
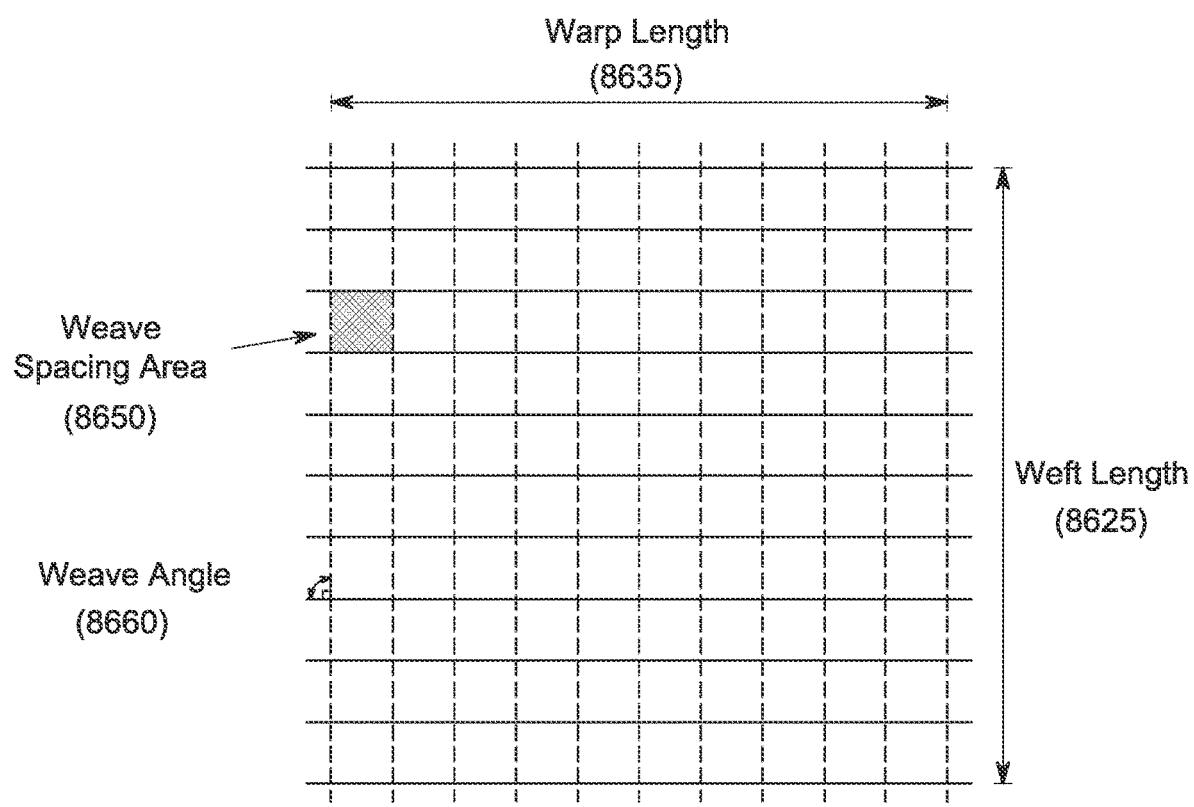
FIG. 86 illustrates a woven fabric and various measurements that can be taken as an indication of resistance to a change in conformation.

That the distance is substantially unchanged after implantation based on testing in a suitable model, such as a sheep model, or a pig model if sheep is not appropriate, for 140 days, indicates that the fabric is indeed a stabilized fabric and resistant to a change in conformation caused by tissue growth. Indeed, it has been found that using a non-stabilized woven fabric, the distance between the first and second intersections (a total of 10 intersections in the warp or weft direction—also referred to herein as the warp length or weft length respectively) could decrease by 10-30%. One way to demonstrate that a fabric or mesh is resistant to changes in conformation caused by tissue growth is to measure the degree of shortening of the distance between warp and/or weft lengths before and after implantation in a suitable model for a suitable time. In FIG. 86, the warp or weft measurement is illustrated. The illustrated weave includes weft fibers 8620 and warp fibers 8630 which are woven together forming intersections 8640. The length of the weft fibers can be determined by measuring the distance between a first and a second intersection spaced apart therefrom such that the total number of intersections is 10 (weft length 8625). If the weft length 8625 before implantation decreases by less than 10% after implantation in a sheep model or if not appropriate in a pig model for a period of 140 days, it is considered resistant to a change in conformation caused by tissue growth. In some embodiments, if the weft length decreases by about 5% or less after that implantation it is considered resistant to a change in conformation caused by tissue growth. Much the same is true when measuring the warp length 8635 which is the length of the warp fiber 8630 measured between a first and a tenth intersection 8640 as well.

It will be appreciated that both warp length 8635 and weft length 8625 changes can be measured and can be measured in a single location or in multiple locations of the fabric. Indeed, warp length 8635 and/or weft length 8625 can be measured at the free edge, near the attachment edge, in the intermediate or moving area or all of these. Analogous measurements can be taken of the relative distance between junctions in a mesh.

There are other techniques that can be used to measure resistance to changes in conformation following implantation as well. The fibers in a woven fabric form gaps between the fibers. As illustrated in FIG. 86, in a simple weave, those gaps may be roughly square or rectangular or square. The area 8650, also referred to as the weave area, can be determined, and that area compared to the area of the same gap following implantation in a sheep model for 140 days. This can be done in for a single gap or multiple gaps. If the area remains substantially the same, that indicates that the fabric or mesh is stabilized and is sufficiently resistant to changes in conformation caused by tissue growth following implantation. However, a reduction in this weave area of less than 10% and indeed, preferably about 5% or less, indicates that the fabric has been stabilized sufficiently to be resistant to changes in conformation caused by tissue growth following implantation. Other visual indicators can come from looking at changes in the angles formed at the fiber intersections, such as illustrated in FIG. 86—see 8660. A change in angle by about 5% or less also indicates a stabilized fabric. The contour of the fabric out of the plane of the fabric—as the fibers are drawn closer together or their positions distorted, the fibers can bow in and out of the plane.

The number of intersections to be fastened by welding, mechanical fastening or adhesive fastening in accordance with the invention can vary with the nature of the fibers used, their thickness, the type of weave and weave density, the polymer used, and the technique used to stabilize the intersections and the type of medical device being constructed. Generally however, the intersections in question, those that will be stabilized, are disposed in a movement area and, in such a movement area, at a minimum, it is expected that a subset of at least about 25% of the intersections within the movement area will be fastened and in other embodiments, at least about 50% of those intersections will be fastened. In still another embodiment, the subset of intersections within the movement area that are fastened is at least about 75% and that number can be as high as at least about 90% or more. Indeed, in some instances, it may be desirable to fasten substantially all the intersections in the movement area.

The placement and distribution of the subset of fastened intersections can vary widely and can be random or in a pattern depending upon fabric used, the medical device in question, and the like. For the leaflets of a replacement heart valve, they are located in the movement area. However, without wishing to be bound by any particular theory of operation, tissue growth comprising cells, tissues and other biological and physiological materials will deposit, attach, grow or accumulate from the attachment edge first and then progress toward the free edge. It is believed that the degree of movement of a particular part of the leaflet impacts the timing, extent and type of tissue growth with it being easier to grow where there is no, or relatively less movement or slower movement.

Figure 85:
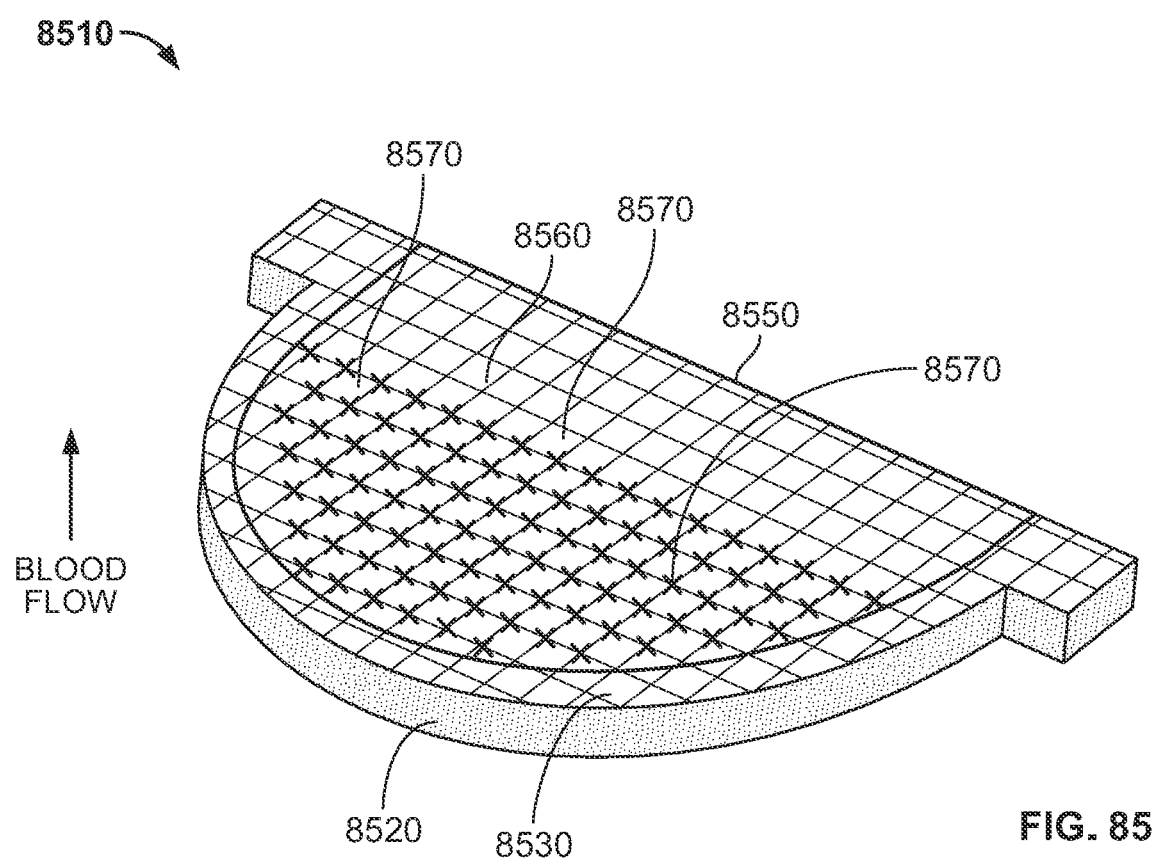
FIG. 85 illustrates a leaflet composed of a woven fabric having an attachment end, a free edge, and a movement area containing a subset of intersections that had been stabilized.

It is possible that when discussing a medical device and the number of intersections fastened, reference is being made to the entirety of the fabric used. But it may also refer to only a portion of the fabric and the number of intersections fastened in that area. Using a leaflet as a non-limiting example, as shown in FIG. 85 the leaflet comprises a free edge 8550 and an attachment edge 8520. The free edge, as its name implies, is not attached, except possibly at its periphery, to any other structure. In contrast, and again as its name implies, the attachment edge 8520, and indeed some surface area adjacent that edge (the attachment end 8530) are generally attached to one or more other structures. If the valve is a collapsible and/or expendable valve like a TAVR or TMVR valve, the attachment end of the leaflet can be attached, directly or indirectly, to a cuff, a self expandible or balloon expandible or both. It could be attached to other structures as well.

There is an intermediate area 8560 between the attachment end 8530 and the free edge 8550 which, in a valve, can often have a belly taking the shape of something like a spinnaker sail or a roughly parabolic structure that approximates the anatomy of a native valve leaflet. This intermediate region 8560, along with the free edge 8550, generally moves during operation as the blood flows past the leaflets and back into the leaflets with the beating of the heart. This area which is subject to movement during operation and includes the free edge and intermediate portions of the leaflet between the free edge and the attachment end contains a subset of all of the intersections that might exist in the fabric that forms the leaflet. And in some embodiments, it is only a number of the intersections of this subset, in this movement area of the leaflet, that are stabilized by being fastened 8570. Thus a leaflet with 90% of its intersections fastened in the movement area means 90% of that subset of intersections are fastened, not that 90% of all of the intersections present in the leaflet are fastened. The attachment end may be attached to a stent, for example, but sutures, and, broadly speaking, this too could "fasten" fiber intersections. But as they are outside of the movement area, in this instance, they are not counted.

Moreover, it will be appreciated that the impact of tissue growth on the conformation of a fabric portion that is sutured to another structure is generally less a concern as it should not cause a change in conformation. Areas of the fabric that are subject to movement or are not otherwise attached to another structure is far more like to exhibit a change in performance or other impact if its conformation changes. So in general, references to stabilizing fabric, or rendering a fabric resistant to changes in conformation will involve portions of the fabric that are able to move or are not directly attached to another structure in use.

A mesh is not woven and does not have intersections formed of fibers crossing one another and to not define gaps. But its structure is very analogous. A mesh is a web or matrix of struts that meet at and define junctions and the space between these structs and junctions are pores or divots. It is therefore intrinsically more stable than an un-stabilized fiber of similar material and physical dimensions—thickness of the struts versus thickness of the fibers, number of junctions versus number of intersections, size and density of pores versus size of fabric gaps and areal density, and the like. Thus, in the context of a stabilized fabric, a mesh need not include further mechanical, chemical, energetic fastening or stabilizing by weaving to be resistant to changes in conformation. That said, additional stability might be obtained by employing some of these same techniques and are therefore contemplated in addition. In one embodiment, the mesh is resistant to changes in conformation caused by tissue growth. And one can tell if the materials selected and the construction of the mesh is sufficient to be relatively resistant to changes in conformation in general and because of tissue growth specifically, in the same way as one does so for a woven fabric. The distance between parallel spaced apart struts or junctions can be determined and the closer that distance remains before and after implantation, (the less the distance between, for example a first and a $10^{th}$ junction changes) the more stable the mesh. If the distance does not change by 10% or more, and preferably, about 5% or less, it is considered sufficiently stable to be resistant to a change in conformation due to tissue growth. Similarly, the area of a pore/divot, or a group of pores/divots will decrease less than 10% and preferably about 5% or less in such a stabilized mesh.

Mechanically fastened means using a mechanical device such as, without limitation, a suture or a staple to bind one or more fiber intersections. Chemically fastening means something, such as, without limitation, using a glue or adhesive to bind one or more of the fiber intersections. Energetically fastening means using one or more types of energy to weld and therefore bind one or more fiber intersections. Stabilized by weaving means altering the nature of the weave and or the nature of the fibers to create additional friction and to restrict relative motion of the fibers at or adjacent one or more of the fiber intersections. This can be done by a number of techniques, such as, without limitation, by increasing the weave density of a localized area of the fabric, using fibers of variable thickness, using fibers of greater than usual thickness, using a denser weave or by controlling the weave pattern.

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the terms "proximal" and "upstream" refer to the inflow end of a prosthetic heart valve and these terms may be used interchangeably. The terms "distal" and "downstream" refer to the outflow end of a prosthetic heart valve and also may be used interchangeably. As used herein, the terms "generally," "substantially," and "about" are intended to mean that slight deviations from absolute are included within the scope of the term so modified. When used herein in the context of a prosthetic heart valve, or a component thereof, the lengthwise or axial direction refers to a direction parallel to a longitudinal axis passing through the center of the stent or heart valve from the inflow end to the outflow end. When used herein in the context of a prosthetic heart valve, or a component thereof, the circumferential direction refers to a direction extending along the circumference of the prosthetic heart valve.

Figure 1B:
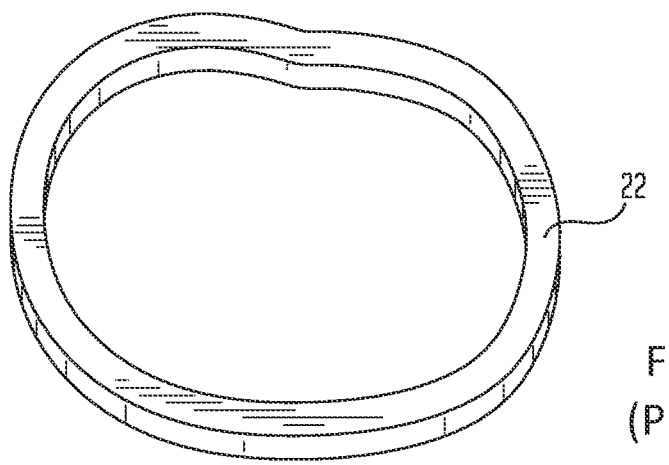
FIG. 1B is a perspective view of a sewing cuff insert of a surgical prosthetic heart valve according to the prior art.
Figure 1C:
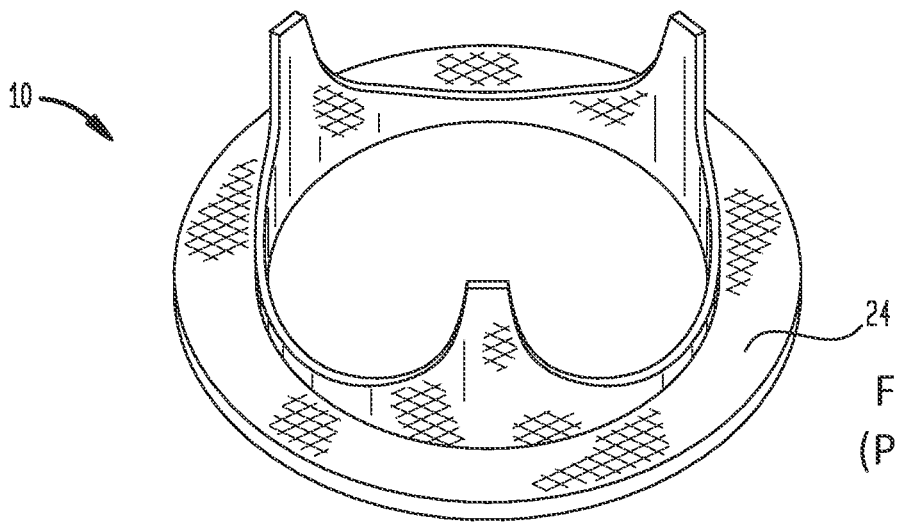
FIG. 1C is a perspective view of the frame and sewing cuff insert of FIGS. 1A-B in an assembled condition and covered by a fabric.

FIGS. 1A-1C illustrate a prior art surgical heart valve 10 and several components thereof. Surgical heart valve 10 may be surgically implanted into a patient to replace a native heart that may be not functioning as intended, such as the aortic valve, mitral valve, pulmonary valve, or the tricuspid valve. Surgical heart valve 10 may have a non-collapsible frame 12, shown in FIG. 1A, having a generally annular shape. Frame 12 may be formed of any suitable biologically compatible material, including titanium, Elgiloy® MP3N, or another metal, which may be laser cut from a tube, or from a biologically compatible polymer, such as PEEK or acetal. Since the valve of the illustrative embodiment is a tricuspid valve (e.g., for use in replacing a patient's aortic valve), frame 12 has three commissure posts 12a, 12b, and 12c that are equally spaced from one another around the circumference of the frame. Each commissure post stands up from the annularly continuous base 16 of frame 12, and they support and/or serve as attachment points for a plurality of prosthetic leaflets (not shown). Although frame 12 is illustrated with three commissure posts 12a-c for supporting a three-leaflet valve assembly, it should be understood that the frame could include more or fewer commissure posts for supporting a corresponding number of prosthetic leaflets. Base 16 of frame 12 may include a blood-inflow edge 18 that is scalloped as one proceeds around the frame to approximately match the natural scallop of the native valve annulus. The frame may also include an annularly continuous blood-outflow edge 20, which merges with and becomes part of each commissure post 12a-c. The inflow edge 18, outflow edge 20, and flexibility of the frame are designed to help ensure proper opening and coaptation of the leaflets of the prosthetic heart valve during use. The prosthetic leaflets may be formed of a biological material, such as bovine pericardium, or from any of the engineered leaflet materials disclosed herein.

Frame 12 may be covered by a fabric covering (not shown), particularly over each commissure post 12a-c. One example of an appropriate covering fabric is reemay fabric, which is a spun form of polyester. A ring 22 (FIG. 1B), which may be formed of silicone, may be positioned around the outside of the inflow edge 18 of frame 12. The entire frame 12 and ring 22 may be completely covered inside and out by a further fabric layer. Subsequently, a layer of tissue 24 may be applied over the fabric layer, including both inside and outside of frame 12 and over ring 22. Tissue layer 24 is typically formed of any mammalian tissue, and in particular any mammalian pericardium tissue, such as porcine, equine, or bovine pericardium. In the completed surgical heart valve 10, the covered ring 22 serves as a sewing cuff for sewing the prosthetic heart valve into the native valve annulus of the patient.

The collapsible/expandable prosthetic heart valves of the disclosure have an expanded condition and may also have a collapsed condition. Although aspects of the disclosure apply to a collapsible/expandable prosthetic heart valve for replacing a native aortic valve, the disclosure is not so limited, and may apply to prosthetic valves for replacing other types of cardiac valves, including, the mitral valve, the tricuspid valve and the pulmonary valve. Nor is the disclosure limited to a specific method of delivery. For example, the collapsible/expandable prosthetic heart valves described herein may be delivered via any suitable transcatheter delivery route, including a transfemoral route, a transvenous route, a transapical route, a transjugular route, a transaortic route, a transsubclavian route, etc. Further, the collapsible/expandable prosthetic heart valves described herein may be delivered via traditional surgical routes, or any suitable minimally invasive route.

Figure 2:
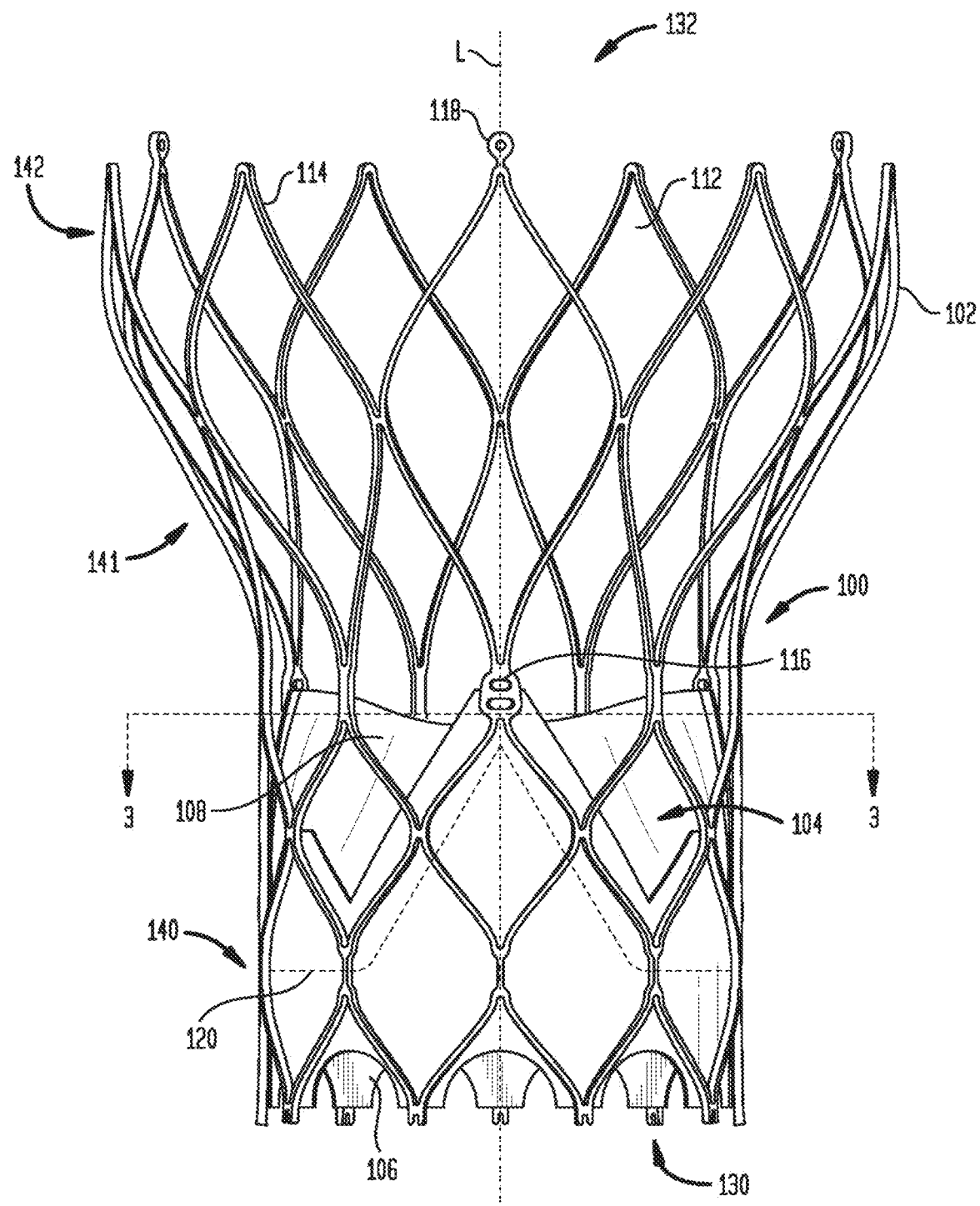
FIG. 2 is a side view of a stent-supported prosthetic heart valve according to the prior art in an expanded condition.

FIG. 2 shows one embodiment of a collapsible/expandable stent-supported prosthetic heart valve 100 according to the prior art, the prosthetic heart valve being shown in an expanded condition. Prosthetic heart valve 100 is designed to replace the function of the native aortic valve of a patient, and includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded condition in comparison to the transverse cross-section of aortic section 142. A transition section 141 may taper outwardly from annulus section 140 to aortic section 142. Each of the sections of stent 102 includes a plurality of cells 112 formed by interconnected struts 114. Each cell 112 may include four struts 114 connected together generally in a diamond shape so as to form a cell that may be readily collapsed and expanded. It will be appreciated that a smaller or larger number of struts may be used to form cells having a different shape. The cells 112 in each section of stent 102 may be connected to one another in one or more annular rows around the stent. For example, as shown in FIG. 2, annulus section 140 may have two annular rows of complete cells 112, with the cells in one annular row offset by one-half cell width in the circumferential direction from the cells in the other annular row. Aortic section 142 and transition section 141 may each have one or more annular rows of complete or partial cells 112. The cells in aortic section 142 may be larger than the cells in annulus section 140 so as to better enable prosthetic valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to the collapsed condition, and shortens in the direction of longitudinal axis L as the stent transitions from the collapsed condition to the expanded condition.

Stent 102 may include one or more retaining elements 118 at outflow end 132, the retaining elements being sized and shaped to cooperate with retaining structures provided on a delivery device (not shown). The engagement of retaining elements 118 with the retaining structures on the deployment device may help maintain prosthetic heart valve 100 in assembled relationship with the deployment device, minimize longitudinal movement of the prosthetic heart valve relative to the deployment device during unsheathing or resheathing procedures, and help prevent rotation of the prosthetic heart valve relative to the deployment device as the deployment device is advanced to the target location and during deployment. One such deployment device is described in U.S. Patent Publication No. 2012/0078352, the disclosure of which is hereby incorporated by reference herein.

Stent 102 may also include a plurality of commissure attachment features 116 for mounting the leaflet commissures of the valve assembly to the stent. As can be seen in FIG. 2, each commissure attachment feature 116 may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141 and may include one or more eyelets or apertures which facilitate the suturing of the leaflet commissures to stent 102. Stent 102 may be formed as a unitary structure, for example, by laser cutting or etching a tube of a superelastic and/or shape-memory metal alloy, such as a nickel-titanium alloy of the type sold under the designation nitinol. It should be understood that stent 102 may include other forms of commissure attachment features, or may omit commissure attachment features, with the prosthetic leaflets being attached to the stent via other mechanisms, such as direct suturing or via intermediary attachment panels. Examples of other attachment modalities may be found in U.S. patent application Ser. No. 16/568,345, filed Sep. 12, 2019, the disclosure of which is hereby incorporated by reference herein.

Prosthetic heart valve 100 includes a valve assembly 104 which, in one embodiment, may be positioned entirely in the annulus section 140 of stent 102. Valve assembly 104 includes a plurality of leaflets 108 that collectively function as a one-way valve by coapting with one another, and a cuff 106 positioned on the luminal surface of stent 102 surrounding leaflets 108. Although cuff 106 is shown in FIG. 2 as being disposed on the luminal or inner surface of annulus section 140, the cuff may be disposed on the abluminal or outer surface of the annulus section, or may cover all or part of either or both of the luminal and abluminal surfaces of the annulus section. As prosthetic heart valve 100 is intended to replace the aortic valve (which ordinarily is a tri-leaflet valve), it is shown in FIG. 2 with three leaflets 108. Adjacent leaflets 108 join one another at leaflet commissures. Each of the leaflet commissures may be sutured to a respective one of the three commissure attachment features 116. Between the leaflet commissures, each leaflet 108 may be sutured to stent 102 and/or to cuff 106 along an attachment edge 120, indicated with broken lines in FIG. 2. Leaflets 108 may be joined to stent 102 and/or to cuff 106 by techniques known in the art other than suturing. Above attachment edge 120, leaflets 108 are free to move radially inward to coapt with one another along their free edges. When prosthetic heart valve 100 is implanted in the native aortic valve annulus, blood flows in an antegrade direction from inflow end 130, past leaflets 108, and toward outflow end 132. This occurs when the pressure in the left ventricle is greater than the pressure in the aorta, forcing leaflets 108 to open. When the pressure in the aorta is greater than the pressure in the left ventricle, leaflets 108 are forced closed and coapt with one another along their free edges, blocking blood from flowing through prosthetic heart valve 100 in a retrograde direction from outflow end 132 to inflow end 130 which allows the left and right coronary arteries to fill and feed blood to the heart muscle. It will be appreciated that prosthetic heart valves according to aspects of the present disclosure may have more or less than the three leaflets 108 and commissure attachment features 116 shown in FIG. 2 and described above.

Cuff 106 may be scalloped at the inflow end 130 of stent 102, and may have a zig-zag structure at its outflow end, following certain stent struts 114 up to commissure attachment features 116 and other stent struts closer to the inflow end of the stent at circumferential positions between the commissure attachment features. When open, leaflets 108 may remain substantially completely within annulus section 140, or they may be designed to extend into transition section 141. In the embodiment shown, substantially the entirety of valve assembly 104 is positioned between the inflow end 130 of stent 102 and commissure attachment features 116, and none of the valve assembly is positioned between the commissure attachment features and the outflow end 132 of the stent.

In operation, prosthetic heart valve 100 may be used to replace a native heart valve, such as the aortic valve, a surgical heart valve, or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into the patient using any known percutaneous procedure, such as a transfemoral, transapical, transvenous, or transseptal delivery procedure. Once the delivery device has reached the target site, the user may deploy prosthetic heart valve 100. Upon deployment, prosthetic heart valve 100 expands into secure engagement within the native aortic annulus. When prosthetic heart valve 100 is properly positioned inside the heart, it works as a one-way valve, allowing blood to flow in one direction and preventing blood from flowing in the opposite direction. (See U.S. Pat. No. 7,585,321 FIGS. 13a-16b and accompanying disclosure; U.S. Pat. No. 6,458,153 FIGS. 20A-20I and accompanying disclosure.)

Figure 3:
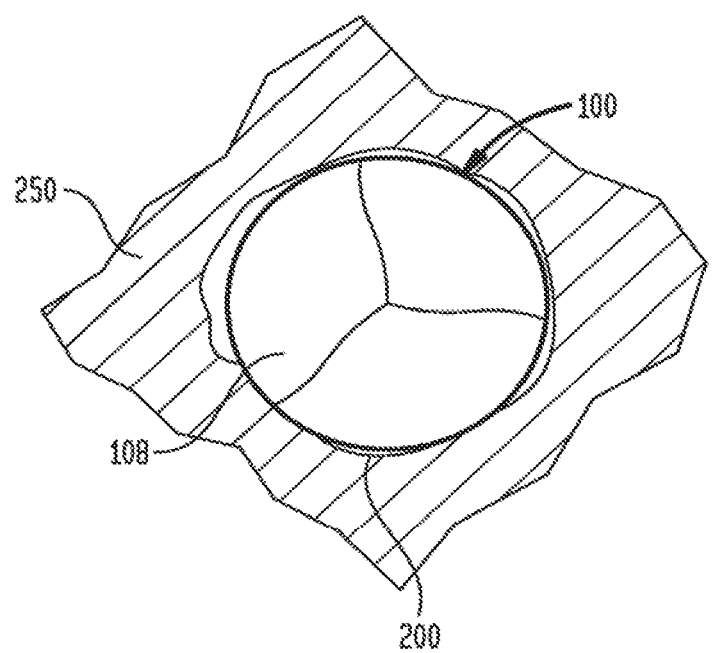
FIG. 3 is a highly schematic transverse cross-section of the prosthetic heart valve taken along line 3-3 of FIG. 2 and implanted in a native valve annulus.

FIG. 3 is a highly schematic transverse cross-section of prosthetic heart valve 100 taken along line 3-3 of FIG. 2 and showing leaflets 108 disposed within native valve annulus 250. As can be seen, the substantially circular annulus section 140 of stent 102 is disposed within a non-circular native valve annulus 250. At certain locations around the perimeter of prosthetic heart valve 100, gaps 200 are formed between the heart valve and native valve annulus 250. Retrograde blood flow through these gaps and around the outside of the valve assembly 104 of prosthetic heart valve 100 can result in PV leak or regurgitation and other inefficiencies which can reduce cardiac performance. Such improper fitment may be due to suboptimal native valve annulus geometry, for example, as a result of the calcification of the tissue of native valve annulus 250 or the presence of unresected native leaflets.

Figure 4:
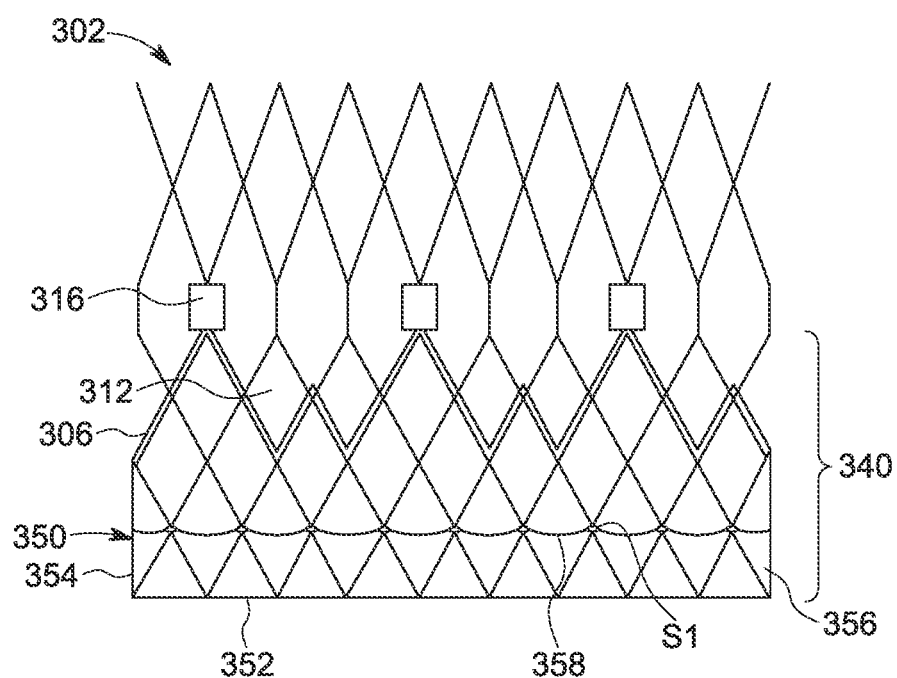
FIG. 4 is a highly schematic developed view of an expanded stent which is illustrated flattened as if it were cut longitudinally, illustrating inner and outer cuffs attached to the stent.

FIG. 4 depicts a collapsible/expandable prosthetic heart valve very similar to that shown in FIGS. 2 and 3, except that it is shown as if cut longitudinally and flattened. The heart valve can include a stent 302 with commissure attachment features 316. A cuff 306 similar or identical to cuff 106 may be positioned on the luminal and/or abluminal surface of stent 302. Indeed, cuff 306 in FIG. 4 is illustrated as being positioned on the luminal or inner surface of stent 302. However, in order to help minimize or eliminate PV leak, for example through the gaps 200 shown in FIG. 3, additional material may be coupled to the exterior of stent 302 as an outer cuff 350. In the illustrated example, outer cuff 350 may have a substantially rectangular shape and may be wrapped around the circumference of stent 302 at the inflow end of the stent so as to overlap in the longitudinal direction of the stent with cuff 306. This is only one embodiment of such an exterior or outer cuff. Outer cuff 350 may be formed as a single piece of material having a proximal edge 352, two side edges 354, 356, and a distal edge 358. Preferably, the proximal edge 352 of outer cuff 350 is coupled to stent 302 and/or to inner cuff 306 at or near the inflow end of the stent, for example by a continuous line of sutures (not shown), with the side edges 354 and 356 of the outer cuff joined to one another, so that retrograde blood flow (flowing from the outflow end toward the inflow end) entering the space between the outer cuff and the inner cuff cannot pass in the retrograde direction beyond the combined cuffs. In order to allow retrograde blood flow to enter the space between outer cuff 350 and inner cuff 306, the distal edge 358 of the outer cuff may be attached to stent 302 and/or to inner cuff 306 at locations that are spaced apart in the circumferential direction. The distal edge 358 of outer cuff 350 may, for example, be sutured to stent 302 at attachment points S1 located where each cell 312 in the proximal-most row of cells intersects with an adjacent cell in that same row. In the illustrated example, since there are nine cells 312 in the proximal-most row, there are nine separate attachment points S1 at which the distal edge 358 of outer cuff 350 is sutured or otherwise attached to stent 302 and/or to inner cuff 306. Retrograde blood flow around the abluminal surface of stent 302 may enter the pocket or space between outer cuff 350 and inner cuff 306 via the spaces between adjacent attachment points S1. Once retrograde blood flow enters this space, outer cuff 350 may tend to billow outwardly, helping to fill any of gaps 200 between the prosthetic heart valve and native valve annulus 250. Although the foregoing description uses the term "inner" in connection with cuff 306, that is merely intended to indicate that cuff 306 is positioned radially inward of outer cuff 350. Inner cuff 306 may be located either on the luminal or abluminal side of stent 302, or on both sides.

Outer cuff 350 may also comprise multiple pieces of material that, when joined together, form a shape and provide a function that are similar to what has been described above. Also, rather than being formed of a single substantially rectangular piece of material that is wrapped around the circumference of stent 302, outer cuff 350 may be formed as a continuous annular web without side edges 354, 356. Preferably, outer cuff 350 has an axial height measured from its proximal edge 352 to its distal edge 358 that is approximately half the axial height of a cell 312 in the proximal-most row of cells in stent 302 as measured along the major axis of the cell between two of its apices when the cell is in an expanded condition. However, outer cuff 350 may have other suitable heights, such as the full axial height of a cell 312 in the proximal-most row of cells, or more or less than the full axial height of a cell 312 in the proximal-most row of cells. Still further, although inner cuff 306 and outer cuff 350 are described above as separate pieces of material joined to stent 302 and to each other, the cuffs may be formed integrally with one another from a single piece of material that is wrapped around the inflow edge of the stent, with the distal edge 358 of the outer portion of the cuff joined to the stent and/or to the inner portion of the cuff at attachment points S1 as described above. With this configuration, the proximal edge 352 of outer cuff 350 does not need to be sutured to stent 302, although it still may be preferable to provide such attachment. The various valve components including, without limitation, inner cuffs, outer cuffs and leaflets, and valve assemblies made therefrom, may be attached to each other and/or to the stent in any conventional manner, including suturing, gluing, molding, welding, heating, cross-linking, and the like. (See U.S. Pat. Nos. 6,821, 297; 6,458,153; 7,585,321; 5,957,949.)

Valve assemblies, such as valve assembly 104 comprising inner cuff 106/306, leaflets 108, as well as outer cuff 350, may be formed of the same or different materials, including any suitable biological material, including "fixed" bovine or porcine tissue, or a polymer such as, for example, polyolefins such as polytetrafluoroethylene (PTFE), polyethylenes including ultra-high molecular weight polyethylene (UHMWPE), and polypropylene, as well as polyurethane, PEEK, polyvinyl alcohol, silicone, or combinations thereof (See U.S. Pub. No. 2018/0055631 A1, the disclosure of which regarding the structure, function and manufacture of a heart valve are hereby incorporated by reference herein.) In accordance with the present disclosure, at least one of the components of a valve, including, without limitation, leaflets or cuffs, valve assemblies, and the like, is produced from an uncoated or coated stabilized fabric, a term which, as noted earlier, includes both a stabilized woven fabric or a mesh as described herein.

The description of surgical heart valve 10 and collapsible/expandable prosthetic heart valve 100 are for context only. Thus, the stabilized fabric materials described herein may be used in surgical heart valves that are similar to surgical heart valve 10 or surgical heart valves that are very different therefrom. Similarly, the presently disclosed stabilized fabric materials may be used in collapsible/expandable prosthetic heart valves that are similar to prosthetic heart valve 100, or prosthetic heart valves that are very different therefrom, such as heart valves having a balloon-expandable stent; heart valves that do not have an aortic section; heart valves in which the stent has an hourglass profile, right cylindrical sections or ovoid cross-sections; heart valves intended to replace other cardiac valves, such as the mitral valve; etc. For example, the stent may be made of a single or multiple bent wires such as illustrated in U.S. Pat. No. 5,411,552 or 5,855,601, forming a zigzag or sinusoidal shape, or may be made from interwoven or intercrossing bars such as shown in U.S. Pat. Nos. 5,545,214 and 7,585, 321. The stent may also be formed of woven materials which can be such as shown in EP 2,926,766, which is hereby incorporated by reference herein for its teaching of a woven stent and for its teachings regarding the mounting of a cuff and/or sac on the interior or exterior of a stent. Often, however, the stent is made from a laser-cut nitinol tube. A balloon-expandable stent may be composed of biocompatible metals known in the art, including but not limited to, cobalt chromium and stainless steel. The stent may be continuous or discontinuous (made in sections that are attached to one another directly or indirectly—see, for example, U.S. Pat. No. 5,957,949). Therefore, the descriptions herein of surgical heart valve 10 and collapsible/expandable prosthetic heart valve 100 should in no way be considered as limiting the features and applications of the coated and uncoated fabric materials disclosed herein.

According to the present disclosure, one or more of the valve components and, in particular, the inner and/or outer cuff(s) and/or one or more leaflets, may be made from a mesh or a woven fabric, a term which includes knitted fabric). As used herein, the term "fabric" refers to a polymer-fiber containing material having filaments, threads, yarns, or other strands (collectively, "fibers") that are interlaced with one another. This term is used interchangeably with the term "woven fabric." However, the term "stabilized fabric" or as the context of the use of the term "fabric" demands, includes not only a woven fabric stabilized as discussed herein but also a mesh. When discussing a woven fabric, the fibers may be formed of any one or more of a variety of materials, including natural materials, polymers, or blends of natural materials and polymers, so long as it includes a majority of polymer fibers. The natural materials may include cotton, wool, hemp, jute, silk, linen, alpaca, cashmere and the like. The polymer fibers may include, for example, polyolefins such as polytetrafluoroethylene (PTFE) (including expanded (e-PTFE), stretched, low molecular weight, medium molecular weight, high molecular weight and ultra-high molecular weight (UHMW)), polyethylenes (including low, medium, high and ultra-high molecular weight polyethylene (UHMWPE—e.g., having an average molecular weight of between about 2 and about 7.5 million atomic mass units)), and polypropylene (including low, medium, high and ultra-high molecular weight polypropylene (UHMWPP)), as well as polyurethane, PEEK, polyvinyl alcohol, silicone, rayon, polyesters, aramid, spandex, or combinations thereof. The fibers may have any cross-sectional shape, including round, rectangular, triangular, polygonal, oval, etc. Moreover, the fibers may be selected to have desired dimensions, such as diameter, width, thickness and/or length. The fibers may also have an irregular, undulating or variable diameter along its length. Fibers are often extruded, and their diameter may be varied during the extrusion process to provide this undulating profile of thicker and thinner regions. The fibers may also be porous or nonporous, and drug-eluting or non drug-eluting. In addition, the fibers may each consist of a single strand or filament, or of multiple strands or filaments. For fibers comprised of multiple strands or filaments, the strands or filaments may be braided, twisted or otherwise joined together in a bundle. (When used herein, the term "fibers" shall include both individual fibers as well as fiber bundles.) The fibers may be selected based on certain properties, such as creep, tensile strength, elastic modulus, strain/elongation, compressibility, flexural rigidity and stiffness, and twist direction and magnitude. Other properties that may influence the selection of certain fibers include melt flow viscosity, percent spin finish, linear density, tenacity, melting temperature, biocompatibility, purity, Denier, color, radiopacity, surface friction and entanglement. The polymers just mentioned herein as being useful for fibers used in the woven fabric and a stabilized woven fabric of the present invention can also be used to produce a mesh for use as a stabilized fabric.

In addition to their mechanical properties, the individual fibers may be uncoated, or they may be coated with another material. In one form of coated fiber, the fiber may be conjugated (i.e., chemically reacted) with another material, for example, a therapeutic drug or a lubricious material. In another form of coated fiber, the fiber may be coated with a polymer or other material. In still another form of coated fiber, a porous fiber may be infused with a polymer, a therapeutic drug, a lubricity-promoting agent or another material. Any known technique may be used to coat the fiber with a polymer or other material, including spray coating, dip coating and the like. Once coated, the fibers may be allowed to dry or, for polymer coatings, the polymer may be solidified by cross-linking. It will be appreciated that, for coated fibers, the coating may be applied uniformly around the surface of the fiber, or it may be applied to only portions of the fiber surface and/or along only portions of the fiber length.

The weave of the fabric may determine the extent of porosity in the fabric. The fabric's porosity corresponds to the number and size of the open areas formed between the fibers as a result of the weaving or knitting process. When used as a component of a prosthetic heart valve, the fabric, when the prosthetic heart valve has been implanted, may be in contact with tissue and may promote a healing response. The porosity of the woven or knitted fabric may allow cells to flow through the valve component, but after blood makes contact with the fabric, the fabric may become less permeable or impermeable.

Expanding on the foregoing, a stabilized fabric may promote cell adhesion, wherein cells may attach to a single fiber of the fabric or to a plurality of fibers of the fabric or to a single strand or multiple strands of a mesh. The cells may adhere or attach to the stabilized fabric without inhibiting the expected performance of the material. Cell adhesion may be aided by the deposition of blood proteins, plasma, coagulation products, fibrin or other materials. In some embodiments, cells may migrate into the prosthetic heart valve from the adjacent tissue and may attach or adhere to the stabilized fabric components. In other embodiments, cells from the blood may be entrapped in the fabric and may attach or adhere to individual fibers of the woven fabric or struts or strands of the mesh.

Figure 5:
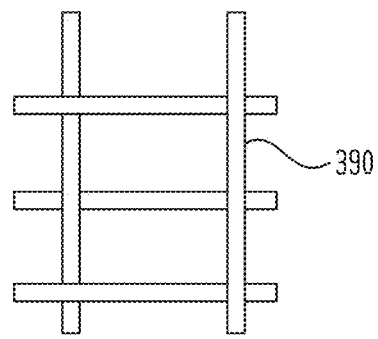
FIG. 5 is an enlarged schematic view of the fibers of a porous uncoated woven fabric.
Figure 6:
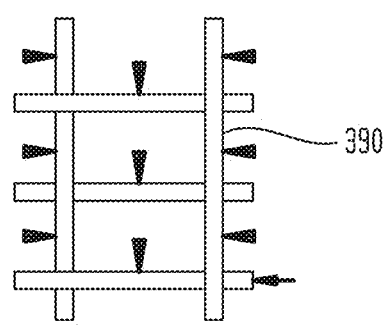
FIG. 6 is an enlarged schematic view of the fibers of a porous uncoated woven fabric, in which the fibers are conjugated with another material.
Figure 7:
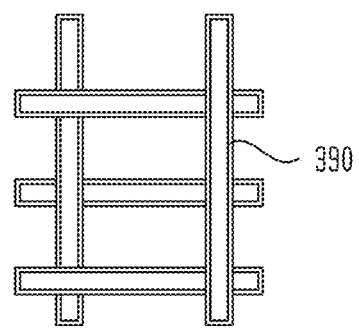
FIG. 7 is an enlarged schematic view of the fibers of a porous uncoated woven fabric, in which the fibers are coated with another material.

The adhesion of cells to the stabilized fabric may also be influenced by the composition of the fibers, the weave, or mesh and whether the fibers or mesh are coated or uncoated, and if coated, the composition of the coating. In some embodiments, porous fibers or a porous mesh may be impregnated with a drug or other material that may either promote or retard cell adhesion. In other embodiments, the individual fibers or the mesh may be either partially or fully conjugated or coated with a polymer, a therapeutic drug and/or another material. FIGS. 5-7 show different embodiments of an uncoated woven fabric. In one embodiment, shown in FIG. 5, the individual fibers 390 of the fabric are uncoated. In another embodiment, shown in FIG. 6, the individual fibers 390 of the fabric may be conjugated with another material, for example, a therapeutic drug, before the fibers are woven or knitted to form the uncoated fabric. In a further embodiment, shown in FIG. 7, the individual fibers 390 of the fabric may be coated with a polymer or other material before the fibers are woven or knitted to form the uncoated fabric. Where the fabric is formed from fibers that have been conjugated or coated with another material, every fiber of the fabric may be so conjugated or coated, either partially or fully, or only some of the fibers of the fabric may be so conjugated or coated. A mesh can be made in a corresponding way.

The woven fabrics or meshes may also be engineered to have certain mechanical properties, such as a desired creep, compression, burst strength, suture retention, flexural rigidity/stiffness, tearing strength, delamination strength, and stretch/elongation. Other properties that may be sought include a specific anisotropy, color, weight, extractable content, permeability, radiation sensitivity, radiopacity, moisture sensitivity, temperature sensitivity, and/or chemical sensitivity. As noted, many of these parameters may be influenced by the particular fibers used to form the woven fabric or the polymers used to produce the mesh, while others may be more influenced by the manner in which the fabric is formed from the fibers or the mesh is produced. In addition, the fabric or mesh may include one or more radiopaque fibers or other features to assist in identifying the location and orientation of one or more features of the prosthetic heart valve or other medical device in which the fabric or mesh is incorporated.

The fabrics may be engineered to have a desired thread count, a desired tensile strength, a desired areal density, and/or a desired thickness, all measured before the medical device incorporating the fabric is implanted in a patient. When the fabric is a woven fabric, it preferably has a thread count of at least about 150, 200, 250, 300, 350, 400, 450, 500, 600, 700, 800, 900, 1000 or more total fibers per square inch per layer of fabric. The thread count need not be symmetrical. For example, one could use a fabric of about 100×50, 100×125, 220×110, 330×170, 360×180, 400×200 and 440×220 fibers in a square inch. In one embodiment, the thread count is from about 200 to about 500 by about 200 to about 500 fibers in a square inch (200-500×200-500), and in another embodiment is from about 300 to about 500 by about 100 to about 300 fibers in a square inch (300-500× 100-300). In some embodiments, the fabric is a high-density weave having more than 300 fibers per square inch. Further, the thread count in one portion of the fabric may be different from the thread count in another portion of the fabric. For example, when the fabric is used to form a leaflet of a prosthetic heart valve, the thread count at the attachment edge may be greater than the thread count in the belly portion or at the free edge of the leaflet. The greater thread count at the attachment edge produces a fabric with greater strength in the region at which the leaflet is attached to the cuff and/or stent and experiences a large amount of stress in use. The density of the weave may be adjusted, and often reduced, to promote flexibility and adhesion of layers, including adhesion through the fabric of a coating on one major surface of the fabric to a coating on the other major surface of the fabric. When the fabric is a knitted fabric, it typically has a lower thread count or stitch density than a woven fabric. Knitted fabrics may have a stitch density of from about 2 to about 750 per square inch or from about 5 to about 500 per square inch.

In some embodiments, the fabric has a tensile strength of at least about 50N, and in other embodiments about 60N. In still other embodiments, the tensile strength is about 70N or more. A tensile strength of at least about 75N may be used, as may a tensile strength of at least about 85N or at least about 100N. A mesh used in producing a stabilized fabric can have these same properties.

In some embodiments, woven or knitted fabric has an areal density of at least about 0.5±0.1 ounces/yard$^2$, in other embodiments, an areal density of at least about 0.65±0.1 ounces/yard$^2$, and in still other embodiments, an areal density of about 0.8±0.05 ounces/yard$^2$. It will be appreciated that weave density and thread counts balance the need for strength, flexibility and porosity. For an uncoated fabric, pore density between woven/knitted fabric fibers should not be large enough to cause appreciable leakage through the fabric. On the other hand, in general, the fewer the number of fibers and/or the larger the number of pores in the fabric, the greater will be the flexibility of the fabric and the more a synthetic fabric leaflet will resemble a healthy native leaflet. Stated another way, the woven or knitted fabric in one embodiment has an areal density of at most about 1.3±0.1 ounces/yard$^2$, and in another embodiment, an areal density of no more than about 1.0±0.1 ounces/yard$^2$. Of course, the weave density could increase locally as a means of stabilizing the woven fabric as described herein.

Obviously, a mesh is not a woven fabric, it is a continuous web of polymer struts that meet at a variety of common locations to form a regular pattern very analogous to a woven fabric. The junctions of the struts are analogous to the intersections of warp and weft fibers and the struts that run between and connect these junctions are analogous to the fibers. And like woven fabrics, struts and their junctions define openings or gaps, which are called divots or pores in case of a mesh. The number of struts and junctions in the web can be configured to provide a density and size of these pores/divots analogous to the gaps and intersections of woven fabrics as noted above. Alternatively, the mesh may contain pores and/or divots having at least one opening having an average area which could range from about 100 microns$^2$ to about 5,000 microns$^2$. In another embodiment, this opening has an average area that ranges from between about range from about 1,000 to about 3,000 microns$^2$. In one embodiment, the mesh has a pore density (divot density) of about 1 to about 25% and in still another embodiment, the pore/divot density is about 5 to about 15%.

In some embodiments, the uncoated fabric or mesh has a thickness of about 10 µm to about 200 µm, and in other embodiments, a thickness of about 20 µm to about 100 µm. In some embodiments, the thickness of the fabric is from about 50 µm to about 100 µm. Thickness is a balance between durability, resilience, and flexibility. At a thickness of about 75 µm, the fabric leaflets of the disclosure are often only about 20% of the thickness of most tissue leaflets used in conventional collapsible heart valves, which are about 300-450 µm thick, or about 10% of the thickness of most tissue leaflets used in surgical heart valves, which are about 400-800 µm thick. In some embodiments, the thickness of the mesh could be as little as 5 µm.

Any of the properties of the stabilized fabric may be selected depending on the particular application. For example, while some parameters may be suitable for stabilized fabrics forming the cuffs and/or leaflets of a collapsible/expandable prosthetic heart valve, stabilized fabrics having other parameters may be better suited for other medical devices described below.

Figure 8:
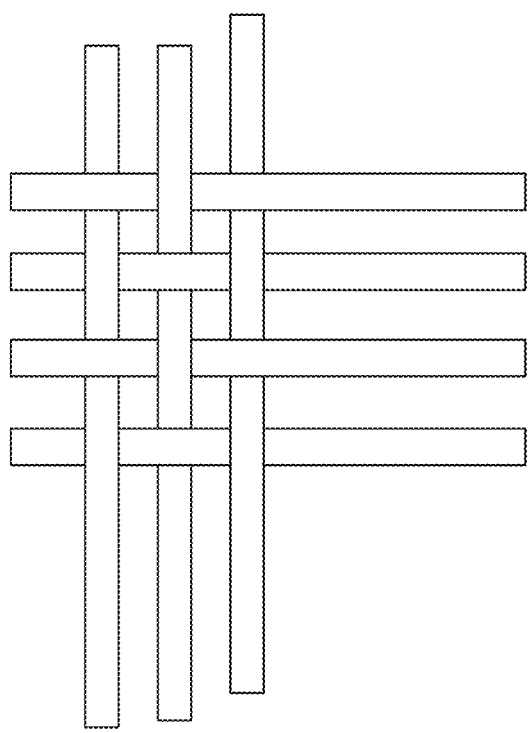
FIG. 8 is an enlarged view of a woven fabric having a plain weave pattern.
Figure 9:
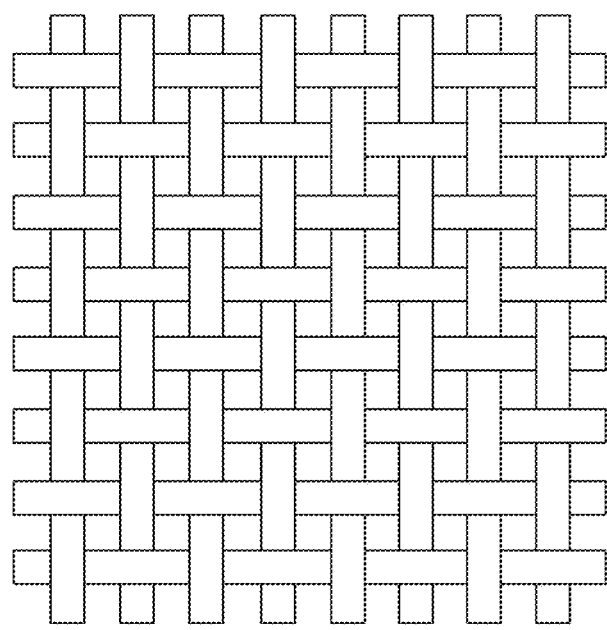
FIG. 9 is a plan view of a woven fabric having a plain weave pattern.
Figure 10:
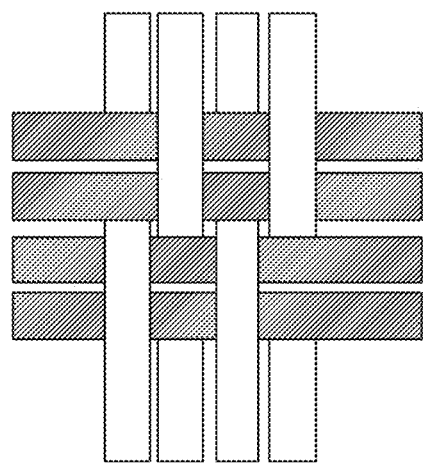
FIG. 10 is a plan view of a woven fabric having a warp rib weave pattern.
Figure 11:
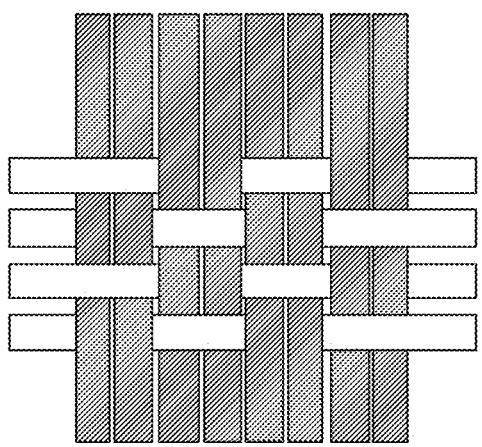
FIG. 11 is a plan view of a woven fabric having a weft rib weave pattern.
Figure 12:
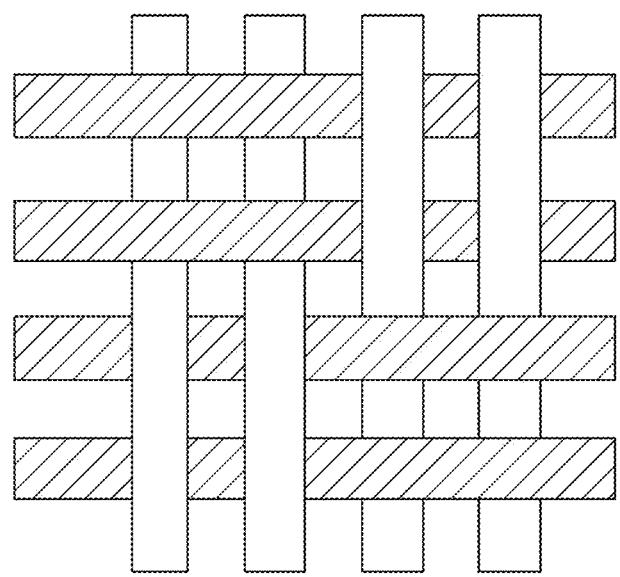
FIG. 12 is a plan view of a woven fabric having a basket weave pattern.
Figure 13:
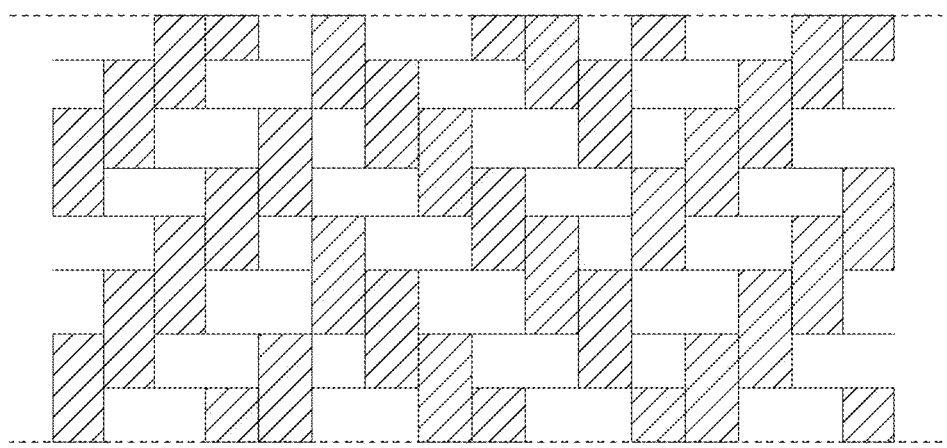
FIG. 13 is a plan view of a woven fabric having a herringbone weave pattern.
Figure 14:
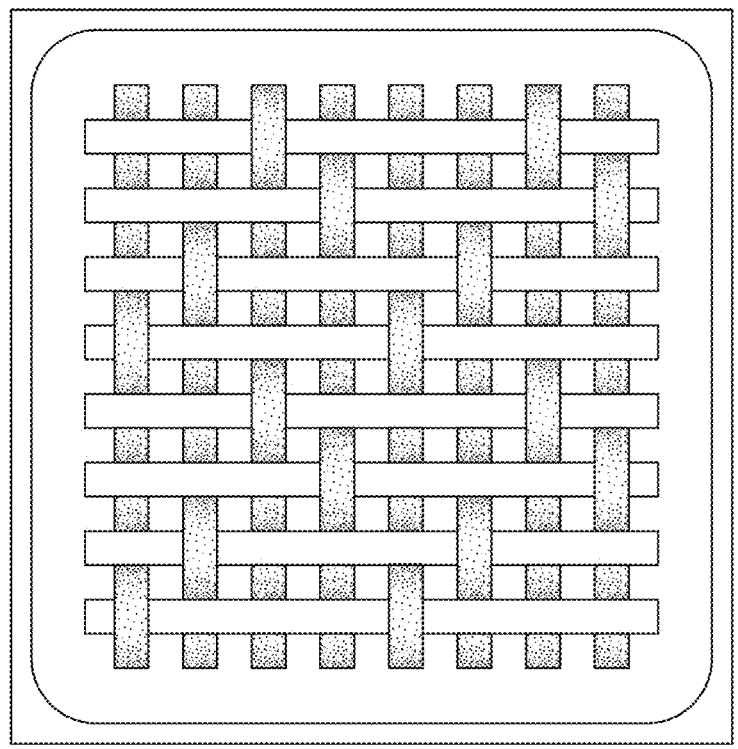
FIG. 14 is a plan view of a woven fabric having a satin weave pattern.
Figure 15:
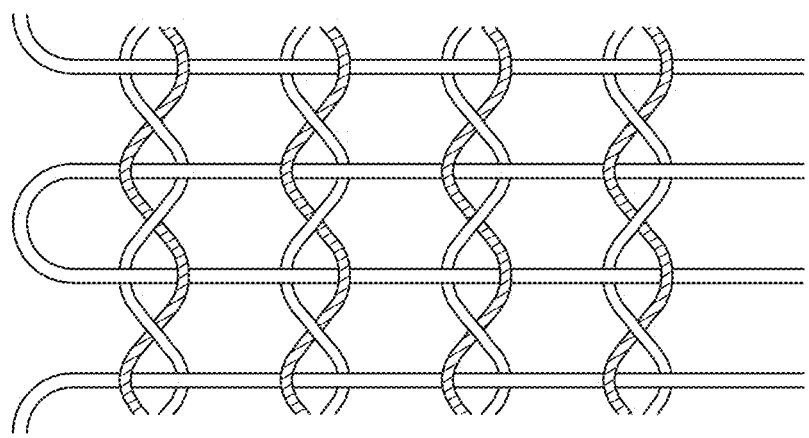
FIG. 15 is a plan view of a woven fabric having a leno weave pattern.
Figure 16:
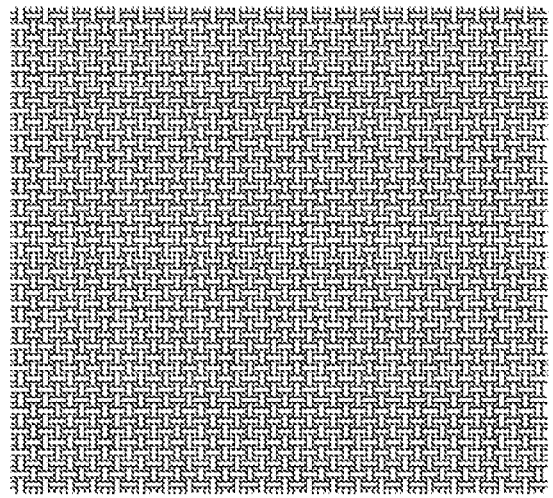
FIG. 16 is a plan view of a woven fabric having a twill weave pattern.

FIGS. 8 to 19 illustrate various techniques that may be used to form a woven fabric. As noted previously, the fabric may be formed by interlacing two or more fibers, or in the case of knit fabrics at least one fiber, which can be accomplished in several ways. Some of the methods for interlacing two or more fibers include weaving, knitting, braiding, plaiting, electro spinning, 3-D printing or entangling the fibers through felting, bonding or lamination. Woven fabrics may be fabricated through various techniques. As used herein in connection with the various weaving techniques, "filling" or "weft" refers to fibers that extend along the width of the fabric, while "warp" refers to fibers that extend along the length of the fabric. A plain weave, shown in FIGS. 8 and 9, is the simplest weaving method in which a single filling fiber is passed over and under each warp fiber, with the pattern in adjacent rows alternating. (Plain weave, Encyclopaedia Brittanica, Dec. 17, 2010, www.britannica.com/technology/plain-weave accessed on Oct. 11, 2019.) One derivative of the plain weave is the rib weave, in which two or more adjacent rows of the filling fiber are passed in the same pattern over and under each warp fiber. (Watson, Kate Heintz et al., *Textiles and Clothing,* 1907, Home Economics Association, p. 77.) Two versions of the rib weave may also be used, the warp rib weave and the weft rib weave shown in FIGS. 10 and 11. The warp rib weave produces a rib or cord in the weft direction, while the weft rib weave produces a rib or cord effect in the warp direction. (*Difference between Warp Rib Weave and Weft Rib Weave*, Define Textile, 2019, www.definetextile.com/2013/05/difference-between-warp-rib-weave-and.html, accessed on Oct. 23, 2019). A weft weave of polyethylene terephthalate (PET) may be particularly desirable for certain applications, such as for cuffs and/or leaflets of prosthetic valves. Another derivative of the plain weave is a basket weave, in which both the filling fiber and the warp fiber run in double or triple strands. (Watson, Kate Heintz et al., *Textiles and Clothing,* 1907, Home Economics Association, p. 77.) That is, in a basket weave, shown in FIG. 12, two or more adjacent rows of the filling fiber are passed in the same pattern over and under two or more adjacent rows of the warp fiber. Another weaving technique that may be used to fabricate a woven fabric is the twill weave, shown in FIG. 16. The twill weave is known for producing a diagonal pattern when the filling fibers are woven over and under two or more adjacent warp fibers. (Twill weave, 2019, www.dictionary.com/browse/twill-weave, accessed on Oct. 11, 2019.) A version of the twill weave includes the herringbone weave, shown in FIG. 13, which resembles a broken zigzag or the bones of a fish. (*What is a Herringbone Weave?*, Shirts of Holland B.V., 2019, sleeve7.com/blog/what-is-a-herringbone-weave/, accessed on Oct. 11, 2019.) Another basic weaving technique is the satin weave which produces a soft, smooth and lustrous face without the appearance of a pattern. (Basic Weaves, Cotton Incorporated, 2019, www.cottonworks- .com/topics/sourcing-manufacturing/weaving/the-art-of-weaving-basic-weaves/, accessed on Oct. 11, 2019). An example of the satin weave is shown in FIG. 14.

Figure 17:
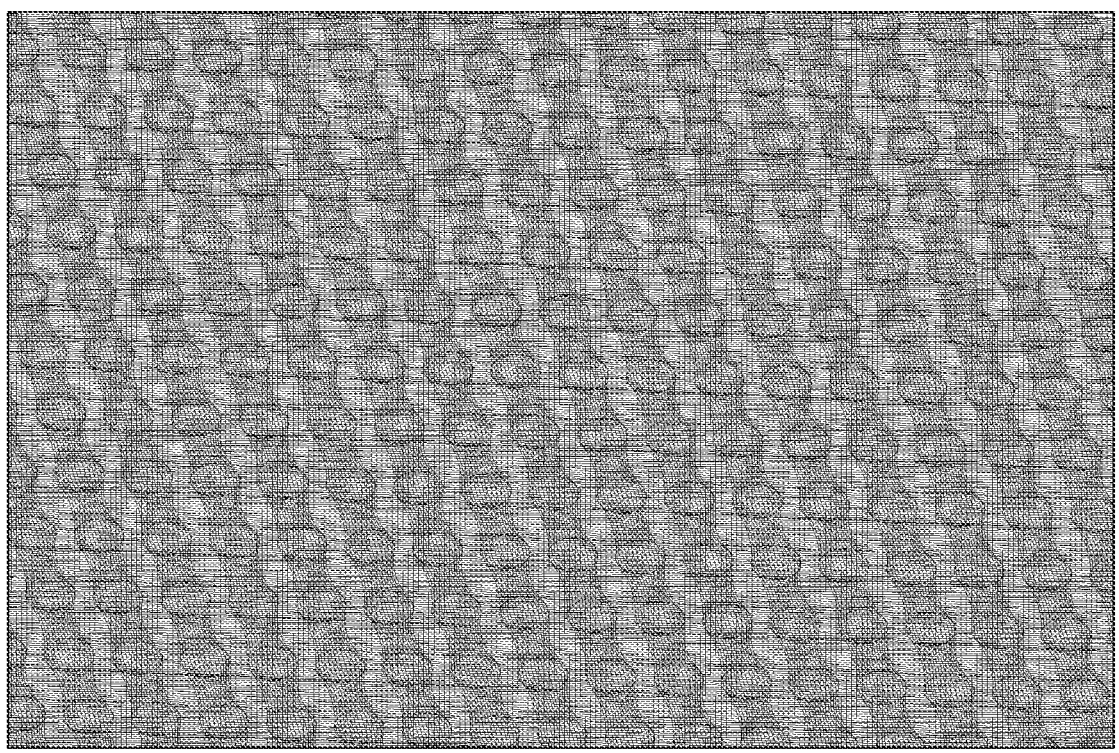
FIG. 17 is a plan view of a woven fabric having a waffle weave pattern.
Figure 18:
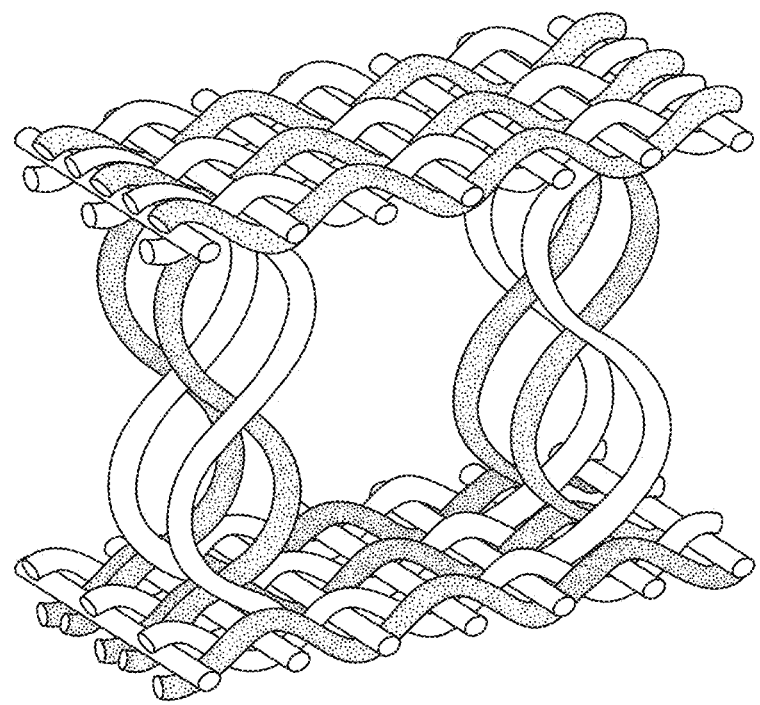
FIG. 18 is a perspective view of a woven fabric having a pile weave pattern.

Additional weaving techniques can be used to form the fabric as well. One additional weaving technique is the leno weave, shown in FIG. 15, a principal of interweaving in which some of the warp ends do not lie parallel to one another, but are twisted partly around other ends. (*Leno Weaves*, Serial 512. Ed. 1., International Textbook Co., www2.cs.arizona.edu/patterns/weaving/monographs/ics512.pdf, accessed on Oct. 11, 2019.) Another weaving technique is the Bedford cord, in which the weave produces longitudinal warp lines in the fabric with fine sunken lines in between. (*Bedford Cords*, Textile School4U. Blog spot-.com, 2013, textile school4u .blog spot.com/2013/12/bedford-cords.html, accessed on Oct. 11, 2019.) A waffle weave as shown in FIG. 17 can also be used by weaving the fabric into a pattern resembling a honeycomb. (*Honeycomb*, The Free Dictionary, www.thefreedictionary.com/waffle+weave, accessed on Oct. 11, 2019.) Also usable is a pile weave, which incorporates a loop pattern into the weave to produce a fabric with a raised, dense surface. (Adam Augustyn, Weaving, 2008, www.britannica.com/technology/weaving#ref290551, accessed on Oct. 11, 2019.) An example of a pile weave is shown in FIG. 18. A jacquard weave is another available technique which produces a fabric on a special loom because of the complex woven-in designs. (Id.) Similarly, a dobby weave requires a special loom attachment to incorporate small, geometric, textured, repeated woven-in designs. (Id.) Tapestry weaving, in which the warp fibers do not show at all, is another available technique. (*Tapestry Weaving Basics,* 2019, www.mirrixlooms.com/pages/tapestry-weaving-basics, accessed on Oct. 11, 2019.) An additional weaving technique is the double cloth weave, in which the fabric is made of two or more sets of warp fibers and one or more sets of weft or filling fibers that are interconnected to form a two-layered fabric. (*Double Cloth, Mar.* 20, 2019, en.wikipedia.org/wiki/Double_cloth#cite_ref-text2-0, accessed on Oct. 11, 2019.)

Figure 19:
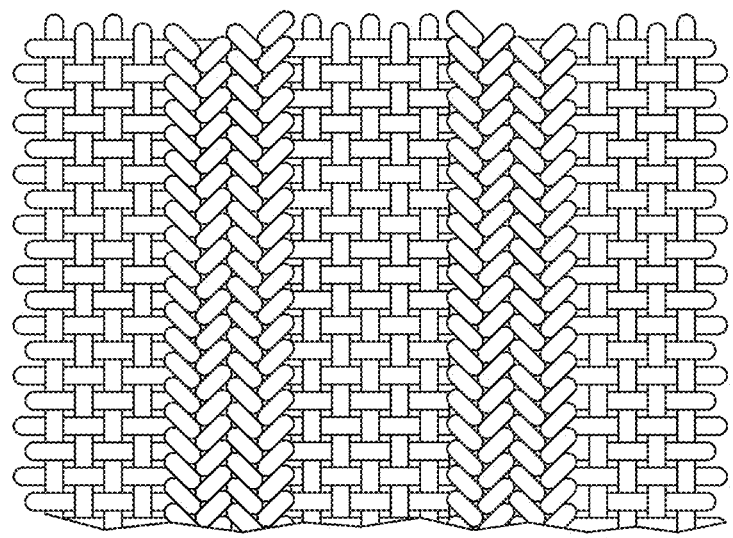
FIG. 19 is a plan view of a woven fabric having a single knit and purl knit patterns.

A variety of knitting techniques may also be used to produce the woven fabric. Knitting involves interlacing loops of at least one fiber. The main fabrics produced by knitting are weft knits, specialized weft knits and warp knits. A weft knit fabric can either be a single knit or a double knit. A single knit fabric is produced by one set of needles, while a double knit fabric is produced by two sets of needles. (Random House Kernerman Webster's College Dictionary, 2010, K Dictionaries Ltd.) The most common example of a single knit fabric is a single jersey. The most common double knit fabrics include rib knit, purl knit, interlock knit, cable fabric, bird's eye, cardigans, Milano ribs and pointelle. Examples of single knit and purl knit fabrics are shown in FIG. 19. The rib knit fabric is known for having a ribbed pattern. (*Rib-knit*, Merriam-Webster, 2019, www.merriamwebster.com/dictionary/rib-knit, accessed on Oct. 11, 2019.) A fabric with an interlock knit is a variation of the rib knit fabric with closely interlocking stitches providing the tightest weave. Fabrics produced with a specialized weft knit include intarsia, jacquard jerseys, knitted terry, knitted velour, sliver knit, fleece and French terry. There are two types of warp knitting commonly used, raschel and tricot. (*Warp knitting*, Sep. 15, 2019, en.wikipedia.org/wiki/Warp_knitting, accessed on Oct. 11, 2019.) Raschel knitting produces fabrics by using latch needles, while tricot knitting uses a bearded needle. (Id.)

No matter their form, woven polymer fabrics or meshes may be coated, either partially or completely, with one or more polymer layers, resulting in a coated fabric. "Coated fabric" in accordance with the disclosure means any of the uncoated fabrics described above, to which a polymer coating, film or layer is deposited or applied, either partially or completely covering at least a portion of one surface or edge of the fabric. The materials used for the fabric, as described previously, can be used for any coating or partial coating. Individual coatings may be the same as or different from one another and from the fabric, and include, without limitation, a PTFE, such as ultra-high molecular weight PTFE (UHMWPTFE) and expanded (e-PTFE) or stretched PTFE, a polyethylene, such as UHMWPE, and a polypropylene, such as UHMWPP, copolymers or block copolymers of polyethylenes and polypropylenes, and combinations or blends thereof. Other polymers which may be used alone or in combination with those mentioned above include, without limitation, polyurethanes, acrylics, polyesters, polyamides, polyimides, vinyl acetates, alkyds, epoxies, silanes, siloxanes, and the like. Homo- and co-polymers of these materials may also be used. A woven fabric could include fibers of one of or more of these materials or fiber bundles of one or more of these materials. Individual layers of a coating could be made of a single one of these materials or of blends/copolymers of them. When more than one coating layer is used, each of the layers may have the same or a different composition.

In some embodiments, the polymer coating may be produced using films that are directionally oriented in the same or in different directions. In one example, a polymer film may be applied to a top side of the fabric in one direction and a second polymer film may be applied to the bottom side of the fabric in a different direction. In another example, if more than one polymer film is applied to the top or bottom side of the fabric, the polymer film on each side of the fabric may be applied in the same direction or in different directions such that one polymer film is oriented differently from the polymer film that it sits on top of. The fabric/coating could further include or be coated with a drug or active pharmaceutical ingredient (API) or the coating could include the API, which gradually elutes from it. API's may include, for example, Sirolimus, Paclitaxel, Everolimus, or any treatment to enhance resistance to calcification. APIs may also include growth factors, such as vascular endothelial growth factor (VEGF) and transforming growth factor (TGF-beta). It may also be coated with, or the coating may include hyaluronan, hyaluronic acid, glycosaminoglycans (GAGs), Heparin, or amino acids for cell attachment sites, and anti-oxidants such as super oxide dismutase or ascorbic acid. In another embodiment, the fabric can be coated with one or more layers (completely or partially) which are composed of one or more bio-absorbable/biodegradable polymers such as, without limitation: poly-glycolic acid; poly-L-lactic acid; copolymers of poly-glycolic acid and poly-L-lactic acid; polycaprolactone; poly-DL lactic acid; polytrimethylene carbonate; polydioxanone; poliglecaprone; and polyglactin, as well as blends, mixtures and copolymers of the foregoing. It may be important that, for example, tissue ingrowth onto a surface be delayed. Applying a coating to an otherwise porous fabric—sufficiently porous to promote cell attachment—might prevent this, depending on many factors including the type of coating. Using a bio-absorbable/biodegradable polymer for the coating could retard cell attachment until the coating erodes or is absorbed. In another embodiment, and as described elsewhere herein, the coating may include an API that is released gradually. Taxol and other drugs have been released from coated stents in a like manner for a variety of reasons, including mitigating the initial stress of placement of the stent. But it may be that an uncoated fabric in contact with the annulus of a heart valve, for example, might be otherwise desirable, such as to allow cell ingrowth to fix the valve in place. Using a thin outermost layer of a cuff material of the disclosure, for example made of one or more bio-absorbable/biodegradable polymers. could facilitate drug release, then get out of the way.

Figure 20:
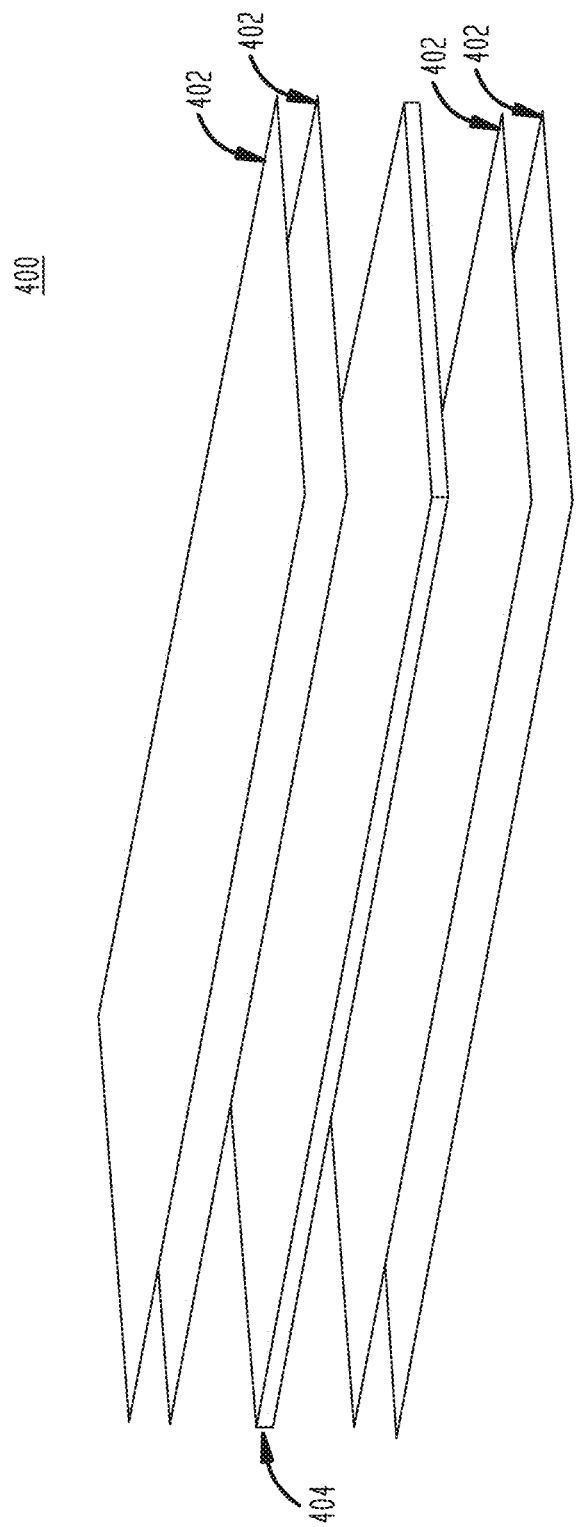
FIG. 20 is an exploded view of a coated woven fabric including a single fabric layer sandwiched between two polymer films or layers adhered to each side of the fabric layer.

FIG. 20 is an exploded view of an exemplary coated fabric 400 in accordance with the present disclosure useful for discussing its general structure in a non-limiting fashion. A completely coated fabric 400 can be created by heat laminating polymer film layers 402 to fabric 404. In FIG. 20, a single fabric layer 404 may be covered on only one side by a single polymer film layer 402, or the fabric layer 404 may be sandwiched between polymer film layers 402, one or two on each side of the fabric (the latter is illustrated). More complex partially coated constructs of coated fabric 400 are also possible. (See FIGS. 21-23C, 34-45B.) Two fabric layers 404 may sandwich a single or multiple polymer film layers 402 and an outer surface of at least one of the two fabric layers 404 may be covered with another polymer film layer 402. It should be noted that the use of the terms "polymer film" and "polymer film layer" herein is not intended to be limited to the application of one or more discrete preformed polymer films to the fabric, but also includes one or more layers of polymer formed directly on the fabric, such as by dip coating, spray coating, 3-D printing and the like.

In some embodiments, up to 20 layers of polymer film may be applied to one or to each side of the fabric layer. In other embodiments, 1 to 10 layers of polymer film may be applied to one or to both sides of the fabric layer. In still other embodiments, 1 to 5 layers of polymer film may be applied to one or to both sides of the fabric layer. Thus, each side of the fabric layer can be covered, completely or partially, by 1, 2, 3, 4, 5, 6, 7, 8, 9, 10, 11, 12, 13, 14, 15, 16, 17, 18, 19, or 20 polymer film layers.

When more than one coating layer is used, the various layers need not each have the same thickness or, as noted previously, the same composition or orientation. While even thicker coatings are possible, generally speaking, the thickness of the coating on each side, whether comprised of 1 layer or 20, may range from about 0.5 µm to about 100 µm, in another embodiment from about 0.5 µm to about 50 µm, and in some further embodiments from about 10 µm to about 40 µm. In one other embodiment, the thickness of the coating on each side may range from about 15 µm to about 30 µm. Very thin polymer layers, i.e., from about 0.50 µm to about 2 µm, may be applied simply to fill the open pores in the fabric or for other reasons.

A resultant coated fabric in accordance with the disclosure often will be thicker than an uncoated fabric. The overall thickness of a coated fabric could be as high as about 500 µm, or even higher (about 1,000 µm), depending on the fabric being used, the type and number of coatings, and the intended use of the fabric. If the coating is being applied just at or adjacent the attachment edge of a leaflet such that it can be sewn through when attaching the leaflet to a cuff and/or stent, it can be relatively thicker as it will not impact the flexibility of the balance of the leaflet. The thickness of the leaflet could also vary along a gradient, such as from the attachment edge to the free edge of the leaflet. In general, the coated fabric will have a maximum thickness in some embodiments of no more than about 500 µm, in other embodiments of no more than about 250 µm, and in still other embodiments of no more than about 200 µm.

It will be appreciated that the thicknesses of the polymer film layers, woven fabrics, coated woven fabric, mesh and coated mesh are dictated by a balancing of properties and functionality. The number of layers of polymer film applied to the fabric or mesh can have an impact on the size to which a collapsible medical device, such as a collapsible prosthetic heart valve, can be collapsed. For non-collapsible devices, such as prosthetic heart valves that are only expandable and surgical heart valves, collapsibility is not a factor dictating thickness. In such instances, other properties may dictate composition, number of layers and thickness, such as, without limitation, rigidity, porosity, stability and flexibility. Of course, there are many other factors involved as well including, without limitation, the size and geometry of the stent or other medical devices to which the coated fabric may be applied or attached.

Figure 67A:
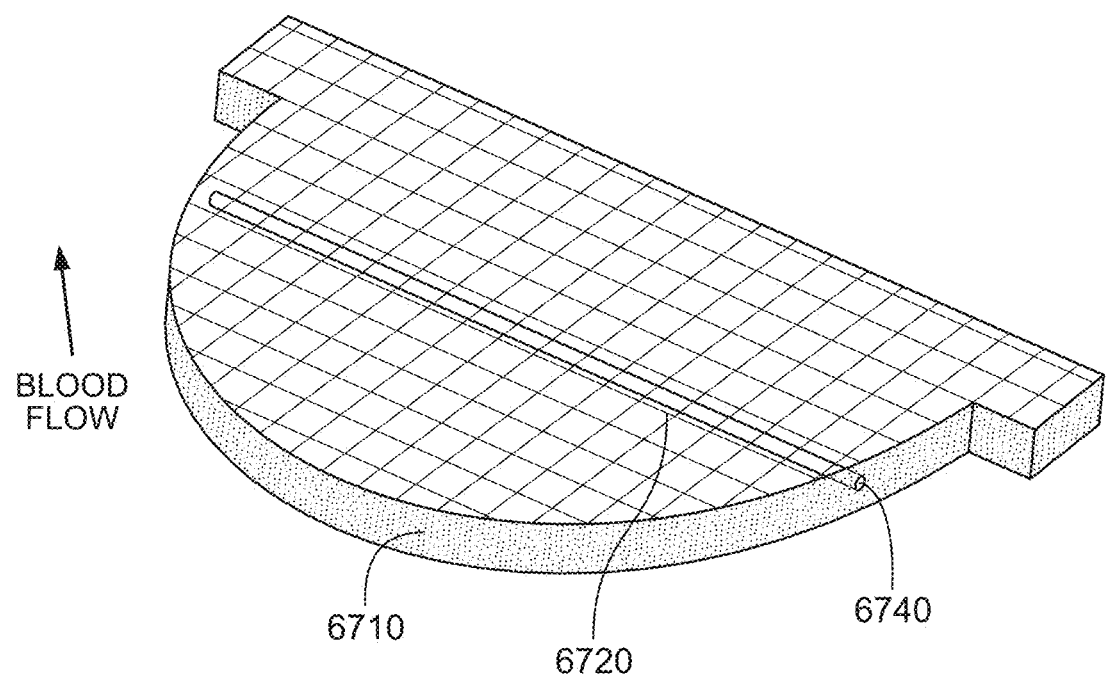
FIG. 67A is a schematic perspective view of a leaflet formed from a stabilized or non-stabilized woven fabric according to the present disclosure including a single wire extending across a major surface of the leaflet and adhered thereto generally along a line which parallels the leaflet's free edge.
Figure 67B:
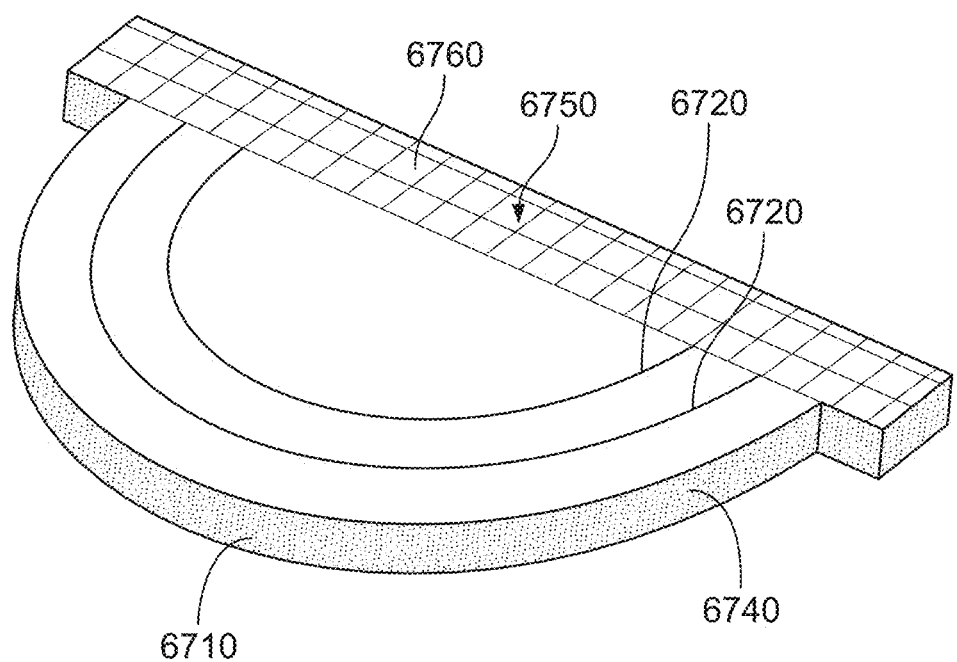
FIG. 67B is a schematic perspective view of a leaflet formed from a stabilized or non-stabilized woven fabric according to the present disclosure including a plurality of concentric semicircular wires roughly paralleling the attachment edge.

Leaflets, cuffs, or other structures of medical devices may be reinforced, weighted, or have their flexibilities altered, or their three-dimensional shape established or preserved by the addition of other features, with or without coatings. That is to say that in addition to coatings or partial coatings or layers, structures such as sutures, wires, denser weaves and the like may also be used for these purposes One such structure that could be used is a suture. A suture could be attached in any number of ways and any number of locations to a woven fabric or mesh. Using a valve leaflet for example, a single stitch could be placed in the middle of a major surface of the leaflet, or in a specific location on the free edge. A series or pattern of a plurality of individual stitches could be used as well. These could provide reinforcement, could alter the flexibility, or provide weight in order to, for example, bias the leaflet into a proper closed position. One or more sutures could be used to form a one or a plurality of suture lines across an entire major surface or a portion of the major surface of a leaflet, including for example along the attachment edge or along the free edge of the leaflet for any of the reasons just described. For example, a row of sutures could be added, of varying number of stiches, in a line or specified shape, across the full length of the leaflet in a single row from the attachment edge to the free edge of a leaflet. A suture line or suture lines could be spaced from but roughly parallel the free edge as well such as shown in FIG. 67A or could be spaced apart from but run roughly parallel to the attachment edge as shown in FIG. 67B This row or suture line could be a continuous or discontinuous row. Where more than one suture line is used, one could be continuous and another discontinuous. The properties of the leaflet in this example can be altered based on the number and density of stiches, the number of sutures applied and the location and pattern in which it (they) are applied. Using several such lines of sutures between the attachment edge and the free edge of a leaflet can alter the stiffness of the leaflet and create flexible zones or "hinges." The use of these sutures could also help impart or preserve the shape in three dimensions of the leaflet or other structure. And the use of sutures and suture lines for these reinforcing, shaping and biasing purposes can be used as a way of stabilizing a woven fabric or in addition to sutures or other structures used to stabilize a fabric.

It should be understood that leaflets and cuffs are often sutured to each other and/or to a stent. Frequently, as few sutures as required are used for this attachment, and in some instances a single suture could be used to attach each of the leaflets. Using a suture in this fashion, the suture is stitched a plurality of times—sometimes 10's or even 100's of times—through the leaflet. Each of these is obviously a stitch. But, a "stitch" in the case of reinforcing, shaping and biasing purposes of a woven fabric leaflet or cuff or a mesh leaflet or cuff refers to a single stitch or knot of a suture material not used to attach, for example, a portion of the leaflet to a cuff, etc. A suture line in this instance is a suture stitched a plurality of times through a cuff or leaflet also not primarily intended to attach the cuff or leaflet to another structure. As used herein, a "continuous" suture line refers to a single suture line formed from a single continuous suture, or multiple sutures that are substantially continuous with one another (e.g. the first suture ends where the second suture beings). On the other hand, a "discontinuous" suture line refers to a suture line formed of two or more sutures, where the sutures are substantially discontinuous with one another (e.g. the second suture begins at a spaced location from where the first suture ends).

One or more sutures could also be stitched to at least a portion of the attachment edge and/or the free edge of a leaflet to provide reinforcement and/or weight and/or to introduce or preserve a shape. The use of sutures here could provide additional strength in an edge that could be sutured or otherwise attached to a cuff and/or stent and can help retard fraying or delamination at the edge. These suture lines could be formed of one or more sutures, can be continuous or discontinuous, and can either be extended in a narrow area or across the entire length of one of these edges.

Instead of or in addition to a coating and/or a suture, localized portions of denser weaves can be used for the purposes just described, using a leaflet as an example—at the attachment edge, the free edge, and/or across at least a portion of the face. As used herein, the phrase "denser weave," "increased weave density," or similar terms refer to a fabric having a weave with more fabric per unit area or per unit volume compared to other areas of the weave. In the example of a fabric leaflet having portions with increased weave density, those portions with the increased weave density may be formed by introducing more fabric in that area during formation of the fabric leaflet, or otherwise after the fabric leaflet is formed with a uniform weave density. For example, after forming a fabric leaflet with a substantially uniform weave density, additional fabric material or fibers may be woven into area where it is desired to increase weave density, or additional pre-woven material may be added onto the fabric leaflet, for example a swatch of fabric may be coupled to the fabric leaflet in areas where it is desired to increase weave density. Note also that an increase weave density can be provided, in a manner of speaking, to a mesh. Fibers can be woven in and out of the pores or openings of a mesh to provide reinforcement, shape or bias.

And in still another aspect of this embodiment, instead of, or in addition to coating, partial coatings, denser weaves, sutures or the like, other reinforcing structures such as wires, including without limitation, steel or nitinol wires, could be used. These structures could be inserted into the weave along the attachment edge, the free edge or across some portion of a major surface of a leaflet, again used only for an example. They could also be applied by gluing, laminating, etc. to a coated or uncoated fabric of the invention. For example, a wire could be disposed between a fabric material and a coating or layer laminated thereto at the free edge of a leaflet. The wire or other reinforcement may extend across the entire edge, just a portion of it, may be continuous or discontinuous. A "continuous" or "discontinuous" wire has a similar definition as the continuous or discontinuous suture line described above, except the reference material is a wire instead of a suture. A suture could be used instead of a wire, or other fiber which is attached by being glued or laminated between the fabric and a layer or partial layer instead of being stitched. A wire could be used as part of the mesh or woven into it.

In addition to, or instead of, reinforcing, shaping and biasing, many of these same structures, and others, can be used to produce a stabilized woven fabric. Specifically, fasteners, such as sutures, welding, adhesives and increases in weave density, as well as other innovations, can also be used to help maintain the geometry and/or relative spacing of the individual fibers in a weave thereby providing additional stability to the woven fabric and retard or control the propensity of it to change conformation after implantation which can impact the intended functions of the medical device. In the case of a collapsible and/or expandable heart valve, or a surgical valve, leaflet retraction proximate free edges of the leaflet could interfere with the completeness of coaptation. The creation and use of stabilized fabrics to reduce this possibility is one aspect of the invention. A mesh could also be used to provide a stabilized fabric where the number, shape and location of the pores/divots and interconnecting struts are resistant to a change in conformation.

Figure 68:
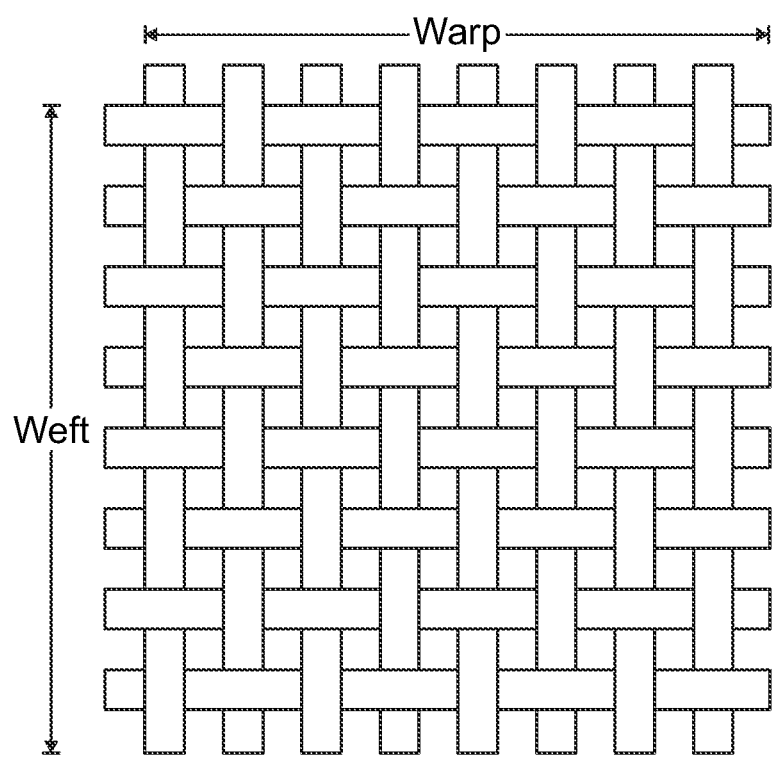
FIG. 68 is an enlarged view of a woven fabric made from polymer fibers showing the warp and weft of the fabric.
Figure 69A:
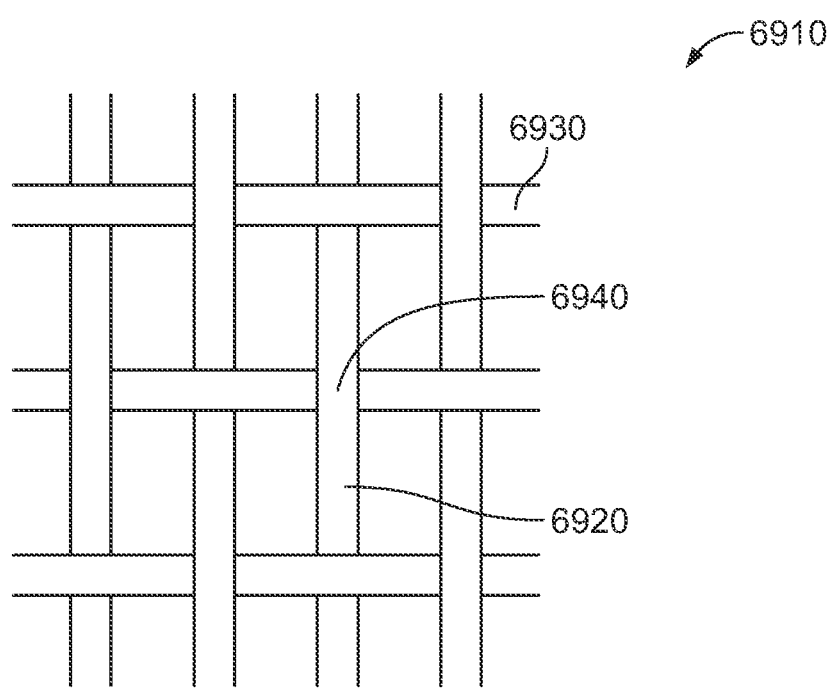
FIG. 69A is an illustration of a woven fabric including the intersections and the gaps between the fibers, for a woven polymer fabric prior to implantation.

FIGS. 5-12 and 16 illustrate relatively simple weaves and FIGS. 17-19 show much more complex weaving patterns. But common to most all woven fabrics is the occurrence of warp and weft fibers. These are illustrated in FIG. 68—the warp fibers tend to be oriented in the length or longitudinal dimension and the weft fibers oriented in the width or transverse direction. For the purposes of this disclosure, the terms warp and weft are just labels used to identify the fibers which are, in this figure, oriented and interwoven perpendicularly to each other. FIG. 69A shows the relative orientation and spacing of a fibers which can be made from, for example, bundles of UHMWPE filaments with the resulting fibers being formed into a fabric. In FIG. 69A, the warp 6930 and weft 6920 fibers cross each other at roughly right angles to form intersections 6940 intersections. The crisscrossing fibers also define a plurality of roughly quadrilateral (square in this instance) gaps or holes of similar size.

Figure 69B:
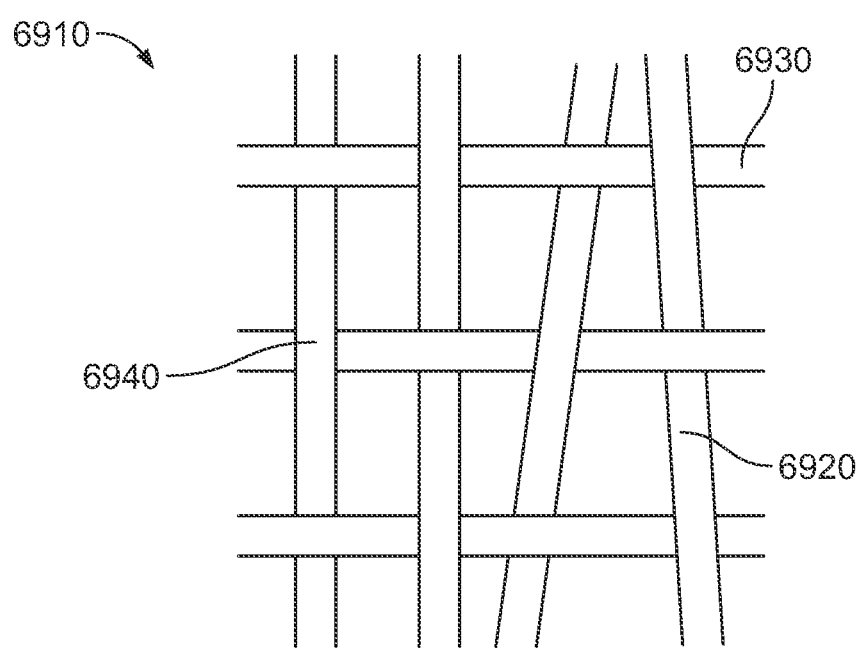
FIG. 69B illustrates possible changes in the conformation of fibers and gaps of the fabric illustrated in FIG. 69A in a woven fabric such as could happen following implantation.

The same fabric, however, may have a very different conformation after implantation as represented by the fabric shown in FIG. 69B. The relative angles at which the warp 6930 and weft 6920 fibers cross might no longer be perpendicular forming right angles and the gaps may no longer form even squares or rectangles as depicted in FIG. 69A. And in some instances, the constituent fibers and/or intersections 6940 could be closer to adjacent fibers or intersections and in other instances they could be farther away from adjacent fibers and intersections. It will be understood that in more complex woven fabrics, warp and weft fibers may not be at right angles, and there could be other fibers in other directions forming part of the weave. But even in those cases, the fabric initially contains a particular conformation, a pattern of woven fibers at intended angles and spacing. Innovations described in this disclosure seek to maintain those initial positions thereby creating a stabilized fabric. And this result may be accomplished no matter what polymer or blend of natural and synthetic fibers, or different types of synthetic fibers, are used. The resulting stabilized fabric may be used in medical devices where a change in conformation such as a relative movement of the fibers can negatively impact performance, such as the retraction of the free edge of prosthetic valve leaflets. This is, as in all such cases a change in conformation relative to the same fabric implanted under like conditions without being stabilized.

Figure 60:
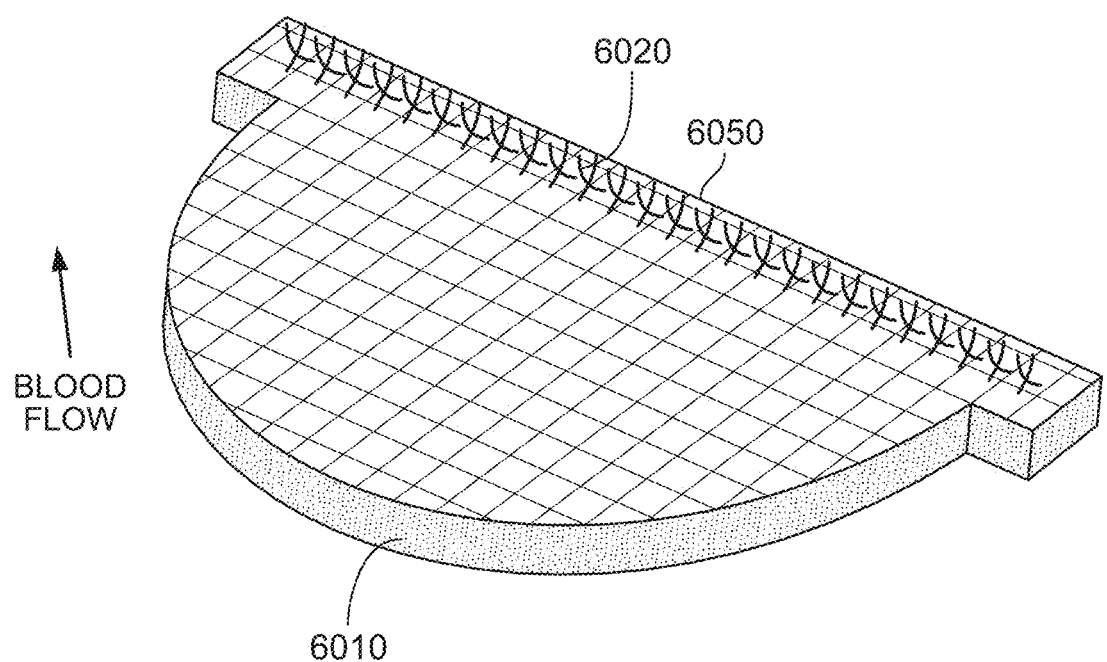
FIG. 60 is a schematic perspective view of a leaflet formed from a stabilized or non-stabilized woven fabric according to the present disclosure including an area of increased weave density extending along and adjacent the free edge of a leaflet.
Figure 61:
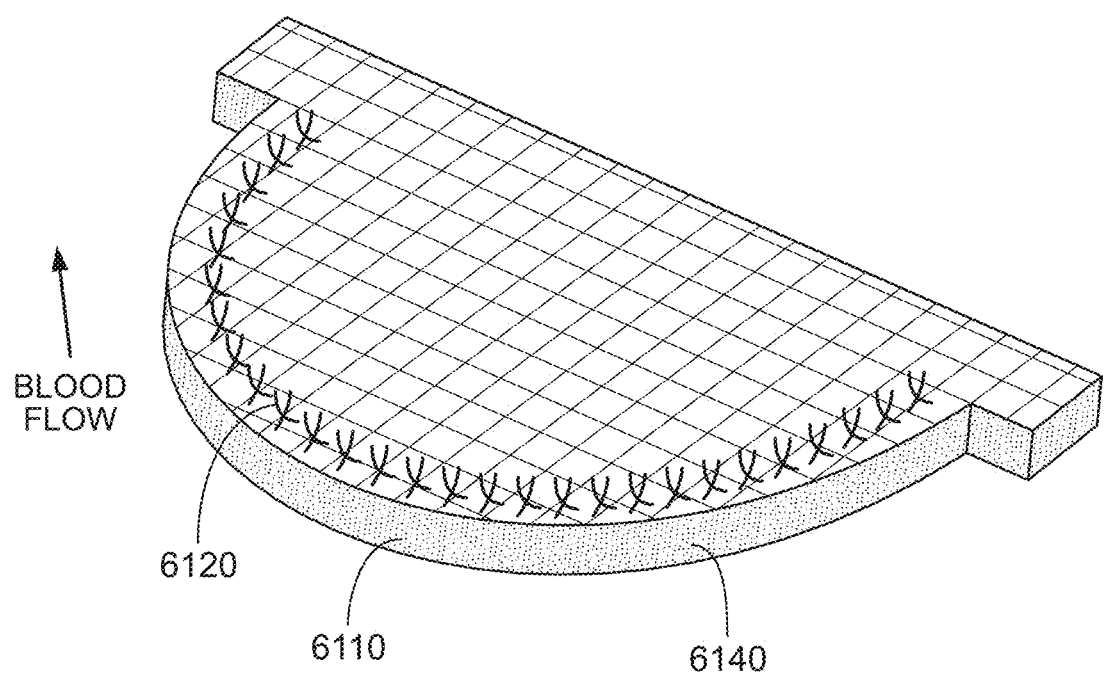
FIG. 61 is a schematic perspective view of a leaflet formed from a stabilized or non-stabilized woven fabric according to the present disclosure including an area of increased weave density extending along the attachment edge of a leaflet.

As noted, one way to accomplish this fabric stabilization is by using a localized denser weave. Relative to the rest of the woven fabric, a higher weave density has more intersections and the fibers in the zone with the high weave density are closer together. Proximity, lack of freedom of movement, and the increased collective friction at the increased number of intersections makes it relatively more difficult to distort the fabric in this region. FIGS. 60 and 61 are schematic perspective views of a leaflet formed from a fabric according to the present disclosure including an area of increased weave density extending along and adjacent the free edge or attachment edge of a leaflet. FIG. 60 shows a leaflet 6010 formed from a fabric according to the present disclosure including an area of increased weave density 6020 extending along and adjacent the free edge 6050 of the leaflet. The area of increased weave density 6020 has higher weave density compared to the remaining portions of the fabric leaflet 6010.

FIG. 61 shows a leaflet 6110 formed from a fabric according to the present disclosure including a localized area of increased weave density 6120 extending along the attachment edge 6140 of a leaflet. The area of increased weave density 6120 has higher weave density compared to the remaining portions of the fabric leaflet 6110. This can provide many of the same functions and advantages as just described for suture lines. In general, weave density and its impact on maintaining the spacing and relative positions and orientations of the fibers, and the desire to retard a change in conformation, must be balanced against the possible increase in stiffness, reduction in flexibility, forces required to load it into a delivery capsule (transcatheter valves), and added weight of that portion of the fabric. But the proper balance can be found. Indeed, the extra weight added adjacent the free edge 6050 can also help maintain the three-dimensional shape of the free edge and can help weight and bias it toward a closed position. This coupled with the propensity of this high-density region to maintain the relative positions of the constituent fibers may reduce changes in conformation when in use—e.g. maintains more closely the original conformation of the fabric relative to a similar piece of fabric implanted which was not stabilized/. It should be understood that when using localized areas of increased weave density in a fabric, it may be preferably to strategically choose where those areas are located to balance many of the factors described above. However, it is still within the scope of this disclosure to have use a high weave density throughout the entire fabric to achieve the desired mitigation of conformation changes. In a related manner, a stabilized fabric can be accomplished by using a particularly densely woven fabric—a fabric with an areal density of about 1.0 ounces/yd$^2$ or more and in particular, more than 1.3 ounces/yd$^2$. Other ways of using the properties of the fibers and how they are woven ("weaving") to provide increased relative stabilization include, without limitation: using fibers with variable or undulating thicknesses, using a variety of thread of more uniform thicknesses, but generally greater thickness than would normally be used, weave pattern, and the like, as described elsewhere.

Filaments when used to produce the stabilized woven fabrics of the invention, those that include fastened intersections, those that are altered but have unaltered intersections, and those based on weaving to provide increased stabilization, generally will have a diameter of about 0.5 to about 20 microns, and in certain embodiments, from about 5 to 15 microns. This assumes that the fibers have a generally circular cross section which may or may not be the case. If other shapes/cross sections are used, an analogous size is contemplated. Another measure that is useful in connection with filaments and fibers is dTex which is short for decitex and is a measure of the mass in grams for every 1,000 meters of fiber. This measurement is often counted in tenths. The filaments may also have a dTex of 0.1 to about 5 and often between about 0.5 to about 2 dTex. In terms of a solid single fiber or a bundle of filaments twisted or otherwise formed into a fiber the dTex could be from about 1 to about 100 dTex and often from about 5 to about 20 dTex.

Synthetic fibers used in any of the stabilized fabrics of the invention may be made from a single filament as just described, a single extruded fiber, or, more commonly, 1 to about 100 filaments and more often about 1 to about 20 filaments bundled, twisted, adhered together and the like. In another embodiment, the number of filaments in a fiber is from about 1 to about 15 filaments. When the fiber has a circular cross section or the bundle has a generally circular cross section, the diameter could range from about 10 to about 150 microns, in another embodiment, from about 10 to 100 microns and in still another embodiment, from about 10 and about 50 microns. However, fibers need not have a substantially circular cross section. It could be more oblong in shape which could be rectangular, ovoid, or more irregular with a thickness that is less than its width. In these situations, the fiber intersections generally comprise a portion of the elongated surfaces of the adjacent fibers being in intimate contact. The width is always the largest dimension and the measurement. Thus it is possible that the thickness of the fabric could be less than the width of a single fiber used to produce it. The fiber thickness can range from about 10 to about 150 microns and in another embodiment from about 25 to about 100 microns while the fiber width could range from about 50 to about 300 microns and in another embodiment, from about 100 to about 200 microns. For further clarity, a weave could be made from warp and weft fibers having a thickness of about 37 microns and a width of about 100 microns. The resulting fabric would have inter-sections having a thickness (and thus the thickness of the fabric) of about 75 microns. Fabric overall thickness, whether coated, partially coated or uncoated, could be as much as 500 microns and as little as about 10 microns. In another embodiment, the overall fabric thickness is from about 10 to about 150 microns and in still another embodiment of about 10 to about 100 microns.

Figure 82A:
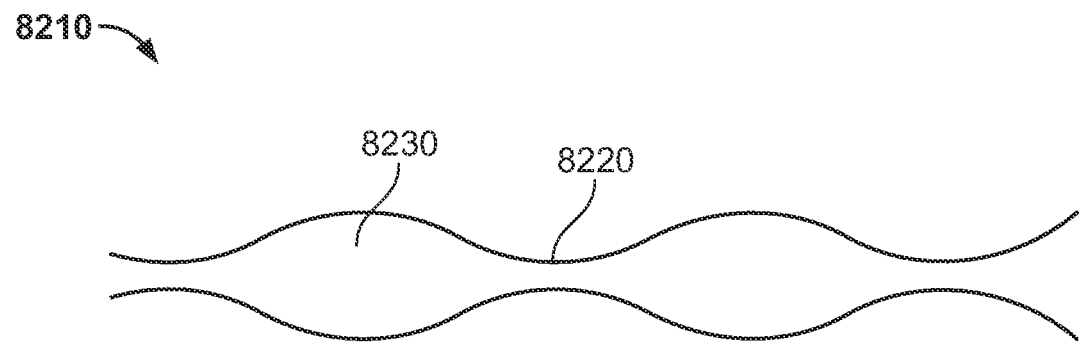
FIG. 82A illustrates a fiber with an undulating diameter.
Figure 82B:
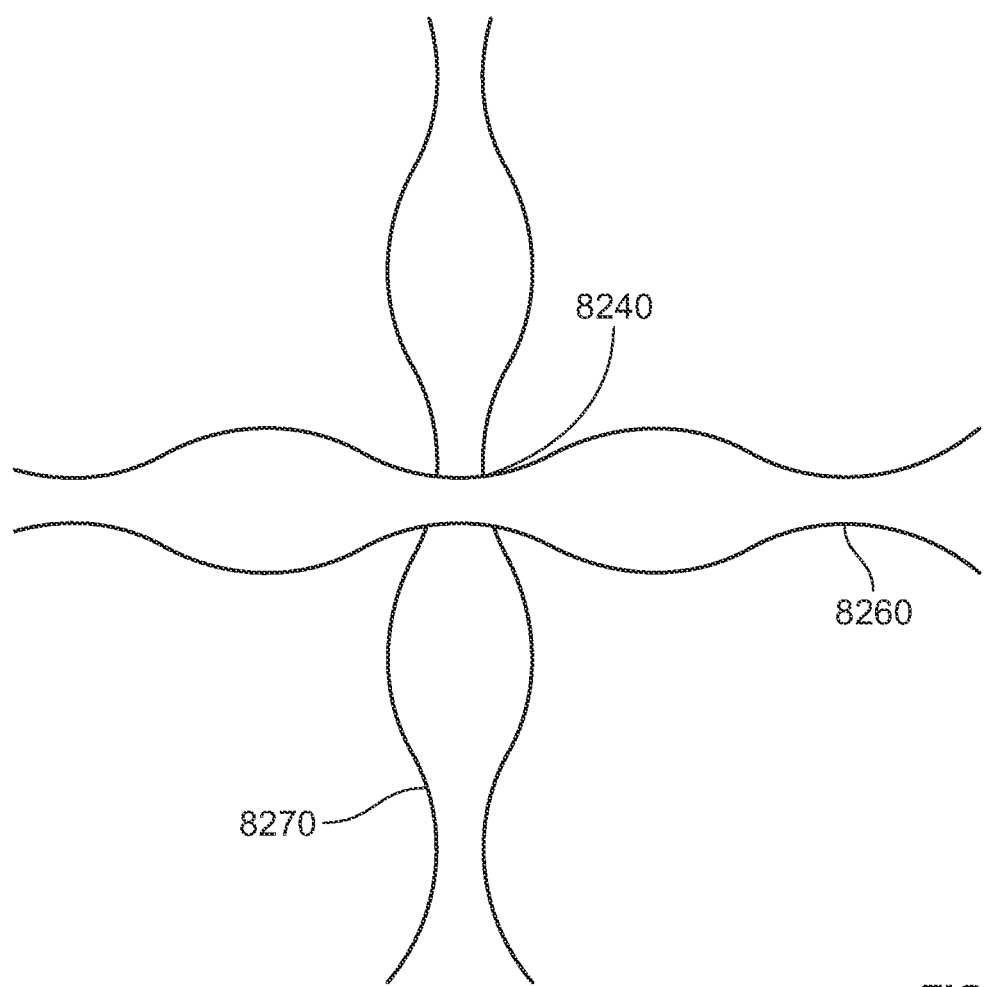
FIG. 82B illustrates the nesting of undulating fibers at an intersection of warp and weft fibers such as shown in FIG. 82B.

In one noted embodiment, the fibers or filaments can be extruded or assembled such that their diameter (diameters where the fiber is made of multiple filaments) may be varied during the extrusion process to provide this undulating profile of thicker and thinner regions. Specifically, in terms of individual filaments, their relative diameter could vary along the length of each filament from about 0.5 to about 20 microns, and in certain embodiments, from about 5 to 15 microns. In terms of a solid single fiber or fiber bundle, the diameter could be up to about 150 microns and if not substantially circular in cross section, a thickness of about 10 to about 150 microns and a width of about 50 to about 200 microns. FIG. 82A illustrates a non-limiting example of a highly enlarged view of a fiber with an undulating profile 8210 having regions of relatively smaller diameter 8220 and relatively thicker diameter 8230. FIG. 82B illustrates how undulating warp 8260 and weft 8270 fibers can nest in a complementary fashion at an intersection 8240 so as to decrease relative movement and increase stability. Where multiple filaments with undulating diameters are used to form a fiber, the result could be an irregular surface which could provide variable diameters and surface irregularities to the resulting fibers. Fibers with these undulations and/or irregularities, when woven into the fabric, increase the friction between fibers and can allow them to "nest" at various intersections making their relative movement more difficult. In another aspect of using weaving to increase stability, the fibers could be woven from relatively thicker fibers such as fibers with a thickness of greater than about 25 microns and width of greater than about 50 microns.

Figure 81:
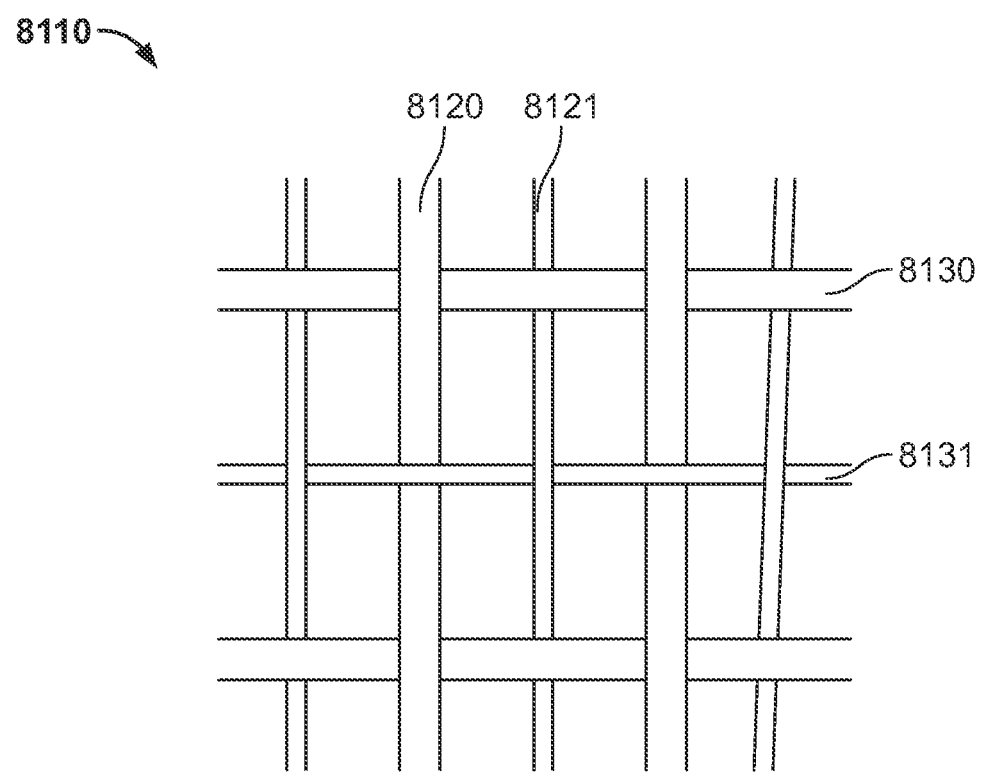
FIG. 81 is a view of a woven fabric made with warp and weft fibers of different thickness.

Alternatively, and as shown in FIG. 81, every other warp and weft fiber could be alternated in width with one being relatively wider warp fibers 8130 and relatively less wide warp fibers 8131 and relatively wider weft fibers 8120 and relatively less wide weft fibers 8121. At least one of the fibers therefore has a width of at least about 100 microns and/or a thickness of at least about 25 microns. Relatively thicker fibers could be used also. Undulating or variable thickness or width fibers could also be used. In another variant, all the warp fibers having a relatively uniform thickness and width are used and every other weft fiber has an undulating surface.

Figure 70:
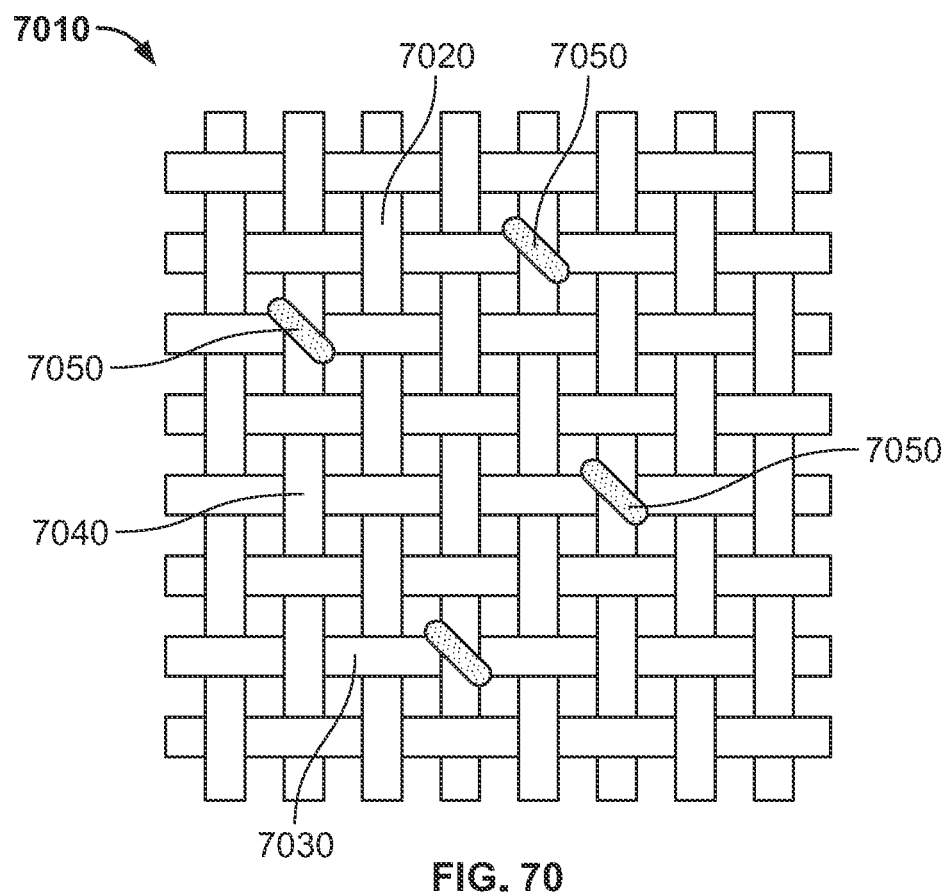
FIG. 70 illustrates the intersections of a stabilized woven synthetic fabric including fasteners across selected intersections.
Figure 71A:
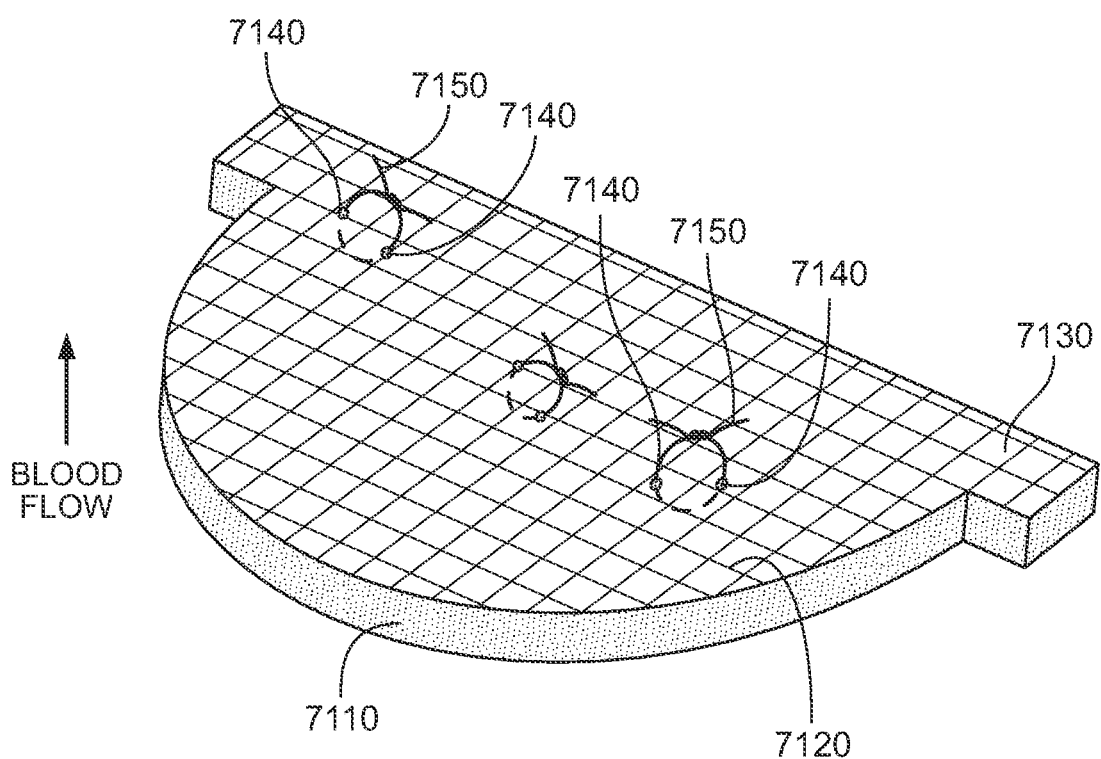
FIG. 71A is a schematic perspective view of a leaflet formed from a stabilized woven fabric according to the present disclosure including a plurality sutures fastening individual fiber intersections.
Figure 71B:
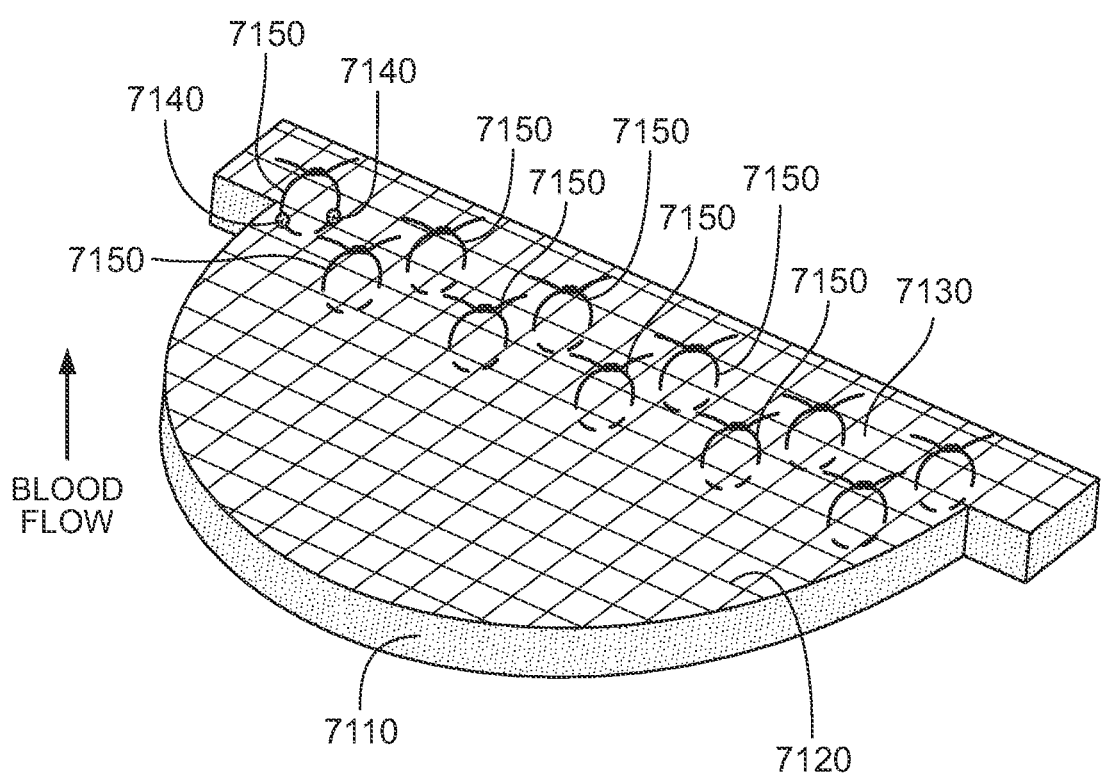
FIG. 71B is a schematic perspective view of a leaflet formed from a stabilized woven fabric according to the present disclosure including a plurality sutures fastening groups of fiber intersections.

Another way to stabilize a woven fabric is "mechanically" to use one or more fasteners such as sutures and staples. On a micro level, individual intersections of fibers, where they crisscross at, for example, right angles (90 degrees), could be sutured together, fastened, or otherwise tied off to make their relative movement more difficult. This is illustrated in FIG. 70 where woven fabric 7010 is composed of warp fibers 7020 and weft fibers 7030. Weft fibers 7030 cross over or under the warp fibers 7020, forming junctions or intersections 7040. Not all such intersections can actually be illustrated and thus only a few of the fibers and intersections are illustrated with the understanding that there could be hundreds of fibers and thousands of intersections per square inch of the fabric. A suture or other fastener 7050 can be applied and tied tightly around some or all of the intersections to reduces or prevent the relative movement of the warp and weft fibers at that intersection. It is also possible to suture or fasten a small region of multiple intersections to form a localized "gather" or "bundle" of intersections. This is illustrated in FIG. 71 where a leaflet 7110 composed of warp 7020 and weft 7030 fibers and comprising fasteners 7150 that ensnare more than a single intersection 7140 which are disposed in a staggered pattern. The action of gathering these intersections can help lock in place the remaining structure of the weave in the areas that surround that gather. The staggering of the gathers formed by multiple staggered fasteners 7150 ensures that at least most of the warp and weft fibers in the area are stabilized at one point or another. Any suitable fastener will do including without limitation, sutures, staples, clips, and hooks/loops.

Figure 72:
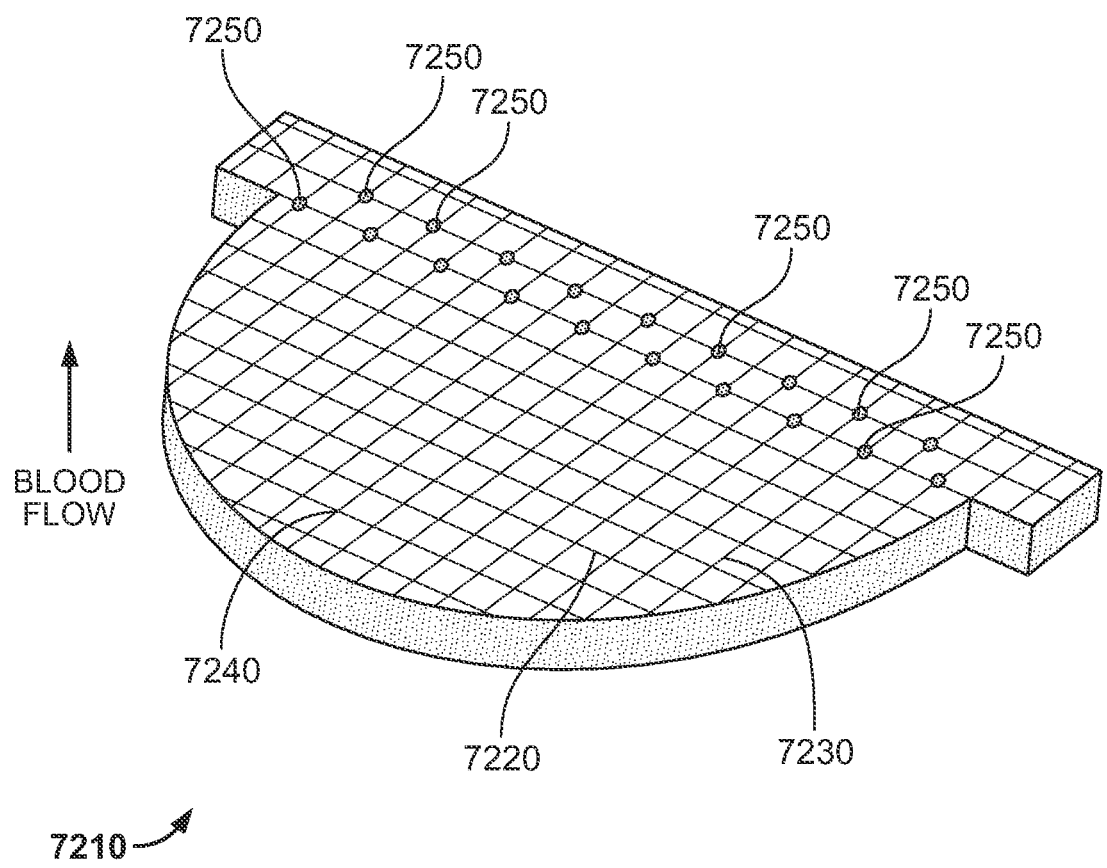
FIG. 72 is a schematic perspective view of a leaflet formed from a stabilized woven fabric according to the present disclosure including a plurality adhesive spots fastening individual fiber intersections.

As illustrated in FIG. 72, a chemical fastener, such as an adhesive could be used to "glue" in place some or all of the intersections so as to maintain and stabilize the intended weave structure. These techniques are forms of "chemically" stabilizing a woven fabric. Leaflet 7210 is made of a woven fabric with multiple intersections 7240 of warp 7220 and weft 7230 fibers where they again crisscross at, for example, right angles (90 degrees). At some, or all of those intersections 7240, a small amount of glue or adhesive 7250 can be applied. The adhesive 7250 can be applied between the two crossing fibers or around their intersection. Alternatively, the fibers could be coated with an adhesive which is activated so that where fibers cross adhesion occurs after a period of time or after activation with heat, light and/or a chemical activator. Adhesives which can be used should be biocompatible and have both sufficient holding force and sufficient flexibility to allow the structure of the fiber to be maintained in substantially its pre-implantation structure. Some useful adhesives include, without limitation: Biological (fibrin, collagen, genipin), silicon and silicon containing polymers, and the like. Polymers can also be used as adhesives. A thermoset resin, or a thermoplastic resin could be melted such that it flows around an intersection or between fibers and where they crisscross and then allowed to harden. A polymer could be applied in a solvent and the solvent driven off. Or a material which can spontaneously cross-link or be induced into cross-linking may be used.

Instead of an art recognized glue or adhesive, one could also use melted synthetic materials (such as UHMWPE, polyester, etc.) applied between polymers or around an intersection, or poured into a gap as noted earlier, and allowed to cool and harden. A polymer dissolved in a solvent system could also be applied in analogous fashion followed by the removal of the solvent. Polymers could also be used and allowed to, or activated to, cross-link.

Figure 73:
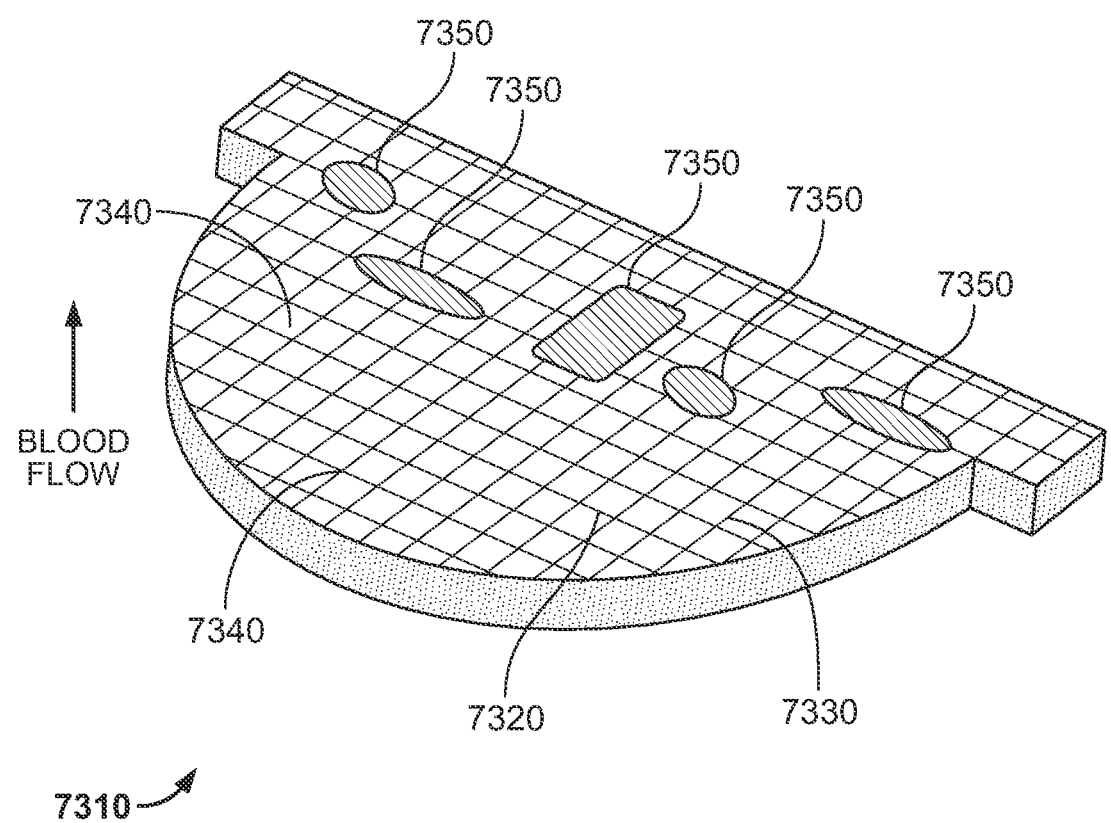
FIG. 73 is a schematic perspective view of a leaflet formed from a stabilized woven fabric according to the present disclosure including a plurality adhesive spots fastening groups of fiber intersections.

As illustrated in FIG. 72, the resulting chemically stabilized intersections 7240 can be arranged in a line, a staggered pattern or some other pattern and some or all of the intersections can be stabilized in this fashion. Instead of gluing individual fiber intersections, groups of such intersections could be glued in common "spots," or "gathers." In FIG. 73, woven fabric leaflet 7310 includes a number of intersections 7340 adhered to each other with a larger common spots of adhesive 7350. A number of such spots could be created in a regular or staggered pattern and the size and shape of the spots can vary.

Figure 83:
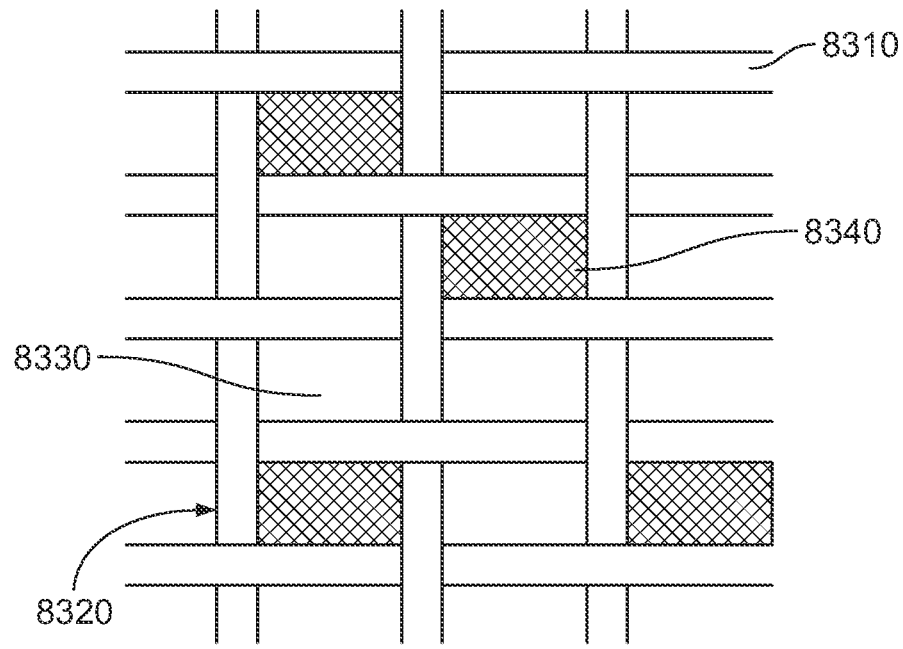
FIG. 83 illustrates a woven fabric with an adhesive or other fastener located in the gaps between adjacent fiber of a stabilized woven fabric.
Figure 84:
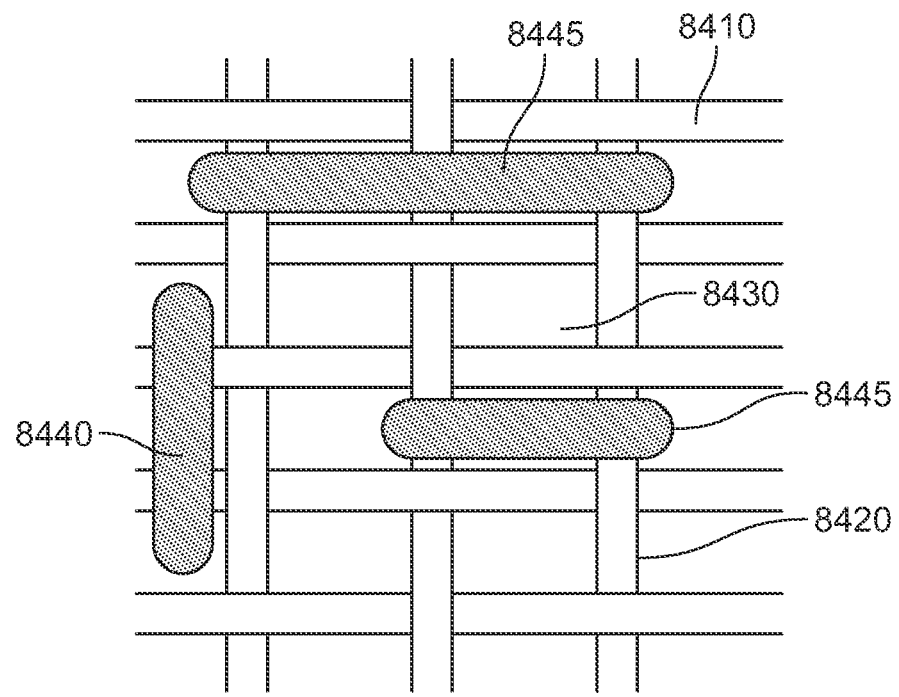
FIG. 84 illustrates a woven fabric with mechanical fasteners located in the gaps between adjacent fiber of a stabilized woven fabric.

Fasteners and adhesives could be used to plug the holes or gaps exiting in woven fabric or by making localized bundles of fibers rather than intersections. As shown in FIG. 83, a woven fabric could include warp fibers 8310 and weft fibers 8320 which together define holes or gaps 8330. Instead of, for example, gluing the intersections of these fibers, an adhesive can be applied into the gap where it fills or at least partially fills the gap and is solidified therein. It therefore glues the warp and weft fibers which define the gap in place and therefore helps provide a stabilized conformation. These glued and therefore filled-in gaps also provide a physical barrier or spacer reducing the movement of adjacent fibers. In FIG. 84, the woven fabric is comprised of warp fibers 8410 and weft fibers 8420 that define gaps 8430. Fasteners 8440/8445 can be fed in and out of gaps, not across an intersection, but from one gap to another across a plurality of warp fibers (8410) or around a plurality of weft fibers (8445). As with the adhesives, the fasteners help fill the gaps but also help to gather warp and weft fibers preserving their conformation. Bundles or larger adhesive spots may involve both stabilized intersections and stabilized gaps.

Figure 74:
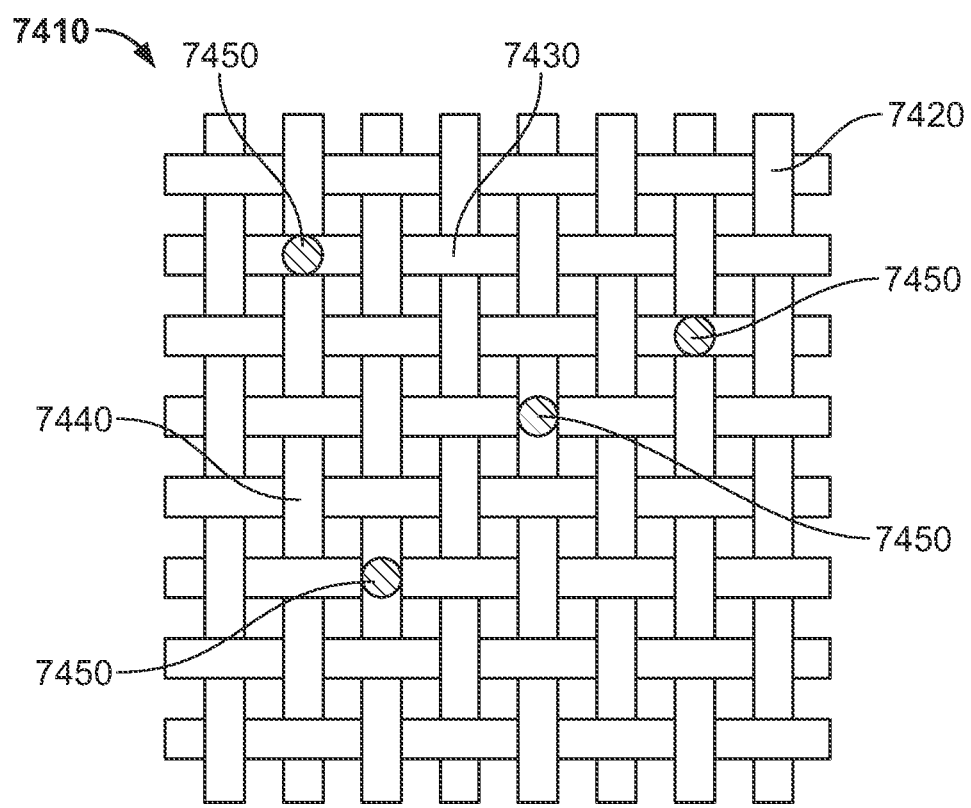
FIG. 74 illustrates a stabilized woven fabric in accordance with the disclosure wherein a number of individual fiber intersections have been welded using energy such as heat and/or pressure.

Finally, energy in the form of heat, pressure, laser, high intensity light, ultrasonics, vibration, gases, radiofrequency, friction, spin welding, electrical current and the like could be used to melt or "weld" fibers together at some or all of their intersections ("energetically" stabilizing). Any known way of doing this can be used. Some illustrative techniques, however, are discussed. FIG. 74 illustrates a fabric 7410 having warp and weft fibers 7420 and 7430 that crisscross at intersections 7440. Energy such as heat and/or pressure, or one of the other welding techniques described, can be applied to one or more of these intersections 7440 to "weld" or "spot weld" 7450 the fibers 7420, 7430 together. Spot welds 7450 could be formed by applying a laser to individual intersections 7440 or groups of such intersections or by applying heat/and or pressure to individual intersections 7440 or a group of intersections in close proximity through other means—a heated tip, heat lamp, opposed heated plates, iron, and the like. And these melted spots or welded spots 7450 can be placed in a regular or staggered pattern. Instead of applying coherent light, heat and/or pressure, sonic devices could be used to create spot welds as well.

Figure 75:
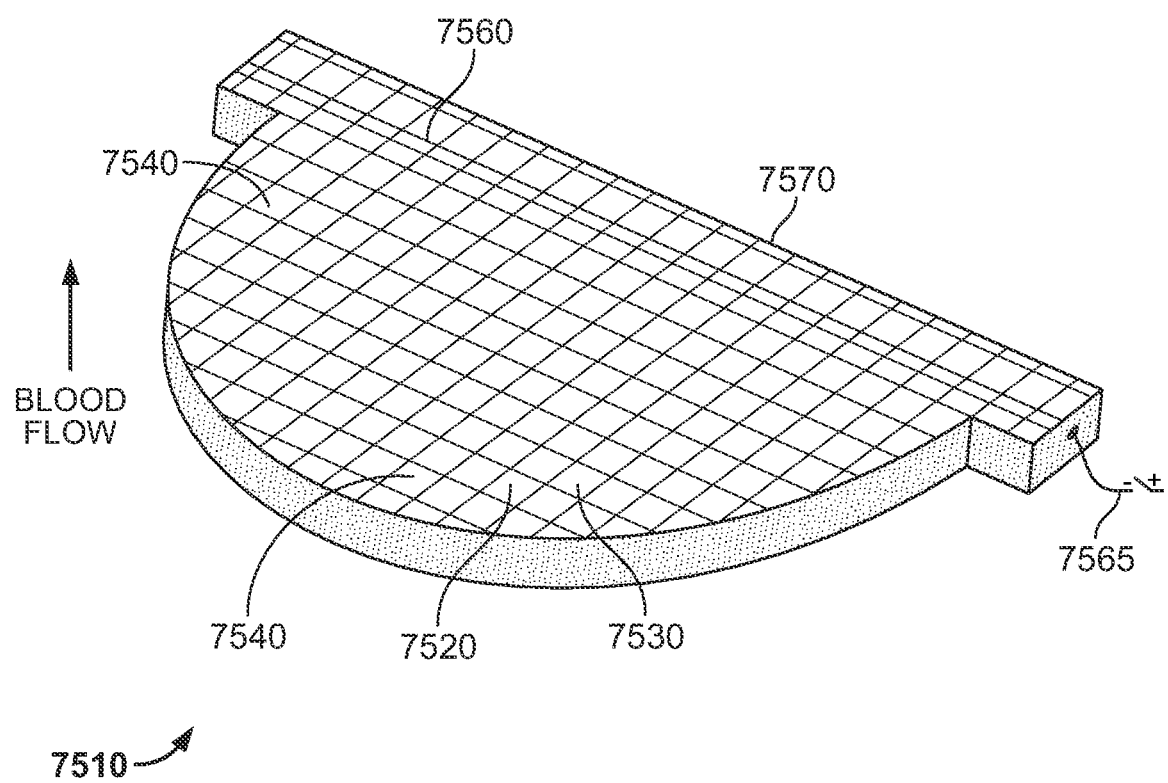
FIG. 75 is a schematic perspective view of a leaflet formed from a stabilized woven fabric according to the present disclosure including a conductive wire woven into the fabric that melted or welded some of the polymer fibers that intersect with it.

In an alternative, shown in FIG. 75, one of the weft fibers 7530 has been replaced with a conductive wire 7560 which is woven into the fabric. The wire could be made of anything that is biocompatible and conducts electricity. The wire can include an extension portion 7565 that extends out of the leaflet where it can be connected to an electrical source. The resistance of the wire will generate heat that can melt the fibers at intersections 7540 all along the length of the wire. The wire can be made of virtually any biocompatible and implantable metal such as Nitinol, titanium, stainless steel and the like. The connection portion 7565 of the wire extending out of the fabric can then be cut and the leaflet assembled to the valve. A wire can also provide reinforcement and weight as noted elsewhere. The wire can be completely uninsulated as shown. However, it is possible to use wires with portions of exposed metal and other portions coated in an insulating material. This is one advantageous way to weld discontinuous spots, just as an example. Using partially insulated wires may provide additional control to forming stabilizing regions and patterning.

Figure 76:
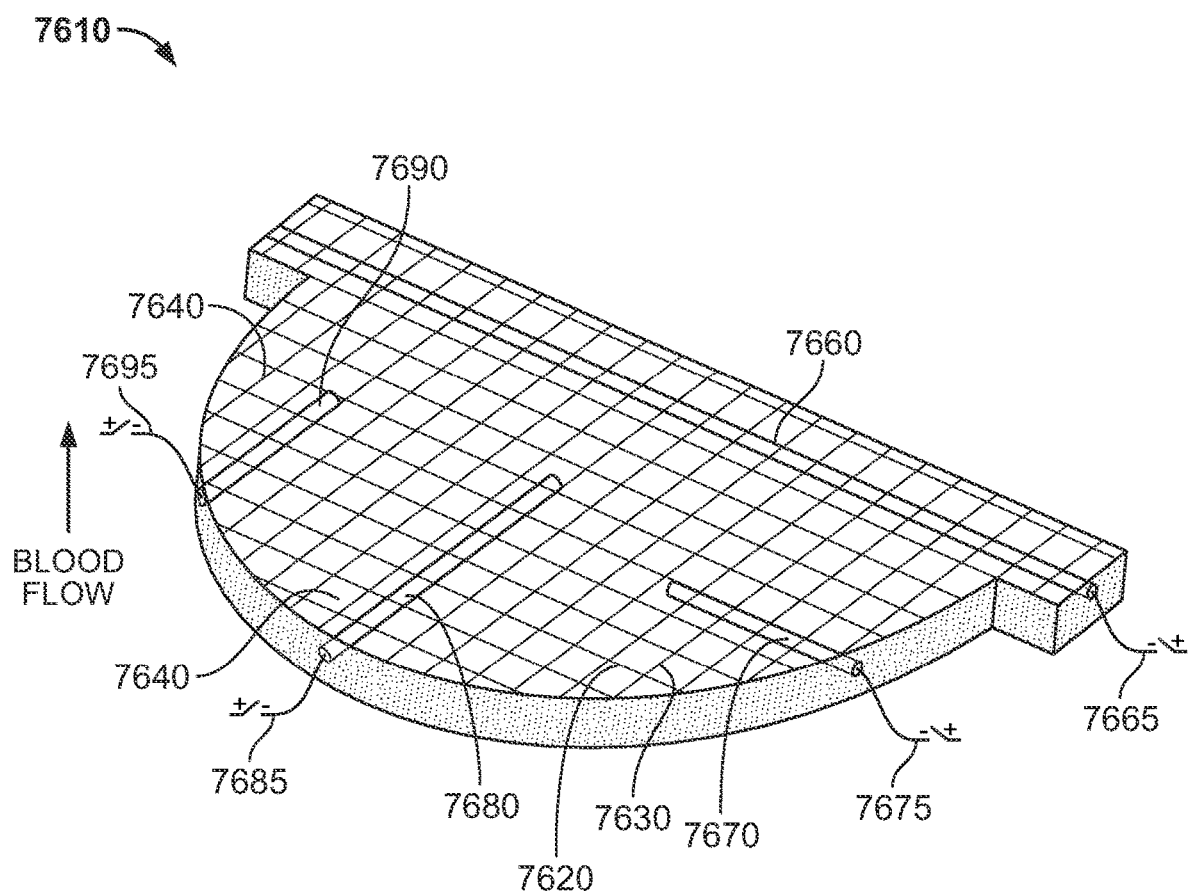
FIG. 76 is a schematic perspective view of a leaflet formed from a stabilized woven fabric according to the present disclosure including a plurality of conductive wires woven into the fabric that melted or welded some of the polymer fibers that intersect with the conductive wires.

FIG. 75 illustrates the use of a wire disposed near the free end 7570 of the leaflet 7510 to create a line of fused intersections. But a wire could also be placed along a surface along and paralleling a warp 7520 or weft 7530 fiber and melted into the fabric or could be woven into an already woven fabric so that it can heat one or more fiber intersections 7540. Wires could also be woven into the fabric in a plurality of locations and orientations so as to provide reinforcement and/or to allow for the localized melting of intersections at the free edge of the leaflet or elsewhere. This is illustrated in FIG. 76 where a plurality of wires 7660, 7670, 7680, 7690 are disposed within the woven fabric as warp 7620 and weft 7639 fibers. The ends 7665, 7675, 7685, 7695 of the wires 7660, 7670, 7680, 7690 can all be connected to an electrical source to provide heating and spot welding at intersections 7640 along their length and then removed. Alternatively, electricity can be applied only to some of these wires.

Figure 78:
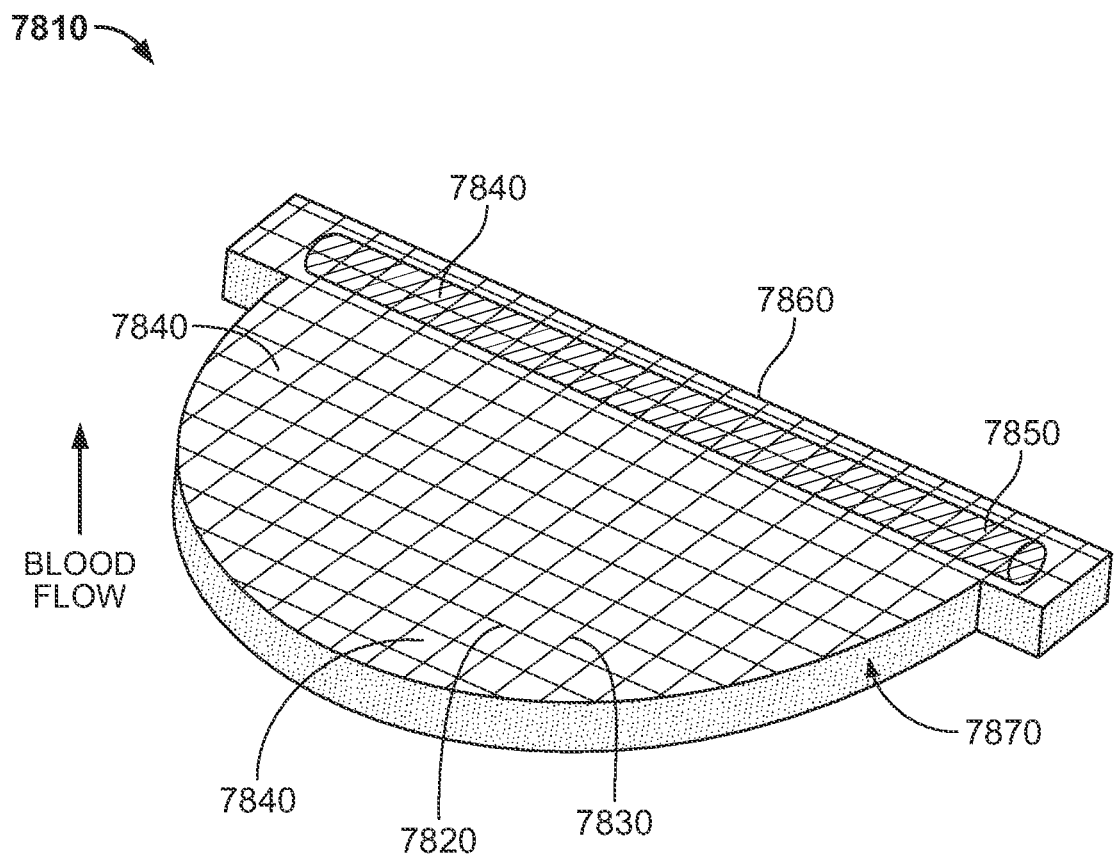
FIG. 78 is a schematic perspective view of a leaflet formed from a stabilized woven fabric according to the present disclosure including an area adjacent its free edge that was exposed to heat and/or pressure to form a melt or weld zone.

Instead of individual intersections or gathers or groups of intersections, heat, pressure, coherent light or sonic waves or other forms of energy can be applied to a localized area as well. As shown in FIG. 78, the free edge 7860 of leaflet 7810 can be exposed to a heated surface that is applied along and adjacent the entire free edge 7860 and for some distance inward therefrom toward the leaflet's attachment edge 7870 creating a melt zone or band 7850. This process applies heat and/or pressure to all or substantially all of the intersections 7840 of warp 7820 and weft 7830 fibers within that zone, but also the interlaced fibers. So care should be taken to apply sufficient energy to the intersections to cause melting while not adversely impacting the free portions of the fibers. Otherwise the material forming the fibers could flow and impact the size and geometry of the gaps to an extent which would adversely impact leaflet performance. In its simplest form, heat and pressure could be applied by a simple heating device such a handheld iron. A heated plate or pair of opposed plates could also be used, or any other heating/pressure device may be suitable.

Figure 77:
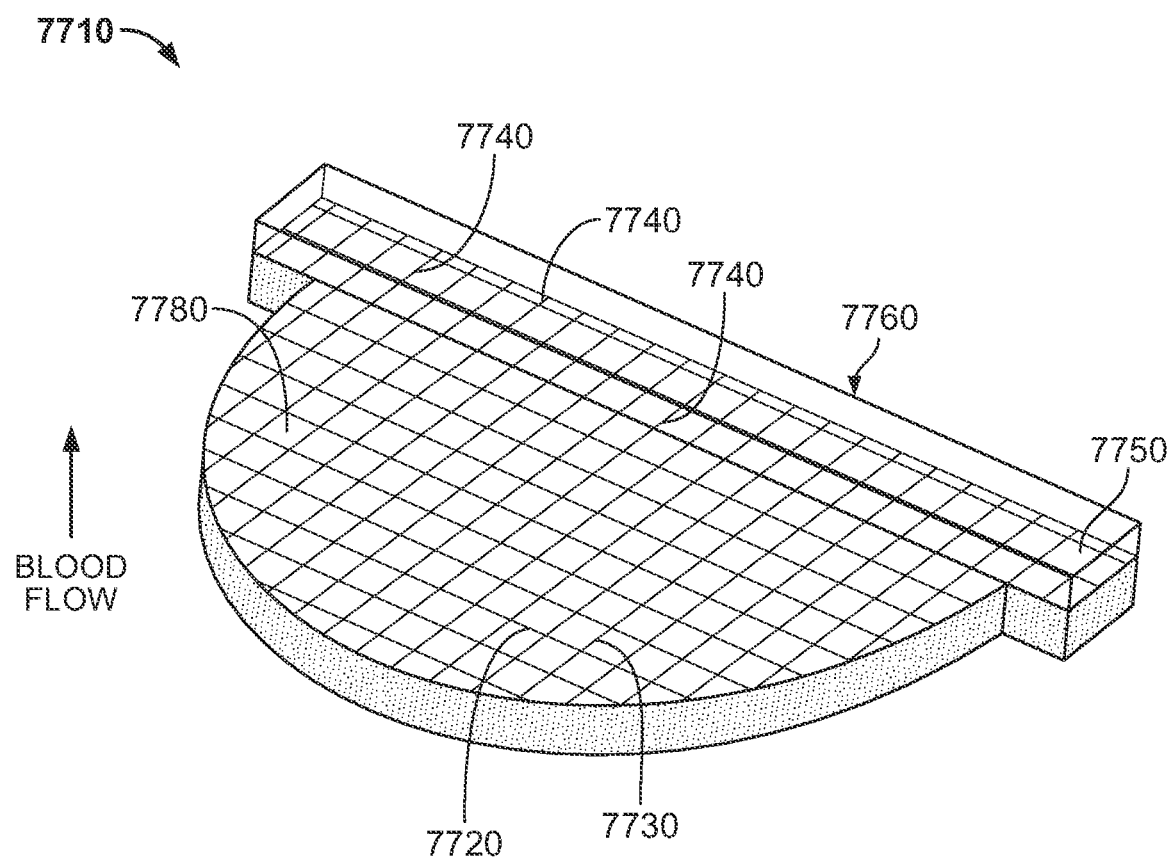
FIG. 77 is a schematic perspective view of a leaflet formed from a stabilized woven fabric according to the present disclosure including a partial coating adjacent the free edge stabilizing the intersections covered by the layer.

In another "bulk" stabilization method, the intersections in a localized area can be stabilized by the application of one or more layers or coating. This can be done at one or more places on the leaflet, but, in particular, one or more layers or coatings could applied to one or each of the major surfaces of the fabric leaflet at and/or adjacent the free edge and/or on the free edge. As shown in FIG. 77, a partial coating layer 7750 is applied to the downstream major surface 7780 of the leaflet 7710 adjacent the free edge 7760, with the coating 7750 covering portions of both warp 7720 and weft 7730 fibers and their intersections 7740. Without wishing to be bound by any particular theory of operation, it is believed that this coating could, in some instances, prevent cells from attaching in that area and that could be sufficient to reduce or eliminate changes in conformation and its impact on coaptation. The location of this coating might also prevent the attachment of cells elsewhere along the surface of the leaflet and prevent them from exercising sufficient influence so as to cause leaflet retraction at the free edge of the leaflet. Alternatively, the coating might not prevent cell attachment, but might interrupt their ability to fully spread and contract the fabric so as to limit their impact sufficiently so as to avoid retraction. And, perhaps, placement of a partial layer 7750 on only the downstream side 7780 of the leaflet 7710 will allow cell attachment on the upstream side, but not on the downstream side of the leaflet. Perhaps that would help reduce a change of conformation as the "pull" from the cells on the upstream side could actually be beneficial in fighting retraction. It could instead, or in addition, prevent a change in conformation by preventing stretching or shrinking of the localized area of the leaflet thereby insulating it from other changes that may occur elsewhere. Any of the coatings or layers discussed herein or techniques for their application can be used.

It will be appreciated that the above discussions of techniques for stabilizing a woven polymer fabric to prevent changes in conformation of a heart valve leaflet. The areas of a leaflet most in need of stabilization often are those areas that are in motion when in use to an appreciable degree. For that reason, much of this discussion focused on the area of the leaflet adjacent to its free edge. However, stabilization might also be needed in other areas of the leaflet that move including the so-called belly of the leaflet—indeed everything but the commissures and the attachment edge, and perhaps the area immediately adjacent those. Regions of the leaflet that move are believed to be most impacted by changes in their properties and in particular changes in their conformation resulting from cell growth on its surfaces. Accordingly, it is preferably these regions; regions that are in motion when in use, are preferably subject to stabilization by fixation of intersections in such areas, by using other weaves in those areas, or by use of the other techniques described herein. Generally, "stabilization" will occur in moving areas of the leaflet and not in other areas. That does not mean that, for an example, a coating or line of sutures cannot be used to reinforce the attachment edge, preventing unravelling, facilitating suturing, or influencing the folding and the like. But, that is generally not considered to be stabilization as it is not an area of the leaflet that tends to be in motion. Occluders, grafts, and other medical devices may not have leaflets. However, they may have regions that are subject to movement, as the body moves, with the passage of blood or other fluids and the like, as well as regions that are relatively immobile and/or attached to another structure. Stabilization will occur in the regions of these structures and devices that are subject to motion in use and generally not in areas that are immobile and/or attached to another structure.

Figure 79:
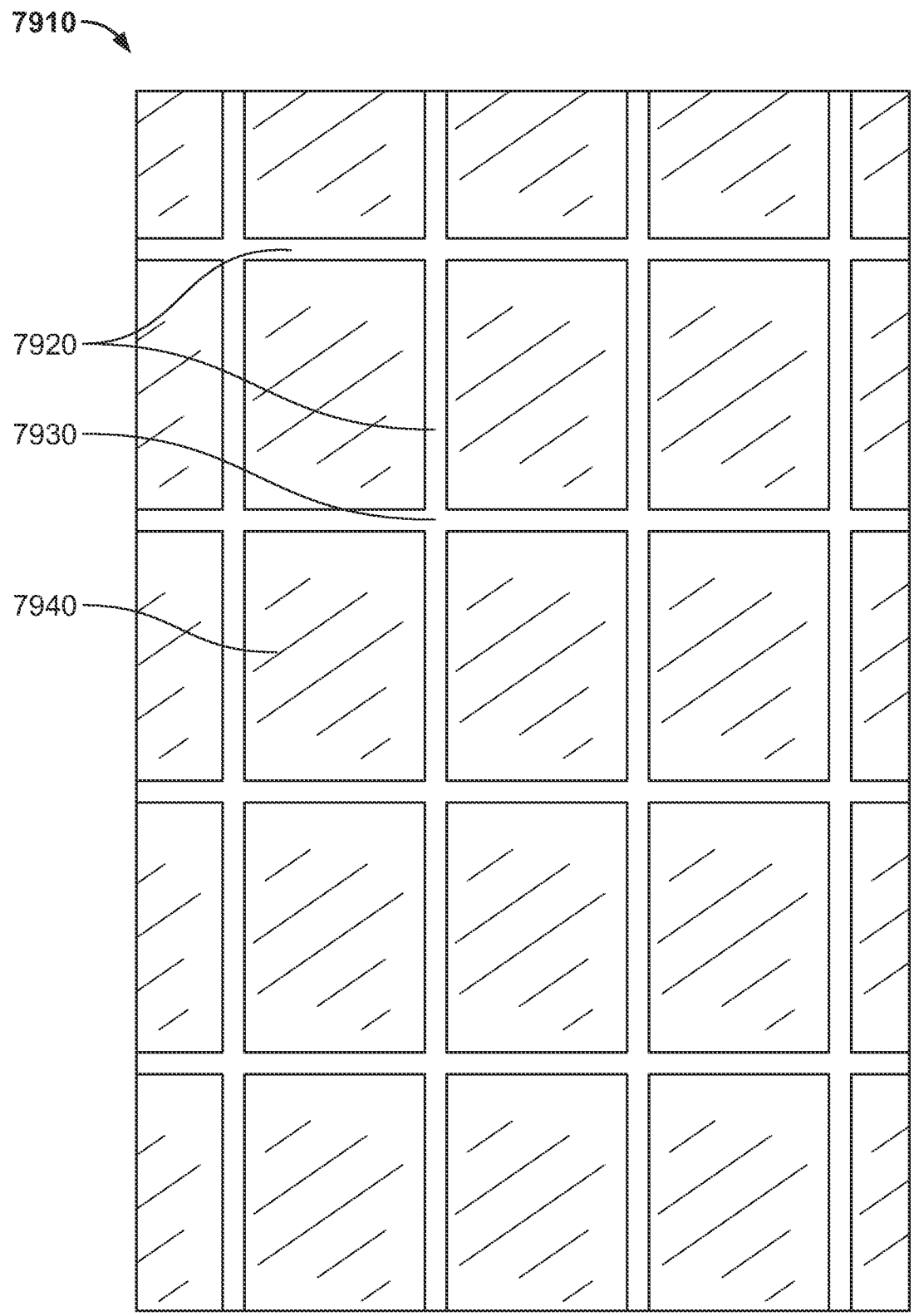
FIG. 79 is a schematic perspective view of a mesh according to the present disclosure.

All of the stabilized fabric embodiments discussed to this point have involved preventing the relative movement of crisscrossing fibers of a woven fabric to maintain their positions, relative angles, contours, and relative spacing. In an alternative embodiment, stabilization can be accomplished by using a mesh instead of using a woven fabric. But stabilized fabrics can also be produced using a mesh which is not a woven fabric. As illustrated in FIG. 79 a mesh 7910 is a nonwoven sheet or matrix with a plurality strands or struts 7920 that meet at and form a plurality of interconnections or junctions 7930 and these struts and junctions define of holes, passages, or pores 7940 of a desired size, location and pattern through its area and/or thickness from one major surface to the other. These pores are analogous to the gaps created between the fibers and intersections of a woven fabric. The stents used in many surgical procedures and in collapsible/expandable heart valves are often laser cut from a tube of steel or Nitinol and can be thought of as a mesh. In a mesh there are no individual fibers to crisscross— one over or under the other and therefore do not have intersections as previously discussed in the case of a woven fabric. And there are no individual fibers that are knotted, woven or braided together. There is only a matrix or web of polymer strands 7920 that interconnect 7930 at various places. All of the polymer material is substantially within the same two-dimensional plane. The mesh can be formed with its plurality of pores 7940 such as by molding in a mold with a plurality of projections that form the pores. It may be formed by placing perforations in a polymer sheet and stretching the sheets to thereby enlarging the pores, or by, for example, having a laser create a pattern of pores in the major surface, in a regular grid or column/row pattern, or in any desired pattern. Instead of pores, which travers the entire thickness of the polymer sheet, the mesh can include divots 7940 which are only open at one end and fluids cannot traverse them.

Figure 80:
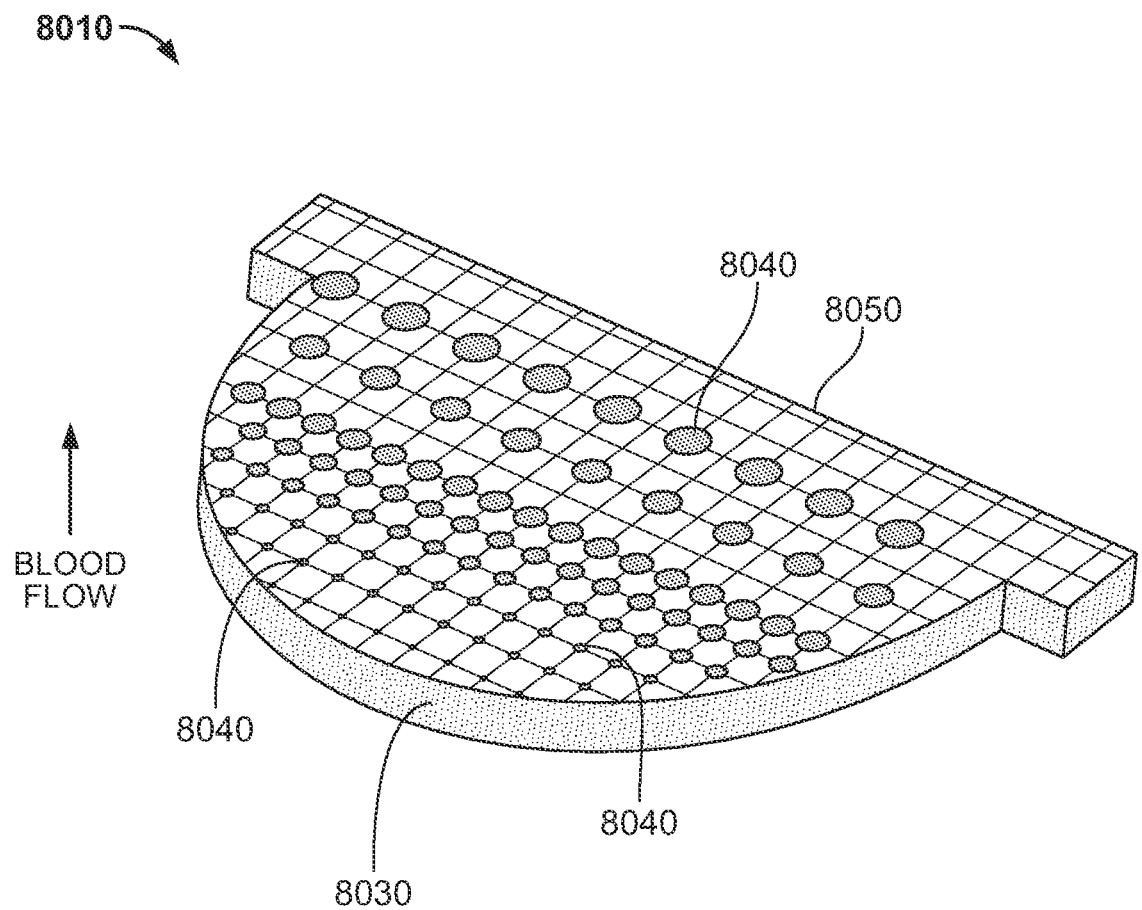
FIG. 80 is a schematic perspective view of a leaflet formed from a mesh according to the present disclosure including a gradient of pore sizes.

The pattern of pores, their size, shape, number, and proximity to each other may be uniform across the length and width of the mesh or may be highly variable, or anywhere in between uniform and highly variable. A mesh could have no pores or divots in one area and a high overall density of pores or divots in another area. As illustrated in FIG. 80, the mesh 8010 could include a gradient of pores 8040, with pores with relatively smaller openings toward the attachment edge 8030 of a leaflet made from the mesh 8010 and pores with relatively larger openings nearer the free edge 8050 of the leaflet, and the pores gradually increasing in the area of their openings between the attachment edge 8030 and the free edge 8050. In a heart valve, of course, the pores should be sufficiently small so as to prevent blood leaking across them, although they could be sized so that there is some leakage initially which is addressed by later cell attachment. The mesh is, in a sense, an already stabilized fabric.

As noted earlier, "pores" are channels traversing the material of the mesh and having openings in both opposed major surfaces. It will be appreciated that the three-dimensional shape of the pores need not be a right cylinder having circular openings. The pores could be any shape such as a triangular cylinder, a quadrilateral cylinder, a pentagonal cylinder or a hexagonal cylinder. And the pores shape could be irregular and varied from pore to pore. The openings to the pores/divots could be as small as about a 1 $micron^2$ across. However, the average area of the openings of each pore/divot will generally range from about 100 $microns^2$ to about 5,000 $microns^2$. In another embodiment, the area ranges from between about range from about 1,000 to about 3,000 $microns^2$. In one embodiment, the mesh has a pore/divot density of about 1 to about 25% and in still another embodiment, the pore/divot density is about 5 to about 15%. In one aspect, the mesh could have pores of two or more different three-dimensional shapes, could include a variety of different shapes, areas, and volumes, and a variable pore density. Moreover, the openings at one end of a pore may differ in area from the area of the openings at the other end.

In another embodiment, instead of pores, the mesh includes divots. A divot is a pore wherein its interior volume is only accessible through a single opening in a single major surface—it is not a pore which is open on both ends. Divots may alternatively be thought of as depressions in the topography of a surface, with the term "opening" referring to the depressed area relative to the adjacent non-depressed area. The divots could have all of their openings on a single side of the mesh or some openings on one side and some the other. There could be an alternating pattern where in a row every other divot faces the opposite direction. Divots could also alternate with pores. In terms of the size, shape, and density of the divots, they may be substantially the same as just noted for the pores. It will be appreciated that for pore/divot density, where pores have different opening sizes at its different ends, or where they alternate with divots, or where divots are on different sides of the mesh, calculations may need to be adjusted. Where the size of the openings are different, they can be averaged, or density can be reported for a single side—where the density is measured using the smallest area of the openings of the pores. Where pores are interspersed with divots, the side with more openings should be used. And where divots are placed on opposite major surfaces, the density is based on either one surface.

In another embodiment, a mesh could be made that looks, in most regards, like a woven fabric. A polymer sheet can be cut or ablated in a pattern so as to form a mesh that closely resembles an otherwise woven fabric. A laser, for example, could ablate not only hole, gaps, pores or divots, but it could selectively ablate a pattern into the sheet's surface resulting in a regular pattern of "hills" and "valleys" where the hills would have the increased thickness that results from fabric fiber crisscrossing and the valleys have a thickness more like that of the fibers extending between intersection. The result can look like a woven fabric. However, it is a mesh as the intersections are not composed of two independent fibers that are stabilized by heat, adhesives, fasteners and the like—they are a solid singular mass of material.

Mesh can be used alone or with other fabrics, stabilized or not. It can be used in place of any of the woven fabrics noted herein, and in any of the surgical devices described herein. In particular it can be used for leaflets or cuffs used in collapsible and/or expandable heart valves in place of other synthetic or biologic materials. It can also used in connection with nonwoven sheets. The mesh can be coated with other material or polymer, such as drug releasing polymers as noted earlier. And a mesh can be coated or laminated as previously described for woven fabrics. It can be used in the same number of layers and have the same relative thicknesses as described herein for woven polymer fabrics as well. Indeed, any laminate or multi-layered construct previously described can have one or all of its woven fabric layers replace with a mesh. And of course an uncoated mesh can be used in place of any uncoated fabric described herein.

These techniques can be combined. A mesh as just described can also include a series of fasteners to retain a group of interconnections or that group of interconnections could be glued or welded together. Similarly, fiber could be woven through the pores of a mesh effectively mimicking increasing the weave density. Or the size, number and spacing of the pores could be altered in a localized area and this also could mimic the effect of increasing or decreasing woven density in a specific area. Returning to woven fabrics, heat could be applied to weld the intersections in a particular area and fasteners could be applied additionally in that area to gather, retain and restrain a group of welded intersections.

Or this sort of area welding could be applied only to an area of a leaflet with increased weave density. These are just examples, any other such combination that achieves these objectives is contemplated.

In still a further embodiment, the medical device, or an element thereof, such as a fabric leaflet, could be constructed or attached so as to form a pleat or fold across a major surface of the leaflet. In particular, this can be accomplished by suturing a gathering of the fabric at the attachment edge and optionally by including structures, cuts or ablations on a major surface of the leaflet in order to form folding zones or pleats.

Producing coated fabrics and/or coated meshes may be accomplished by any known method. U.S. Pat. No. 2,852,811, for example, describes methods for casting thin plastic films, particularly those composed of polytetrahaloethylene. U.S. Pat. No. 4,610,918 describes the production of fluoropolymer coated textiles and U.S. Pat. No. 7,109,135 relates to a woven fabric sandwiched between PTFE layers. In some embodiments, the polymer layers may be extruded via any extrusion mechanism known to those of skill in the art and applied or laminated to fabrics using heat and pressure, such as rollers. In some embodiments, polymer layers may be bonded to fabric layers using an adhesive or adhesion promoting agent. The polymer layers may also be formed in situ by spray coating or dip coating the fabric layers, or a side thereof, with a polymer that will dry, or that can be cross-linked, to form a layer or layers. The coatings and partial coatings may also be applied by 3D printing. The coated fabric may also include intermediate materials or layers intended to improve adhesion between the polymer layers and the fabric layers.

FIGS. 21-23, 34-42 and 47-67B illustrate certain exemplary structures that can result from the formation of a partial coating. The partial coatings forming these structures can, of course, be applied to a fabric layer in a manner similar to complete coatings. For example, polymer films of the desired shape and size can be placed where desired and glued, laminated, etc. in place; liquid polymer can be molded to the shape desired; or an edge of the fabric can be dip coated. However, a partial coating may also be achieved by fully coating a major surface of the fabric layer (or a partially or fully coated fabric layer) and then removing unwanted portions of that coating or unwanted portions of specific layers by ablating, melting, evaporating, cutting, eroding or frictionally removing (sanding, grinding, rubbing). Thus ribs, reinforced areas adjacent an attachment region, and structures at or adjacent the free edge used to resist wear can all be formed by removing the coating material between those structures.

Ablation can also be used to provide a pattern in a coated surface or to impart other surface features. Ablation could be used, for example, to taper the thickness of a leaflet, just for example, from an attachment edge to the free edge. This is accomplished by progressively ablating the coating layer(s) from one edge to the other, deeper and deeper, thus removing more and more of the coating. As another example, ablation could be used to remove a portion of the coating(s) in a selected area, such as in the portion of a leaflet that will form its belly when in use in a heart valve, to provide additional flexibility to that region. Other surface patterns may also be developed. In addition, surface roughening, such as to promote cell adhesion generally or in specific areas of the surface, may be employed.

When ablation is used, it may be preferable to use a single thicker coating layer rather than multiple layers. In other circumstances, the topmost layers that will be selectively ablated could be composed of one polymer material, with one or more under layers that are not to be removed or patterned being composed of a different polymer material. Indeed, while these processes for removing portions of a full coating have just been described in connection with forming partial coatings, they may also be used to provide patterns and/or surface features in complete coatings where no portion of the major surface of the fabric is substantially uncoated. See, for example, FIG. 37, which contains a full coating 3751 disposed between fiber layer 3740 and an additional coating feature 3750 adjacent the free edge 3730. Layer 3750 could be applied to polymer layer 3571 or it could be formed by ablating away a portion of a top layer leaving only portion 3750.

The polymer layer or layers may therefore form a pattern or relief on one or both sides of a fabric layer. They may vary thickness; provide rigidity or additional cohesion to specific regions; retard fraying; reinforce shape, stretch, or friction; alter porosity; provide or encourage cell attachment or prohibit it in specific areas; enhance coaptation; and the like.

Figure 21:
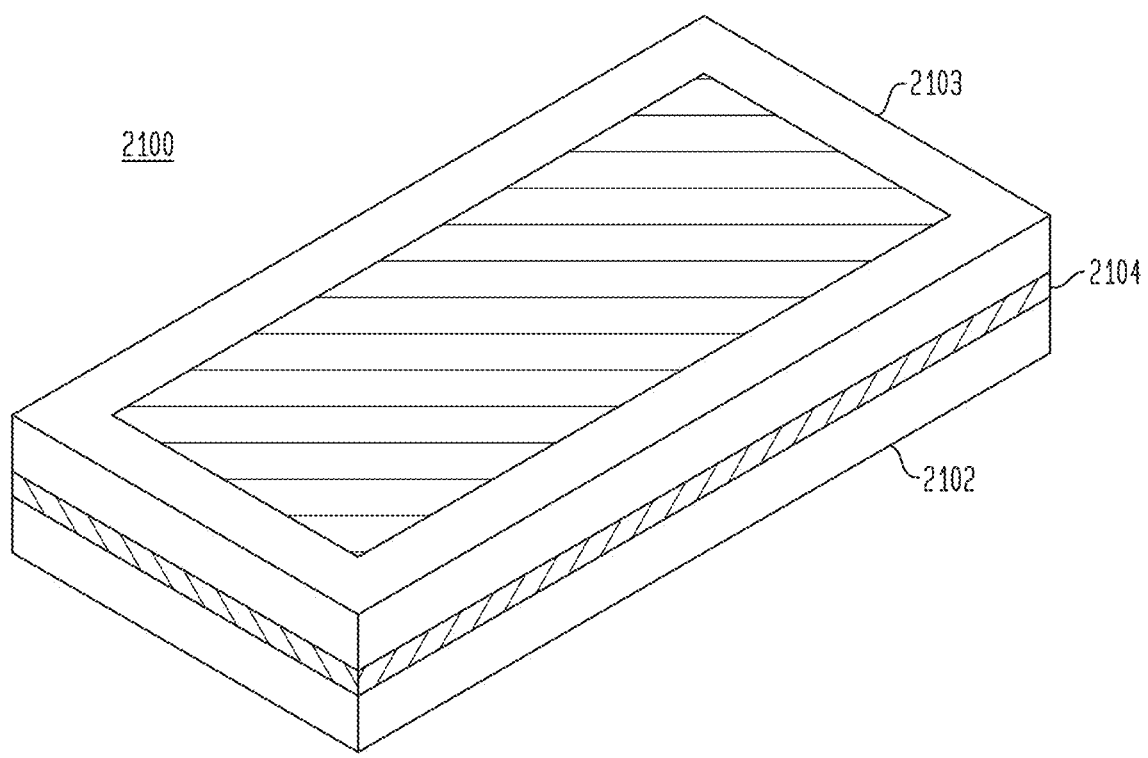
FIG. 21 is a perspective view of a woven fabric having a polymer film or layer on the edges of the top surface of the fabric layer.

FIG. 21 illustrates a non-limiting example of a coated fabric 2100 which may be patterned as shown. A fabric layer 2104 may be discontinuously coated with a polymer layer 2103 such that only the area a few millimeters from each edge of the top major surface of the fabric layer 2104 is polymer coated—forming a structure looking like a picture in a frame, as shown in FIG. 21. The bottom major surface of the fabric layer 2104 may be continuously coated with a polymer layer 2102. The reverse may also be possible. A checkerboard pattern, a series of strips, concentric circles or other shapes may be laminated, printed, etched, masked, coated or otherwise formed onto one or more major surfaces of the fabric. Each of these patterns can be formed by using differing thicknesses and/or different numbers of layers of polymer. The entire upper surface of a fabric could be coated. Alternatively, different portions of the surface could be coated with different thicknesses and/or different numbers of layers of polymer. This can be done to provide a coated fabric with areas of greater or lesser porosity, areas of greater or lesser surface irregularity or roughness, areas of different texture, and/or areas of greater flexibility or rigidity. Controlled coating of the fabric may also provide preferred movement or folding, reinforcement of certain areas, greater wear resistance, areas in which it is harder for a tear to form or propagate near a suture, or a combination of any of these.

Figure 22:
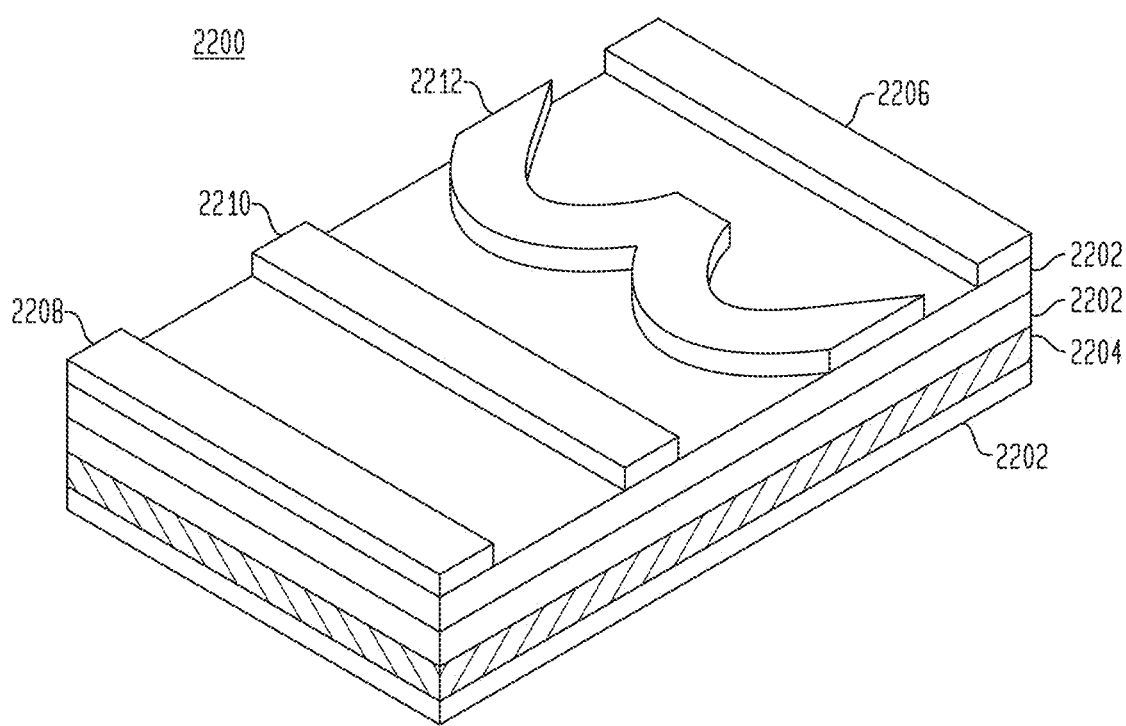
FIG. 22 is a perspective view of a woven fabric having a structured upper surface and a different number of polymer layers on each side of the fabric layer.

FIG. 22 illustrates another example of a partially coated fabric 2200 in which a fabric layer 2204 may be coated on its entire lower surface with a single polymer layer 2202. However, two continuous polymer layers 2202 may be applied to the upper surface of fabric layer 2204, and a third polymer layer may be printed or otherwise applied thereto in a discontinuous fashion over the continuous layers. A portion of this third layer may be, in this example, applied to the continuous layers 2202 so as to overlie two opposed edges 2206 and 2208 of the coated fabric 2200. This could be done to reinforce those areas of the coated fabric that may be attached with, for example, sutures, to the luminal and abluminal surfaces of a stent and wrapped around the inflow end of the stent to provide internal and external cuffs. Another portion of the third layer may include a curved portion 2212 to help reinforce that portion of the resulting inner cuff at which leaflets will likely be attached. The third layer may also include another strip 2210 located in the area of the coated fabric 2200 which will actually wrap around the inflow end of the stent to help prevent abrasion upon contact between the cuffs and the stent and to provide a sturdier portion for suturing to the inflow end of the stent.

Figure 23A:
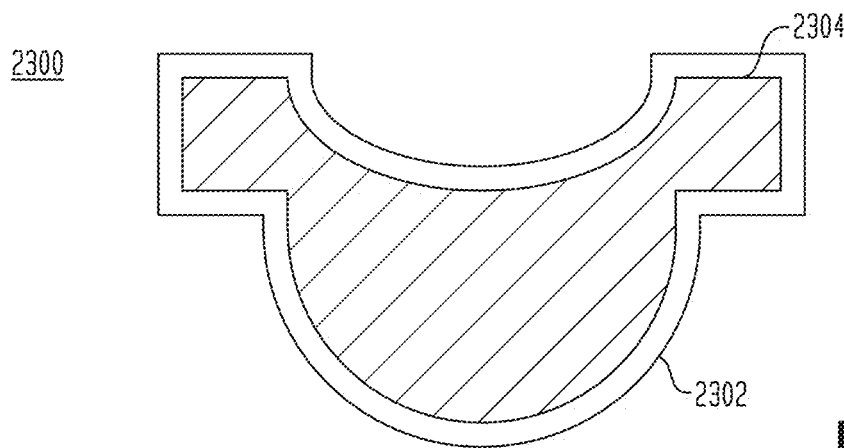
FIG. 23A is a plan view of a woven fabric leaflet coated on the edges of the woven fabric layer.
Figure 23B:
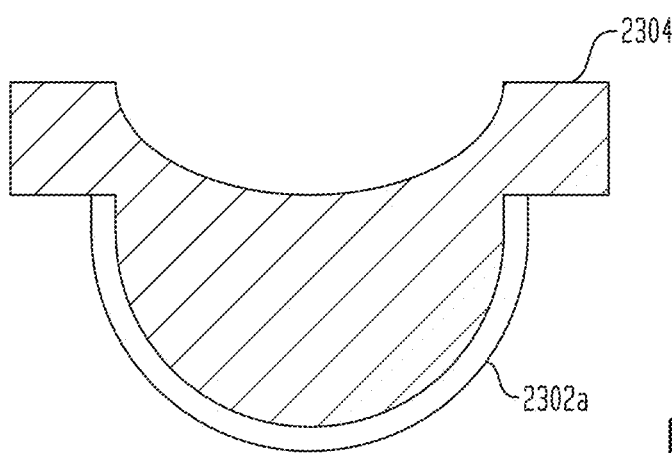
FIG. 23B is a plan view of the underside of the woven fabric leaflet partially coated along the sewing or attachment edge.
Figure 23C:
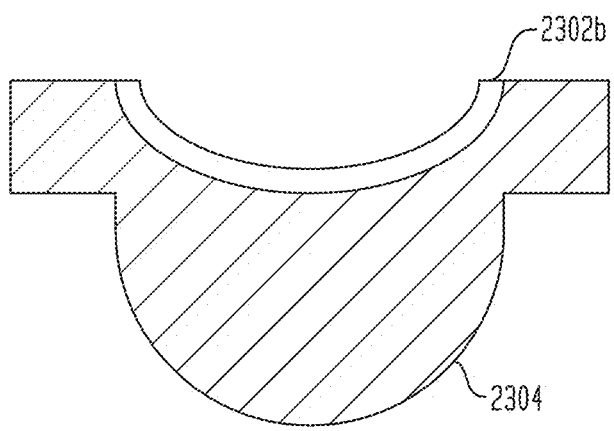
FIG. 23C is a plan view of the top side of the woven fabric leaflet partially coated along the free edge.

FIGS. 23A-23C, for example, illustrate a patterned coated fabric for use in a leaflet 2300. The fabric layer 2304 may be discontinuously coated with a polymer layer 2302 such that only the area a few millimeters from each edge of the fabric layer is coated. The pattern as just described may be used for a leaflet in which only the attachment edge and the free edge of the leaflet are coated, as shown in FIG. 23A. In some embodiments, the pattern as just described for a leaflet may have a fabric layer discontinuously coated with a polymer layer such that an area extending about 10 mm from the attachment edge and the free edge is coated with the polymer. In other embodiments, the coating areas may not be uniform and the fabric 2304 may be coated in an area extending about 10 mm from the attachment edge with polymer 2302a and in an area extending about 5 mm from the free edge with polymer 2302b, as is shown in FIG. 23B and FIG. 23C, respectively. FIG. 23B illustrates the underside (or upstream surface) of the leaflet which attaches to the stent, while FIG. 23C illustrates the other side (or downstream surface) of the leaflet. The reverse may also be possible when used for a leaflet.

Figure 24:
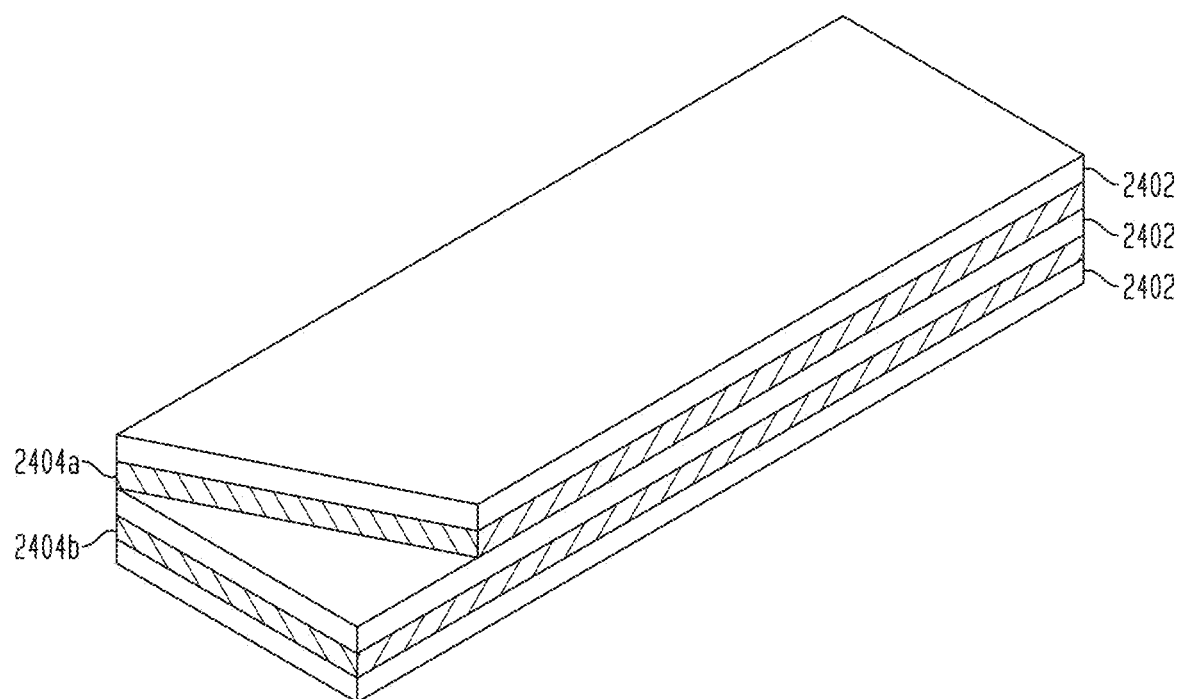
FIG. 24 is a perspective view of a coated woven fabric having multiple layers of woven fabric and at least one polymer layer between each fabric layer.

FIG. 24 illustrates a coated fabric composed of multiple polymer layers and multiple fabric layers. The fabric layers may be oriented such that their warp fibers either are oriented substantially parallel to the longitudinal edges of the coated fabric (not on a bias), or at a bias of between about 30 degrees and about 60 degrees relative to the longitudinal edges of the coated fabric. The coated fabric with multiple polymer layers and multiple fabric layers may be formed by alternating each polymer layer with a fabric layer such that each fabric layer has a polymer layer on both its top surface and its bottom surface. In FIG. 24, a first fabric layer 2404a is oriented at about a 45 degree bias relative to the longitudinal edges of the coated fabric, while second fabric layer 2404b is not oriented on a bias. Each fabric layer 2404a, 2404b may be coated with a polymer layer 2402.

Figure 25:
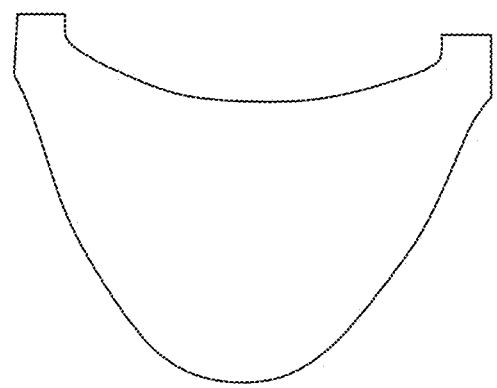
FIG. 25 is a plan view of a heart valve leaflet fabricated from woven UHMWPE fibers.
Figure 26:
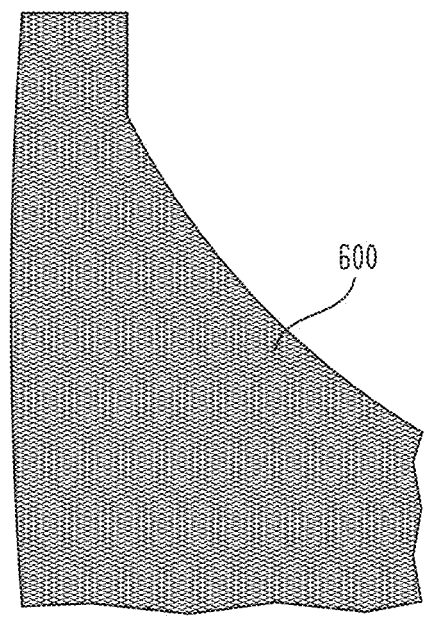
FIG. 26 is an enlarged view of a portion of the heart valve leaflet of FIG. 25.

FIGS. 25 and 26 depict a heart valve leaflet fabricated from a fabric composed of UHMWPE fibers. The fabric may be cut to a desired geometry by stamping, mechanical cutting, laser cutting or other known techniques. As shown in FIG. 25, the UHMWPE fabric is cut to produce a heart valve leaflet having fibers 600 oriented at a 45 degree angle relative to the direction from the attachment edge to the free edge of the leaflet. FIG. 26 shows an enlarged portion of the heart valve leaflet of FIG. 25 showing the edge quality of the heart valve leaflet produced by laser cutting. The laser cutting may melt the edges of the leaflets to effectively create a single, continuous seam. There may be a preference for a smooth transition between the main leaflet body and the edges of the leaflet. If the transition is not smooth, blood cells may encounter a relatively large amount of shear stress at the transition point, which can activate the blood cells, creating a potential for undesirable thrombus formation. The edges of the leaflet may be coated with a polymer as described above to ensure a smooth transition between the main leaflet body and the edges of the leaflet. In still further embodiments, at least one of the leaflets may be composed of a woven or knitted fabric that is coated or uncoated and fabricated such that its fibers are at a bias angle of between about 30 degrees and about 60 degrees relative to a line that extends perpendicular to the free edge of the leaflet when the leaflet is in a flattened condition or lies within a plane (e.g., before the leaflet is attached to the valve assembly). In another embodiment, all of the leaflets may be fabricated with their fibers at that same relative bias. In still a further embodiment, the leaflets may not all be fabricated with their fibers at that same bias. In one such instance, all of the leaflets may be fabricated with their fibers on a bias of between about 30 degrees and about 60 degrees relative to a line that extends perpendicular to the free edge of the leaflet, but the fibers of at least one of the leaflets are not on the same bias as the fibers of the other leaflets of the valve assembly. In still another such embodiment, the fibers of at least one such leaflet are biased at between about 30 degrees and about 60 degrees relative to a line that extends perpendicular to the free edge of the leaflet and the fibers of at least one other leaflet are not.

FIGS. 28-46A further illustrate the structural diversity of coated and uncoated synthetic fabrics useful in medical devices in accordance with the present disclosure. This diversity is illustrated by using leaflets and cuffs useful in the construction of collapsible/expandable heart valves. It should be understood, however, that these structures are illustrative and that the fabric materials depicted can be used in other medical devices and their shape, thickness, and composition may be adjusted to suit that particular purpose.

Figure 28:
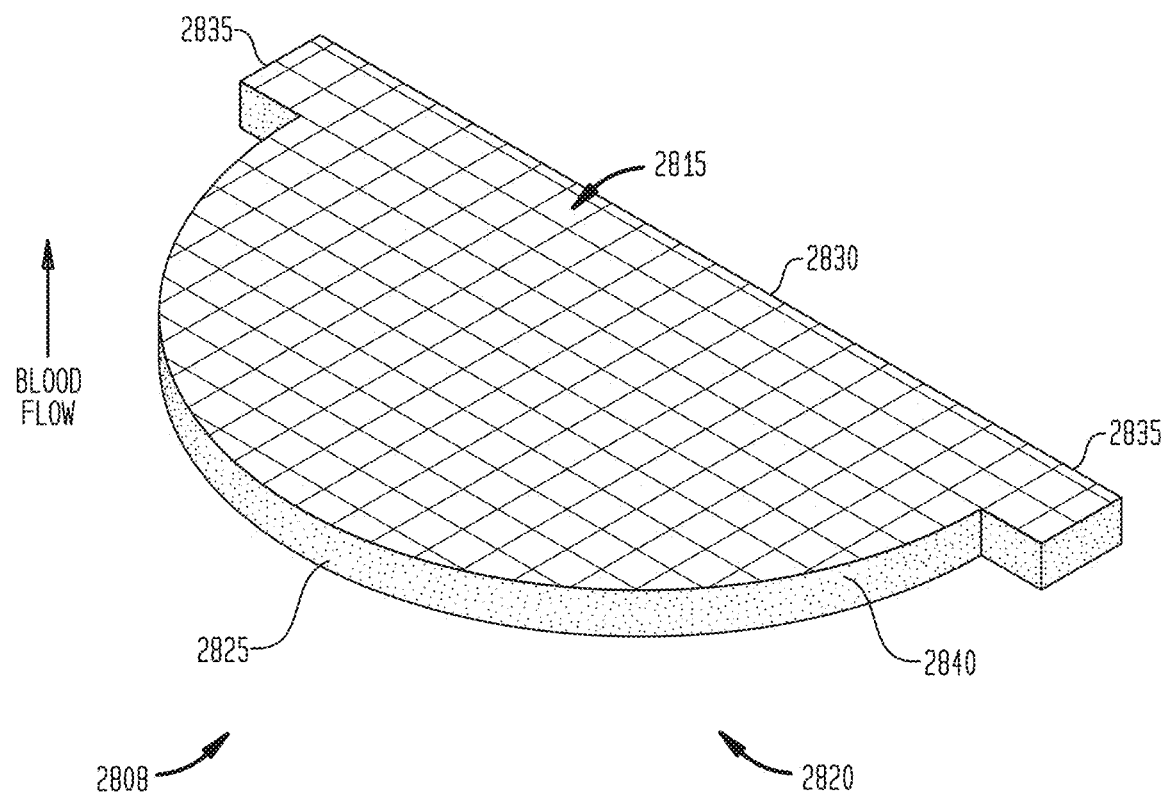
FIG. 28 is a schematic perspective view of a leaflet formed from a stabilized or non-stabilized uncoated woven fabric according to the present disclosure.

Looking at FIG. 28, leaflet 2808, an uncoated leaflet, consists only of a fabric 2840. Leaflet 2808 includes a first major surface or downstream surface 2815 and a second major surface or upstream surface 2820. Leaflet 2808 is similar to leaflet 108 shown in FIG. 2 attached to a stent so as to form a one-way valve assembly. The actual surface illustrated in FIG. 2 is the first major surface or downstream surface as blood flows into the valve from the inflow or annulus end 130 to the outflow or aortic end 132. Blood flows from upstream to downstream and, accordingly, the first major surface is considered the downstream side with the downstream surface 2815 and the opposite major surface is the upstream surface 2820. Stated in another way, the downstream surface 2815 is the major surface generally facing the outflow or aortic end 132 of the stent when the valve leaflets are in a closed position during use. The upstream surface 2820 generally faces the inflow or annulus end 130 of the stent when the leaflets are in the closed position.

Leaflet 2808 has a free edge 2830, an attachment edge 2825, and a plurality of tabs or flaps 2835. Generally, the leaflet is attached to the cuff and/or to the stent at or adjacent the attachment edge 2825. The tabs 2835 often form commissures at which two adjacent leaflets meet. Each tab 2835 is often attached to an adjacent tab of an adjacent leaflet and/or to the stent at, for example, a commissure attachment feature such as element 116 in FIG. 2. While much of the fabric moves during operation of the prosthetic heart valve, the greatest degree of movement is experienced by the free edge 2830. It is pushed out of the way from the center of the valve toward the luminal surface of the stent when blood is flowing, and is pushed back toward the center of the valve where it engages or coapts with other leaflets when the valve is closed.

As noted, the fabric leaflet 2808 in FIG. 28 is uncoated, and it can be composed of any uncoated at least partially synthetic fabric as disclosed herein. Leaflet 2808 is illustrated as a single layer of fabric, although multiple layers of fabric could be stacked directly atop one another and attached to one another by suitable methods, such as gluing, stitching, spot welding, and the like.

Figure 29:
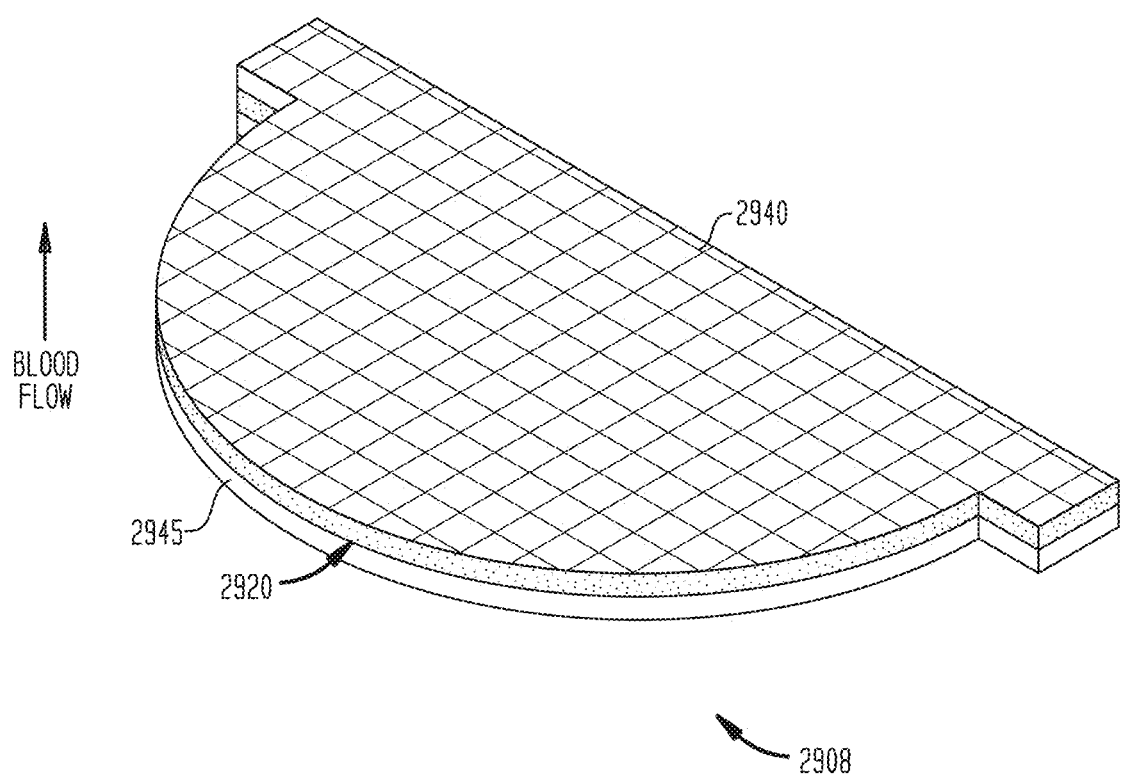
FIG. 29 is a schematic perspective view of a leaflet formed from a stabilized or non-stabilized coated woven fabric according to the present disclosure.

FIG. 29 illustrates a coated fabric and is generally of the same structure and composition as that illustrated in FIG. 28, other than the coating. The leaflet 2908 in FIG. 29 includes a fabric layer 2940, which can be composed of any of the fabrics disclosed herein, as well as a polymer layer 2945. In FIG. 29, polymer layer 2945 is generally coextensive with the shape and size of fabric layer 2940 and is attached to the upstream surface 2920 of the fabric layer. Fabric layer 2940 and polymer layer 2945 are illustrated as being of roughly the same thickness, however, that need not be the case. Multiple fabric layers and/or multiple polymer layers are possible and contemplated as described elsewhere herein. Moreover, the leaflet 2908 in FIG. 29 is illustrated with the downstream surface not covered by a polymer layer. It can, however, be covered by one or more polymer layers as well. Indeed, this concept is illustrated in FIG. 30.

Figure 30:
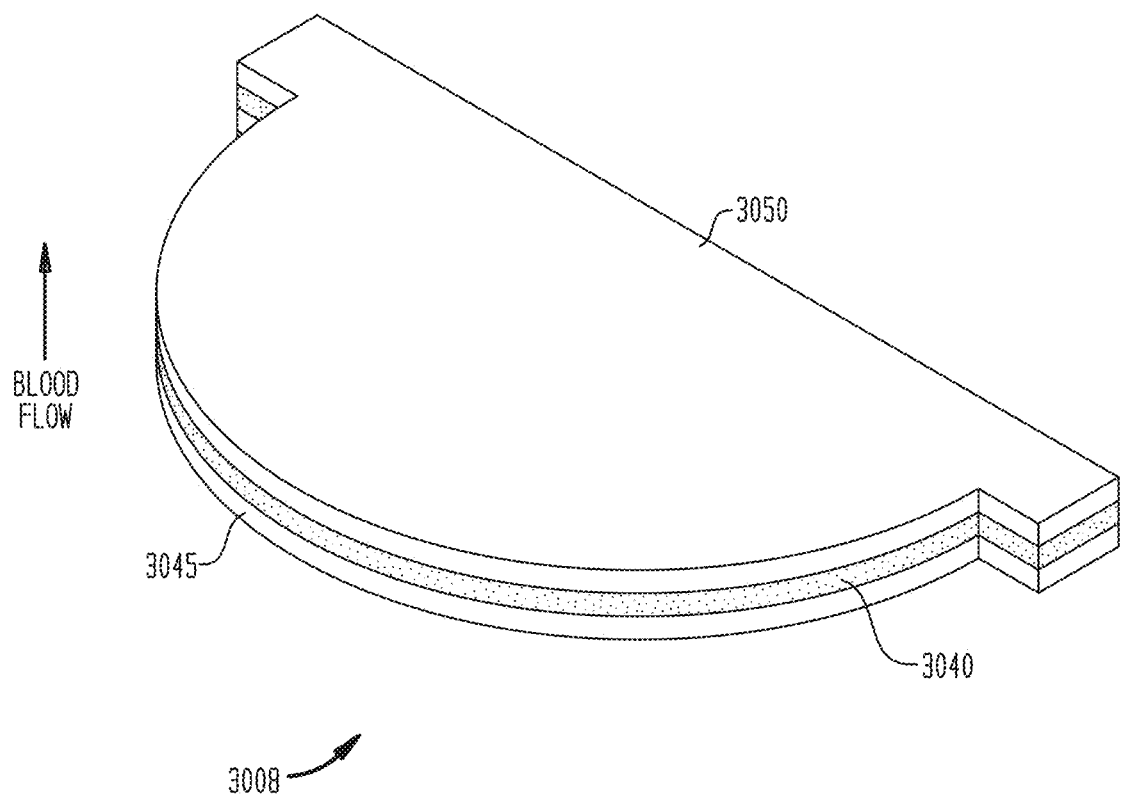
FIG. 30 is a schematic perspective view of a leaflet formed from another stabilized or non-stabilized coated woven fabric according to the present disclosure.

FIG. 30 illustrates a valve leaflet 3008 as generally described in FIGS. 28 and 29 comprised of a fabric layer 3040, a first polymer layer 3045 covering the entire upstream surface of the fabric layer and a second polymer layer 3050 covering the entire downstream surface of the fabric layer. As before, the individual layers can be made of any of the fabrics and any of the polymer coating materials described herein. While a leaflet having three layers is illustrated, more layers are possible, and the layers may be of varying thicknesses.

Figure 31:
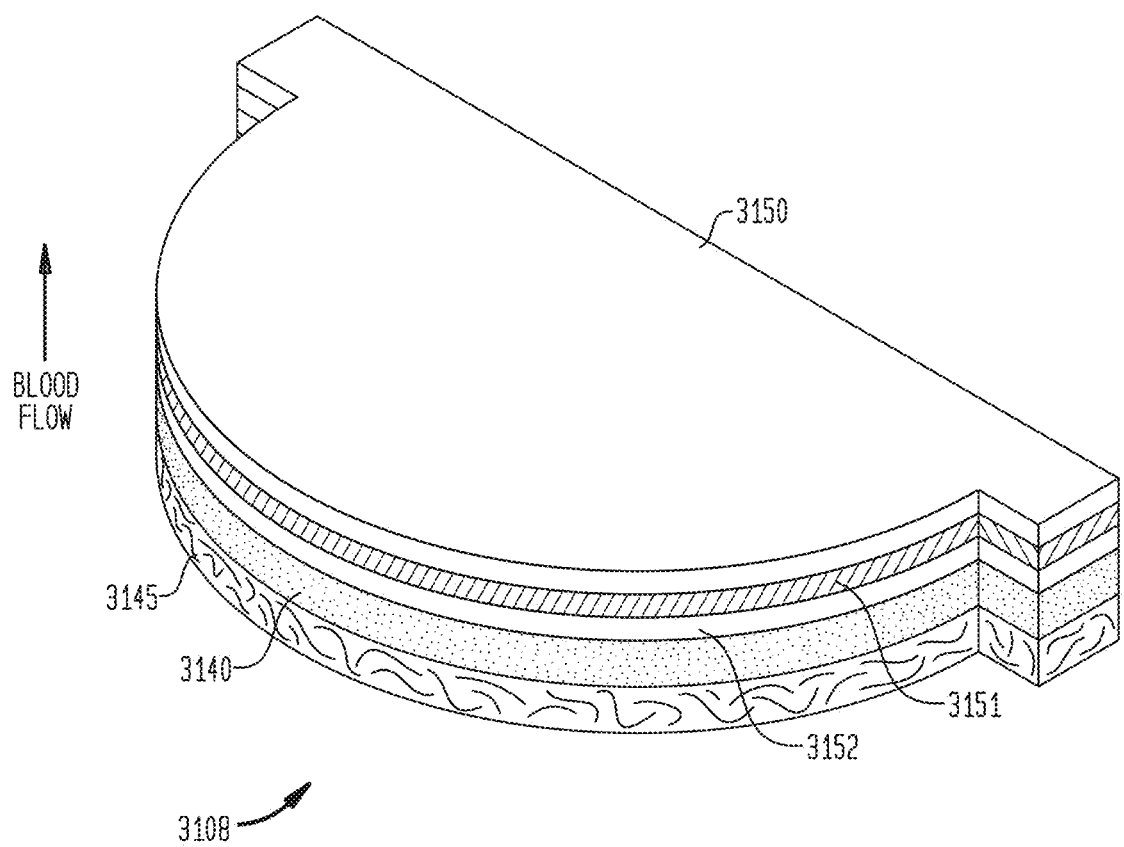
FIG. 31 is a schematic perspective view of a leaflet formed from another stabilized or non-stabilized coated woven fabric according to the present disclosure.

Similarly, FIG. 31 illustrates a leaflet 3108 as described in connection with FIGS. 28-30. Leaflet 3108 has a multilayered structure in which the fabric layer 3140 is coated on both of its major surfaces with at least one polymer layer. Leaflet 3108 contains a fabric layer 3140 as discussed herein, and a single polymer layer 3145 covering the entire upstream surface of the fabric layer. There are, however, three polymer layers covering and attached to, directly or indirectly, the entire downstream surface of leaflet 3108. The most downstream or outermost layer 3150 may be made of ultra-high molecular weight polyethylene (UHMWPE), the next adjacent layer 3151 may be made of low density polyethylene, and the third and final layer 3152 situated against the fabric layer 3140 may also be composed of UHMWPE.

The three polymer layers 3150, 3151, and 3152 illustrated in FIG. 31 have roughly the same combined thickness as polymer layer 3145 disposed on the upstream surface of fabric layer 3140. This need not be the case. Each of the individual polymer layers may be thin or thick and their combination may be thicker or thinner than polymer layer 3145 or fabric layer 3140. Moreover, while three polymer layers are illustrated, as discussed elsewhere herein, the number of layers that can be applied to any one major surface of the fabric layer can be as many as 20 layers.

Figure 32:
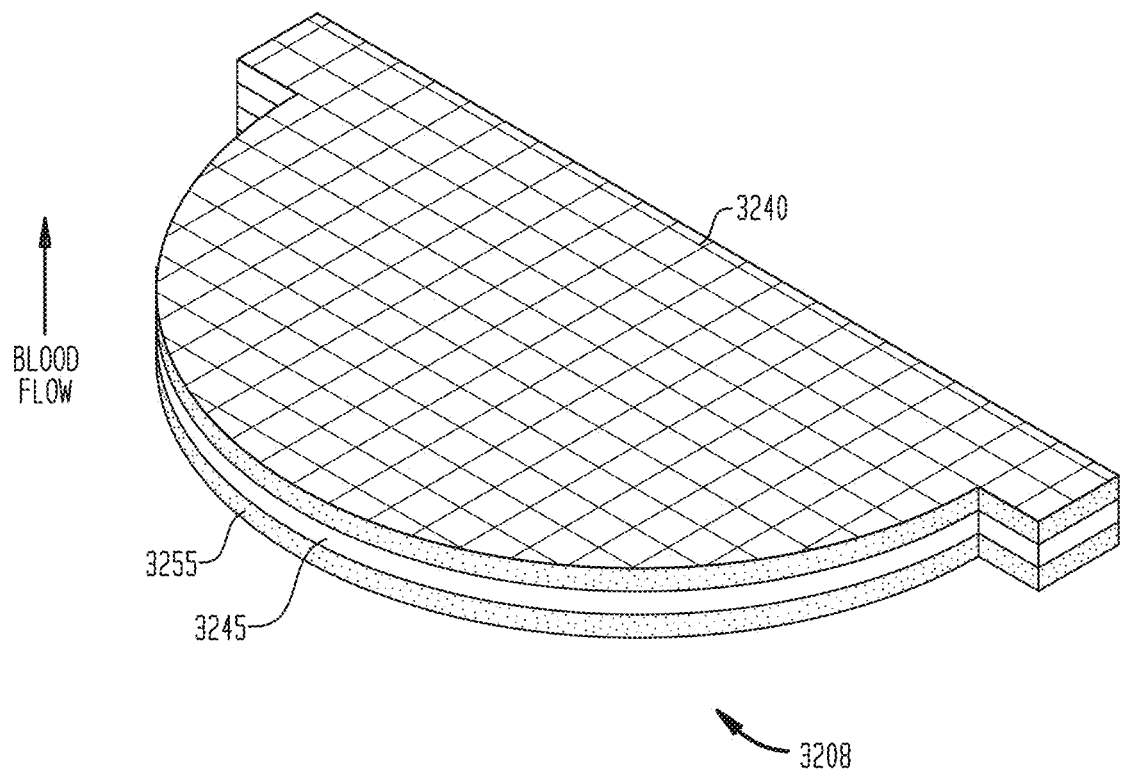
FIG. 32 is a schematic perspective view of a leaflet formed from another stabilized or non-stabilized coated woven fabric according to the present disclosure.

FIG. 32 shows another construction of a leaflet generally discussed and illustrated in FIGS. 28-31. Leaflet 3208, however, includes two fabric layers separated by, and each attached to, a polymer layer disposed between them. Specifically, fabric layer 3240 forms a downstream side of leaflet 3208 and fabric layer 3255 forms the upstream side of the leaflet. Fabric layers 3240 and 3255 may be the same as one another, or may be different from one another in composition, thread count, fiber orientation, weave pattern, thickness, etc. A polymer layer 3245 is disposed between and is coextensive with the second (upstream) major surface of fabric layer 3240 and the first (downstream) major surface of fabric layer 3255. Fabric layers 3240 and 3255 may be the same as or different from one another in composition, structure, thickness, etc., and each may be a single layer or multiple layers independently of one another. While a single polymer layer 3245 is illustrated between the fabric layers, this layer could be composed of multiple polymer layers having the same or different structures, thicknesses, and compositions.

Figure 33:
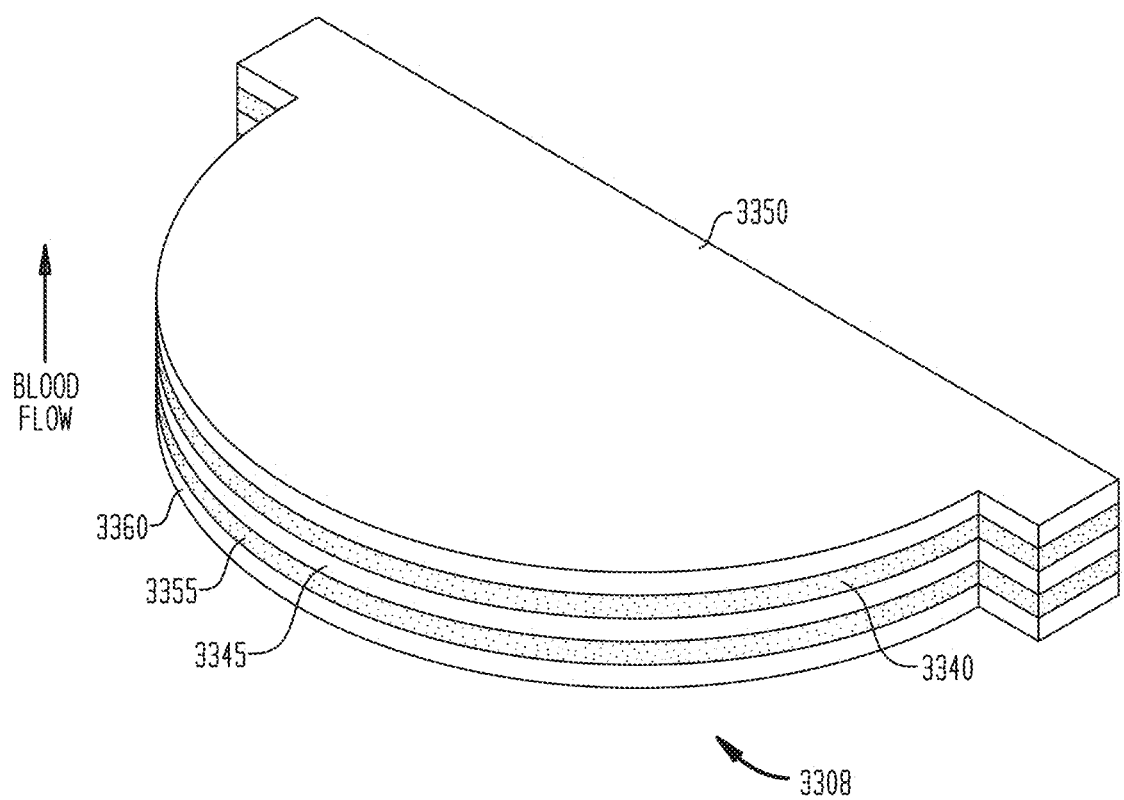
FIG. 33 is a schematic perspective view of a leaflet formed from another stabilized or non-stabilized coated woven fabric according to the present disclosure.

FIG. 33 illustrates yet another possible construction of a fabric leaflet, as generally described in connection with FIGS. 28-32. Leaflet 3308 is constructed with two fabric layers 3340 and 3355, and a polymer layer 3345 disposed between them. Additionally, the downstream surface of fabric layer 3340 is covered with a polymer layer 3350 and the upstream surface of fabric layer 3355 of leaflet 3308 is also covered with a polymer layer 3360. Fabric layers 3340 and 3355 may be the same as one another, or may be different from one another in composition, thread count, fiber orientation, weave pattern, thickness, etc. Similarly, polymer layers 3345, 3350 and 3360 may be the same as one another or may be different from one another in structure, composition, thickness, etc.

Figure 34:
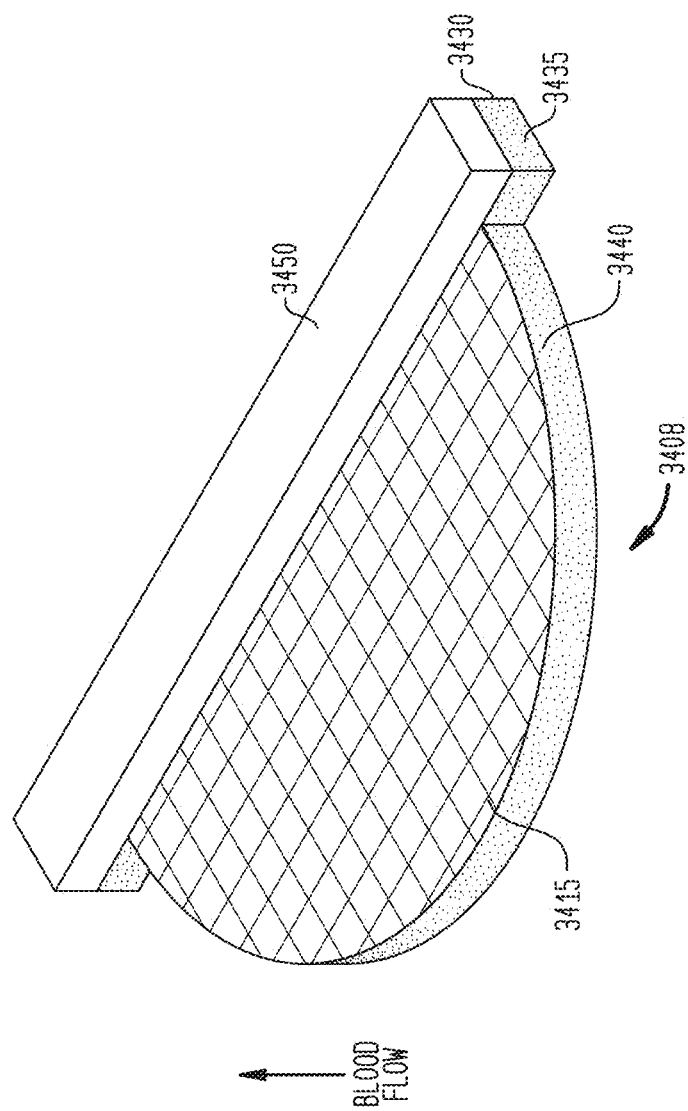
FIG. 34 is a schematic perspective view of a leaflet formed from a partially coated stabilized or non-stabilized woven fabric according to the present disclosure.

FIG. 34 illustrates a partially coated leaflet 3408. Leaflet 3408 comprises a fabric layer 3440. Any fabric described in accordance with the disclosure may be used including an already stabilized woven fabric or a mesh. Leaflet 3408 also includes a partial polymer coating 3450 disposed as a single layer on its downstream surface 3415 adjacent the free edge 3430 of the leaflet. This partial polymer layer 3450 is illustrated as being the same width as tabs 3435 and roughly the same thickness as fabric layer 3440. However, that need not be the case. Polymer layer 3450 may be wider or narrower across the downstream face 3415 of fabric layer 3440 and may be thicker or thinner than the fabric layer. That said, layer 3450 is often thinner than and not as wide as the fabric layer. Multiple polymer layers and fabric layers may be used as opposed to the single layers illustrated. The partial coating 3450 adjacent the free edge 3430 of leaflet 3408 may serve one or more purposes. For example, it may help add weight to bias the leaflet back into a closed position, it may help the leaflet retain its intended shape, and may promote or prevent cell attachment and proliferation adjacent the free edge 3430.

Figure 34A:
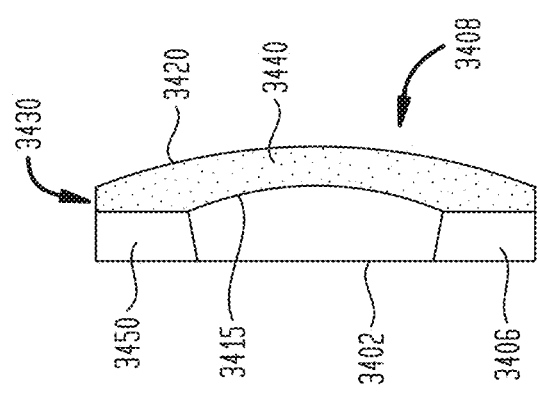
FIG. 34A is a schematic partial cross-section of a stent and a valve assembly incorporating the leaflet of FIG. 34.

FIG. 34A is a partial cross-section of a stent and a valve assembly similar to those shown in FIG. 2. A portion of the stent 3402 is illustrated in cross-section with an internal cuff 3406 attached to a luminal surface of the stent. Leaflet 3408 is attached to cuff 3406 and/or stent 3402 at or adjacent its attachment edge 3425, which may be sutured to the cuff and/or stent. Leaflet 3408 is illustrated in its open position as it extends generally downstream to accommodate blood flow from the inflow end of the stent to the outflow end past the upstream surface 3420 of the leaflet. Partial coating 3450 is disposed on the downstream surface 3415 of the leaflet edge adjacent the free edge 3430 of fabric layer 3440 (which could be any form of stabilized or un-stabilized woven fabric or a mesh) and is illustrated engaging the luminal surface of stent 3402. Partial coating 3450 therefore prevents direct contact of the fabric layer 3440 and any layer disposed on the downstream surface of the fabric layer with the inner surface of the stent during blood flow, thereby providing additional wear resistance and helping to prevent the fraying of the free edge 3430 of the fabric layer. In addition to providing resistance to wear, such partial coating 3450 could also help maintain the shape of the leaflet and its ability to coapt with other leaflets, despite cell ingrowth on the downstream surface 3415 of the leaflet. Without partial coating 3450, inter-cellular attachment could exert forces that could tend to pull the free edge out of proper position. Instead of, or in addition to, a partial coating 3450 on the downstream surface 3415, a similar partial coating may be applied to the upstream surface 3420 of the leaflet, adjacent the free edge 3430 or otherwise, to resist the deformation of the leaflet due to cellular ingrowth.

Partial polymer layer 3450 is shown extending fully across the entirety of the free edge 3430 of leaflet 3408 between tabs 3435. This need not be the case. Partial polymer layer 3450 may be provided adjacent free edge 3430 but not overlying tabs 3435. Further, partial polymer layer 3450 may be a discontinuous layer of two, three, or more coated portions forming in essence a dashed line adjacent free edge 3430. Still further, layer 3450 may be formed of spots or dots formed intermittently adjacent free edge 3430. Each dot or each dash may have a different thickness and/or may be composed of a different composition.

Figure 35:
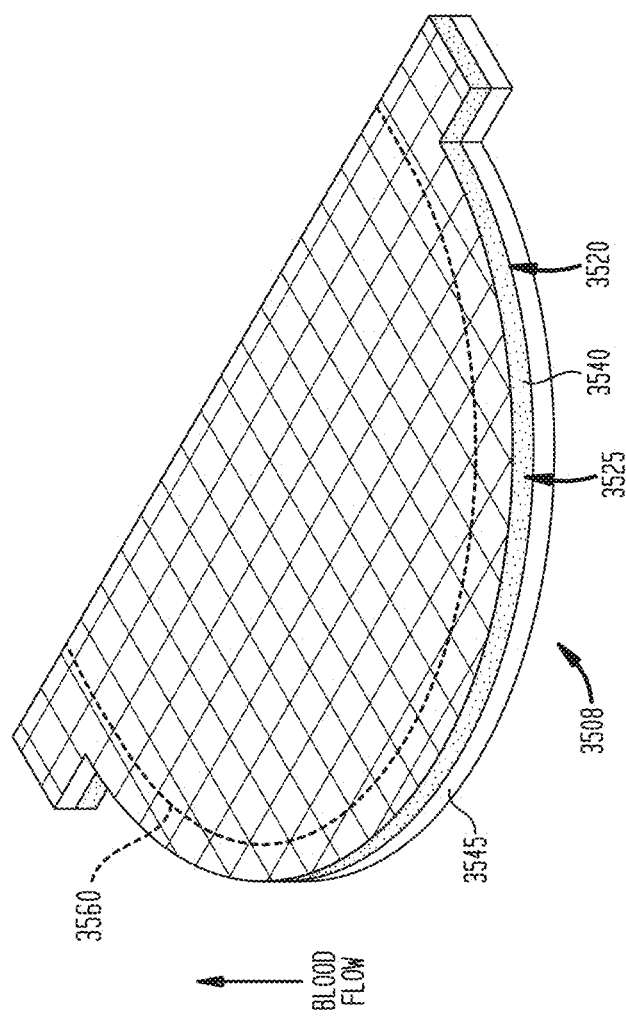
FIG. 35 is a schematic perspective view of a leaflet formed from another partially coated stabilized or non-stabilized woven fabric according to the present disclosure.
Figure 35A:
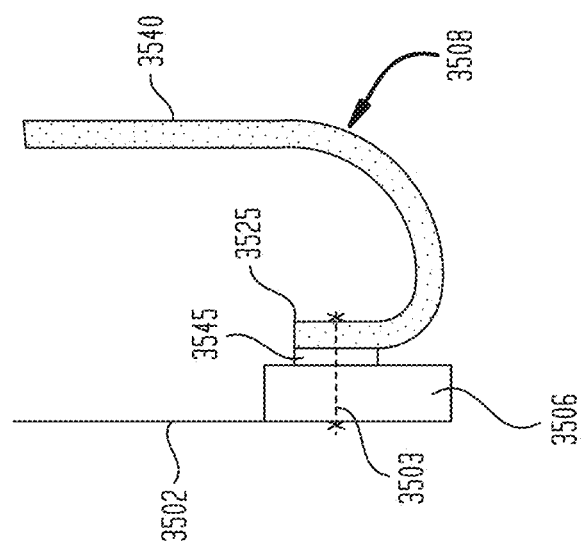
FIG. 35A is a schematic partial cross-section of a stent and a valve assembly incorporating the leaflet of FIG. 35.

FIG. 35 illustrates another embodiment of the fabric leaflets generally illustrated in FIGS. 28-34. Leaflet 3508 includes a fabric layer 3540 (which includes an already stabilized woven fabric or a mesh), and a polymer layer 3545 disposed on its upstream surface 3520. Polymer layer 3545, however, does not cover the entirety of the upstream surface 3520 of fabric layer 3540. It is a relatively narrower layer in width and runs adjacent the attachment edge 3525, extending inwardly therefrom for some predefined width. An illustrative width is shown using the dashed semicircular line 3560 in FIG. 35. FIG. 35A is a partial cross-section of a stent 3502 and a valve assembly similar to those illustrated in FIG. 2. Attached to a luminal surface of stent 3502 is a cuff 3506. Leaflet 3508 as shown is composed of fabric layer 3540, which is rolled or folded adjacent its attachment edge 3525 for attachment purposes. Disposed between fabric layer 3540 and cuff 3506 is polymer layer 3545, which is provided adjacent the attachment edge 3525 of fabric layer 3540. As is true for FIG. 34A, leaflet 3508 is illustrated in the open position, e.g., a position that would be roughly when blood is flowing through the valve from the inflow end of the stent to the outflow end. Leaflet 3508 may be attached via a suture 3503 anchoring both fabric layer 3540 and polymer layer 3545 to cuff 3506 and/or stent 3502.

As was true for the partial layer 3450 in FIG. 34, the partial layer 3545 need not be a single layer nor need it be the same thickness or composition as fabric layer 3540. As was previously described, its width need not extend over the entire upstream surface 3520 of fabric layer 3540. Indeed, generally, it may be provided with sufficient width only to allow a suture therethrough. Partial layer 3545 may provide additional reinforcement and/or may help prevent fraying when suturing leaflet 3508 to cuff 3506 and/or stent 3502. It may serve other purposes as well.

Partial polymer layer 3545 is illustrated as being disposed on the upstream surface 3520 of fabric layer 3540. Fabric layer 3540 may be a woven fabric, a stabilized woven fabric or a mesh. However, it may be disposed on the downstream surface or on both the upstream and downstream surfaces to provide additional reinforcement and/or other advantages. Partial layer 3545 also is illustrated as covering the entire attachment edge and tabs of leaflet 3508. That need not be the case. It need not be provided at the tabs and/or may be provided as discontinuous dashes or spots of varying compositions, number of layers and thicknesses as previously discussed in connection partial layer 3450 in FIG. 34.

Figure 36:
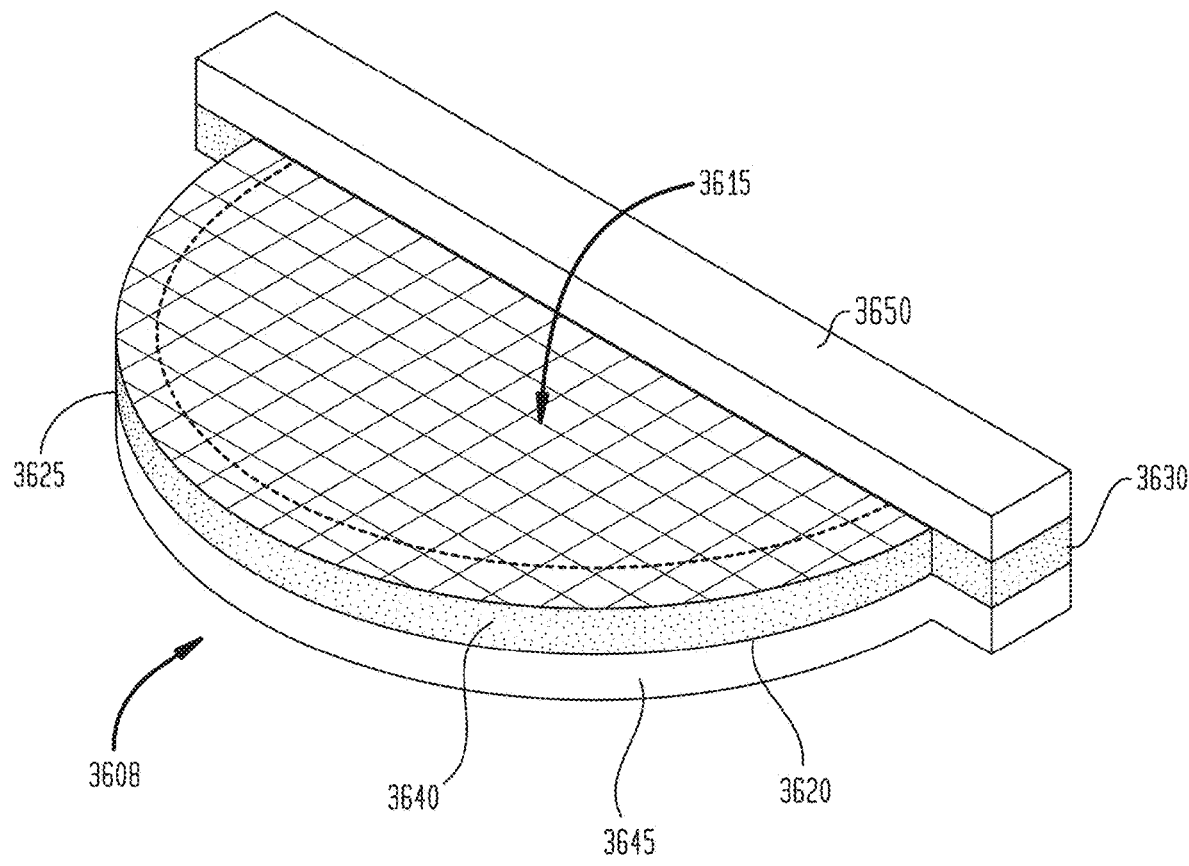
FIG. 36 is a schematic perspective view of a leaflet formed from another partially coated stabilized or non-stabilized woven fabric according to the present disclosure.

FIG. 36 is an amalgam of the leaflets illustrated previously in FIGS. 34 and 35. It includes a fabric layer 3640 having attached to its downstream surface 3615 a partial polymer layer 3650 adjacent its free edge 3630. It also includes a partial polymer layer 3645 on the upstream surface 3620 of fabric layer 3640 adjacent the attachment edge 3625. Fabric layer 3640 may be a woven fabric, a stabilized woven fabric or a mesh.

Figure 37:
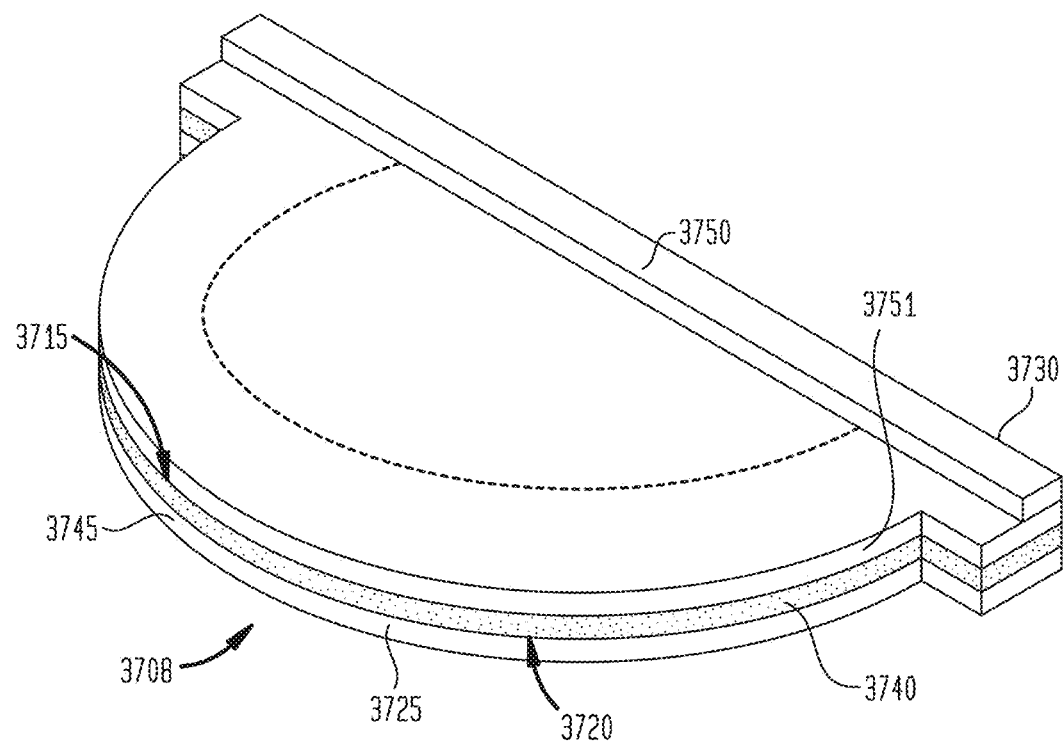
FIG. 37 is a schematic perspective view of a leaflet formed from another partially coated stabilized or non-stabilized woven fabric according to the present disclosure.

FIG. 37 illustrates another embodiment of a leaflet such as described in FIGS. 28-36. Leaflet 3708 includes a fabric layer 3740 having a polymer layer 3751 applied to its entire downstream surface 3715. Adjacent the free edge 3730 is a further partial polymer layer 3750 applied atop/upon layer 3751. Partial layer 3750 may be any layer as previously described, such as, for example, partial layer 3450 in FIG. 34. Leaflet 3708 also includes a partial polymer layer 3745 attached to the upstream surface 3720 of fabric layer 3740 adjacent the attachment edge 3725, generally as described for partial polymer layer 3545 in FIG. 35. Fabric layer 3740 may be a woven fabric, a stabilized woven fabric or a mesh.

As illustrated in FIG. 37, however, the width of polymer layer 3745 adjacent the attachment edge 3725 is much greater than the width of polymer layer 3750 adjacent the free edge 3730 of leaflet 3708. This is meant merely to illustrate the fact that there are partial layers on various surfaces of a leaflet and that they may independently have different widths.

Figure 38:
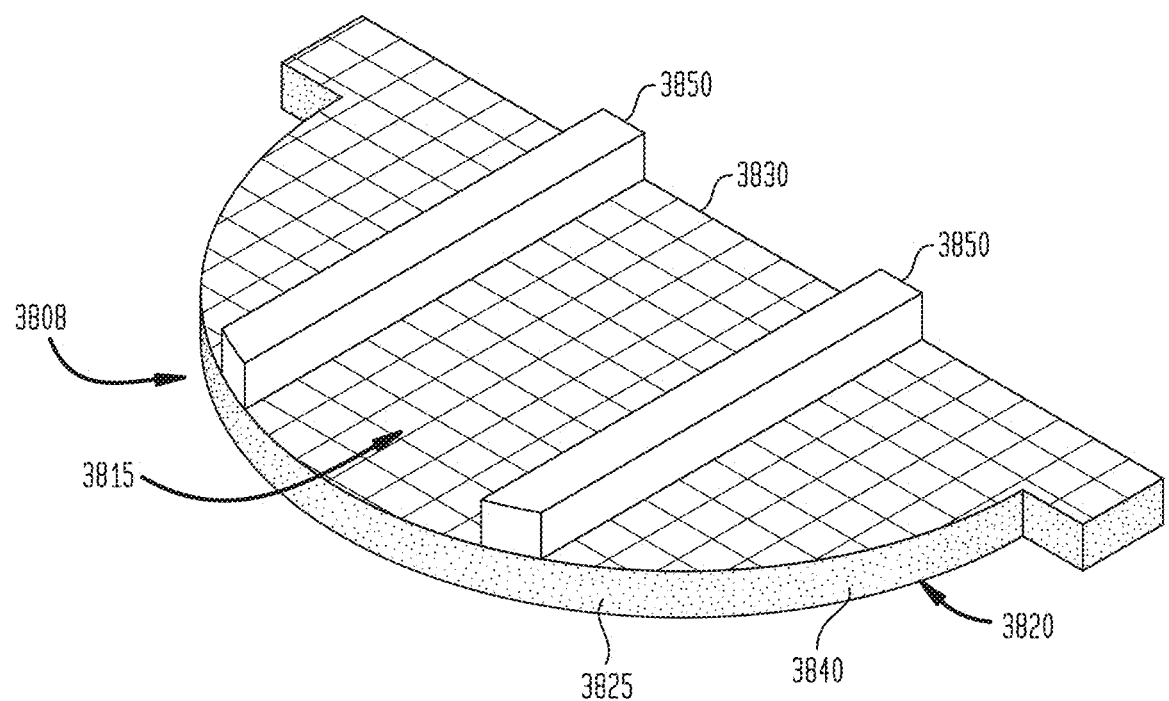
FIG. 38 is a schematic perspective view of a leaflet formed from another partially coated stabilized or non-stabilized woven fabric forming ribs according to the present disclosure.

FIG. 38 illustrates another embodiment of a leaflet 3808 generally as described in FIGS. 28-37. Leaflet 3808 contains a fabric layer 3840 similar to the fabric layers previously described. Fabric layer 3840 may be a woven fabric, a stabilized woven fabric or a mesh. Disposed on the downstream surface 3815 of the leaflet are one or more "ribs" or reinforcing strips 3850 composed of a partial polymer layer. These ribs are shown as running from approximately the attachment edge 3825 to the free edge 3830 of leaflet 3808. Reinforcing ribs 3850 may provide weight and structure to bias the leaflet from an open position back to a closed position. They may also provide some measure of structural rigidity and reinforcement to leaflet 3808. While shown as extending from the attachment edge 3825 of the leaflet to the free edge 3830, that may not be the case. They may extend from attachment edge 3825 approximately halfway along the downstream surface 3815 of the leaflet toward the free edge 3830. Similarly, they may extend from adjacent free edge 3830 approximately 30% of the way along the downstream surface of fabric layer 3840 toward the attachment edge 3825. Ribs 3850 may be of any length, thickness, width, number of polymer layers and composition.

While ribs 3850 are shown applied to the downstream surface 3815 of fabric layer 3840, they could be applied to the upstream surface 3820 thereof instead of, or in addition to, their application to the downstream surface. Moreover, the entire downstream surface of the leaflet in FIG. 38 may be coated with an additional polymer layer (not shown) to provide a smooth, if undulating, surface topography. A similar polymer layer could be provided on the upstream surface of the leaflet if ribs 3850 were applied to upstream surface 3820.

Figure 39:
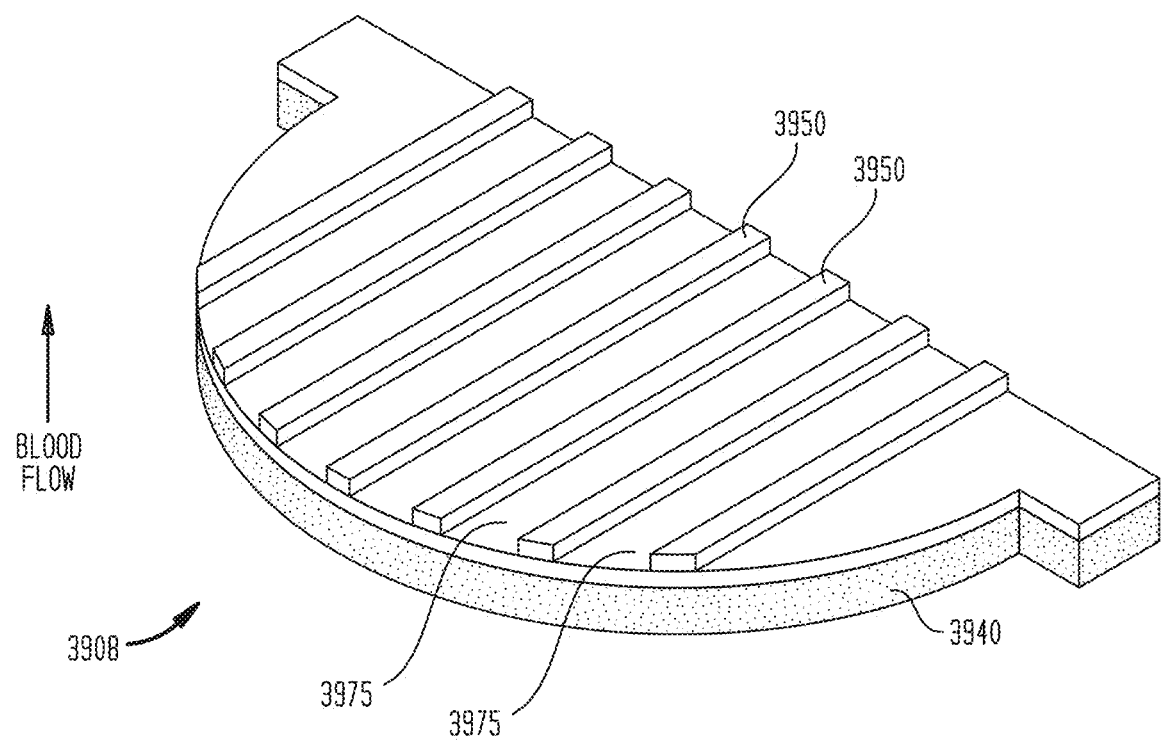
FIG. 39 is a schematic perspective view of a leaflet formed from another partially coated stabilized or non-stabilized woven fabric forming ribs according to the present disclosure.

This concept of reinforcing ribs is further illustrated in FIG. 39 in which leaflet 3908 contains a plurality of ribs 3950 again extending from adjacent the attachment edge to the free edge of fabric layer 3940. Fabric layer 3940 may be a woven fabric, a stabilized woven fabric or a mesh. In addition to providing reinforcement, shape and biasing as previously described in connection with the leaflet in FIG. 38, the spaces 3975 between ribs 3950 may act as folding regions helping to provide a controlled fold of the leaflet when the prosthetic heart valve is collapsed for loading into a catheter for transcatheter or transapical delivery. In a variant hereof, leaflet 3908, or any leaflet described herein, whether coated or uncoated, may be scored on its upstream surface or downstream surface, such as with a laser, to produce a pattern on the surface. Such pattern may facilitate folding of the leaflet during collapsing of the prosthetic heart valve, may increase the flexibility of the leaflet for opening and closing during use, or may improve the performance of the leaflet in other ways.

Figure 40:
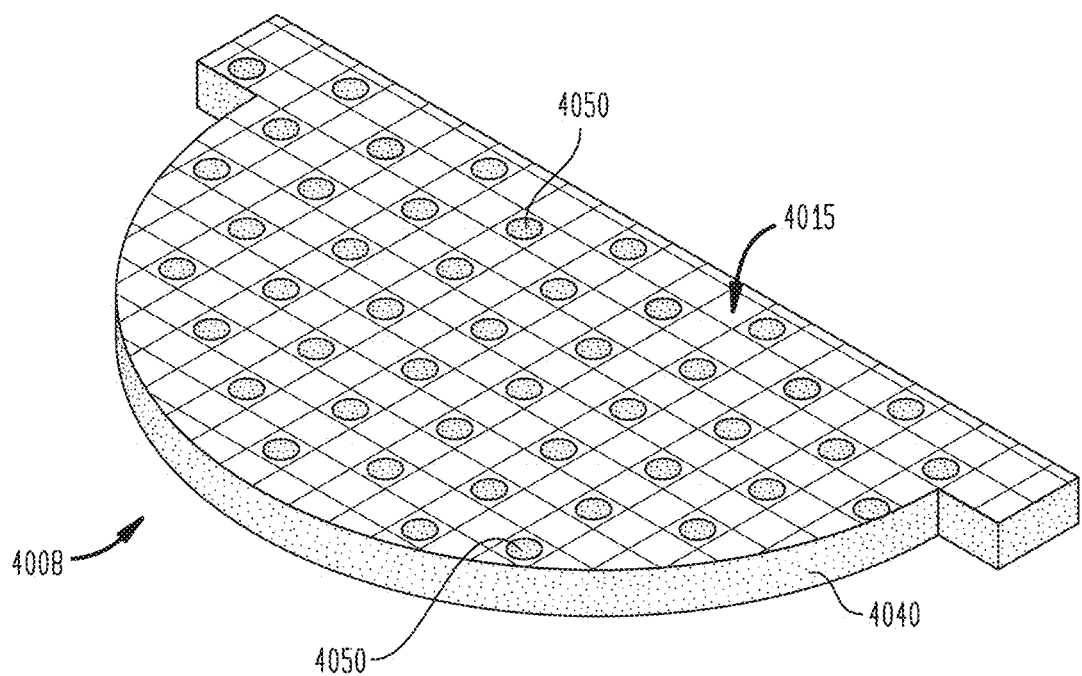
FIG. 40 is a schematic perspective view of a leaflet formed from another partially coated stabilized or non-stabilized woven fabric forming spots according to the present disclosure.

FIG. 40 illustrates another leaflet embodiment. Here, leaflet 4008 comprises a fabric layer 4040 having a downstream surface 4015 to which are attached one or more polymer dots or spots 4050. Fabric layer 4040 may be a woven fabric, a stabilized woven fabric or a mesh. Like the polymer ribs illustrated in FIGS. 38 and 39, the spots 4050 may provide weight to help bias the leaflet to a closed position in operation. Spots 4050 may also provide selective reinforcement and/or abrasion resistance. While shown as spots or dots in FIG. 40, these spots could be present in any number and in any shape such as, without limitation, crosses, lines, dashes, polygons, etc. In this instance, spots may be spots of adhesive or bundles of intersections as well providing both biasing weight and stability to a woven fabric if used to form the leaflet.

FIGS. 41, 41A, and 41B illustrate other partial coating arrangements for a leaflet. In FIG. 41, partial polymer coatings are disposed on the downstream surface 4115 of the fabric layer 4140 of leaflet 4108. Fabric layer 4140 may be a woven fabric, a stabilized woven fabric or a mesh. A first semicircular polymer coating area 4150 of a predetermined width may be comprised of five individual polymer layers, which may be the same or different in composition and thickness. Disposed relatively inwardly toward the free edge 4130 of leaflet 4108 is a second concentric semicircular partial coated area 4151 comprised of three different polymer layers. These layers may have the same composition and thickness or a different composition and/or thickness from those used in partial coated area 4150. They may have the same or a different width as well. Finally, further inwardly and closer free edge 4130 is partial coated area 4152 composed of a single polymer layer. Partial coated area 4152 may be made of one of the polymers used in partial coated areas 4150 or 4151 or may be made of a different material altogether. It may have a width that is the same as or different from areas 4150 and 4151. The area directly adjacent free edge 4130 in this embodiment is uncoated. This entire structure could be coated with an additional continuous layer that would provide a smoother surface, albeit one gradually getting thinner from the attached edge 4125 to free edge 4130.

FIG. 41A shows a similar construction, however, coating area 4151 is disposed on the upstream surface 4120 of the leaflet as opposed to the downstream surface 4115. Partial coated area 4150 composed of five individual polymer layers and partial coated area 4152 composed of a single polymer layer are disposed on the downstream surface 4115.

FIG. 41B shows a similar construction, however, instead of being semicircular or forming a rainbow, the coated areas are formed in parallel strips, with the first strip 4150 running roughly parallel to the free edge 4130 composed of five individual polymer layers, the next strip 4151 composed of three layers and the last area 4152 composed of a single layer.

Figure 42:
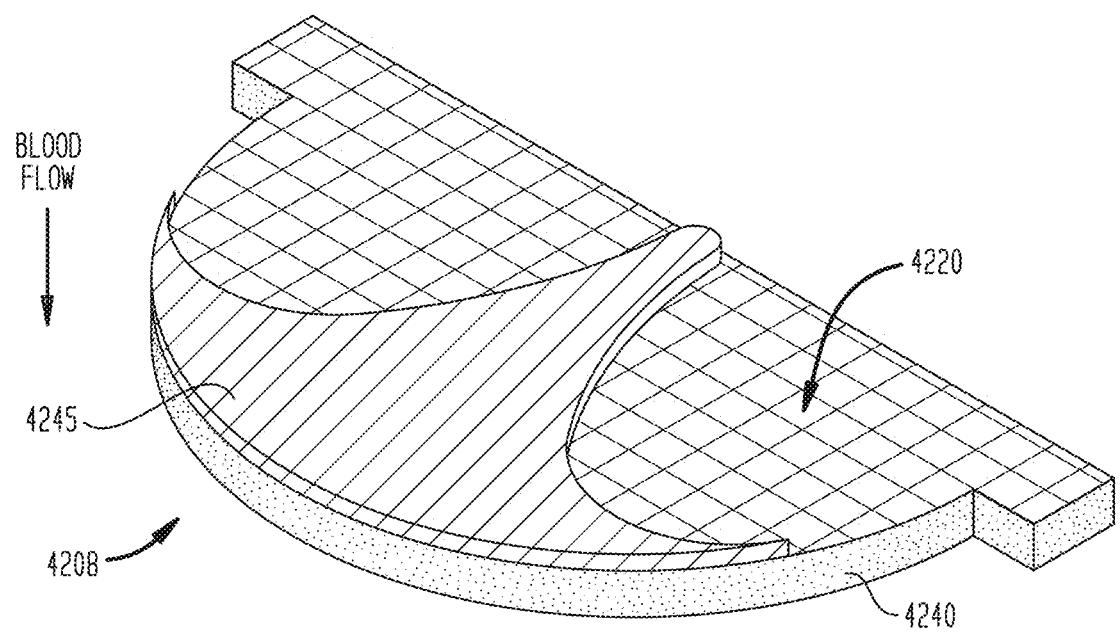
FIG. 42 is a schematic perspective view of a leaflet formed from another partially coated stabilized or non-stabilized woven fabric according to the present disclosure.

FIG. 42 illustrates a partial coating on a fabric leaflet 4208 disposed on the upstream side of the leaflet. In particular, leaflet 4208 is shown comprising a fabric layer 4240 and applied to its upstream surface 4220 is a reinforcing partial polymer coating 4245. This structure is made of a partial coating of at least one polymer layer, and possibly a plurality of polymer layers, in any shape or size as described in FIGS. 28-41. Fabric layer 4240 may be a woven fabric, a stabilized woven fabric or a mesh.

Figure 43:
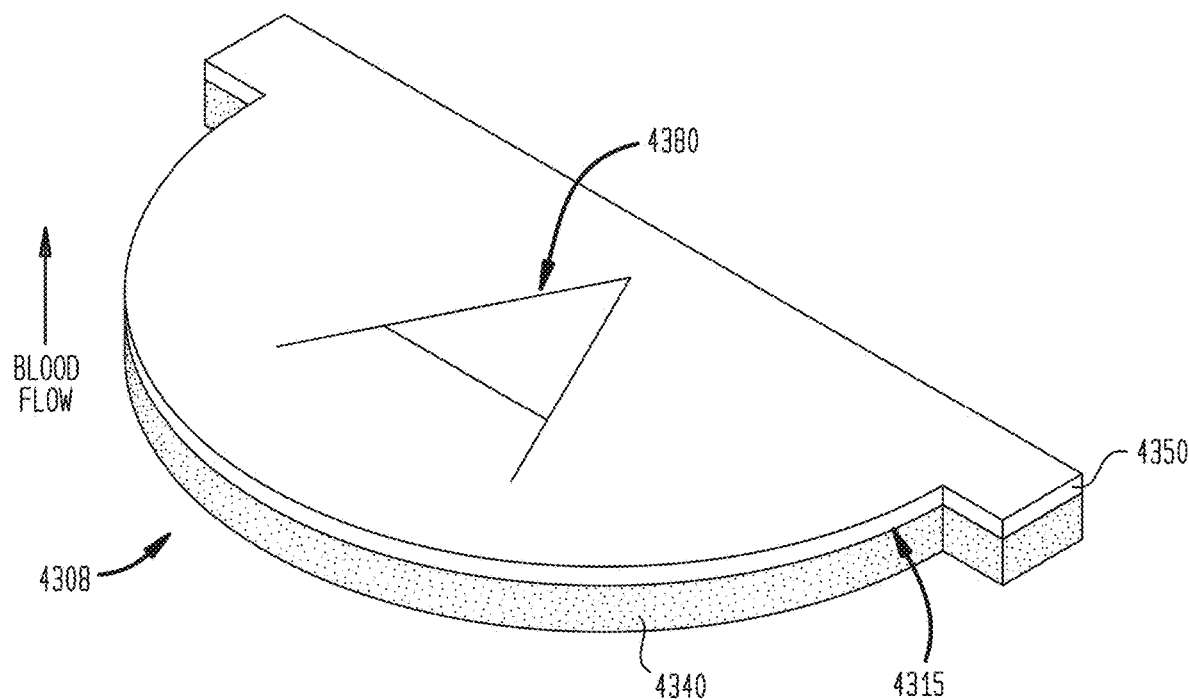
FIG. 43 is a schematic perspective view of a leaflet formed from another coated stabilized or non-stabilized woven fabric incorporating indicia according to the present disclosure.
Figure 43A:
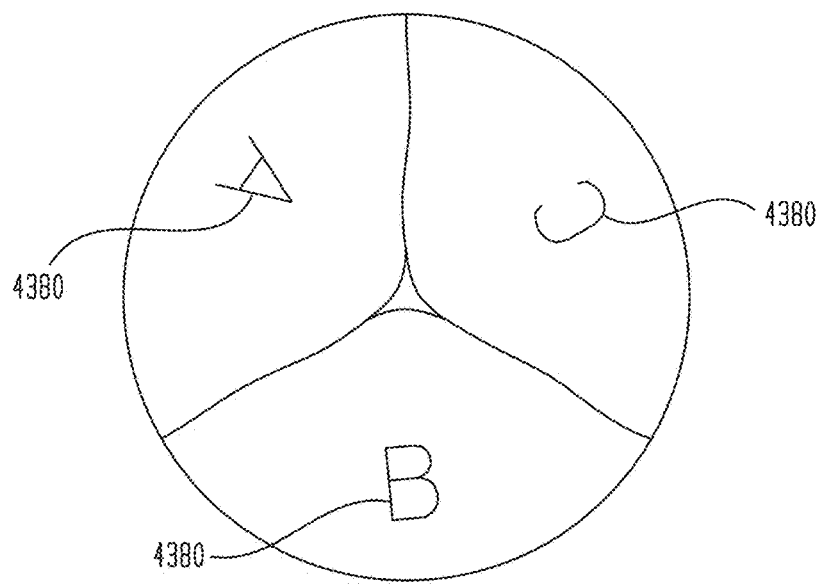
FIG. 43A is a highly schematic transverse cross-section of a prosthetic heart valve incorporating a plurality of the leaflets of FIG. 43.

The leaflet 4308 in FIGS. 43 and 43A is similar in structure to a leaflet described in connection with FIG. 29, except that the polymer layer 4350 is disposed on the downstream surface 4315 of fabric layer 4340. Fabric layer 4340 may be a woven fabric, a stabilized woven fabric or a mesh. Leaflet 4308, however, contains one or more indicia 4380 that may be apparent visually to the naked eye, may be radiopaque to make it visible during surgery when the device is implanted within a patient's anatomy, or both. Indicia 4380 may help a surgeon position and orient the valve as needed and may assist in visualizing the movement of the leaflet to show an operable valve. Letters are used as the indicia 4380 in FIG. 43, but numbers, Roman numerals, symbols, or any other relevant indicia may be used as well. FIG. 43A is a view of a coapted set of leaflets such as shown in FIG. 3. It illustrates the use of a plurality of indicia 4380 individually on each leaflet 4308. The indicia may be embedded within polymer layer 4350, may be sandwiched between adjacent polymer layers, or may be disposed between polymer layer 4350 and fabric layer 4340.

Figure 44:
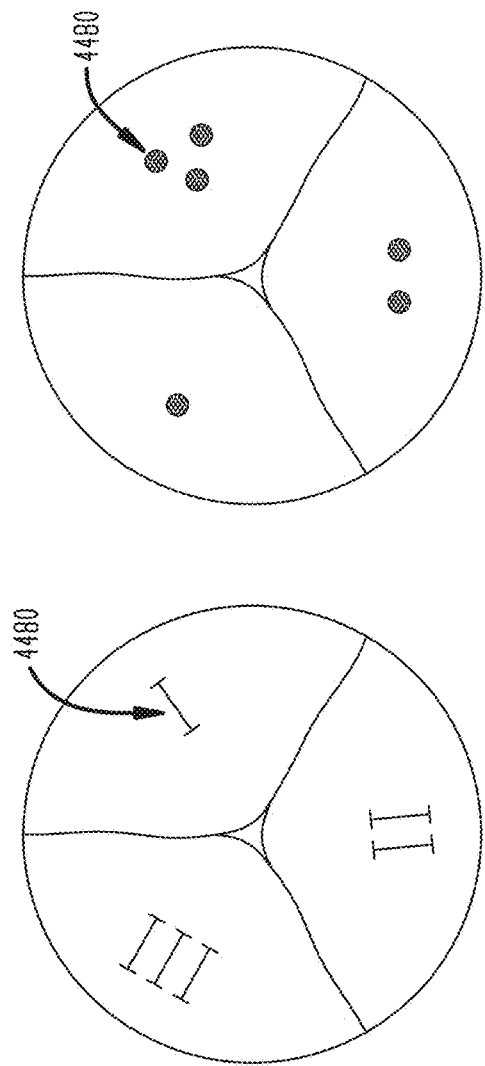
FIG. 44 is a schematic perspective view of a leaflet formed from another uncoated stabilized or non-stabilized woven fabric incorporating indicia according to the present disclosure.
Figure 44C:
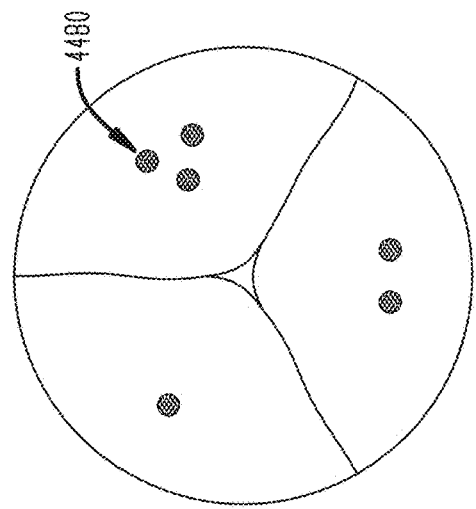
FIGS. 44A-44C are highly schematic transverse cross-sections of a prosthetic heart valve incorporating a plurality of the leaflets of FIG. 44 with different indicia.
Figure 44B:
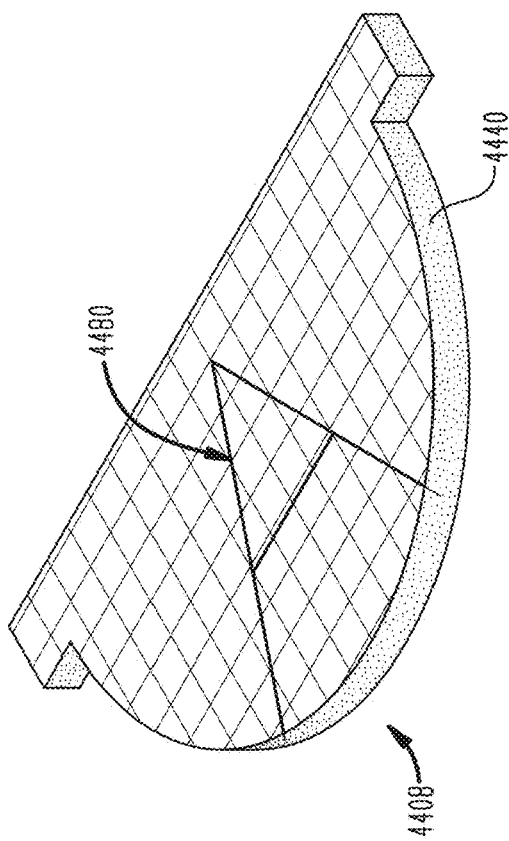
Figure 44A:
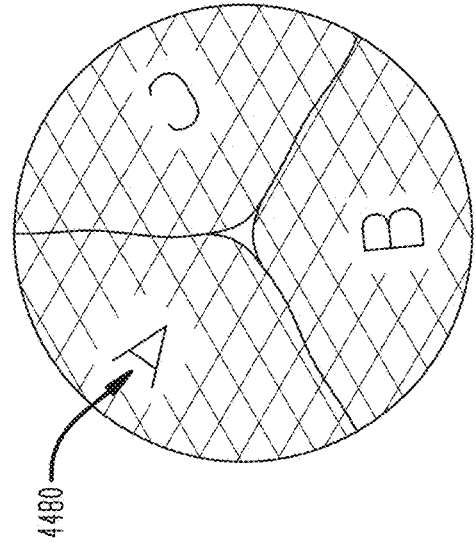

FIGS. 44, 44A, 44B, and 44C illustrate an embodiment similar to that shown in FIG. 43. Leaflet 4408, however, is an uncoated fabric composed entirely of fabric layer 4440. Woven into that fabric, melted or otherwise embedded into the fabric, or glued or otherwise applied to a surface of the fabric may be visual and/or radiopaque indicia 4480. FIG. 44A shows an embodiment like that shown in FIG. 43A, in which indicia 4480 constitute a plurality of letters. FIG. 44B shows indicia 4480 as Roman numerals, and FIG. 44C shows the indicia as a series of dots. These indicia could also be made using wires that are used to spot weld various intersections of a woven fabric as noted elsewhere.

Figure 45:
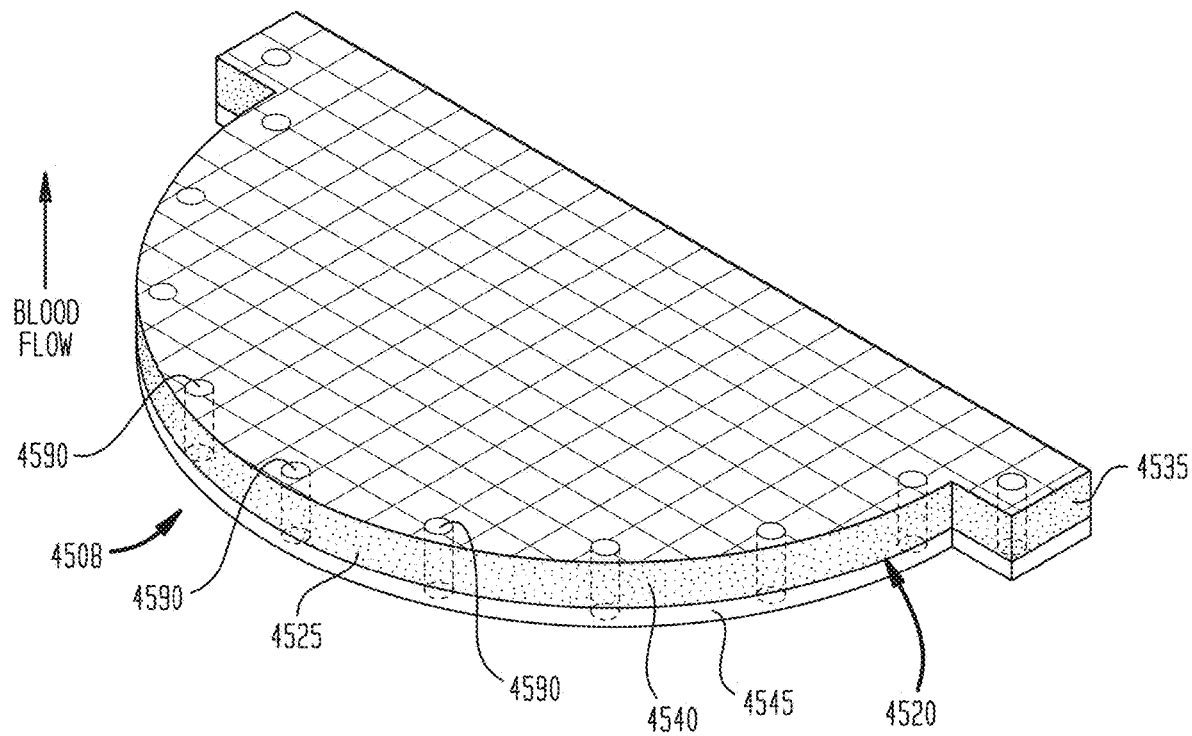
FIG. 45 is a schematic perspective view of a leaflet formed from another partially coated stabilized or non-stabilized woven fabric incorporating holes according to the present disclosure.
Figures 45A, 45B:
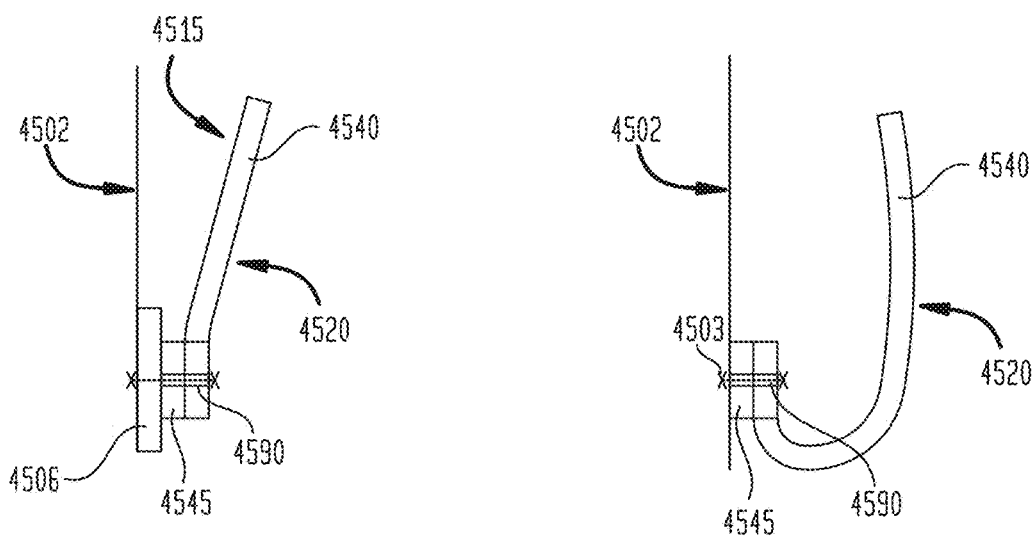
FIG. 45A is a schematic partial cross-section of a stent and a valve assembly including a cuff and the leaflet of FIG. 45.
FIG. 45B is a schematic partial cross-section of a stent and a valve assembly incorporating the leaflet of FIG. 45.

FIGS. 45, 45A and 45B illustrate a leaflet as previously described in connection with FIG. 35. Leaflet 4508 includes a fabric layer 4540 and attached to its upstream surface 4520 adjacent attachment edge 4525 is a polymer layer 4545, which partially coats the upstream surface 4520 of the fabric layer. Fabric layer 4540 may be a woven fabric, a stabilized woven fabric or a mesh. Additionally, leaflet 4508 includes a number of holes 4590 disposed adjacent attachment edge 4525 and through both fabric layer 4540 and partial polymer layer 4545. These holes 4590 may facilitate suturing, lacing or other attachment of leaflet 4508 to the support structure. Holes 4590 may also be formed in the leaflet tabs 4535 to facilitate the attachment or lacing of the leaflet commissures to one another by aligning the holes in adjacent leaflet tabs, as well as the attachment of the leaflets to the stent. Holes 4590 may be formed by laser drilling, a process that locally melts the polymer fabric and polymer layer forming a smooth, tough, abrasion resistant surface, much like a grommet, that can provide resistance to damage caused by the passage of sutures therethrough during the suturing process. These holes or grommets 4590 may be coated with a more lubricous coating or polymer material that is permanent or one that can be removed to further improve the suturing process and prevent damage to the leaflet. Moreover, the laser drilling process may melt the various layers together in a localized area, which could help prevent fraying or damage. While laser drilled holes have been described, the holes may be produced by any other means as well, such as molding, mechanical or water jet drilling, and the like.

FIG. 45A shows a partial cross-sectional view of a stent with an attached valve assembly as previously described. In this view, stent 4502 has a cuff 4506 attached to its luminal surface. Leaflet 4508 composed of fabric layer 4540 contains a partial polymer layer 4545 on its downstream surface 4515, which is disposed between the cuff and the fabric layer

4540. Fabric layer 4540 may be a woven fabric, a stabilized woven fabric or a mesh. Leaflet 4508 contains grommets 4590 through which the leaflet is sutured or laced to cuff 4506, stent 4502, or both. Grommets may also be formed in a pattern in cuff 4506 to facilitate the attachment of the cuff to the stent. FIG. 45B shows a similar arrangement in which the device contains no cuff and a partial polymer layer 4545 is disposed on the upstream side 4520 of leaflet 4508, as illustrated in FIG. 45. Grommets 4590 are provided through both fabric layer 4540 and partial polymer layer 4545, enabling the leaflet to be sutured or laced via suture 4503 to the stent 4502. Grommets have been described here in connection with partially coated leaflets. However, these grommets could be formed in fully coated or completely uncoated leaflets, in coated or uncoated cuffs, and in any portion of a medical device that may be attached to a support structure by a suture.

Figure 46:
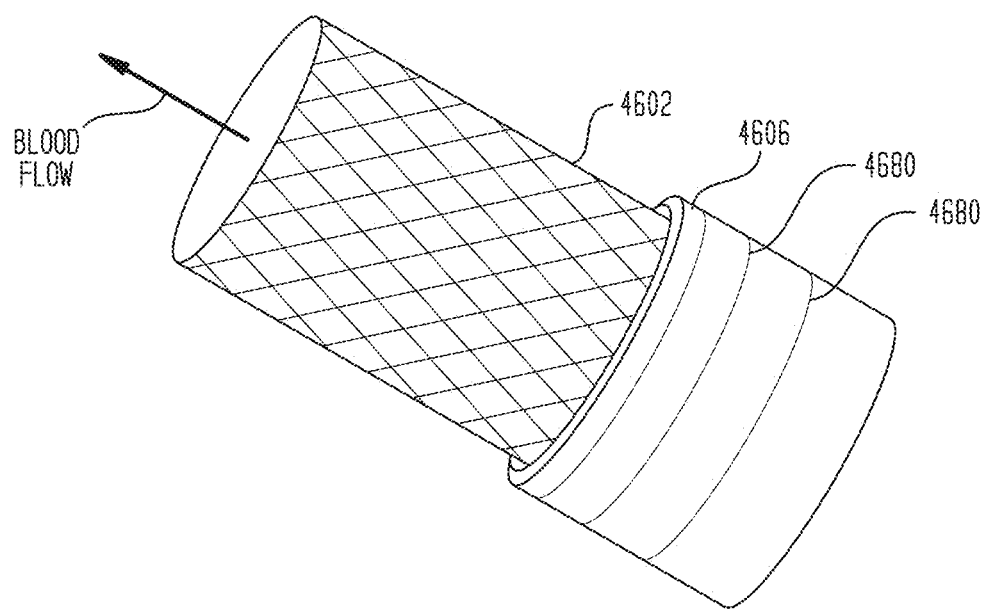
FIG. 46 is a schematic perspective view of a stent having a cuff formed from a coated stabilized or non-stabilized woven fabric incorporating radiographic bands according to the present disclosure.
Figure 46A:
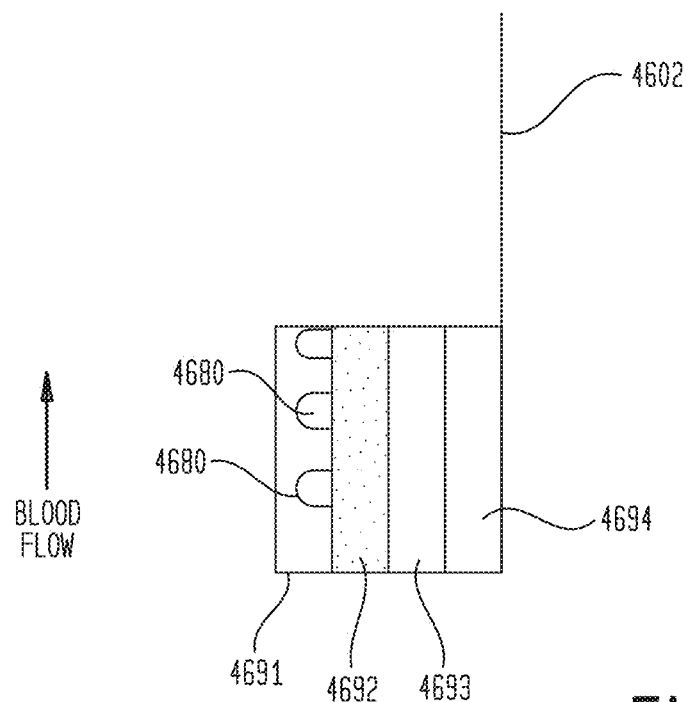
FIG. 46A is a schematic partial cross-section of the stent and cuff of FIG. 46.

FIG. 46 illustrates a stent 4602 containing a cuff 4606 on its abluminal or exterior surface. Cuff 4606 contains a plurality of indicia, in this case, radiopaque bands 4680 disposed at various intervals to assist the surgeon in placement of the prosthetic valve. The structure of cuff 4606 is illustrated in more detail in FIG. 46A. Attached to the exterior of stent 4602, and provided for illustrative purposes only, cuff 4606 has four layers. The outermost layer 4691 is a polymer layer covering the entire exterior surface of cuff 4606. The next innermost layer is a fabric layer 4692. Disposed between the fabric layer 4692 and outermost polymer layer 4691 are the circumferential radiopaque and/or visual indicia 4680. Between the fabric layer 4692 and stent 4602 are two additional polymer layers 4693 and 4694. Each of layers 4691, 4693 and 4694 may be composed of the same or different polymer materials or may have the same or different dimensions and thicknesses as previously described in connection with the leaflets described in FIGS. 28-45. The fabric layers may be a woven fabric, a stabilized woven fabric or a mesh.

Figure 47:
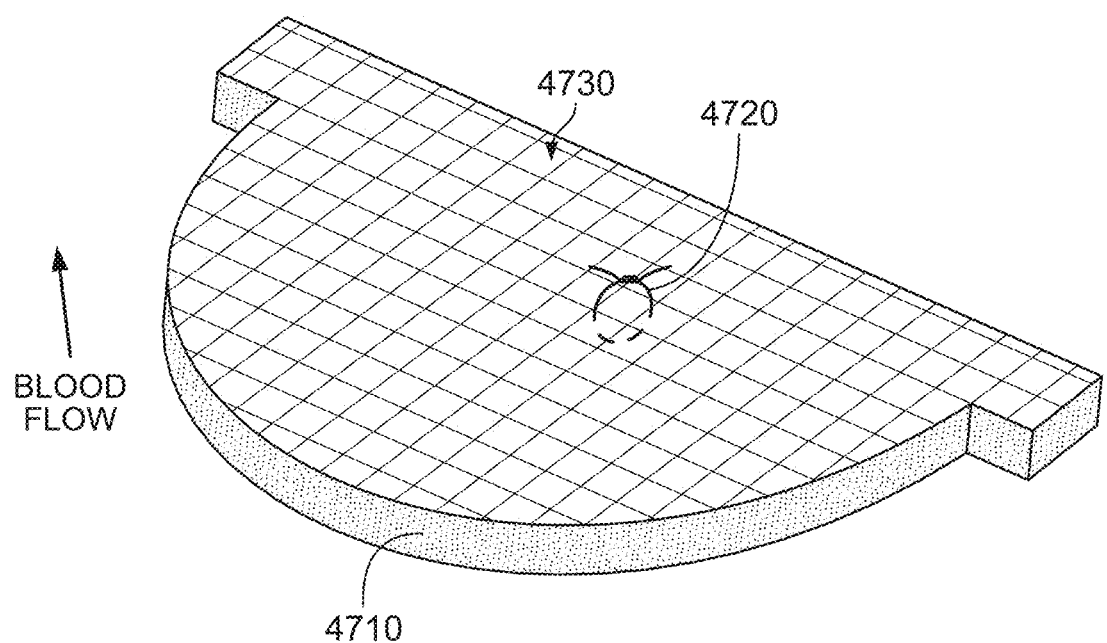
FIG. 47 is a schematic perspective view of a leaflet formed from a stabilized or non-stabilized woven fabric according to the present disclosure including a single stitch in a major surface of a leaflet.

FIG. 47 shows a leaflet 4710 formed from a woven fabric according to the present disclosure including a single stitch 4720 disposed through a major surface 4730 of the leaflet. A mesh could be used instead of a woven fabric.

Figure 48:
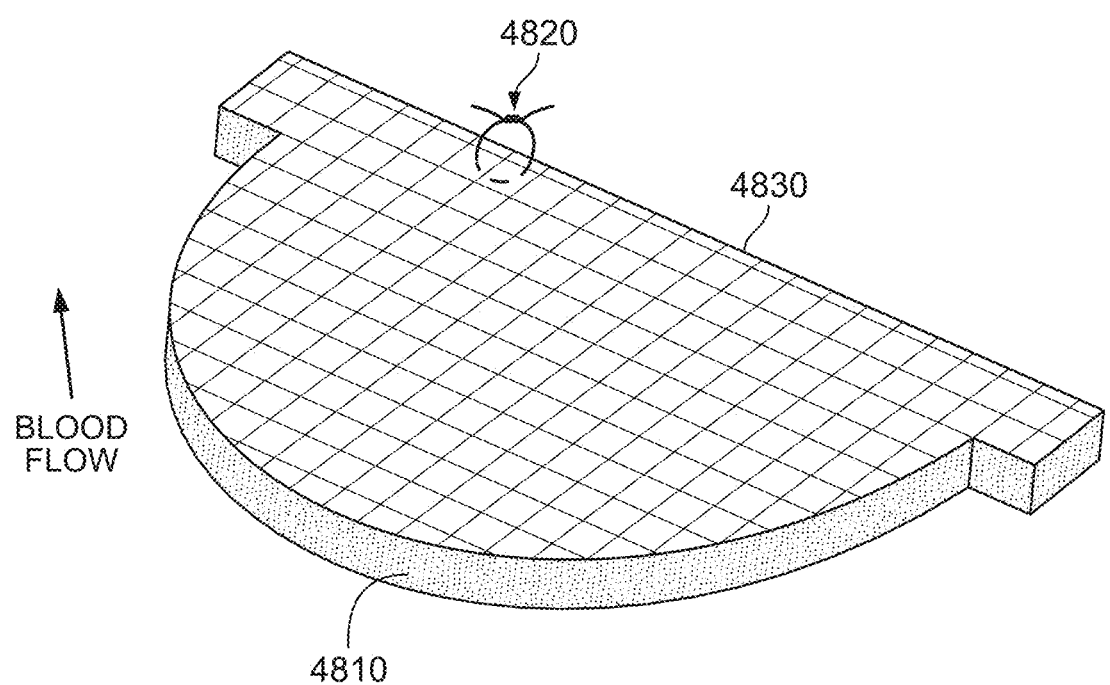
FIG. 48 is a schematic perspective view of a leaflet formed from a stabilized or non-stabilized woven fabric according to the present disclosure including a single stitch in the free edge of a leaflet.

FIG. 48 shows a leaflet 4810 of a leaflet formed from a fabric according to the present disclosure including a single stitch 4820 in the free edge 4830 of the leaflet. The fabric layer may be a woven fabric, a stabilized woven fabric or a mesh.

Figure 49:
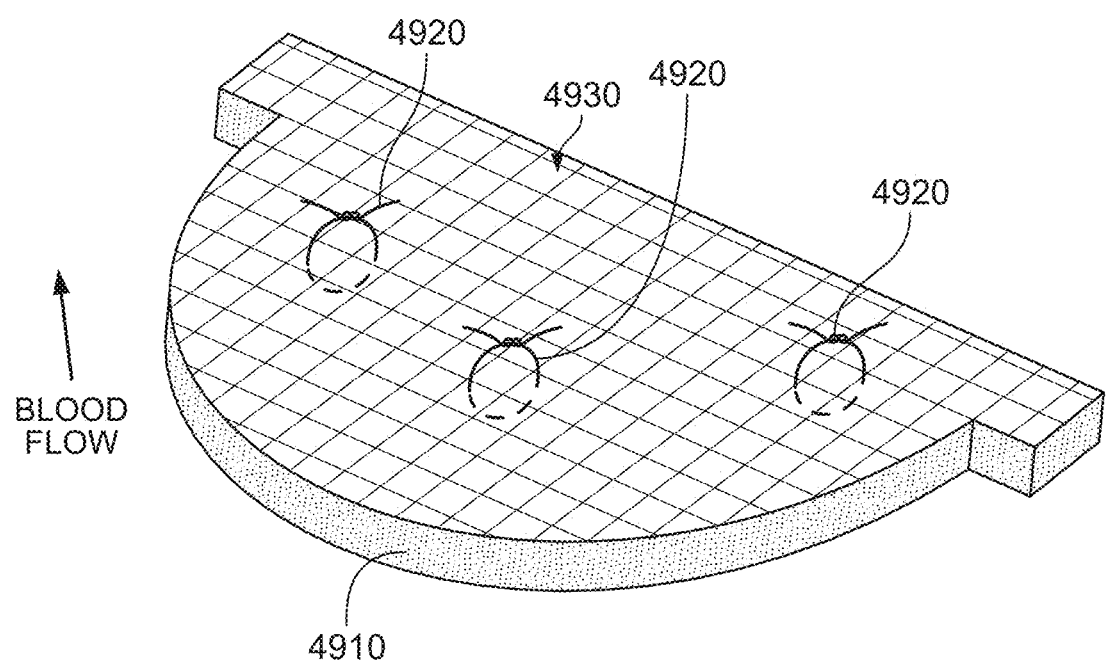
FIG. 49 is a schematic perspective view of a leaflet formed from a stabilized or non-stabilized woven fabric according to the present disclosure including multiple stitches on a major surface of a leaflet.

FIG. 49 shows a leaflet 4910 of a leaflet formed from a fabric according to the present disclosure including multiple stitches 4920 on a major surface 4930 of the leaflet. The fabric layer may be a woven fabric, a stabilized woven fabric or a mesh.

Figure 50:
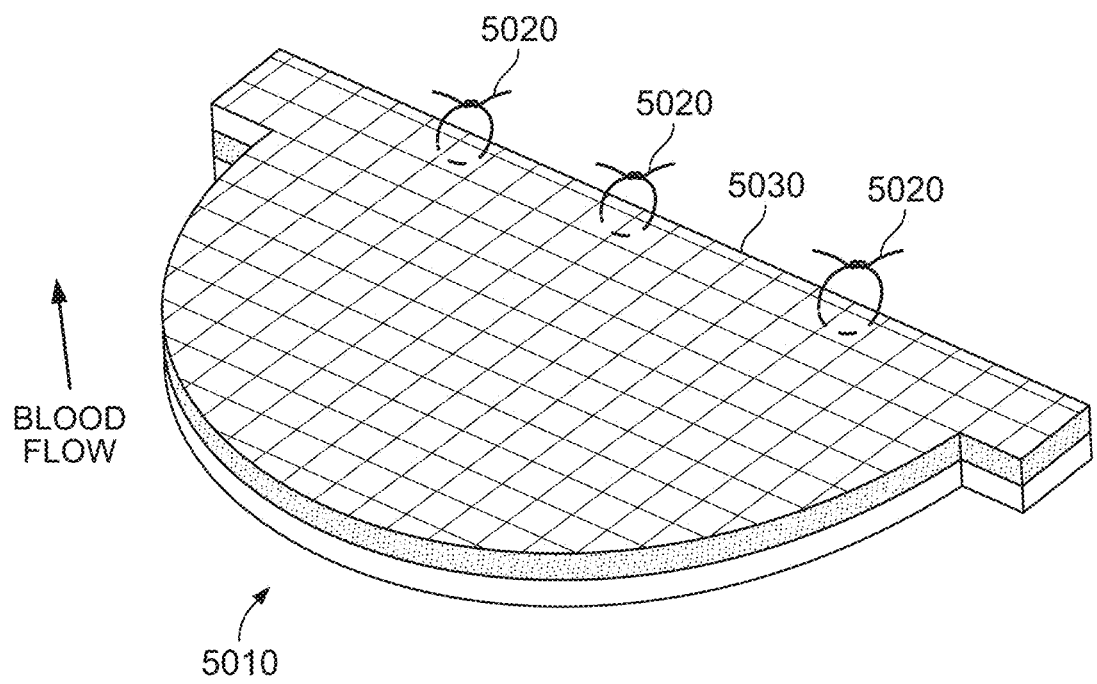
FIG. 50 is a schematic perspective view of a leaflet formed from a stabilized or non-stabilized woven fabric according to the present disclosure including a woven fabric layer and coating layer having multiple stitches in the free edge of a leaflet.

FIG. 50 shows a leaflet 5010 formed from a fabric according to the present disclosure including multiple stitches 5020 along the free edge 5030 of the leaflet. Leaflet 5010 is illustrated with a partial or complete coating and/or layer positioned on one major surface of the fabric layer. Stitches 5020 may pass through the fabric, the coating, or both. The fabric layer may be a woven fabric, a stabilized woven fabric or a mesh.

Figure 51:
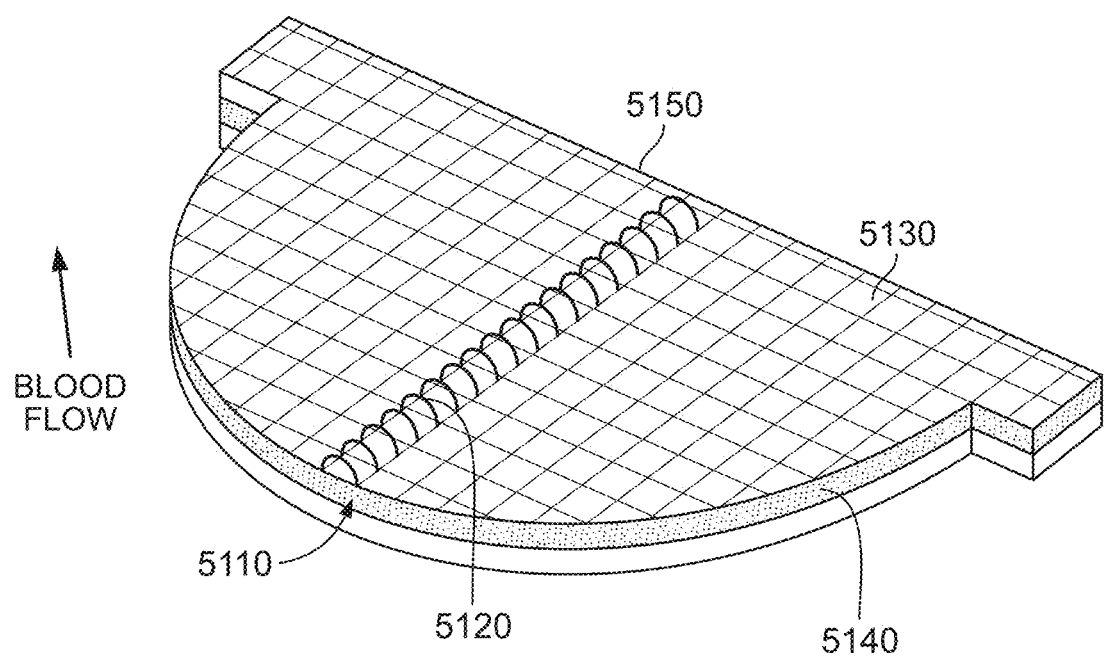
FIG. 51 is a schematic perspective view of a leaflet formed from a stabilized or non-stabilized woven fabric according to the present disclosure including a woven fabric layer and coating layer having a single suture line extending across a major surface of a leaflet from the attachment edge to the free edge.

FIG. 51 shows a leaflet 5110 formed from a fabric according to the present disclosure including a suture line 5120 extending across a major surface 5130 of the leaflet from the attachment edge 5140 to the free edge 5150. Leaflet 5110 is illustrated with a partial or complete coating and/or layer positioned on the fabric as noted in FIG. 50. Suture line 5120 may pass through the fabric, the coating, or both. By varying the density and number of the stitches, by varying their relative width, and by using sutures of different materials and constructions, one can impart varying degrees of reinforcement, impart or preserve a three dimensional shape, such as the "belly" or "spinnaker" like shape of a native leaflet, or may bias the leaflet into a closed position. The fabric layer may be a woven fabric, a stabilized woven fabric or a mesh.

Figure 52:
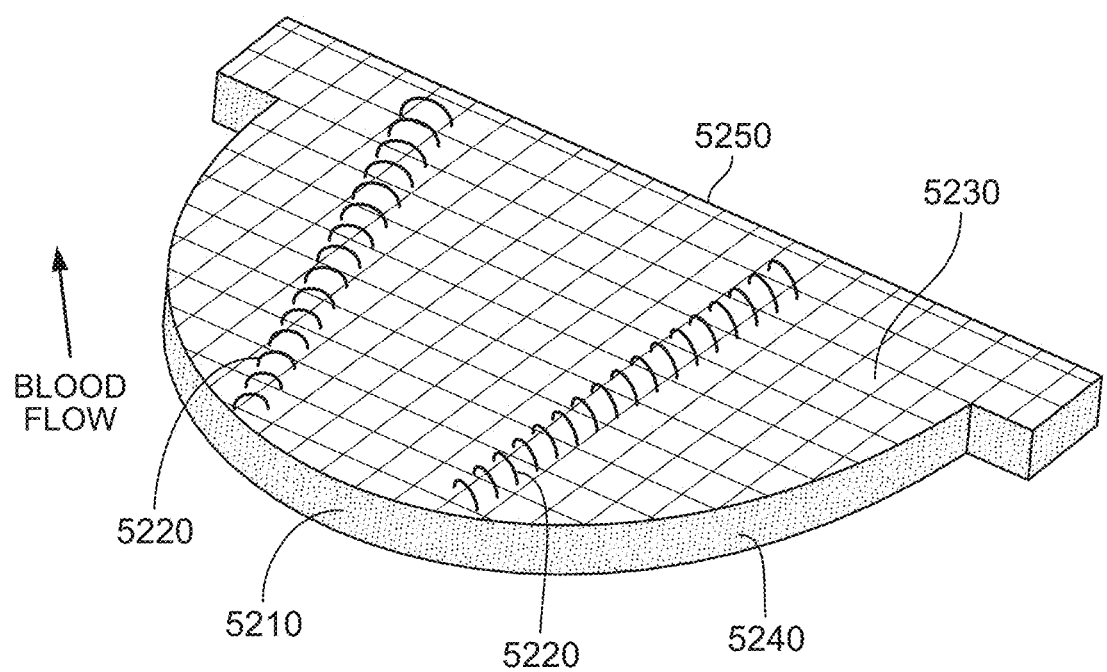
FIG. 52 is a schematic perspective view of a leaflet formed from a stabilized or non-stabilized woven fabric according to the present disclosure including a plurality of suture lines extending across a major surface of a leaflet from the attachment edge to the free edge.

FIG. 52 shows a leaflet 5210 formed from a fabric according to the present disclosure including a plurality of suture lines 5220 extending across a major surface 5230 of the leaflet from the attachment edge 5240 to the free edge 5250. The fabric layer may be a woven fabric, a stabilized woven fabric or a mesh.

Figure 53:
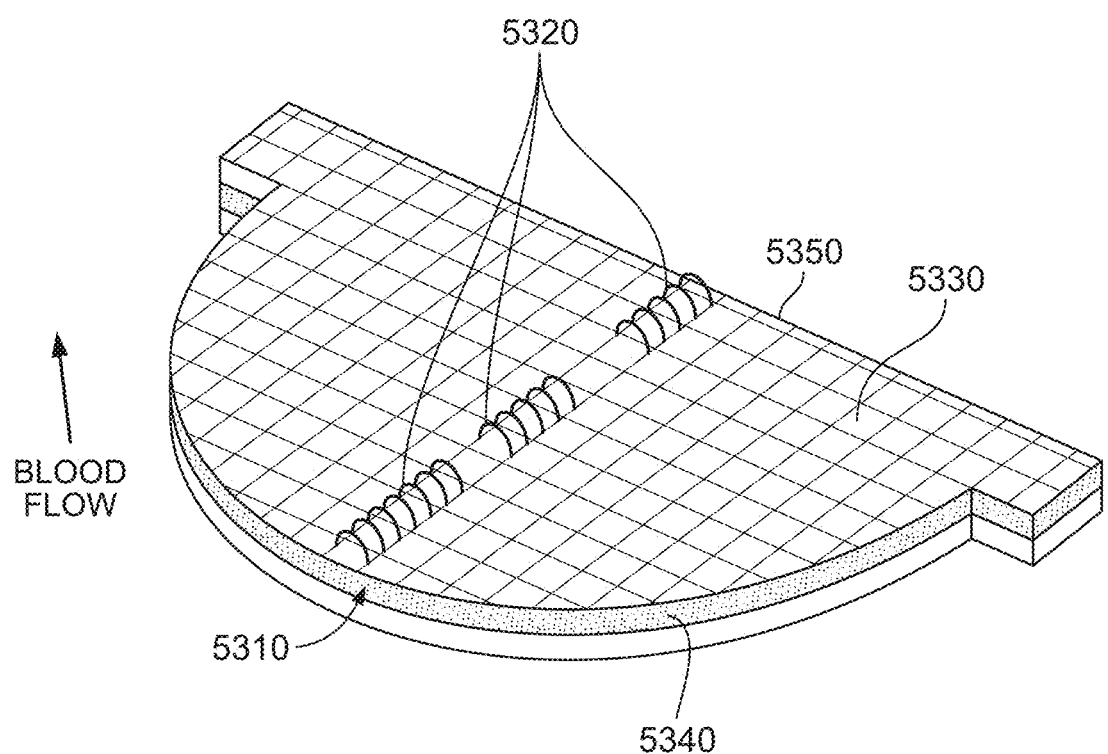
FIG. 53 is a schematic perspective view of a leaflet formed from a stabilized or non-stabilized woven fabric according to the present disclosure including a fabric layer and coating layer having a discontinuous suture line extending across a major surface of a leaflet from the attachment edge to the free edge.

FIG. 53 shows a leaflet 5310 formed from a fabric according to the present disclosure including a discontinuous suture line 5320 extending across a major surface 5330 of the leaflet from the attachment edge 5340 to the free edge 5350. Leaflet 5310 is illustrated with a partial or complete coating and/or layer positioned on the fabric. Suture line 5320 may pass through the fabric, the coating, or both. In additions to the functions described in connection with FIG. 51, the use of discontinuous sutures can create regions of relatively greater and lesser flexibility along the suture line. The fabric layer may be a woven fabric, a stabilized woven fabric or a mesh.

Figure 54:
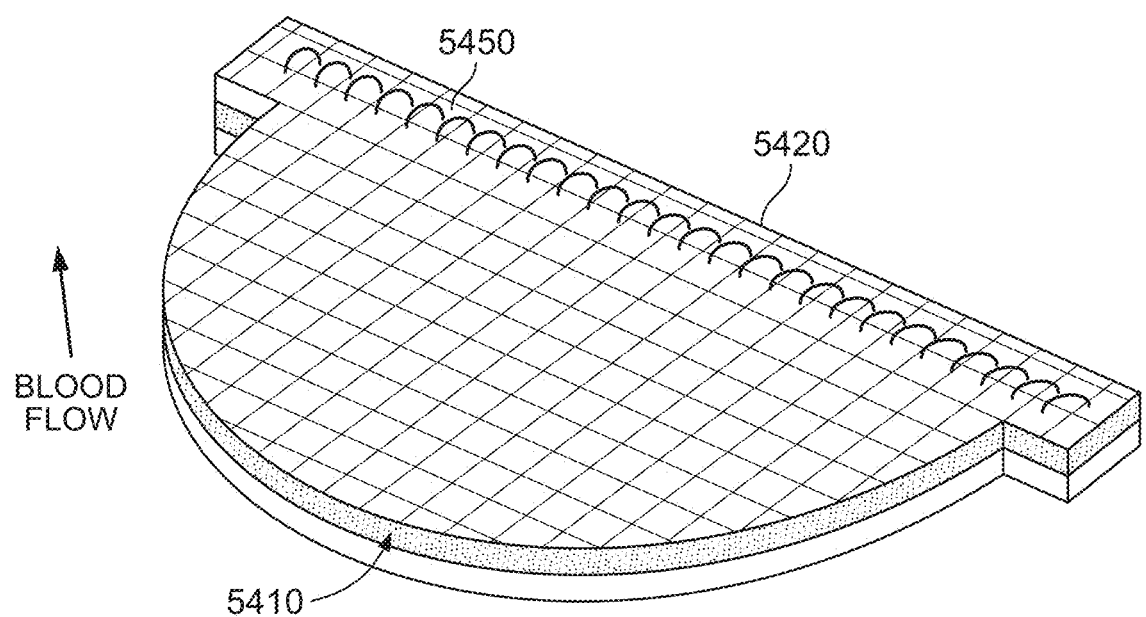
FIG. 54 is a schematic perspective view of a leaflet formed from a stabilized or non-stabilized woven fabric according to the present disclosure including a fabric layer and coating layer having a single suture line extending along the free edge of a leaflet.

FIG. 54 shows a leaflet 5410 formed from a fabric according to the present disclosure including a suture line 5420 extending along the free edge 5450 of the leaflet. Leaflet 5410 is illustrated with a partial or complete coating and/or layer positioned on the fabric. Suture line 5420 may pass through the fabric, the coating, or both. The fabric layer may be a woven fabric, a stabilized woven fabric or a mesh.

Figure 55:
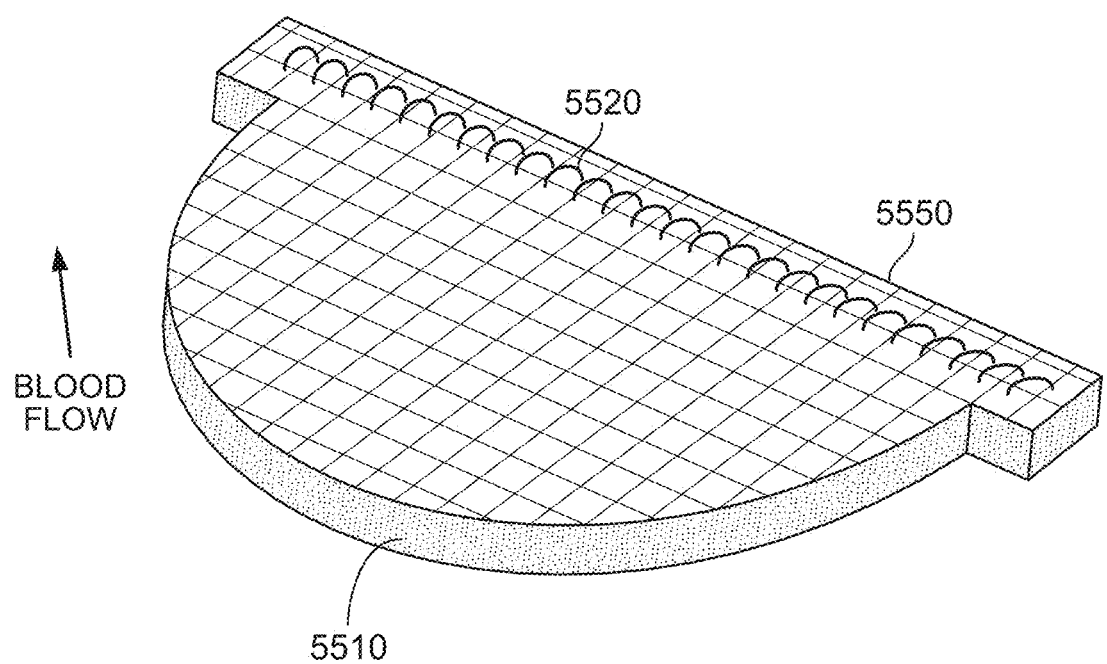
FIG. 55 is a schematic perspective view of a leaflet formed from a stabilized or non-stabilized woven fabric according to the present disclosure including a discontinuous suture line extending along the free edge of a leaflet.

FIG. 55 shows a leaflet 5510 formed from a fabric according to the present disclosure including a discontinuous suture line 5520 extending along the free edge 5550 of the leaflet. The fabric layer may be a woven fabric, a stabilized woven fabric or a mesh.

Figure 56:
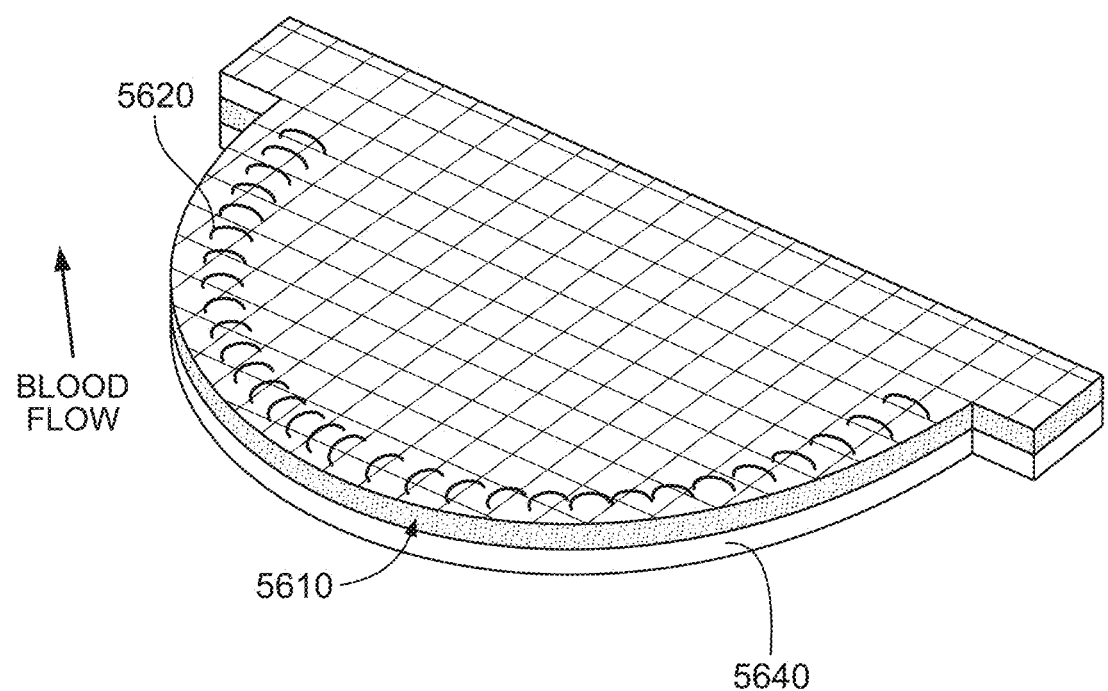
FIG. 56 is a schematic perspective view of a leaflet formed from a stabilized or non-stabilized woven fabric according to the present disclosure including a woven fabric layer and coating layer having a single suture line extending along the attachment edge of a leaflet.

FIG. 56 shows a leaflet 5610 formed from a fabric according to the present disclosure including a suture line 5620 extending along the attachment edge 5640 of the leaflet. In addition to the functions noted above for suture lines, this suture line can in addition or instead provide benefits in attaching the leaflet by providing reinforcement through which attachment sutures will pass. It could also assist in preventing the fabric from unravelling over time. The fabric layer may be a woven fabric, a stabilized woven fabric or a mesh.

Figure 57:
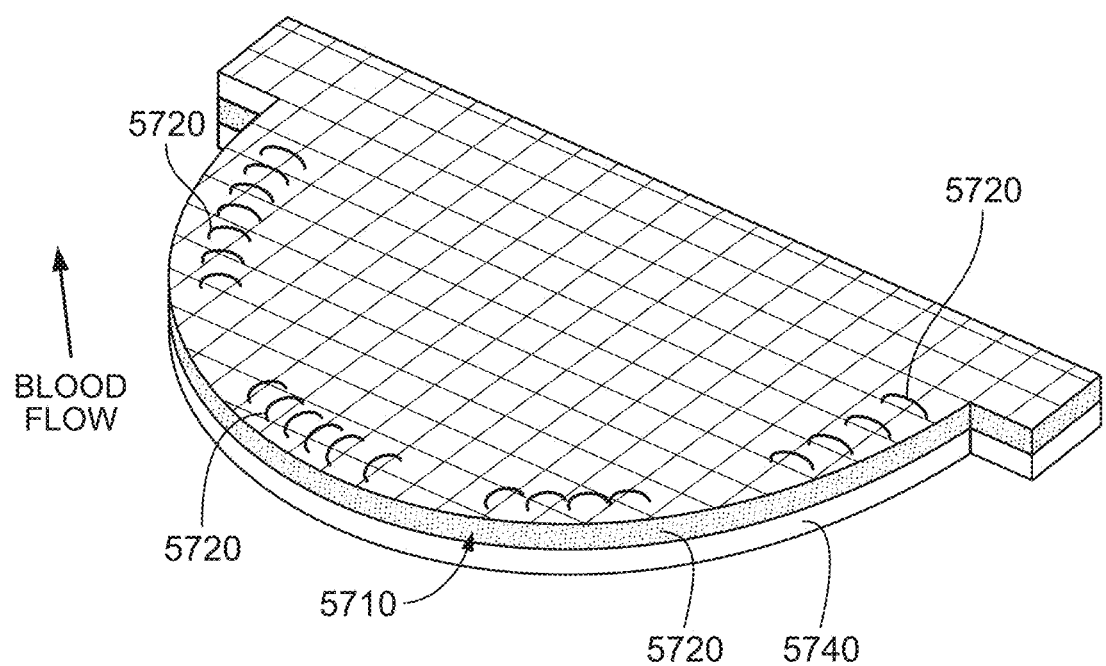
FIG. 57 is a schematic perspective view of a leaflet formed from a stabilized or non-stabilized woven fabric according to the present disclosure including a woven fabric layer and coating layer having a discontinuous suture line extending along the attachment edge of a leaflet.

FIG. 57 shows a leaflet 5710 formed from a fabric according to the present disclosure including a discontinuous suture line 5720 extending along the attachment edge 5740 of the leaflet. Leaflet 5710 is illustrated with a partial or complete coating and/or layer positioned on the fabric. Suture line 5720 may pass through the fabric, the coating, or both. As also described in connection with other suture lines, the gaps here can provide regions of relative flexibility. The fabric layer may be a woven fabric, a stabilized woven fabric or a mesh.

Figure 58:
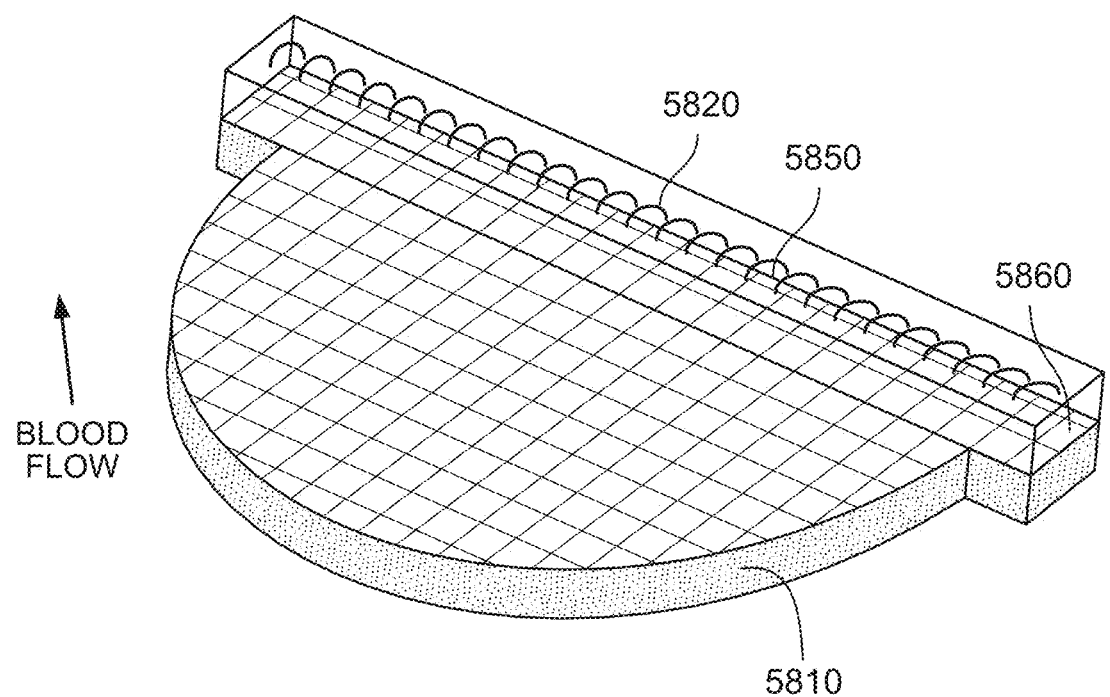
FIG. 58 is a schematic perspective view of a leaflet formed from a stabilized or non-stabilized woven fabric according to the present disclosure including a single suture line extending along the free edge of a leaflet through a partial coating layer.

FIG. 58 shows a leaflet 5810 formed from a fabric according to the present disclosure including a suture line 5820 extending along the free edge 5850 of the leaflet through a partial coating layer 5860 as well as the fabric layer it covers. The fabric layer may be a woven fabric, a stabilized woven fabric or a mesh.

Figure 59:
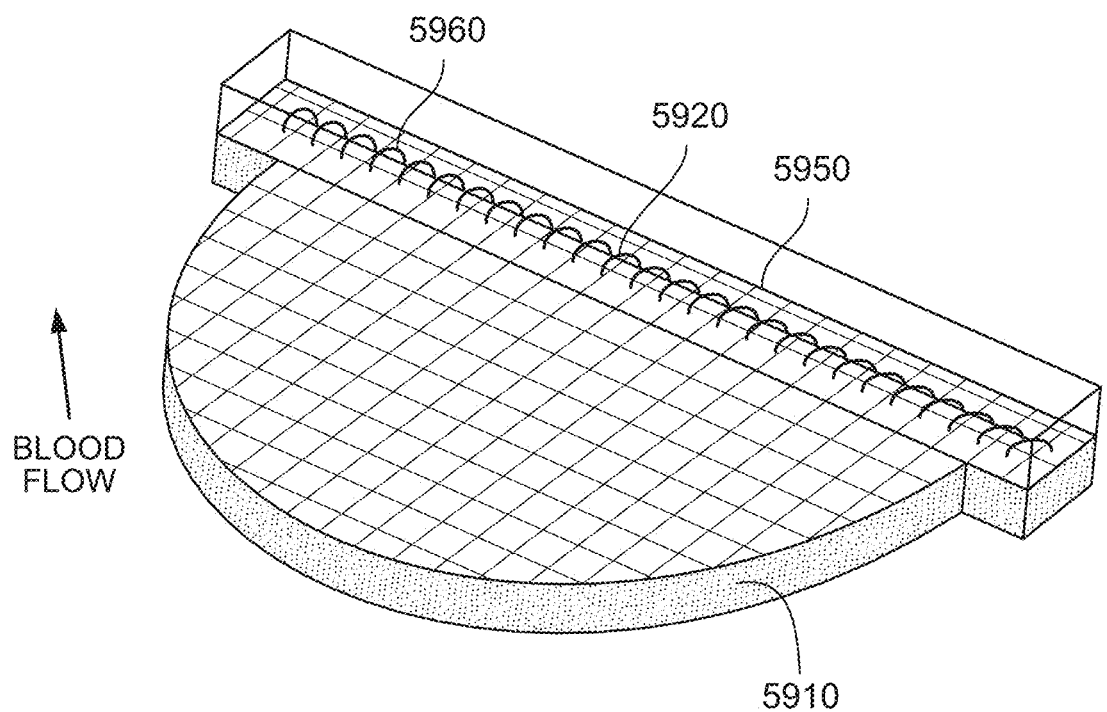
FIG. 59 is a schematic perspective view of a leaflet formed from a stabilized or non-stabilized woven fabric according to the present disclosure including a single suture line extending along the free edge of a leaflet disposed underneath a partial coating layer.

FIG. 59 shows a leaflet 5910 formed from a fabric according to the present disclosure including a suture line 5920 extending along the free edge 5950 of a leaflet, the suture line being disposed underneath a partial coating layer 5960 and laced through the polymer fabric. The fabric layer may be a woven fabric, a stabilized woven fabric or a mesh.

Figure 62:
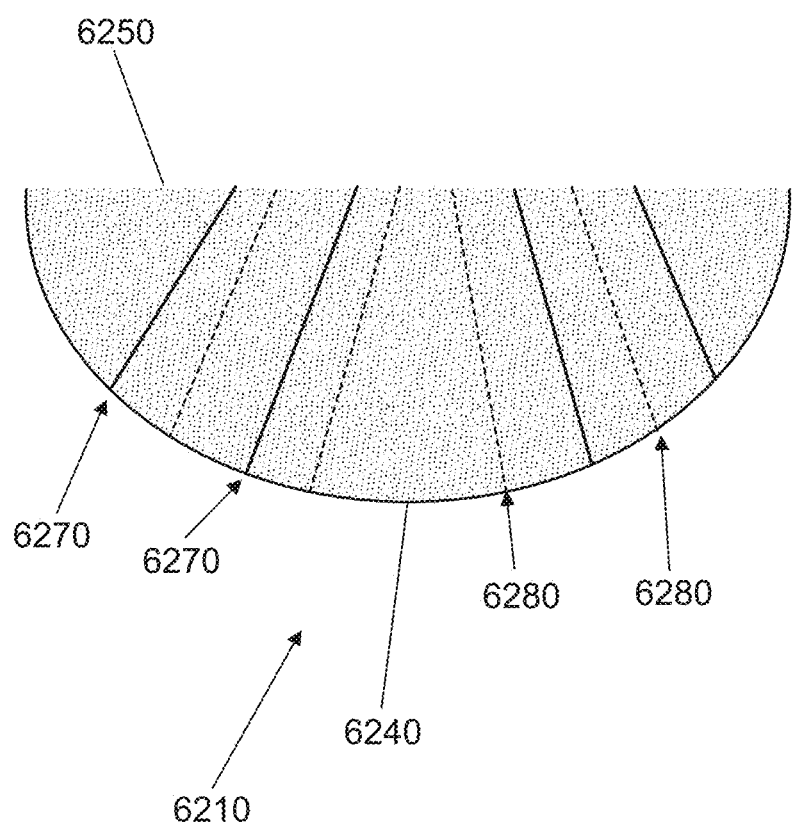
FIG. 62 is a schematic view of a leaflet formed from a stabilized or non-stabilized woven fabric according to the present disclosure including a pleat formed therein.

FIG. 60 shows a leaflet 6010 formed from a fabric according to the present disclosure including an area of increased weave density 6020 extending along and adjacent the free edge 6050 of the leaflet. The area of increased weave density 6020 has higher weave density compared to the remaining portions of the fabric leaflet 6010. This can provide many of the same functions and advantages as just described for suture lines, FIG. 61 shows a leaflet 6110 formed from a fabric according to the present disclosure including an area of increased weave density 6120 extending along the attachment edge 6140 of a leaflet. The area of increased weave density 6120 has higher weave density compared to the remaining portions of the fabric leaflet 6110. This can provide many of the same functions and advantages as just described for suture lines, FIG. 62 shows a leaflet 6210 formed from a fabric according to the present disclosure including a pleat formed therein. In the illustrated embodiment, the pleats are formed by fold lines 6270, 6280. Fold lines 6270 are folds in which the vertex is pointed in first direction which is visible in FIG. 62, with fold lines 6280 having the vertex pointed in the opposite direction. The pleats formed by the fold lines 6270, 6280 may unfold when a load is exerted on the leaflet 6210 during loading and may reform during valve opening. The pleats may be formed by folding a first portion of the fabric over a second portion of the fabric. The ultimate goal of using one or more pleats may be to reduce strain in the leaflet 6210. The pleats can be folded into the leaflet 6210 such that they fully expand to their original structure once deployed. The pleats may be formed in any suitable fashion. For example, the fabric material may be gathered and/or folded to form a pleat, with the material being tacked down using a suture or grommet such that while expanded, the pleat maintains its shape to some degree. Pleats may also be facilitated by scoring or partial ablation (e.g. via a laser). If the pleats are tacked down, it may be preferable to tack the pleats only at the ends of the pleat, although in some circumstances the pleats may be tacked down in other or additional locations, such as along a middle portion of the pleat. In the illustrated embodiment, the fold lines 6270, 6280 forming the pleats generally extend from the attachment edge 6240 to the free edge 6250, although other locations and/or directions of the pleats may be suitable in other embodiments. The fabric layer may be a woven fabric, a stabilized woven fabric or a mesh.

Figure 63:
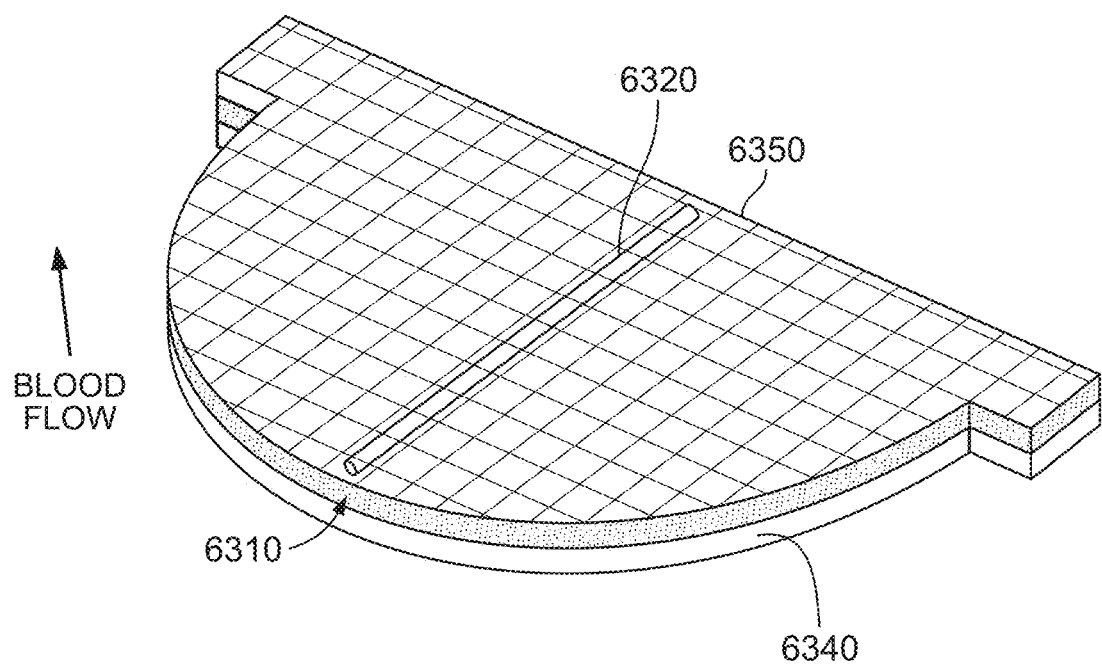
FIG. 63 is a schematic perspective view of a leaflet formed from a stabilized or non-stabilized woven fabric according to the present disclosure including a woven fabric layer and coating layer having a single wire extending from the attachment edge to the free edge of a leaflet.

FIG. 63 shows a leaflet 6310 formed from a fabric according to the present disclosure including a wire 6320 extending from the attachment edge 6340 to the free edge 6350 of the leaflet. Leaflet 6310 is illustrated with a partial or complete coating and/or layer positioned on the fabric. Wire 6320 may be positioned through the fabric, the coating, or both. It may be adhered on top of the fabric layer as illustrated or laminated between the fabric layer and the coating layer. The fabric layer may be a woven fabric, a stabilized woven fabric or a mesh. The wire could be used to conduct energy to weld intersections and stabilize the fabric.

Figure 64:
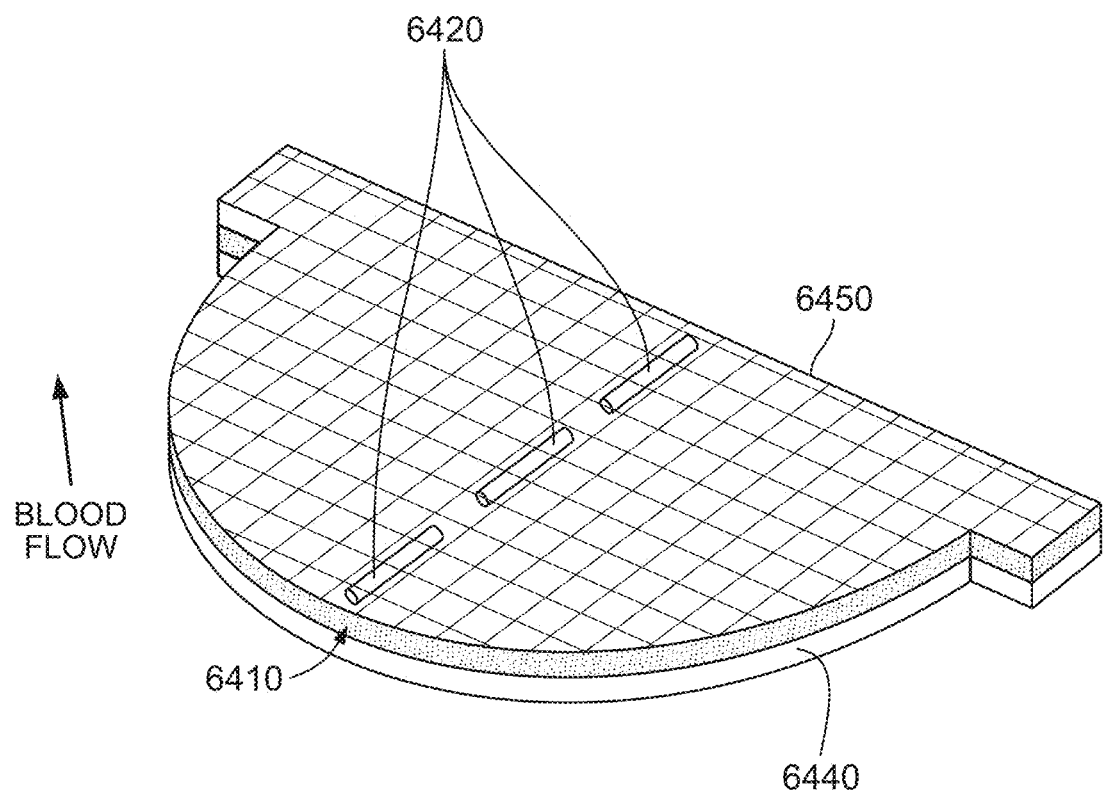
FIG. 64 is a schematic perspective view of a leaflet formed from a stabilized or non-stabilized woven fabric according to the present disclosure including a woven fabric layer and coating layer having a discontinuous wire extending from the attachment edge to the free edge of a leaflet.

FIG. 64 shows a leaflet 6410 formed from a fabric according to the present disclosure including a discontinuous wire 6420 extending from the attachment edge 6440 to the free edge 6450 of the leaflet. Leaflet 6410 is illustrated with a partial or complete coating and/or layer positioned on the fabric. Wire 6420 may be positioned through the fabric, the coating, through both, between the fabric and the coating or on one of the major surfaces. The fabric layer may be a woven fabric, a stabilized woven fabric or a mesh. The wire could be used to conduct energy to weld intersections and stabilize the fabric.

Figure 65:
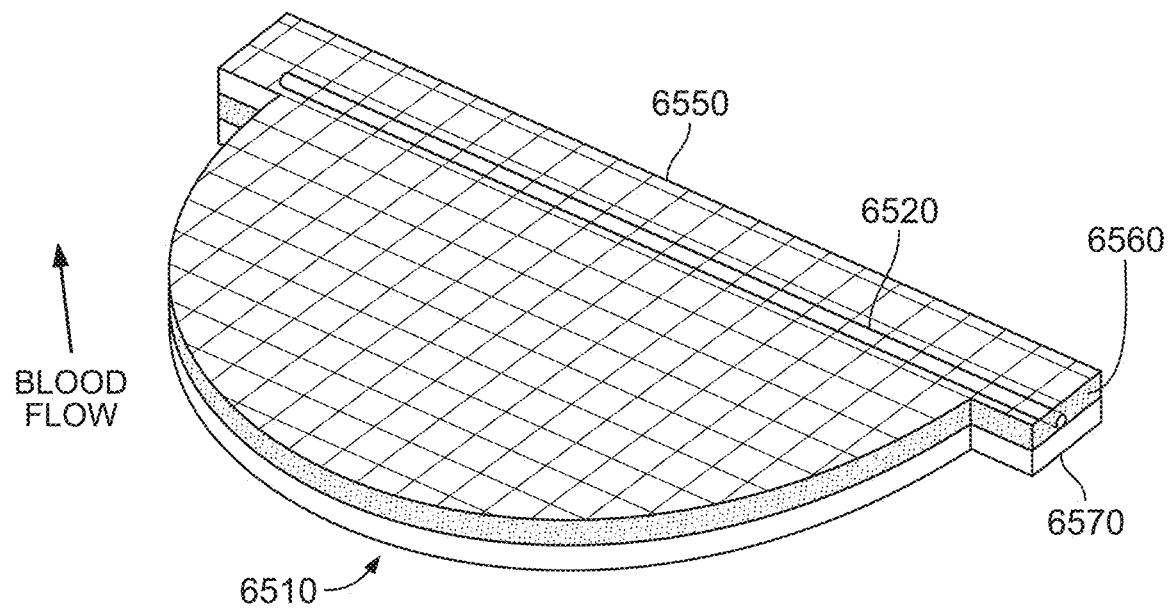
FIG. 65 is a schematic perspective view of a leaflet formed from a stabilized or non-stabilized woven fabric according to the present disclosure including a woven fabric layer and coating layer having a single wire extending across and generally along the free edge of the leaflet, the single wire being disposed between the woven fabric layer and a partial coating layer.

FIG. 65 shows a leaflet 6510 formed from a fabric according to the present disclosure including a wire 6520 extending across a major surface of the leaflet and along the free edge 6550 of the leaflet, the wire being disposed between the fabric layer 6560 and a partial coating layer 6570. The fabric layer may be a woven fabric, a stabilized woven fabric or a mesh. The wire could be used to conduct energy to weld intersections and stabilize the fabric.

Figure 66:
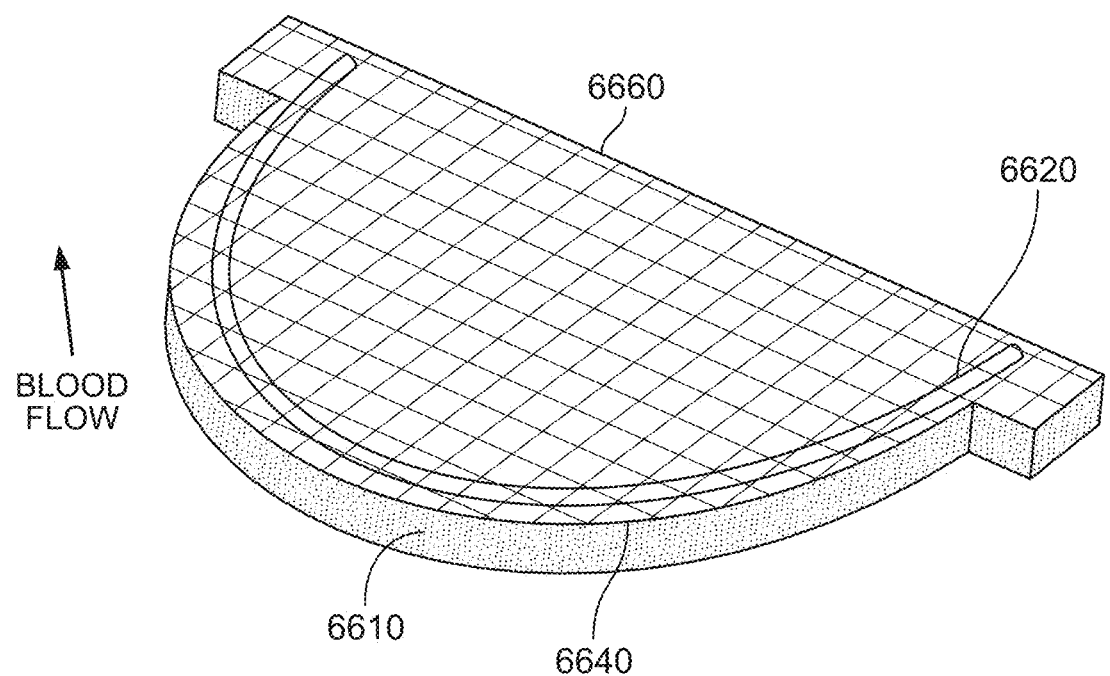
FIG. 66 is a schematic perspective view of a leaflet formed from a stabilized or non-stabilized woven fabric according to the present disclosure including a single wire extending across a major surface of the leaflet and generally along the attachment edge of a leaflet.

FIG. 66 shows a leaflet 6610 formed from a fabric according to the present disclosure including a wire 6620 extending across a major surface of the leaflet and along the attachment edge 6640 of the leaflet. In the illustrated embodiment, the ends of the wire 6620 extend to the free edge 6660, although in other embodiments the ends of the wire may be spaced a distance from the free edge. The fabric layer may be a woven fabric, a stabilized woven fabric or a mesh. The wire could be used to conduct energy to weld intersections and stabilize the fabric.

FIG. 67A illustrates the use of a wire 6720 adhered to a major surface of a fabric layer spaced apart from, but aligned roughly parallel to the free edge 6750 of leaflet 6710. Both of the free ends of this wire intersect the attachment edge 6740. One such wire is shown but other rows of wire, continuous or discontinuous, may also be used. Instead of a wire, as illustrated, this could also be accomplished with a series of stitches, suture line(s), or an area of increased weave density. As shown in FIG. 67B, several of these structures 6720 ould also be placed roughly conforming to or paralleling the contour of the attachment edge 6740 spaced apart from each other. In this illustration, two such wires are disposed in a roughly concentric patters with their ends running between the fabric and a partial coating 6760 disposed at the free edge 6750 of leaflet 6710. The fabric layer may be a woven fabric, a stabilized woven fabric or a mesh. The wire could be used to conduct energy to weld intersections and stabilize the fabric.

The uses of partial coatings or patterned full coatings to provide abrasion resistance to the free edge of leaflets, to help facilitate the attachment of the leaflets to a supporting structure by reinforcing and preventing the unraveling of attachment edges, to provide reinforcing structures, folding zones, etc., and to provide indicia, have been described mainly in terms of leaflets and, to a lesser extent, cuffs designed for use in collapsible/expandable valves. However, some of the described structures, such as grommets and indicia, may be incorporated in both coated and uncoated fabrics for use in other collapsible/expandable valves. They may all be used as well in constructing leaflets and cuffs or other structures for surgical valves—those sewn in place using open heart surgery. And they may be used in other medical devices as described herein.

One coated fabric which may be useful for some applications is composed of five layers, two polymer layers (each about 20 µm thick) laminated to one side of a woven fabric and two other polymer layers (each about 20 µm thick) laminated to the other side of the same fabric. These polymer layers may be, for example, made of Dyneema Purity® membrane 55501 available from DSM Biomedical (www.dsmbiomedical.com). Dyneema Purity® membrane 55501 is composed of UHMWPE and is said to be known for uses in the medical device industry. The properties of Dyneema Purity® membrane 55501 are specified in its Product Data Sheet from DSM Biomedical dated June 2015.

Other materials, a greater or lesser number of layers, layers of variable thicknesses, and different woven fabrics may be used instead. For example, Dyneema Purity® TG dtex10 TS450 may be an example of a suitable fiber for use in producing the fabrics disclosed herein, including for cuffs and/or leaflets of a prosthetic heart valve. The properties of Dyneema Purity® TG dtex10 TS450 are specified in its Product Data Sheet from DSM Biomedical dated September 2013. That fabric may be used in uncoated form, or may include Dyneema Purity® membrane 55501 as one or more polymer coating layers.

After the desired fabric material has been created and shaped or cut, it will typically need to be connected to a supporting structure (such as a stent if the material is intended for use as a cuff and/or prosthetic leaflets). The attachment may be accomplished through any one of a number of suitable methods, including suturing, heat bonding, weaving or knitting directly to the supporting structure, gluing, wrapping, electrospinning, laminating, mechanical attachment such as hooks, hook-and-loop fasteners, being sandwiched between two supporting structures, or being bonded directly to the supporting structure, such as integrating the fabric to the supporting structure while the supporting structure is in a non-set state (e.g., a liquid) in which curing the supporting structure results in the fabric being integrated into the supporting structure.

In attaching fabric-based components to a stent and/or to another support structure of a medical device, the fabric may be attached such that the fibers are oriented in a particular direction. This consideration applies both to uncoated fabrics, as well as coated fabrics described below. Most woven fabrics are produced using fibers that are woven at right angles to each other. These fabrics may be cut and attached to the support structure such that the direction of at least one of the fibers in the weave is substantially parallel to the longitudinal axis of the support structure, and another fiber is oriented generally perpendicular to the longitudinal axis of the support structure. Alternatively, these fabrics may be mounted to the support structure such that the fibers are generally oriented on a bias, i.e., at an oblique angle, relative to the longitudinal axis of the support structure. The fabrics may, for example, be used to form an inner cuff and/or an outer cuff of a collapsible/expandable heart valve or the skirt or other fabric covering of a surgical heart valve. When used for an inner cuff or an outer cuff of a collapsible/expandable heart valve, the oblique angle may be between about 30 degrees and about 60 degrees relative to the longitudinal axis of the support structure when the heart valve is in an expanded use condition. In some embodiments, the fabric may be oriented such that the fibers are oriented at about 45 degrees relative to the longitudinal axis of the support structure when the heart valve is in an expanded use condition. (See EP 2,949,292, the disclosure of which is hereby incorporated by reference herein for its teaching of the manufacture and attachment of a woven fabric at an oblique angle relative to the longitudinal axis of a stent.)

One aspect of the disclosure is a collapsible/expandable heart valve which may be implanted through a catheter or trocar, the heart valve including a valve assembly comprising a coated or uncoated fabric as described herein, and in particular, a heart valve in which the coated or uncoated fabric is used to form the leaflets and/or cuffs shown in FIGS. 28-46A. In one such embodiment, the outer cuff may be made of a coated or uncoated fabric of the disclosure. In another such embodiment, the inner cuff may be made of a coated or uncoated fabric of the disclosure. In still another such embodiment, both the inner and outer cuffs may be made of a coated or uncoated fabric of the disclosure. In still a further embodiment, the inner cuff may be coated while the outer cuff is not. In another embodiment, the inner cuff may be uncoated and the outer cuff may be coated. The fabric used may be a non-stabilized fabric, a stabilized woven fabric or a mesh.

In another embodiment, at least one leaflet may be made from a coated or uncoated fabric material in accordance with the disclosure. In another embodiment, some, but not all of the leaflets may be made from a coated or uncoated fabric material in accordance with the disclosure. It is also contemplated that all leaflets may be produced from a coated or uncoated fabric material in accordance with the disclosure. In one desirable embodiment, all of the leaflets may be made of the same uncoated fabric of the disclosure. In another embodiment, all of the leaflets may be made of the same coated fabric of the disclosure. The fabric used may be a non-stabilized fabric, a stabilized woven fabric or a mesh.

It is also an embodiment of this aspect of the disclosure that at least one cuff and at least one leaflet of the valve assembly may be composed of a coated or uncoated fabric of the disclosure. In one further embodiment, both the at least one cuff and the at least one leaflet of the valve assembly may be made of a coated fabric in accordance with the disclosure. In another embodiment, both the cuff and the leaflet may be made from an uncoated fabric in accordance with the present disclosure. The fabric used may be a non-stabilized fabric, a stabilized woven fabric or a mesh.

While the disclosure above provides for the use of uncoated and/or coated fabrics for prosthetic leaflets, inner cuffs, and/or outer cuffs of collapsible/expandable and surgical prosthetic cardiac valves, the concepts may be similarly or identically applied to other prosthetic valves, such as prosthetic venous valves. Prosthetic venous valves may have generally similar structures and components as those described for the prosthetic heart valves, including a stent, one or more prosthetic leaflets, and optionally inner and/or outer cuffs. If the stent is self-expandable or balloon expandable, the stent may maintain a desired position within the vasculature via a friction fit. If the stent is non-collapsible, it may be sutured or otherwise fixed at the desired position within the vasculature. The one or more prosthetic leaflets may be coupled to the stent and/or to an inner and/or outer cuff attached to the stent, for example via sutures. The prosthetic leaflets may allow blood to flow in substantially only one direction within the vasculature. The inner and/or outer cuffs may assist in enhancing sealing to help prevent blood from flowing in the retrograde direction past the prosthesis and may also aid in coupling the one or more prosthetic leaflets to the stent. The prosthetic leaflets, inner cuffs, and outer cuffs of the prosthetic venous valves may be formed of any of the materials described above for similar components of the prosthetic cardiac valves, for example including the uncoated and/or coated fabrics described herein. The fabric used may be a non-stabilized fabric, a stabilized woven fabric or a mesh.

The uncoated and/or coated fabrics described herein may have still further applications, for example with occluders, which may also be referred to as closure devices. Such occluders may be used to treat any suitable abnormality or condition, including patent foramen ovale ("PFO"), atrial septal defect ("ASD"), ventricular septal defect ("VSD"), patent ductus arteriosus ("PDA"), and left atrial appendage ("LAA") closure. Occluders may have various different configurations depending on factors such as the type of abnormality to be occluded, the location of the target site, the condition of the patient's vasculature or cardiac anatomy, and the practitioner's preferences. The occluders described herein have a collapsed condition and an expanded condition. For example, in the embodiment shown in FIG. 27A, a closure device 2000 has a first expanded volume portion 2010 and a second expanded volume portion 2020 that are substantially perpendicular to a central axis extending along closure device 2000. The first expanded volume portion 2010 may be proximate a first end of closure device 2000, with the second expanded volume portion 2020 spaced axially from the first expanded volume portion 2010 and proximate a second end of closure device 2000. The first expanded volume portion 2010 may be connected to the second expanded volume portion 2020 via an axial portion 2030. The fabric used may be a non-stabilized fabric, a stabilized woven fabric or a mesh.

Figure 27A:
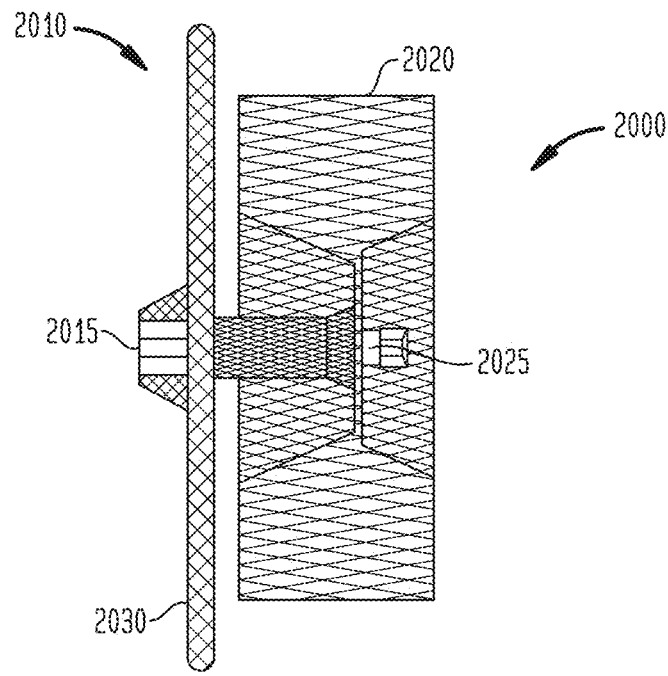
FIG. 27A is a longitudinal cross-section of a medical closure device according to an embodiment of the disclosure.

As depicted in FIG. 27A, the first expanded volume portion 2010 in the expanded condition may have the shape of a thin disk, and is intended to help maintain the closure device 2000 in position at the target site, as described in greater detail below. The second expanded volume portion 2020 in the expanded condition may, in some cases, be a generally cylindrical body that is substantially thicker in the axial direction than the first expanded volume portion 2010 and axially disposed toward the second end. The second expanded volume portion 2020 when expanded may be sized to be somewhat larger in diameter (e.g., about 10-30% larger) than the inside diameter of the vessel, cavity, or lumen to be occluded to facilitate anchoring of the device to prevent dislodgement, but not so large when collapsed as to not fit in the vessel, cavity or lumen. The fabric used may be a non-stabilized fabric, a stabilized woven fabric or a mesh.

At the same time, in the expanded condition, the first expanded volume portion 2010 of the closure device 2000 may have a diameter that is larger than the diameter of the second expanded volume portion 2020. This larger diameter is intended to abut the wall surrounding the abnormal aperture to prevent device movement further into the aperture and to assist in sealing the aperture. For example, the first expanded volume portion 2010 may be oversized so as to overlie the ostium or opening of the LAA in a position adjacent to, and in flush contact with, the wall of the atrium. The first expanded volume portion 2010 may also be flexible so as to be capable of conforming to the curvature of the wall of the atrium in LAA applications or other cardiac or vascular structures in other applications. Although one configuration of the first and second expanded volume portions 2010, 2020 is described above and shown in the figures, various other configurations and sizes may be used depending on the particular application or condition to be treated. For example, one or both expanded volume portions 2010, 2020 may be thin disks or disks having a convex distal end, or the device may include a smaller diameter cylindrical portion between two larger diameter disks. Moreover, the depth or thickness of the first and/or second expanded volume portions may depend on the thickness and number of layers used to make the closure device 2000.

The first expanded volume portion 2010, the second expanded volume portion 2020, and the axial portion 2030 may each be formed of a shape-memory alloy, such as braided nitinol, to facilitate collapsing the closure device 2000 for minimally invasive delivery, and to facilitate expansion to a pre-set shape upon delivery of the closure device 2000 to the intended location. A first coupling 2015 may be disposed adjacent the first expanded volume portion 2010 and may enable connection of a delivery device or other device to closure device 2000. For example, first coupling 2015 may include internal or external threads that mate with corresponding threads of another device. A second coupling 2025, similar to the first coupling 2015, may be disposed adjacent to or within the second expanded volume portion 2020. Second coupling 2025 may also include internal or external threads for connection to corresponding threads of another device. It should be understood that other coupling mechanisms, such as press-fit or snap-fit arrangements, may be utilized in first and second couplings 2015, 2025. Additional details of closure device 2000 and similar devices are described in U.S. Pat. No. 8,758,389, the disclosure of which is hereby incorporated by reference herein.

Figure 27B:
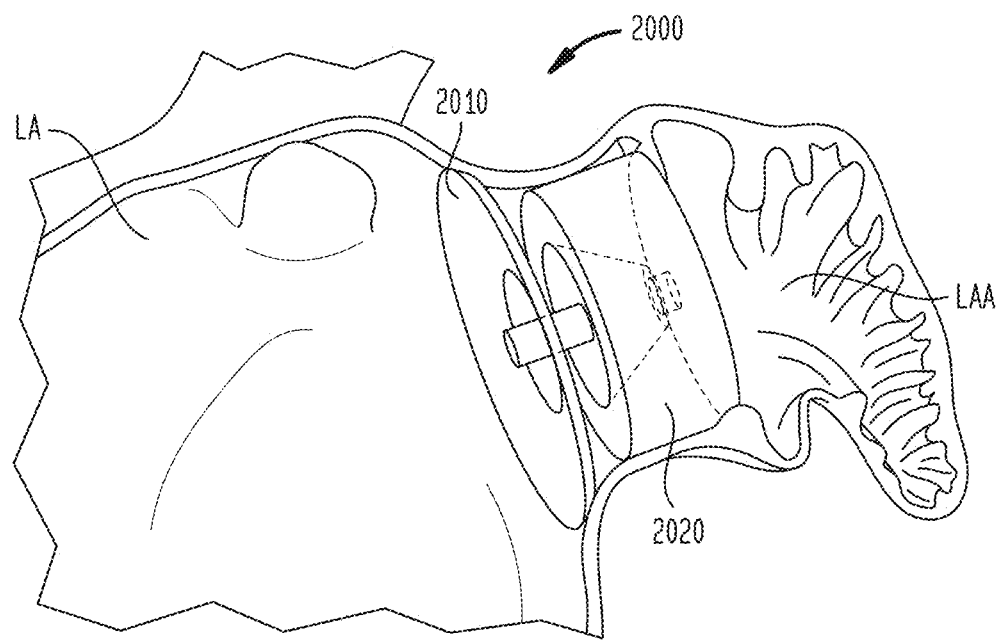
FIG. 27B is a highly schematic view of the medical closure device of FIG. 27A implanted into a left atrial appendage.

FIG. 27B is a schematic view of closure device 2000 positioned within the LAA of a left atrium LA. In patients with certain conditions, such as atrial fibrillation, blood clots may tend to form in the LAA. Implanting a device such as closure device 2000 may lead to partial or complete occlusion of the LAA, thus reducing the risk of thrombi breaking off the LAA and entering the blood stream. In order to help better occlude the LAA, it may be desirable to include fabrics on the interior surface, exterior surface, or both surfaces of the closure device 2000. For example, part or all of the outer surface, and/or part or all of the inner surface, of closure device 2000 may include one or more layers of the uncoated and/or coated fabrics described herein. Such fabrics may help better and/or more quickly occlude the LAA. In some embodiments, if portions of closure device 2000 are formed of two or more layers of braided metal, such as braided nitinol, uncoated and/or coated fabrics of the present disclosure may be included between the two or more layers of braided metal. Other closure devices, such as PFO closure devices, may similarly include uncoated and/or coated fabrics of the present disclosure on part or all of an exterior surface and/or on part or all of an interior surface (and/or between multiple layers of braided mesh if present), for similar purposes as described in connection with closure device 2000.

The uncoated and/or coated fabrics described herein may also be used to form the entirety, or portions, of various types of prosthetic vascular conduits. The fabric used may be a non-stabilized fabric, a stabilized woven fabric or a mesh. For example, a prosthetic aortic graft may be implanted into the aorta to treat a weakened portion of the aorta resulting from a thoracic aneurysm. Prosthetic vascular conduits may be used to perform a bypass to reroute the path of blood flow, for example as a lower extremity bypass, a cardiac bypass in conjunction with open heart surgery, or to serve as an access point to the circulatory system, such as for hemodialysis. Prosthetic vascular conduits may also be used as arteriovenous ("AV") shunts. AV fistulas are abnormal connections between an artery and vein, although they may be surgically created in order to assist with hemodialysis treatment. When an AV fistula is surgically created, an AV shunt formed from the uncoated and/or coated fabrics described herein may be implanted to provide the desired connection between the artery and vein. Prosthetic vascular conduits are typically cylindrical in shape and have been formed of PTFE or Dacron. However, prosthetic vascular grafts may instead be formed of the uncoated and/or coated fabrics described herein.

In addition to the above uses, the fabrics described herein may have additional uses. For example, hernias occur when there is an opening or a weakness in the muscle and/or connective tissue through which organs begin to push. Hernias are frequently treated with a fabric mesh that provides closure and support of the weakness and/or opening that forms the hernia. The mesh acts to patch the hernia, and is frequently formed of a plastic material. Such patches may instead be formed of the uncoated or coated fabrics disclosed herein, whether the patches are continuous or formed as a mesh. And while hernia repair is one exemplary use of patches formed of the uncoated or coated fabrics disclosed herein, such patches may be used in any other suitable procedure, including skin patches, vaginal patches, and/or cardiac patches to provide the desired support to the underlying anatomy. The fabric used may be a non-stabilized fabric, a stabilized woven fabric or a mesh.

In some embodiments, the fabrics described herein may be used to form adhesion barriers. Adhesion barriers are medical implants that may be used to reduce abnormal internal scarring following surgery. The uncoated or coated fabrics of the adhesion barriers may act to separate internal tissues and/or organs while they heal post-surgery. The fabric used may be a nonstabilized fabric, a stabilized woven fabric or a mesh.

While the above-described embodiments of devices that incorporate the uncoated or coated fabrics described herein are generally directed to devices intended to be permanently implanted into the body, the fabrics may be used for various types of medical devices that are used in medical procedures, but not intended to be implanted at all, or not intended to be implanted for longer than the surgical procedure. One such example is an embolic protection device. Generally, an embolic protection device may be used to prevent emboli that are dislodged during a medical procedure from entering the vasculature. Typically, embolic protection devices either capture dislodged emboli so that the emboli can be removed from the body, or otherwise deflect emboli from entering high-risk vasculature (such as the carotid arteries) so that the emboli are able to pass through the vasculature where there may be a lower risk of complications from the emboli. Embolic protection devices may include various types of filters that allow blood to pass through the filter, but are formed as meshes or with pore sizes small enough to trap emboli therein, or otherwise to deflect emboli. Such embolic protection devices may be formed of the fabrics described herein. Examples of embolic protection devices are disclosed in greater detail in U.S. Patent Pub. Nos. 2014/0249567 and 2018/0116780, the disclosures of which are hereby incorporated by reference herein. While the fabrics described herein may be used with short-term filters such as those described immediately above, they may also be used in permanently implanted filters, such as inferior vena cava ("IVC") filters, whether or not the IVC filter is intended to be retrievable. IVC filters typically have a central base and a plurality of legs that extend outwardly from the base to form an overall conical shape, with the legs intended to make contact with the interior surface of the lumen of the IVC to help support the IVC filter in place. The IVC filter functions by allowing blood to flow around the filter, while trapping emboli that pass into the filter, preventing the emboli from causing blockages in the vasculature downstream of the IVC filter. The IVC filters may be formed of a metal or other biocompatible material and the uncoated and coated fabrics described herein may encapsulate portions or all of the IVC filter, or in other embodiments the IVC filter may be formed entirely of the coated fabrics described herein. It should be understood that for IVC filters, or any other application disclosed herein, specific parameters of the disclosed fabrics, such as dimensions, as well as fabrication methods, may be altered to suit the particular application. The fabric used may be a non-stabilized fabric, a stabilized woven fabric or a mesh.

Various medical devices, including collapsible and expandable prosthetic heart valves, have been described above which may incorporate the fabrics described herein. The fabric used may be a non-stabilized fabric, a stabilized woven fabric or a mesh. Although the prosthetic collapsible and expandable heart valves have generally been described in connection with a prosthetic aortic valve, those heart valves may be designed for replacing any heart valve. For example, collapsible and expandable prosthetic mitral valves may include an outer stent portion to anchor into the mitral valve annulus, and an inner stent portion to house the prosthetic leaflets, with the inner stent connected to the outer stent, for example so that the inner stent is substantially mechanically isolated from the outer stent. In such embodiments, the outer stent portion may include features to help secure the prosthetic mitral valve within the mitral valve annulus, and the inner stent portion may be substantially cylindrical (e.g. a right cylinder) so that the valve assembly may have a generally circular profile in cross section. The fabrics described herein may be used for prosthetic leaflets of the prosthetic mitral valve and/or for any cuffs or skirts on the prosthetic mitral valve, which may include inner cuffs and/or outer cuffs of the inner stent portion and the outer stent portion, as well as any other cuff or skirt portions, such as cuff portions that connect the inner stent portion to the outer stent portion. Prosthetic mitral valves having inner and outer stent portions are described in greater detail, for example, in U.S. Patent Publication Nos. 2017/0196688 and 2019/0328525, and U.S. Pat. No. 10,052,204, the disclosures of which are hereby incorporated by reference herein.

According to an aspect of the disclosure, a prosthetic heart valve comprises:
 an expandable stent extending in a longitudinal direction between an inflow end and an outflow end;
 a cuff coupled to a luminal surface of the stent; and
 a plurality of prosthetic leaflets coupled to at least one of the cuff and the stent and having an open condition and a closed condition, the plurality of prosthetic leaflets adapted to allow blood to flow from the inflow end toward the outflow end when in the open condition and to retard blood from flowing from the outflow end toward the inflow end when in the closed condition, each of the plurality of leaflets being formed of a stabilized fabric;
 wherein the stabilized fabric is a mesh of ultra-high molecular weight polyethylene (UHMWPE), PTFE or PP with pores or divots with openings with an area of from about 100 microns$^2$ to about 5,000 microns$^2$ and in a further embodiment, from about 1,000 to about 3,000 microns$^2$ and a pore density/divot density of about 1 to about 25% and in still another embodiment, about 5 to about 15%. It the stabilized fabric is a woven fabric, it has a first group of fibers extending in a first direction of the fabric and a second group of fibers extending in a second direction of the fabric different than the first direction, the first group of fibers and the second group of fibers being interlaced in an ordered arrangement and defining intersections and gaps, the first group of fibers and the second group of fibers both being composed of UHMWPE, PTFE or PP, at least one layer of the fabric having a thread count of between about 300 and about 500 fibers by between about 100 and about 300 fibers per square inch, the fabric having a thickness of between about 50 μm and about 100 μm; and/or
 each of the plurality of prosthetic leaflets includes a free edge adapted to move as the plurality of prosthetic leaflets transitions between the open condition and the closed condition, and an attachment edge directly attached to at least one of the cuff and the stent; and/or when each of the plurality of leaflets is in a flattened condition, the first group of fibers extend in the first direction at an angle of between about 30 degrees and about 60 degrees relative to a line that extends perpendicular to the free edge; and/or the stabilized fabric is not coated by a polymer coating; and/or the stabilized fabric is at least partially coated with a first polymer coating; and/or the stabilized fabric has a tensile strength of between about 50 N and about 100 N before coating; and/or the stabilized fabric having an areal density of between about 0.5 ounces/yard$^2$ and about 1.0 ounces/yard$^2$; and/or the stabilized fabric having an areal density of greater than about 1.3 ounces/yard$^2$; and/or each of the plurality of prosthetic leaflets includes a free edge adapted to move as the plurality of prosthetic leaflets transitions between the open condition and the closed condition, and an attachment edge directly attached to at least one of the cuff and the stent; and/or a polymer coating wherein the polymer coating is disposed on the first major surface adjacent the attachment edge or on the second major surface adjacent the attachment edge; and/or the attachment edge is directly attached to the at least one of the cuff and the stent via one or more sutures extending through a polymer coating; and/or at least some portions of the first major surface are not coated by the polymer coating, and at least some portions of the second major surface are not coated by the polymer coating; and/or the polymer coating is disposed adjacent the attachment edge on the second major surface, at least some other portions of the second major surface remaining uncoated by the polymer coating, and the polymer coating is disposed adjacent the free edge on the first major surface, at least some other portions of the first major surface remaining uncoated by the polymer coating; and/or portions of the first major surface adjacent the free edge are coated by the polymer coating, at least some other portions of the first major surface remaining uncoated by the polymer coating, and portions of the second major surface adjacent the free edge are not coated by the polymer coating; and/or the second major surface is entirely uncoated by the polymer coating; and/or portions of the second major surface adjacent the free edge are coated by the polymer coating, at least some other portions of the second major surface remaining uncoated by the polymer coating, and portions of the first major surface adjacent the free edge are not coated by the polymer coating; and/or the polymer coating is disposed adjacent the free edge on the second major surface, at least some other portions of the second major surface remaining uncoated by the polymer coating, and the polymer coating is disposed adjacent the free edge on the first major surface, at least some other portions of the first major surface remaining uncoated by the polymer coating; and/or the polymer coating is disposed in a plurality of strips on the second major surface so that portions of the second major surface between adjacent ones of the plurality of strips are uncoated by the polymer coating, each of the plurality of strips extending in a direction from the attachment edge toward the free edge.

According to another aspect of the disclosure, a prosthetic heart valve comprises:

an expandable stent having a luminal surface; and a valve assembly attached to the luminal surface of the stent, the valve assembly including a cuff and a leaflet, the leaflet having a first major surface, an opposed second major surface, an attachment edge, a free edge, and a plurality of tabs, the leaflet composed of an uncoated stabilized woven fabric composed of a polymer, the woven fabric having a thread count of 300-500×100-300 fibers per square inch, an areal density of between 0.5 and 1.0 ounces/yd$^2$, a thickness of between about 20 and about 250 μm, and a tensile strength of between about 50 N and about 100 N; and/or a valve assembly attached to the luminal surface of the stent, the valve assembly including a cuff and a leaflet, the leaflet having a first major surface, an opposed second major surface, an attachment edge, a free edge, and a plurality of tabs, the leaflet composed of an uncoated polymer mesh with pores or divots with openings with an area of from about 100 microns$^2$ to about 5,000 microns$^2$ and in a further embodiment, from about 1,000 to about 3,000 microns$^2$ and a pore density/divot density of about 1 to about 25% and in still another embodiment, a pore density/divot density of about 5 to about 15%; and/or the polymer is polytetrafluoroethylene ("PTFE"); and/or the polymer is low density PTFE, high density PTFE, or ultra-high molecular weight PTFE ("UHMWPTFE"); and/or the polymer is stretched PTFE or expanded PTFE; and/or the polymer is polyethylene ("PE"); and/or the polymer is low density PE, high density PE, or ultra-high molecular weight PE ("UHMWPE"); and/or the polymer is polypropylene ("PP"); and/or the polymer is low density PP, high density PP, or ultra-high molecular weight PP ("UHMWPP"); and/or the polymer is a copolymer or block polymer of PE and PP; and/or the polymer is a polyurethane, an acrylic, a polyester, a polyamide, a polyimide, a vinyl acetate, an alkyd, an epoxy, a silane, or a siloxane; and/or the stabilized woven fabric has an areal density of about 0.5 ounces/yd$^2$; and/or the stabilized woven fabric has an areal density of about 0.8 ounces/yd$^2$; and/or the stabilized woven fabric has an areal density of about 1.0 ounces/yd$^2$; and/or the stabilized woven fabric has an areal density of greater than about 1.0 ounces/yd$^2$; and/or the stabilized woven fabric has an areal density of greater than about 1.3 ounces/yd$^2$; and/or the woven fabric has a thickness of between about 50 and about 100 μm; and/or the woven fabric has a thickness of between about 75 μm; and/orthe woven fabric has a tensile strength of about 75N; and/or the woven fabric has a thread count of 440×220 fibers per square inch; and/or at least one grommet is disposed in the attachment edge or in one of the plurality of tabs.

According to a further aspect of the disclosure; a prosthetic heart valve comprises:

an expandable stent having a luminal surface; and a valve assembly attached to the luminal surface of the stent, the valve assembly including a cuff and a leaflet, the leaflet having a first major surface, an opposed second major surface, an attachment edge, a free edge, and a plurality of tabs, both the cuff and the leaflet composed of a woven fabric composed of a first polymer, the leaflet further comprising a coating composed of a second polymer disposed on at least one of the first major surface and the second major surface; and/or the woven fabric has an areal density of between 0.5 and 1.0 ounces/yd$^2$; and/or the woven fabric has an areal density of about 0.5 ounces/yd$^2$; and/or the woven fabric has an areal density of about 0.8 ounces/yd$^2$; and/or the woven fabric has an areal density of about 1.0 ounces/yd$^2$; and/or the woven fabric, including the coating, has a thickness of between about 20 and about 250 µm; and/or the woven fabric, including the coating, has a thickness of between about 50 and about 100 µm; and/or the woven fabric, including the coating, has a thickness of between about 75 µm; and/or the woven fabric has a tensile strength of between about 50 N and about 100 N; and/or the woven fabric has a tensile strength of about 75 N; and/or the woven fabric has a thread count of 300-500×100-300 fibers per square inch; and/or the woven fabric has a thread count of 440×220 fibers per square inch; and/or the first polymer is polytetrafluoroethylene ("PTFE"); and/or the first polymer is low density PTFE, high density PTFE, or ultra-high molecular weight PTFE ("UHMWPTFE"); and/or the first polymer is stretched PTFE or expanded PTFE; and/or the first polymer is polyethylene ("PE"); and/or the first polymer is low density PE, high density PE, or ultra-high molecular weight PE ("UHMWPE"); and/or the first polymer is polypropylene ("PP"); and/or the first polymer is low density PP, high density PP, or ultra-high molecular weight PP ("UHMWPP"); and/or the first polymer is a copolymer or block polymer of PE and PP; and/or the first polymer is a polyurethane, an acrylic, a polyester, a polyamide, a polyimide, a vinyl acetate, an alkyd, an epoxy, a silane, or a siloxane; and/or the second polymer is polytetrafluoroethylene ("PTFE"); and/or the second polymer is low density PTFE, high density PTFE, or ultra-high molecular weight PTFE ("UHMWPTFE"); and/or the second polymer is stretched PTFE or expanded PTFE; and/or the second polymer is polyethylene ("PE"); and/or the second polymer is low density PE, high density PE, or ultra-high molecular weight PE ("UHMWPE"); and/or the second polymer is polypropylene ("PP"); and/or the second polymer is low density PP, high density PP, or ultra-high molecular weight PP ("UHMWPP"); and/or the second polymer is a copolymer or block polymer of PE and PP; and/or the second polymer is a polyurethane, an acrylic, a polyester, a polyamide, a polyimide, a vinyl acetate, an alkyd, an epoxy, a silane, or a siloxane; and/or the coating is composed of between 1 and 20 coating layers having a total coating thickness of between about 5 µm and about 50 µm; and/or at least one grommet is disposed in the attachment edge or in one of the plurality of tabs; and/or the stabilized fabric further comprises at least one partial coating adjacent the free edge of each leaflet and/or the if the fabric is a woven fabric it is stabilized by a fastener, an adhesive or a weld applied to at least one intersection of a warp and weft fiber And in yet another embodiment of the disclosure, there is provided a replacement heart valve as described above in the foregoing paragraphs which is specifically designed to replace or repair a native aortic, native pulmonary, native tricuspid, or native mitral valve, the replacement heart valve being made using a stabilized fabric which is either a mesh or a stabilized woven fabric stabilized by: a fastener to fasten at least one fiber intersection; an adhesive to glue at least one fiber intersection; weld created by the application of energy to at least one intersection; an increased localized weave density; having an areal density of greater than about 1.0 ounces/yard$^2$ and in another embodiment, more than 1.3 ounces/yard$^2$; fibers with a non-uniform cross-section along their length; at least one partial coating; a fastener to fasten adjacent or parallel fibers other than at an intersection; and/or an adhesive gluing adjacent or parallel fibers other than at an intersection.

Methods of making these heart valves include forming a mesh into at least one leaflet or a cuff and creating a valve assembly from the leaflet or cuff produced from that mesh. These methods could also include producing a at least one leaflet or cuff from a stabilized woven fabric stabilized by: a fastener to fasten at least one fiber intersection; an adhesive to glue at least one fiber intersection; weld created by the application of energy to at least one intersection; an increased localized weave density; having an areal density of greater than about 1.0 ounces/yard$^2$ and in another embodiment, more than 1.3 ounces/yard$^2$; fibers with a non-uniform cross-section along their length; at least one partial coating; a fastener to fasten adjacent or parallel fibers other than at an intersection; and/or an adhesive gluing adjacent or parallel fibers other than at an intersection, and creating a valve assembly from the leaflet or cuff produced from that stabilized fabric. In one embodiment of such a prosthetic mitral valve, the prosthetic mitral valve comprises a self-expandable or balloon-expandable stent that includes a first inner stent portion having a generally cylindrical shape and a second outer stent portion attached to the first inner stent portion. The second outer stent portion is disposed generally surrounding the first inner stent portion. When implanted into a native mitral valve annulus, the second outer stent portion engages the native valve annulus and at least partially mechanically isolates the first inner stent portion from being deformed by the anatomy of the native valve annulus or calcification of the native valve. Thus, the first inner stent portion retains its generally cylindrical shape. Moreover, the prosthetic mitral valve includes a valve assembly that is substantially only attached to the first inner stent portion. The valve assembly comprises at least one cuff attached to a surface of the stent and two or three prosthetic leaflets attached to the cuff and/or the luminal surface of the first inner stent portion. The cuff(s) and/or prosthetic leaflets are composed of a coated or uncoated woven polymer fabric itself composed of one or more layers of ultra-high molecular weight polyethylene or polytetrafluoroethylene. At least one layer of the woven polymer fabric exhibits one of the following properties: an ultimate tensile strength of from about 25 to about 250 MPa; a tear strength of from about 10 to about 40 lbF; a permeability of from about 10 to about 1,200 mL/cm2/min; a suture retention of from about 30 to about 70 N; a stiffness/flexural rigidity of from about 0.001 to about 4 cm; or a stretch of from about 3 to about 50%. The prosthetic leaflets have a thickness of from about 50 μm to about 350 μm and the cuff has a thickness of from about 5 μm to about 200 μm. And in some additional aspects of this embodiment, the at least one of the prosthetic leaflets or the cuff further comprises a wire, stitch, a suture line or grommet. In the case of a stitch or a suture line, they are not provided to substantially attach the cuff or prosthetic leaflet to another structure of the replacement heart valve.

In yet another set of embodiments, the disclosure encompasses a stabilized replacement heart valve comprising: a transapical or trans-catheter valve which includes a self-expandable, balloon-expandable stent, or a surgical valve that includes a frame. A valve assembly is attached to the stent or frame. The valve assembly includes a cuff and 2 to 4 leaflets. The leaflets are made of a stabilized fabric as recited herein. In some aspects of this set of embodiments, the leaflets are composed of a woven polymer fabric having a thickness of between about 5 μm and about 500 μm and having a plurality of warp and weft fibers that meet at and define intersections. As shown in FIG. 85, the leaflets 8510 each have a free edge 8550, an attachment end 8530 which includes the attachment edge 8520 as well as some additional area proximate to the attachment edge and a movement area 8560 subject to movement during operation with the movement area which generally includes the free edge 8550 and intermediate portions of the leaflet between the free edge 8550 and the attachment end 8530. This movement area 8560 includes a subset of the woven fabric's intersections which are mechanically fastened, chemically fastened or energetically fastened and thereby stabilized 8570. As shown in FIG. 85, a subset of more than 50% of the intersections 8570 in the movement area 8560 have been stabilized by, in this case, the application of energy to those intersections individually or as a group. In the example illustrated in FIG. 85, the subset of stabilized intersections 8570 is disposed at, and radiates from, the attachment end 8530 toward the free edge 8550. However, as illustrated, there is a region of the movement area 8560 without such stabilized intersections which is proximate to the free edge 8550. This need not be case. The stabilized intersections can be disposed adjacent the free edge and not the attachment edge, dispose in regions spaced apart from either the attachment end and the free edge, and the like. And they may be disposed in any patter or randomly. Moreover, in some instances the subset of fastened intersections within the movement area of the leaflets comprises at least about 25% of the intersections in the movement area, in other instances at least about 50% of the intersections in the movement area, and in still other instances the subset comprises at least about 75% of the intersections in the movement area. Indeed, in some instances, the subset comprises at least about 90% of the intersections in the movement area.

In some instances the leaflets of the stabilized replacement heart valve include within their movement areas a sufficient number of intersections in movement area that are mechanically fastened, chemically fastened or energetically fastened so as to render the movement area of the leaflets resistant to changes in conformation caused by tissue growth onto or into the leaflets. Often, this can be established by measuring the distance between a first fastened intersection within the subset and a second parallel intersection fastened intersection within the subset spaced apart from the first fastened intersection (a total of 10 intersections including the first and second intersections) in either the warp or weft direction (See 8635 and 8625 respectively in FIG. 86) and determining that it has decreased by less than 10% after implantation in a sheep model, or if a sheep in not the most appropriate model, a pig model, for 140 days when compared to the warp and/weft lengths of same or similar intersections in a substantially identical woven fabric before implantation. In some instances, being resistant to changes in conformation caused by tissue growth onto or into the leaflets can be established by a decrease of about 5% or less after implantation using the same test method.

In some of the embodiments of this set of embodiments, the stabilized intersections are created by a plurality of welds which are produced by the application of heat, pressure, a laser, high intensity light, ultrasonics, vibration, a gas, a plasma, radiofrequency, friction, spin welding or electrical current. The woven fabric used for these leaflets can have any of the following properties before stabilization: (i) an ultimate tensile strength between 25 MPa and 250 MPa; (ii) a tear strength of between 10 lbF and 40 lbF; (iii) a permeability of between 10 mL/cm$^2$/min- and 1,200 mL/cm$^2$/min; (iv) a suture retention of between 30 N and 70 N; (v) a stiffness/flexural rigidity of between 0.001 cm and 4 cm; and (vi) a stretch of between 3% and 50%. The woven fabric may have at least one of: an areal density of between 0.5 and 1.3 ounces/yard$^2$ or a thread count of about 300-500×100-300 fibers per square inch before and after stabilization, and in some of this set of embodiments, an areal density of at least 0.65±0.1 ounces/yard$^2$ and at most about 1.0±0.1 ounces/yard$^2$ and a thread count of about 400-500× 200-300 fibers per square inch. In still further aspects of these embodiments, the woven fabric leaflets have an areal density of at least 0.65±0.1 ounces/yard$^2$ and at most about 1.0±0.1 ounces/yard$^2$ and a thread count of about 400-500× 200-300 fibers per square inch. In some additional embodiments of this set of embodiments, the woven fabric leaflets have a maximum thickness of approximately 100 μm.

The cuff and leaflets of the stabilized replacement heart valves discussed herein and specifically the warp and weft fibers can be made from, inter alia, polyolefins, halogenated polyolefins, polyurethanes, PEEK, polyvinyl alcohols, silicones, rayons, polyesters, aramids, spandex, or combinations, blends and copolymers thereof. In particular, the warp and weft fibers are composed of polyolefins or halogenated polyolefins selected from the group consisting of a polyethylene, a polypropylene and a polytetrafluoroethylene as well as combinations, blends and copolymers thereof and in particular can be selected from the group consisting of ultra-high molecular weight polyethylene, ultra-high molecular weight polypropylene or expanded polytetrafluoroethylene as well as combinations, blends and copolymers thereof.

In another of this set of embodiments, the disclosure relates to a method of stabilizing a replacement heart valve comprising the steps of: (a) providing leaflets composed of a woven polymer fabric having a thickness of between about 5 μm and about 500 μm, having at least one of an areal density of between 0.5 and 1.3 ounces/yard$^2$ or a thread count of about 300-500×100-300 fibers per square inch, and having a plurality of warp and weft fibers that meet at and define intersections, the leaflets having a free edge, an attachment end and a movement area subject to movement during operation, the movement area including the free edge and intermediate portions of the leaflet between the free edge and the attachment end; (b) energetically welding a subset of at least about 50% of the intersections within the movement area by applying heat, pressure, laser light, high intensity light, ultrasonics, vibration, a gas, a plasma, radiofrequency, friction, spin welding or electrical current thereto to form a plurality of welded intersections; and (c) attaching the leaflets to a support so as to form a replacement heart valve. In some cases, the stabilized replacement heart valve will include leaflets wherein the subset comprises at least about 75% of the intersections in the movement area and in other instances, at least about 90% of the intersections in the movement area.

Similar methods are contemplated for making a stabilizing a replacement heart valve using a mesh as discussed below comprising the steps of: (a) providing leaflets composed of a polymer mesh having a thickness of between about 1 µm and about 500 µm, containing a plurality of pores or divots having openings with an average area ranging from about 100 microns$^2$ to about 5,000 microns$^2$ and having a pore density or divot density of about 1 to about 25%, the mesh comprising a matrix of struts that meet at and define junctions, the leaflets having a free edge, an attachment end and a movement area subject to movement during operation, the movement area including the free edge and intermediate portions of the leaflet between the free edge and the attachment end and (b) attaching the leaflets to a self-expandable or balloon-expandable stents or a frame so as to form a replacement heart valve.

In still others of this set of embodiments, the stabilized replacement heart valve has leaflets composed of a woven polymer fabric having a thickness of between about 5 µm and about 500 µm and having a plurality of warp and weft fibers that meet at and define intersections. The leaflets also has a free edge, an attachment end and a movement area subject to movement during operation with the movement area including the free edge and intermediate portions of the leaflet between the free edge and the attachment end. These leaflets are stabilized by using fibers of: a undulating or variable diameter or thickness/width; a uniform diameter or width/thickness; an increased localized weave density which is up to about 50% greater than that of other portions of the leaflet and in some further embodiments, between about 20-40% greater than that of other portions of the leaflet.; an areal density of greater than 1.3 ounces/yard$^2$; or a weave selected from Plain weave, Rib weave, Basket weave, Twill Weave, Herringbone weave, Satin weave, Sateen weave, Leno weave, Oxford Weave, Bedford cord weave, Waffle weave, Pile weave, Jacquard weave, Dobby weave, Crepe weave, Lappet weave, Tapestry Weave, Striped weaves, Checquered weaves, or Double cloth weave.

In some further embodiments of this set of embodiments, the stabilized replacement heart valves described herein contemplate a self-expandable, balloon-expandable stent or frame; and a valve assembly attached to the stent or frame. The valve assembly comprising a cuff and 2 to 4 leaflets and the leaflets are composed of a polymer mesh having a thickness of between about 1 µm and about 500 µm. The mesh is made from a matrix of struts that meet at and define junctions and the struts and junctions together define a plurality of pores or divots. The pores or divots each have at least one opening and the openings have an average area ranging from about 100 microns$^2$ to about 5,000 microns$^2$ and have a pore density or divot density of about 1 to about 25%. The leaflets have a free edge, an attachment end and a movement area subject to movement during operation, the movement area including the free edge and intermediate portions of the leaflet between the free edge and the attachment end. The stabilized replacement heart valve produced using a mesh can be resistant to a change in conformation caused by tissue growth on and into the mesh which can be determined by a change in the distance between a first strut or junction and a second strut or junction spaced apart from and parallel to the first strut before and after implantation using the same model, timing and procedure described previously for fastened woven fabrics. If the decrease is less than 10% and more preferably about 5% or less, than the mesh can be considered resistant to a change in conformation caused by tissue growth on and into the mesh. In some other instances, the mesh has a maximum thickness of approximately 150 µm and in other instances from about 5 to about 100 microns. The polymers that can be used are the same as previously described in the context of a stabilized woven fabric noted above. In particular, the mesh can be composed of a polyolefin selected from the group consisting of ultra-high molecular weight polyethylene, ultra-high molecular weight polypropylene or expanded polytetrafluoroethylene as well as combinations, blends and copolymers thereof, and the mesh contains a plurality of pores or divots having openings with an average area ranging from about 1,000 microns$^2$ to about 3,000 microns$^2$ and having a pore density or divot density of about 1 to about 15%.

The stabilized replacement heart valve described above can be designed for replacing and repairing a native aortic valve, a native mitral valve, a native pulmonary valve, or a native tricuspid valve. In one particular embodiment of this set of embodiments, the stabilized replacement heart valve is a mitral valve and is constructed from a self-expandable or balloon-expandable stents including a first inner stent portion having a generally cylindrical shape and a second outer stent portion generally surrounding the first inner stent portion, the second outer stent portion attached to the first inner stent portion so that when the stabilized replacement heart valve is implanted into a native mitral valve annulus, the second outer stent portion engages the native mitral valve annulus and at least partially mechanically isolates the first inner stent portion from being deformed by the anatomy of the native mitral valve annulus or calcification of the native mitral valve such that the first inner stent portion retains its generally cylindrical shape, the valve assembly being substantially only attached to the first inner stent portion. The leaflets are composed of the stabilized fabrics, either the stabilized woven fabric or the mesh, described above.

To this point, leaflets have been described. But all of the materials described in the preceding paragraphs can instead, or in addition, be used to produce a cuff disposed on a luminal surface of the stent, an abluminal surface of the stent, or both. In particular, the cuff can be composed of a woven polymer fabric having a thickness of between about 5 µm and about 500 µm and having a plurality of warp and weft fibers that meet at and define intersections a subset of which may be mechanically fastened, chemically fastened or energetically fastened and thereby stabilized. In certain of this set of embodiments, the cuff's subsets of intersections are energetically fastened by a plurality of welds. And in some other embodiments of this set, the cuff is on the abluminal surface and it includes one or more structures to reduce paravalvular leaks around the abluminal surface of the stent.

Although the present disclosure has been made with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims. For example, features of one embodiment described above may be combined with features of other embodiments described above.

The invention claimed is:

1. A stabilized replacement heart valve, comprising:
   an expandable stent or frame; and
   a valve assembly attached to the stent or frame, the valve assembly comprising a cuff and 2 to 4 leaflets, the leaflets being composed of a polymer mesh having a thickness of between about 1 µm and about 500 µm, the mesh including a matrix of struts that meet at and define junctions and a plurality of pores or divots having openings with an average area between about 100 microns$^2$ and about 5,000 microns$^2$ such that the mesh has a pore density or a divot density of about 1% to about 25% of the total area of the mesh, the leaflets having a free edge, an attachment end and a movement area subject to movement during operation, the movement area including the free edge and intermediate portions of the leaflet between the free edge and the attachment end.

2. The stabilized replacement heart valve of claim 1, wherein the distance between a first strut or junction and a second strut or junction spaced apart from the first strut or junction does not decrease by 10% or more after implantation in a sheep model for 140 days.

3. The stabilized replacement heart valve of claim 1, wherein the mesh has a maximum thickness of approximately 150 µm.

4. The stabilized replacement heart valve of claim 1, wherein the mesh is composed of a material selected from the group consisting of polyolefins, halogenated polyolefins, polyurethanes, PEEK, polyvinyl alcohols, silicones, rayons, polyesters, aramids, spandex, or combinations, blends and copolymers thereof.

5. The stabilized replacement heart valve of claim 4, wherein the mesh is composed of polyolefins or halogenated polyolefins selected from the group consisting of a polyethylene, a polypropylene and a polytetrafluoroethylene, as well as combinations, blends and copolymers thereof.

6. The stabilized replacement heart valve of claim 5, wherein the mesh is composed of a polyolefin selected from the group consisting of ultra-high molecular weight polyethylene, ultra-high molecular weight polypropylene or expanded polytetrafluoroethylene, as well as combinations, blends and copolymers thereof.

7. The stabilized replacement heart valve of claim 2, wherein the mesh is composed of a material selected from the group consisting of polyolefins, halogenated polyolefins, polyurethanes, PEEK, polyvinyl alcohols, silicones, rayons, polyesters, aramids, spandex, or combinations, blends and copolymers thereof.

8. The stabilized replacement heart valve of claim 7, wherein the mesh is composed of polyolefins or halogenated polyolefins selected from the group consisting of a polyethylene, a polypropylene and a polytetrafluoroethylene, as well as combinations, blends and copolymers thereof.

9. The stabilized replacement heart valve of claim 8, wherein the mesh is composed of a polyolefin selected from the group consisting of ultra-high molecular weight polyethylene, ultra-high molecular weight polypropylene or expanded polytetrafluoroethylene, as well as combinations, blends and copolymers thereof.

10. The stabilized replacement heart valve of claim 2, wherein the distance between a first strut or junction and a second strut or junction spaced apart from the first strut or junction decreases by about 5% or less after implantation in a sheep model for 140 days, and the mesh is composed of a polyolefin selected from the group consisting of ultra-high molecular weight polyethylene, ultra-high molecular weight polypropylene and expanded PTFE and contains a plurality of pores or divots having openings with an average area between about 1,000 microns$^2$ and about 3,000 microns$^2$ such that the mesh has a pore density or divot density of about 5% to about 15% of the total area of the mesh.

11. The stabilized replacement heart valve of claim 1, wherein the replacement heart valve is configured to replace or repair a native aortic valve.

12. The stabilized replacement heart valve of claim 1, wherein the replacement heart valve is configured to replace or repair a native mitral valve.

13. The stabilized replacement heart valve of claim 1, wherein the replacement heart valve is configured to replace or repair a native mitral valve and the stent or frame includes a first inner stent portion having a cylindrical shape and a second outer stent portion surrounding the first inner stent portion, the second outer stent portion being attached to the first inner stent portion so that when the stabilized replacement heart valve is implanted into a native mitral valve annulus, the second outer stent portion engages the native mitral valve annulus and at least partially mechanically isolates the first inner stent portion from being deformed by the anatomy of the native mitral valve annulus or calcification of the native mitral valve such that the first inner stent portion retains its cylindrical shape, the valve assembly being attached only to the first inner stent portion.

14. The stabilized replacement heart valve of claim 13, wherein the cuff is disposed on a luminal surface of the first inner stent portion or the second outer stent portion and is composed of a cuff mesh having a thickness of between about 1 µm and about 500 µm and a plurality of pores or divots having openings with an average area between about 100 microns$^2$ and about 5,000 microns$^2$ such that the cuff mesh has a pore density or a divot density of about 1% to about 25% of the total area of the mesh.

15. The stabilized replacement heart valve of claim 13, wherein the cuff is disposed on an abluminal surface of the second outer stent portion and is composed of a cuff mesh having a thickness of between about 1 µm and about 500 µm and a plurality of pores or divots having openings with an average area between about 100 microns$^2$ and about 5,000 microns$^2$ such that the cuff mesh has a pore density or a divot density of about 1% to about 25% of the total area of the mesh.

16. The stabilized replacement heart valve of claim 15, wherein the cuff includes structure to reduce paravalvular leaks around the abluminal surface of the second outer stent portion.

* * * * *